US011471490B2

(12) United States Patent
Andresen et al.

(10) Patent No.: US 11,471,490 B2
(45) Date of Patent: Oct. 18, 2022

(54) T CELLS SURFACE-LOADED WITH IMMUNOSTIMULATORY FUSION MOLECULES AND USES THEREOF

(71) Applicant: Torque Therapeutics, Inc., Cambridge, MA (US)

(72) Inventors: Thomas L. Andresen, Vanlose (DK); De-Kuan Chang, Cambridge, MA (US); Douglas S. Jones, Bellevue, WA (US); Jesse Lyons, Cambridge, MA (US); Jonathan D. Nardozzi, Watertown, MA (US); Ulrik B. Nielsen, Quincy, MA (US); Michael Feldhaus, Grantham, NH (US)

(73) Assignee: Torque Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/628,342

(22) PCT Filed: Jul. 3, 2018

(86) PCT No.: PCT/US2018/040777
§ 371 (c)(1),
(2) Date: Jan. 3, 2020

(87) PCT Pub. No.: WO2019/010219
PCT Pub. Date: Jan. 10, 2019

(65) Prior Publication Data
US 2020/0330514 A1 Oct. 22, 2020

Related U.S. Application Data

(60) Provisional application No. 62/657,455, filed on Apr. 13, 2018, provisional application No. 62/620,107, filed on Jan. 22, 2018, provisional application No. 62/620,418, filed on Jan. 22, 2018, provisional application No. 62/598,433, filed on Dec. 13, 2017, provisional application No. 62/528,411, filed on Jul. 3, 2017.

(51) Int. Cl.
| | |
|---|---|
| *A61K 35/17* | (2015.01) |
| *A61K 38/20* | (2006.01) |
| *A61P 35/00* | (2006.01) |
| *C07K 14/54* | (2006.01) |
| *C07K 14/715* | (2006.01) |
| *C07K 16/28* | (2006.01) |
| *C12N 5/16* | (2006.01) |
| *C12N 15/88* | (2006.01) |
| *A61P 37/06* | (2006.01) |
| *A61K 39/395* | (2006.01) |
| *C07K 14/765* | (2006.01) |
| *C12N 5/0783* | (2010.01) |
| *A61K 9/00* | (2006.01) |
| *A61K 47/65* | (2017.01) |
| *A61K 39/00* | (2006.01) |

(52) U.S. Cl.
CPC .......... *A61K 35/17* (2013.01); *A61K 38/2086* (2013.01); *A61K 39/39541* (2013.01); *A61P 35/00* (2018.01); *A61P 37/06* (2018.01); *C07K 14/5434* (2013.01); *C07K 14/5443* (2013.01); *C07K 14/7155* (2013.01); *C07K 14/765* (2013.01); *C07K 16/289* (2013.01); *C07K 16/2812* (2013.01); *C07K 16/2815* (2013.01); *C07K 16/2845* (2013.01); *C07K 16/2866* (2013.01); *C12N 5/0637* (2013.01); *C12N 5/163* (2013.01); *C12N 15/88* (2013.01); *A61K 9/0019* (2013.01); *A61K 47/65* (2017.08); *A61K 2039/505* (2013.01); *C07K 2317/31* (2013.01); *C07K 2317/55* (2013.01); *C07K 2319/31* (2013.01); *C07K 2319/33* (2013.01); *C12N 2501/2315* (2013.01)

(58) Field of Classification Search
CPC ....... A61K 35/17; A61K 38/204; A61K 38/20
See application file for complete search history.

(56) References Cited

U.S. PATENT DOCUMENTS

| | | | |
|---|---|---|---|
| 5,405,940 | A | 4/1995 | Boon et al. |
| 5,650,150 | A | 7/1997 | Gillies |
| 6,617,135 | B1 | 9/2003 | Gillies et al. |
| 7,615,223 | B2 | 11/2009 | Thorpe et al. |
| 7,872,107 | B2 | 1/2011 | Webster et al. |
| 7,879,319 | B2 | 2/2011 | Gillies et al. |
| 7,906,118 | B2 | 3/2011 | Chang et al. |
| 8,034,352 | B2 | 10/2011 | Chang et al. |
| 8,119,101 | B2 | 2/2012 | Byrd et al. |
| 8,163,291 | B2 | 4/2012 | Chang et al. |

(Continued)

FOREIGN PATENT DOCUMENTS

| | | |
|---|---|---|
| EP | 1071468 A2 | 1/2001 |
| EP | 1418184 A1 | 5/2004 |

(Continued)

OTHER PUBLICATIONS

Bergholdt et al., "Genetic and Functional Evaluation of an Interleukin-12 Polymorphism (IDDM18) In Families With Type 1 Diabetes", Journal of Medical Genetics, 2004, vol. 41, No. 4, e39-e39, pp. 1-7.

(Continued)

*Primary Examiner* — Prema M Mertz
(74) *Attorney, Agent, or Firm* — Goodwin Procter LLP

(57) ABSTRACT

Immunostimulatory fusion molecules that include an immune cell targeting moiety and a cytokine molecule, pharmaceutical and formulations thereof, and methods of using and making the same, are disclosed.

30 Claims, 71 Drawing Sheets

Specification includes a Sequence Listing.

(56) References Cited

U.S. PATENT DOCUMENTS

| | | |
|---|---|---|
| 8,188,239 B2 | 5/2012 | Hansen et al. |
| 8,246,960 B2 | 8/2012 | Chang et al. |
| 8,258,268 B2 | 9/2012 | Wu et al. |
| 8,455,625 B2 | 6/2013 | Neri et al. |
| 8,617,557 B2 | 12/2013 | Penichet et al. |
| 8,986,699 B2 | 3/2015 | Hansen et al. |
| 9,139,657 B2 | 9/2015 | Hansen et al. |
| 9,441,043 B2 | 9/2016 | Chang et al. |
| 9,550,838 B2 | 1/2017 | Chang et al. |
| 9,580,485 B2 | 2/2017 | Wulhfard |
| 9,707,300 B2 | 7/2017 | Govindan et al. |
| 9,931,413 B2 | 4/2018 | Chang et al. |
| 10,377,829 B2 | 8/2019 | Chang et al. |
| 10,561,738 B2 | 2/2020 | Govindan et al. |
| 10,597,464 B2 | 3/2020 | Labrijn et al. |
| 10,696,722 B2 | 6/2020 | Kim et al. |
| 10,696,723 B2 | 6/2020 | Winston et al. |
| 11,084,863 B2 | 8/2021 | Bernett et al. |
| 2003/0175270 A1 | 9/2003 | Penninger |
| 2007/0003514 A1 | 1/2007 | Penichet et al. |
| 2009/0257991 A1 | 10/2009 | Li et al. |
| 2010/0297060 A1 | 11/2010 | Gillies et al. |
| 2011/0020273 A1 | 1/2011 | Chang et al. |
| 2011/0165122 A1 | 7/2011 | Shahangian et al. |
| 2012/0093769 A1 | 4/2012 | Chang et al. |
| 2012/0237442 A1 | 9/2012 | Rossi et al. |
| 2012/0276608 A1 | 11/2012 | Chang et al. |
| 2013/0078182 A1 | 3/2013 | Goldenberg et al. |
| 2013/0203115 A1 | 8/2013 | Schrum et al. |
| 2013/0230517 A1 | 9/2013 | Grewall et al. |
| 2014/0294758 A1 | 10/2014 | Gillies |
| 2014/0294759 A1 | 10/2014 | Chu et al. |
| 2015/0307628 A1 | 10/2015 | Kim et al. |
| 2016/0039920 A1 | 2/2016 | Casi et al. |
| 2016/0102135 A1 | 4/2016 | Escobar-Cabrera |
| 2016/0145355 A1 | 5/2016 | Saha et al. |
| 2016/0158378 A1 | 6/2016 | Park et al. |
| 2016/0168269 A1 | 6/2016 | Nielsen et al. |
| 2016/0175397 A1 | 6/2016 | Umana et al. |
| 2016/0176969 A1 | 6/2016 | Bernett et al. |
| 2016/0250350 A1 | 9/2016 | McBride et al. |
| 2016/0355600 A1 | 12/2016 | Moore et al. |
| 2017/0037131 A1 | 2/2017 | Bernett et al. |
| 2017/0080104 A1 | 3/2017 | Irvine et al. |
| 2017/0291934 A1 | 10/2017 | Reed et al. |
| 2017/0369568 A1 | 12/2017 | Witte et al. |
| 2018/0162939 A1 | 6/2018 | Ma et al. |
| 2019/0000989 A1 | 1/2019 | Leszczyniecka et al. |
| 2019/0062394 A1 | 2/2019 | Yarlagadda et al. |
| 2019/0071500 A1 | 3/2019 | Kley et al. |
| 2019/0194283 A1 | 6/2019 | Hauskins et al. |
| 2019/0255108 A1 | 8/2019 | Ma et al. |
| 2019/0263877 A1 | 8/2019 | Yeung et al. |
| 2019/0352335 A1 | 11/2019 | Jeong et al. |
| 2020/0048322 A1 | 2/2020 | Li et al. |
| 2020/0102363 A1 | 4/2020 | Mishra et al. |
| 2020/0188433 A1 | 6/2020 | Soon-Shiong et al. |
| 2020/0190213 A1 | 6/2020 | Preyer et al. |
| 2020/0223918 A1 | 7/2020 | Ma et al. |
| 2020/0230250 A1 | 7/2020 | Park et al. |
| 2020/0283534 A1 | 9/2020 | Ma et al. |
| 2020/0306301 A1 | 10/2020 | Andresen et al. |
| 2020/0308242 A1 | 10/2020 | Lowe et al. |
| 2020/0317787 A1 | 10/2020 | Li et al. |
| 2021/0017247 A1 | 1/2021 | Jones et al. |
| 2021/0246227 A1 | 8/2021 | Loew et al. |
| 2021/0301015 A1 | 9/2021 | Tseng |

FOREIGN PATENT DOCUMENTS

| | | |
|---|---|---|
| EP | 2525820 A1 | 11/2012 |
| EP | 3889183 A1 | 10/2021 |
| WO | WO-2002088334 A1 | 11/2002 |
| WO | WO-2003048334 A2 | 6/2003 |
| WO | WO-2006107786 A2 | 10/2006 |
| WO | WO-2007075270 A2 | 7/2007 |
| WO | WO-2010059253 A3 | 5/2010 |
| WO | WO-2011066342 A2 | 6/2011 |
| WO | WO-2012040323 A2 | 3/2012 |
| WO | WO-2013/052484 A1 | 4/2013 |
| WO | WO-2013/082254 A1 | 6/2013 |
| WO | WO-2014145907 A1 | 9/2014 |
| WO | WO2014204762 A1 | 12/2014 |
| WO | WO-2014209804 A1 | 12/2014 |
| WO | WO-2015048498 A3 | 7/2015 |
| WO | WO2016179288 A1 | 11/2016 |
| WO | WO-2016187514 A1 | 11/2016 |
| WO | WO-2016210293 A1 | 12/2016 |
| WO | WO-2017027843 A1 | 2/2017 |
| WO | WO-2017093408 A1 | 6/2017 |
| WO | WO-2017102010 A1 | 6/2017 |
| WO | 2016/113395 A1 | 7/2017 |
| WO | WO-2018030806 A1 | 2/2018 |
| WO | WO2019010222 A2 | 1/2019 |
| WO | WO2019010224 A1 | 1/2019 |
| WO | WO-2019209965 A2 | 10/2019 |
| WO | WO-2019222294 A1 | 11/2019 |
| WO | WO-2019222296 A1 | 11/2019 |
| WO | WO-2020024922 A1 | 2/2020 |
| WO | WO-2020047473 A1 | 3/2020 |
| WO | WO-2020088631 A1 | 5/2020 |
| WO | WO-2020102745 A1 | 5/2020 |
| WO | WO-2020123602 A1 | 6/2020 |
| WO | WO-2020205808 A1 | 10/2020 |
| WO | WO-2020221135 A1 | 11/2020 |
| WO | WO-2020247843 A2 | 12/2020 |
| WO | WO-2020255014 A1 | 12/2020 |
| WO | WO-2020259536 A1 | 12/2020 |
| WO | WO-2021001289 A1 | 1/2021 |
| WO | WO-2021041715 A2 | 3/2021 |

OTHER PUBLICATIONS

International Search Report and Written Opinion in International Application No. PCT/US2018/040777 dated Oct. 29, 2018.

International Preliminary Report on Patentability in International Application No. PCT/US2018/040777 dated Sep. 9, 2019.

Hombach, et al., "Targeting two co-operating cytokines efficiently shapes immune responses," OncoImmunology, Mar. 1, 2013, pp. e23205 1-3, vol. 2, No. 3.

Young, et al., "Antibody-cytokine fusion proteins for treatment of cancer: engineering cytokines for improved efficacy and safety," Semin Oncol, Oct. 2014, pp. 623-636, vol. 41, No. 5.

"Review Invivogen: Engineered Fc Regions," Invivogen (2011) https://www.invivogen.com/review-engineered-pfuse-chig.

Bootz and Neri, "Immunocytokines: a Novel Class of Products for the Treatment of Chronic Inflammation and Autoimmune Conditions," Drug Discov. Today 21:180-189 (2016).

Chaudhary and Elkord, "Regulatory T Cells in the Tumor Microenvironment and Cancer Progression: Role and Therapeutic Targeting," Vaccines 4:28 (2016).

Corthay, "How do Regulatory T Cells Work?" Scand. J. Immunol. 70:326-336 (2009).

Czajkowsky et al., "Fc-fusion Proteins: New Developments and Future Perspectives," EMBO Mol. Med. 4:1015-1028 (2012).

Francois et al., "Construction of a bispecific antibody reacting with the alpha- and beta-chains of the human IL-2 receptor," J. Immunol. 150:4610-4619 (1993).

Gunasekaran et al., "Enhancing antibody Fc heterodimer formation through electrostatic steering effects," J. Biol. Chem. 285:19637-19646 (2010).

Ha et al., "Immunoglobulin Fc Heterodimer Platform Technology: from Design to Applications in Therapeutic Antibodies and Proteins," Front. Immunol. 7:394 (2016).

Kiefer and Neri, "Immunocytokines and Bispecific Antibodies: Two Complementary Strategies for the Selective Activation of Immune Cells at the Tumor Site," Immunol. Rev. 270:178-192 (2016).

Klein et al., "Progress in overcoming the chain association issue in bispecific heterodimeric IgG antibodies," MABS 4:653-663 (2012).

(56) References Cited

OTHER PUBLICATIONS

Low et al., "Oral and Pulmonary Delivery of FSH—Fc Fusion Proteins via Neonatal Fc Receptor-mediated Transcytosis," Hum. Reprod. 20:1805-1813 (2005).
Neri and Sondel, "Immunocytokines for Cancer Treatment: Past, Present, and Future," Curr. Opin. Immunol. 40:96-102 (2016).
Noris et al., "Regulatory T Cells and T Cell Depletion: Role of Immunosuppressive Drugs," J. Am. Soc. Nephrol. 18:1007-1018 (2007).
Pechtner et al., "A New Approach to Drug Therapy: Fc-Fusion Technology," Prim. Health Care 7:2167-1079 (2017).
Peng et al., "A Single-Chain IL-12 lgG3 Antibody Fusion Protein Retains Antibody Specificity and IL-12 Bioactivity and Demonstrates Antitumor Activity," 163:250-258 (1999).
Schmidt et al., "Molecular Mechanisms of Treg-Mediated T Cell Suppression," Front. Immunol. 3:51 (2012).
Sondel and Gillies, "Current and Potential Uses of Immunocytokines as Cancer Immunotherapy," Antibodies 1:149-171 (2012).
Strohl, "Fusion Proteins for Half-Life Extension of Biologies as a Strategy to Make Biobetters," BioDrugs 29:215-239 (2015).
Tzeng et al., "Antigen Specificity Can be Irrelevant to Immunocytokine Efficacy and Biodistribution," PNAS 112:3320-3325 (2015).
Vazquez-Lombardi et al., "Molecular Engineering of Therapeutic Cytokines," Antibodies 2:426-451 (2013).
Akdis et al., "Interleukins (from IL-1 to IL-38), Interferons, Transforming Growth Factor β, and TNF-α: Receptors, Functions, and Roles in Diseases," J. Allergy Clin. Immunol. 138:984-1010 (2016).
Fallon et al., "The Immunocytokine NHS-IL12 as a Potential Cancer Therapeutic," Oncotarget 5: 1869-1884 (2014).
Hutmacher et al., "Antibody-cytokine fusion proteins: Biopharmaceuticals with immunomodulatory properties for cancer therapy," Adv. Drug Deliv. Rev. 141:67-91 (2019).
Kermer et al., "Combining Antibody-Directed Presentation of IL-12 and 4-1BBL in Trifunctional Fusion Protein for Cancer Immunotherapy," Mol. Cancer Ther. 13: 112-121 (2013).
Murer et al., "Antibody-cytokine fusion proteins: a novel class of biopharmaceuticals for the therapy of cancer and of chronic inflammation," N. Biotechnol. 52: 42-53 (2019).
Paoloni et al., "Defining the Pharmacodynamic Profile and Therapeutic Index of NHS-IL12 Immunocytokine in Dogs with Malignant Melanoma," PLoS One 10(6):e0129954 (2015).
Robinson-Mosher et al., "Designing Cell-Targeted Therapeutic Proteins Reveals the Interplay between Domain Connectivity and Cell Binding," Biophys. J. 107: 2456-2466 (2014).
Rudman et al., "A Phase 1 Study of AS1409, a Novel Antibody-Cytokine Fusion Protein, in Patients with Malignant Melanoma or Renal Cell Carcinoma," Clin. Cancer Res. 17:1998-2005 (2011).
Runbeck et al., "Utilizing Immunocytokines for Cancer Therapy," Antibodies 10:10 (2021).
Singh et al., "Combining Adoptive Cellular and Immunocytokine Therapies to Improve Treatment of B-Lineage Malignancy," Cancer Res. 67: 2872-2880 (2007).
Weidle et al., "Genetically Engineered Fusion Proteins for Treatment of Cancer," Cancer Genom. Proteom. 9:357-372 (2012).
Xu et al., "Combination Therapy with NHS-muIL12 and Avelumab (anti-PD-L1) Enhances Antitumor Efficacy in Preclinical Cancer Models," Clin. Cancer Res. 23:5869-5880 (2017).
U.S. Appl. No. 16/628,363, filed Jan. 3, 2020, Andresen et al.
U.S. Appl. No. 16/628,374, filed Jan. 3, 2020, Jones et al.
U.S. Appl. No. 17/293,995, filed May 14, 2021, Andresen et al.
U.S. Appl. No. 17/599,948, filed Sep. 29, 2021, Jones.
Clement et al., "Anti-CD8 antibodies can trigger CD8+ T cell effector function in the absence of TCR engagement and improve peptide -MHCI tetramer staining," J. Immunol. 187:654-663 (2011).
Denkberg et al., "Critical role for CD8 in binding of MHC tetramers to TCR: CD8 antibodies block specific binding of human tumor-specific MHC-peptide tetramers to TCR," J. Immunol. 167:270-276 (2001).
Nagaraj et al., "Human cytokine-induced killer cells have enhanced in vitro cytolytic activity via non-viral interleukin-2 gene transfer," Genet. Vaccines Ther. 2:12 (2004).
Wooldridge et al., "Anti-CD8 antibodies can inhibit or enhance peptide-MHC class I (pMHCI) multimer binding: this is paralleled by their effects on CTL activation and occurs in the absence of an interaction between pMHCI and CD8 on the cell surface," J. Immunol. 171:6650-6660 (2003).

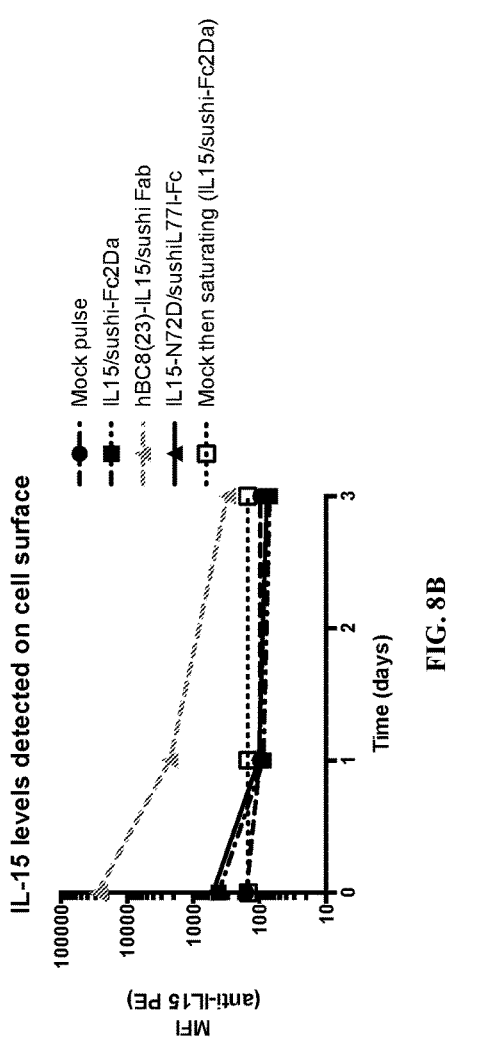
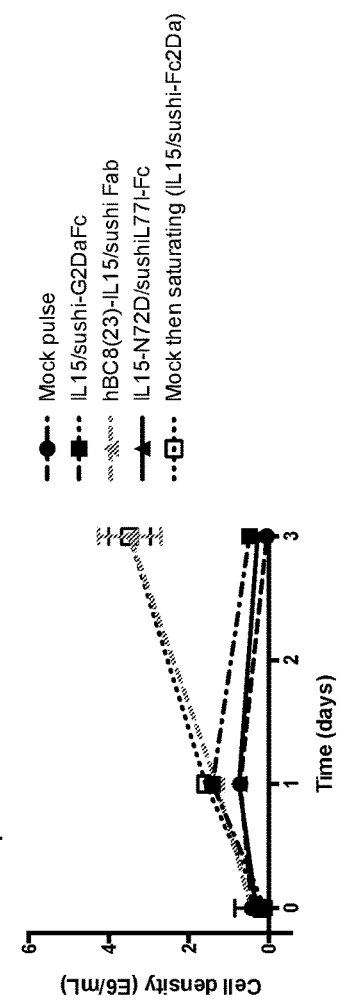
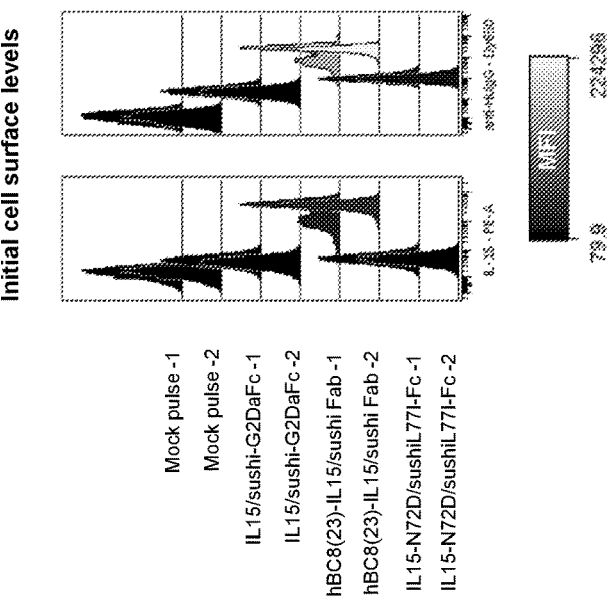
FIG. 8A
FIG. 8B
FIG. 8C

Mouse:

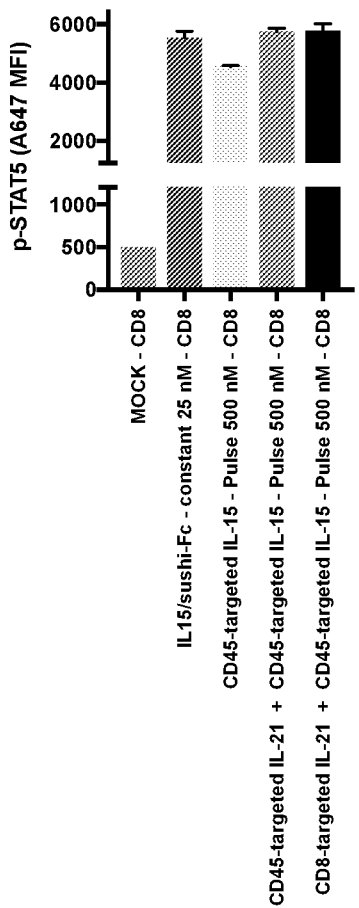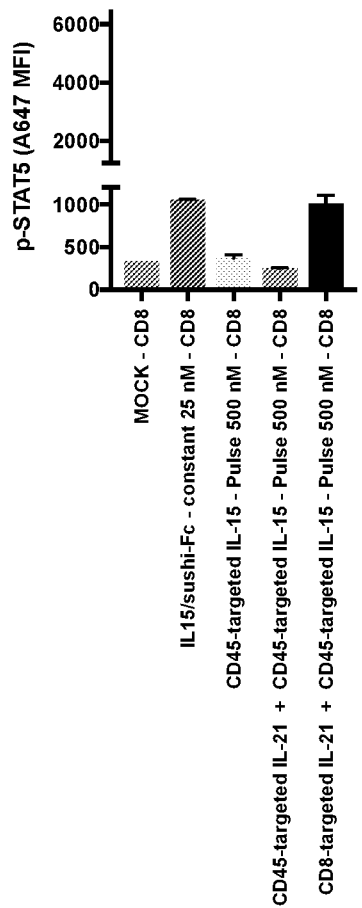
FIG. 27A
FIG. 27B

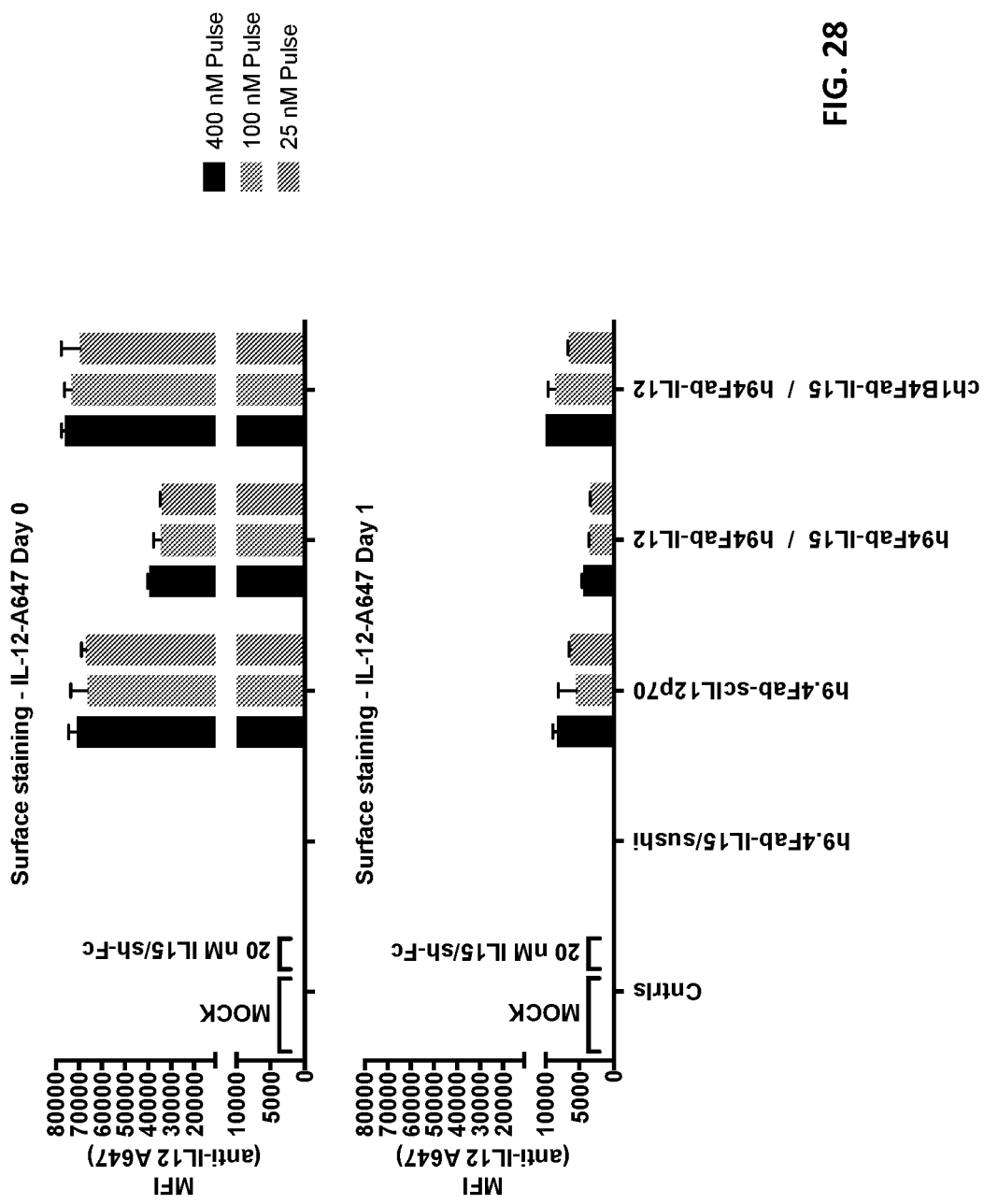

T CELLS SURFACE-LOADED WITH IMMUNOSTIMULATORY FUSION MOLECULES AND USES THEREOF

CROSS-REFERENCE TO RELATED APPLICATIONS

This application is a U.S. National Phase application under 35 U.S.C. 371 of International Application No. PCT/US2018/040777, filed Jul. 3, 2018, which claims priority to and the benefit of U.S. Provisional Application Nos. 62/528,411 filed Jul. 3, 2017, 62/598,433 filed Dec. 13, 2017, 62/620,418 filed Jan. 22, 2018, 62/620,107 filed Jan. 22, 2018 and 62/657,455 filed Apr. 13, 2018, the entire disclosure of each of which is incorporated OK TO EP herein by reference.

SEQUENCE LISTING

The ASCII text file submitted herewith via EFS-Web, entitled "174285_010800_sequence.txt" created on May 29, 2020, having a size of 231,711 bytes, is hereby incorporated by reference in its entirety.

FIELD

The present disclosure relates generally to immunostimulatory fusion molecule engineered to comprise an immune stimulating moiety and an immune cell targeting moiety. Methods for making and using the same are also provided.

BACKGROUND

Cytokines participate in the regulation of the immune system. When used in cancer therapy, cytokines can act as immunomodulatory agents that have anti-tumor effects and which can increase the immune response towards some types of tumors. However, rapid blood clearance and lack of tumor specificity require systemic administration of high doses of the cytokine in order to achieve a concentration of the cytokine at the tumor site and other relevant tissues (e.g., lymph nodes and spleen) sufficient to activate an immune response or have an anti-tumor effect. These high levels of systemic cytokine can lead to severe toxicity and adverse reactions.

Thus, the need still exists for cytokine compositions with improved properties, e.g., having greater therapeutic effectiveness and a reduction in the number and severity of the side effects of these products (e.g., toxicity, destruction of non-tumor cells, among others).

SUMMARY

The present disclosure provides, inter alia, an immunostimulatory fusion molecule (IFM; used interchangeably with "tethered fusion") comprising an immune stimulating moiety and an immune cell targeting moiety.

In one aspect, an immunostimulatory fusion molecule is provided, comprising:
(a) an immunostimulatory cytokine molecule; and
(b) an immune cell targeting moiety comprising an antigen-binding fragment of an antibody having an affinity to an antigen on the surface of a target immune cell,
wherein the immunostimulatory cytokine molecule is operably linked to the antigen-binding fragment.

In another aspect, an immunostimulatory fusion molecule is provided, comprising:
(a) an immunostimulatory cytokine molecule; and
(b) an immune cell targeting moiety comprising an antibody having an antigen-binding site specific for an antigen on the surface of a target immune cell, wherein the antibody comprises a light chain having a C-terminus and an N-terminus, and a heavy chain having a C-terminus and an N-terminus, wherein the light chain is linked to the heavy chain by a disulfide bond,
wherein the immunostimulatory cytokine molecule is operably linked to the antibody at the C-terminus of the light chain, the N-terminus of the light chain, or the N-terminus of the heavy chain portion.

In another aspect, an immunostimulatory fusion molecule is provided, comprising:
(a) an IL-12 molecule; and
(b) a T cell targeting moiety comprising a Fab fragment having an antigen-binding site specific for a CD45 cell surface receptor;
wherein the Fab fragment and the IL-12 molecule are operably linked together as a fusion molecule.

In some embodiments, the immune cell targeting moiety targets a T cell selected from an effector T cell, a CD4+ T cell, a CD8+ T cell, and a CTL. In some embodiments, the antigen is a CD45 receptor expressed on the cell surface of the T cell. In some embodiments, the immune cell targeting moiety comprises a Fab fragment, F(ab')2, Fv, a single chain Fv of anti-CD45 antibodies BC8, 4B2, GAP8.3 or 9.4, or humanized version of any of the foregoing. In some embodiments, the immunostimulatory cytokine molecule comprises an IL-12, a single chain IL-12, a subunit of IL-12, or a variant form any of the foregoing. The immunostimulatory fusion molecule can further include a single-chain Fv having an affinity to an antigen on the surface of the target immune cell, wherein optionally the single-chain Fv has an affinity to the same antigen as the antigen-binding fragment. In some embodiments, the single-chain Fv has an affinity to a different antigen than the antigen-binding fragment. In some embodiments, the antigen-binding fragment is a Fab fragment, which optionally comprises a light chain and a heavy chain fragment optionally linked by a disulfide bond, and wherein the immunostimulatory cytokine molecule is operably linked to the Fab fragment at a C-terminus of the light chain, an N-terminus of the light chain, a C-terminus of the heavy chain fragment, or an N-terminus of the heavy chain fragment.

In some embodiments, the immunostimulatory cytokine molecule is operably linked to the antigen-binding fragment by a linker. In some embodiments, the linker is selected from a cleavable linker, a non-cleavable linker, a peptide linker, a flexible linker, a rigid linker, a helical linker, and a non-helical linker, e.g., a peptide linker comprising a Gly and a Ser. In some embodiments, the peptide linker is a $(GGGS)_N$ (SEQ ID NO: 124) or $(GGGGS)_N$ (SEQ ID NO: 125) linker, wherein $_N$ indicates the number of repeats of the motif and is an integer selected from 1-10.

In some embodiments, the antigen-binding fragment has an affinity to a CD45 receptor and comprises:
(a) a light chain variable amino acid sequence corresponding to the variable domain in the antibody portion of the amino acid sequence shown in SEQ ID NO: 82, or an amino acid sequence at least 85%, 90%, 95%, or higher identity to the variable domain of SEQ ID NO: 82; and/or
(b) a heavy chain variable amino acid sequence corresponding to the variable domain of amino acid sequence shown in SEQ ID NO: 79, or an amino acid sequence at least 85%, 90%, 95%, or higher identity to the variable domain of SEQ ID NO: 79.

In some embodiments, the cytokine molecule comprises an IL-12 molecule having an amino acid sequence corresponding to the amino acid sequence shown in SEQ ID NO: 50, or an amino acid sequence at least 85%, 90%, 95%, or higher identity to the cytokine portion of SEQ ID NO: 50.

In some embodiments, the cytokine molecule comprises a single-chain IL-12 molecule having an IL-12A subunit linked to an IL-12B subunit through a linker having an amino acid sequence corresponding to the amino acid sequence shown in SEQ ID NO: 70, or an amino acid sequence at least 85%, 90%, 95%, or higher identity to the cytokine portion of SEQ ID NO: 70.

In some embodiments, the linker comprises a peptide linker having an amino acid sequence corresponding to the amino acid sequence in SEQ ID NO: 36, or an amino acid sequence at least 85%, 90%, 95%, or higher identity to the cytokine portion of SEQ ID NO: 36.

In some embodiments, the single-chain Fv has an amino acid sequence corresponding to the Fv portion of SEQ ID NO: 80, or an amino acid sequence at least 85%, 90%, 95%, or higher identity to the Fv portion of SEQ ID NO: 80.

In some embodiments, the Fab fragment comprises a light chain having a variable domain (VL) and a constant domain (CL) and a heavy chain fragment having a variable domain (VH) and a constant domain (CH1), wherein the light chain and heavy chain fragment are optionally linked by a disulfide bond, and wherein the light chain and heavy chain fragment each comprise a C-terminus and an N-terminus. In some embodiments, the IL-12 molecule is operably linked to the C-terminus or the N-terminus of the light chain or the heavy chain fragment.

In some embodiments, the immunostimulatory fusion molecule further comprises a peptide linker having a first terminus fused to the IL-12 molecule and a second terminus is fused to the Fab fragment, thereby operably linking the IL-12 molecule and the Fab fragment.

Also provided herein is an isolated nucleic acid molecule encoding any one of the immunostimulatory fusion molecule disclosed herein.

Also provided herein is a vector comprising one or more nucleic acids encoding a polypeptide corresponding to the amino acid sequence of SEQ ID NO: 36, 50, 70, 79, 80, or 82, or an amino acid sequence at least 85%, 90%, 95%, or higher identity to SEQ ID NO: 36, 50, 70, 79, 80, or 82.

Also provided herein is a host cell comprising the nucleic acid molecule or the vector disclosed herein.

A further aspect relates to a modified immune cell comprising:
(a) an immunostimulatory fusion molecule comprising
  (i) an immunostimulatory cytokine molecule; and
  (ii) an immune cell targeting moiety having an affinity to a cell surface antigen; and
(b) a target immune cell expressing or otherwise displaying the cell surface antigen,
wherein the immunostimulatory fusion molecule is bound to the surface of the immune cell through interaction with the cell surface antigen.

Another aspect relates to a modified immune cell comprising a healthy and/or non-malignant immune cell and the immunostimulatory fusion molecule disclosed herein bound thereto.

Another aspect relates to a method of preparing modified immune cells, comprising:
(a) providing a population of immune cells; and
(b) incubating the immunostimulatory fusion molecule of disclosed herein with the population of immune cells so as to permit targeted binding of the immunostimulatory fusion molecule thereto, thereby producing a population of immune cells having immunostimulatory fusion molecules bound on the cell surface.

Another aspect relates to a composition for use in immune cell therapy, the composition comprising:
(a) a plurality of immunostimulatory fusion molecules, each fusion molecule comprising
  (i) an immunostimulatory cytokine molecule; and
  (ii) an immune cell targeting moiety having an affinity to a cell surface antigen of a T cell;
(b) a population of T cells expressing or otherwise displaying the cell surface antigen, wherein the plurality of immunostimulatory fusion molecules are bound to the surface of the T cells through interaction with the cell surface antigen; and
(c) a pharmaceutically acceptable carrier, excipient, or stabilizer.

Another aspect relates to a pharmaceutical composition comprising the immunostimulatory fusion molecule disclosed herein and a pharmaceutically acceptable carrier, excipient, or stabilizer.

Also provided herein is a method for the treatment of cancer in a human subject, the method comprising administering to the human subject a cell therapeutic composition, the composition comprising:
(a) a plurality of immunostimulatory fusion molecules, each fusion molecule comprising
  (i) an immunostimulatory cytokine molecule; and
  (ii) an immune cell targeting moiety having an affinity to a cell surface antigen of a T cell; and
(b) a population of T cells that homes to a cancer cells or a tissue in which cancer cells exist, and wherein the T cells express the cell surface antigen,
wherein the plurality of immunostimulatory fusion molecules are bound to the surface of the T cells, and wherein the cytokine molecule acts in vivo upon the population of T cells and/or other immune cells in the human subject to stimulate an immune response against the cancer.

In some embodiments, the population of T cells comprise primary T cells, expanded primary T cells, T cells derived from PBMC cells, T cells derived from cord blood cells, T cells autologous to the human subject, T cells allogeneic to the human subject, genetically-engineered T cells, CAR-T cells, effector T cells, activated T cells, CD8+ T cells, CD4+ T cells, and/or CTLs. In some embodiments, the cell therapeutic composition is administered to the human subject in a cell therapy course selected from an adoptive cell therapy, CAR-T cell therapy, engineered TCR T cell therapy, an antigen-trained T cell therapy, or an enriched antigen-specific T cell therapy.

In some embodiments, the immunostimulatory fusion molecule disclosed herein can further include a nanoparticle, a liposome and/or a biodegradable polymer. In some embodiments, the nanoparticle comprises a protein nanogel, a nucleotide nanogel, a polymer nanoparticle, or a solid nanoparticle. In some embodiments, the nanoparticle comprises a protein nanogel. In some embodiments, the nanoparticle optionally comprises at least one polymer, cationic polymer, or cationic block co-polymer on the nanoparticle surface. In some embodiments, the nanoparticle comprises a nanogel that is cross linked by a reversible linker that is sensitive to redox (disulfide) or pH (hydrolysable groups) or enzymes (proteases).

In an aspect, a composition is provided, comprising:
(a) an immunostimulatory fusion molecule comprising
(i) an immunostimulatory cytokine molecule; and
(ii) an immune cell targeting moiety having an affinity to a cell surface antigen;
(b) a target immune cell expressing or otherwise displaying the cell surface antigen, wherein the immunostimulatory fusion molecule is bound to the surface of the immune cell through interaction with the cell surface antigen; and
(c) a nanoparticle, nanogel, or liposome.

In another aspect, an immunostimulatory fusion molecule (IFM) is provided, comprising:
(i) a cytokine molecule selected from one or more of IL-15, IL-2, IL-6, IL-7, IL-12, IL-18, IL-21, IL-23, or IL-27, including; and
(ii) an immune cell targeting moiety having an affinity with an immune cell surface receptor on the immune cell, wherein the immune cell targeting moiety is selected from an antibody or antigen-binding fragment thereof, a non-antibody scaffold, or a ligand that binds to the immune cell surface receptor, wherein the immune cell surface receptor is selected from one or more of CD45, CD4, CD8, CD3, CD11a, CD11b, CD11c, CD18, CD25, CD127, CD19, CD20, CD22, HLA-DR, CD197, CD38, CD27, CD196, CXCR3, CXCR4, CXCR5, CD84, CD229, CCR1, CCR5, CCR4, CCR6, CCR8, CCR10, CD16, CD56, CD137, OX40, or GITR;
wherein the cytokine molecule and the immune cell targeting moiety are operably linked together as a fusion molecule.

In some embodiments, the cytokine molecule can comprise IL-15 and/or IL-12. The immune cell targeting moiety can comprise an antibody or a ligand that binds to CD45.

In another aspect, an immunostimulatory fusion molecule (IFM) is provided, comprising:
(i) a cytokine molecule selected from IL-12 and/or IL-15, or an variant form thereof; and
(ii) an immune cell targeting moiety having an affinity with an immune cell surface receptor on the immune cell, wherein the immune cell targeting moiety is selected from an antibody or antigen-binding fragment thereof, a non-antibody scaffold, or a ligand that binds to the immune cell surface receptor, wherein the immune cell surface receptor is CD45;
wherein the cytokine molecule and the immune cell targeting moiety are operably linked together as a fusion molecule.

In some embodiments, the cytokine molecule is IL-12 and/or IL-15. The immune cell targeting moiety can comprise an antibody or antigen-binding fragment thereof that binds to CD45.

In some embodiments, the immune cell is a healthy and/or non-malignant immune cell. In various embodiments, the IFM can further include a linker for operably linking the targeting moiety and the cytokine molecule. For example, the linker can be selected from: a cleavable linker, a non-cleavable linker, a peptide linker, a flexible linker, a rigid linker, a helical linker, or a non-helical linker, preferably a peptide linker that optionally comprises Gly and Ser, wherein preferably the peptide linker is a $(GGGS)_N$ or $(GGGGS)_N$ linker, wherein $N$ indicates the number of repeats of the motif and is an integer selected from 1-10.

Also provided herein is a pharmaceutical composition comprising the IFM disclosed herein and a pharmaceutically acceptable carrier, excipient, or stabilizer.

Another aspect relates to a modified immune cell, comprising a healthy and/or non-malignant immune cell and the IFM disclosed herein bound or targeted thereto.

A further aspect relates to a method of in vitro preparation of modified immune cells, comprising:
providing a plurality of healthy and/or non-malignant immune cells; and
incubating the IFM disclosed herein with the plurality of healthy and/or non-malignant immune cells so as to permit targeted binding of the IFM thereto, thereby producing a plurality of modified immune cells.

Another aspect relates to a method of providing a cell therapy, comprising:
providing a plurality of healthy and/or non-malignant immune cells;
incubating the IFM disclosed herein with the plurality of healthy and/or non-malignant immune cells so as to permit targeted binding of the IFM thereto, thereby producing a plurality of modified immune cells; and
administering the plurality of modified immune cells to a subject in need thereof;
wherein preferably the cell therapy is administered in the absence of pre-conditioning of the subject, wherein said pre-conditioning comprises CPX (cyclophosphamide) or other lymphodepletion conditioning chemotherapy.

In some embodiments, the cell therapy can be used for treating a cancer, preferably a solid tumor cancer or a hematological cancer. The solid tumor cancer can be one or more of ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof. The hematological cancer can be one or more of leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sézary syndrome, Waldenström macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm.

In various embodiments, the cell therapy can be selected from an adoptive cell therapy, CAR-T cell therapy, engineered TCR T cell therapy, a tumor infiltrating lymphocyte therapy, an antigen-trained T cell therapy, an enriched antigen-specific T cell therapy or NK cell therapy. In certain embodiments, the plurality of healthy and/or non-malignant immune cells are autologous to the subject.

In another aspect, the disclosure provides a particle, e.g., a nanoparticle, that comprises an IFM as described herein, e.g., nanoparticle that comprises a protein (e.g., a protein nanogel). In one embodiment, the particle comprises the same IFM. In other embodiments, the particle comprises one or more different types of IFM. Nanoparticles and methods of making are disclosed in PCT International Application No. PCT/US2017/037249 filed Jun. 13, 2017, e.g., on pages 57-79, which is incorporated herein by reference in its entirety. In certain embodiments, such nanoparticles can be used in connection with the backpack technology as disclosed in, e.g., U.S. Publication No. 2017/0080104, U.S. Pat. No. 9,603,944, (S. Publication No. 2014/0081012, and PCT Application No. PCT/US2017/037249, each of which is incorporated herein by reference in its entirety.

In some embodiments, the immune stimulating moiety is chosen from a cytokine molecule, an agonist of a costimulatory molecule, or an inhibitor of a negative immune regulator, e.g., an inhibitor of a checkpoint inhibitor.

In some embodiments, the immune stimulating moiety is a cytokine molecule. In certain embodiments, the cytokine molecule includes a cytokine, e.g., includes a cytokine chosen from one or more of IL-2, IL-6, IL-7, IL-9, IL-12, IL-15, IL-18, IL-21, IL-23, or IL-27, including variant forms thereof (e.g., a cytokine derivative, a complex comprising the cytokine molecule with a polypeptide, e.g., a cytokine receptor complex, and other agonist forms thereof). In one embodiment, the cytokine molecule is an IL-15 molecule.

In other embodiments, the immune stimulating moiety is an agonist of a costimulatory molecule, e.g., a costimulatory molecule chosen from CD137, OX40, CD28, GITR, VISTA, anti-CD40, or CD3. In some embodiments, the agonist of the immune stimulatory molecule is an agonist antibody molecule against, or an agonist ligand of, CD137, OX40, GITR, CD3, or CD28.

In yet other embodiments, the immune stimulating moiety is an inhibitor of a negative immune regulator, e.g., an inhibitor of a checkpoint inhibitor, e.g., a checkpoint inhibitor chosen from PD-1, PD-L1, LAG-3, TIM-3, or CTLA-4. In some embodiments, the inhibitor of the negative immune regulator is an antibody molecule or a ligand. For example, the inhibitor of the checkpoint inhibitor, e.g., the antibody molecule, binds to and/or inhibits PD-1, PD-L1, LAG-3, TIM-3, or CTLA-4.

In some embodiments, the immune cell targeting moiety is capable of binding to an immune cell surface target, thereby targeting the immune stimulating moiety to the immune cell, e.g., an immune effector cell (e.g., a lymphocyte). Without wishing to be bound by theory, binding of the immune cell targeting moiety to the immune cell surface target is believed to increase the concentration, e.g., the concentration over time, of the immune stimulating moiety, e.g., cytokine molecule, with its corresponding receptor, e.g., a cytokine receptor, on the surface of the immune cell, e.g., relative to the association of the free cytokine molecule with its cytokine receptor. In some embodiments, the immune cell surface target is abundantly present on the surface of an immune cell (e.g., outnumbers the number of receptors for the cytokine molecule present on the immune cell surface). In some embodiments, the immune cell targeting moiety can be chosen from an antibody molecule or a ligand molecule that binds to an immune cell surface target, e.g., a target chosen from CD4, CD8, CD11a, CD19, CD20 or CD45. In one embodiment, the immune cell targeting moiety comprises an antibody molecule or a ligand molecule that binds to CD45. In other embodiments, the immune cell targeting moiety binds to an immune checkpoint inhibitor, such as PD-1, PD-L1, LAG-3, TIM-3, or CTLA-4. In embodiments where an immune checkpoint inhibitor is targeted, the immune cell targeting moiety may bind to, or may bind to and inhibit, the immune checkpoint inhibitor. In embodiments, the targeting moiety is believed to specifically deliver and/or increase the concentration of the cytokine molecule to the surface of an immune cell, thereby resulting in one or more of increased localization, distribution and/or enhancing the cell surface availability of the cytokine molecule. In embodiments, the IFM does not substantially interfere with the signaling function of the cytokine molecule. Such targeting effect results in localized and prolonged stimulation of proliferation and activation of the immune cells, thus inducing the controlled expansion and activation of an immune response.

Thus, provided herein are, inter alia, IFMs that include the aforesaid moieties, pharmaceutical compositions thereof and formulations, e.g., nanoparticles that comprise the IFMs (e.g., a protein nanogel as described herein), nucleic acids encoding the same, methods of producing the aforesaid molecules, and methods of treating a disorder, e.g., a cancer, an infectious disorder or an autoimmune disorder, using the aforesaid IFMs and compositions thereof.

Accordingly, in one aspect, the disclosure provides an immunostimulatory fusion molecule (IFM) comprising an immune stimulating moiety (e.g., a cytokine molecule, an agonist of a costimulatory molecule, or an inhibitor of a negative immune regulator), and an immune cell targeting moiety.

In some embodiments, the immune stimulating moiety, e.g., the cytokine molecule, is connected to, e.g., covalently linked to, the immune cell targeting moiety (e.g., directly or indirectly, e.g., via a peptide linker). In some embodiments, the immune cell targeting moiety of the IFM binds to a surface target, e.g., surface receptor, on an immune cell, e.g., an immune effector cell. In embodiments, the IFM associates, e.g., links together, the immune stimulating moiety, e.g., the cytokine molecule, and the immune cell targeting moiety to the immune cell, e.g., the effector immune cell. In some embodiments, the IFM increases the concentration of the cytokine molecule of the IFM (e.g., the concentration of the cytokine molecule of the IFM over time, e.g., a specified period of time) on the surface of the immune cell. In embodiments, the increased concentration of the cytokine molecule of the IFM on the surface of the immune cell results in one or more of: (i) increased localization (e.g., level) of the cytokine molecule of the IFM to the immune cell surface, e.g., relative to the free cytokine molecule; (ii) enhanced cell surface availability (e.g., concentration (e.g., level or amount) and/or duration of exposure) of the cytokine molecule of the IFM, e.g., relative to the free cytokine molecule; (iii) increased cytokine signaling in a targeted population of immune cells, e.g., a population of cells expressing a preselected surface target, e.g., a surface target as described herein, e.g., relative to the free cytokine molecule; (iv) prolongs cytokine signaling in the targeted cell population (e.g., increases the duration of cytokine signaling by at least 8 hours, e.g., 24 hours), e.g., relative to the free cytokine molecule; (v) causes immunostimulation; (vi) increases immune cell activation of and/or expansion, e.g., of the targeted population of immune cells; or (vii) shows reduced side effects, e.g., a lower systemic toxicity, compared to the free cytokine molecule. In some embodiments, the IFM changes, e.g., increases, any of (i)-(vii) to a greater extent than the free cytokine molecule, e.g., by at least 8 hours, e.g., 24 hours. In one embodiment, the cytokine molecule is an IL-15 molecule as described herein, and the immune cell targeting moiety is an anti-CD45 antibody molecule. e.g., an antibody or antibody fragment that binds to CD45 as described herein.

In a related aspect, the disclosure provides a composition, e.g., an IFM, comprising a cytokine molecule, e.g., an TL-15 molecule, coupled to, e.g., fused to, an immune cell targeting moiety. In embodiments, the immune cell targeting moiety binds to a target or a receptor on the immune cell. In embodiments, the immune cell targeting moiety includes, or is, an antibody molecule, e.g., an antibody or an antibody fragment, e.g., an anti-CD45 antibody molecule (e.g., an IgG, a Fab, scFv), that binds a CD45 receptor on a cell, e.g., an immune cell (e.g., an immune effector cell, such as a lymphocyte). In embodiments, the composition, e.g., an IFM, associates, e.g., links together, the cytokine molecule and the immune cell targeting moiety to the immune cell, e.g., the effector immune cell. In embodiments, the anti-CD45 antibody binding to the cell increases the association of the IL-15 molecule with the cell and improves one or more of IL-15 signaling, immunostimulation, over time, e.g., relative to a free IL-15 molecule (an IL-15 molecule not found in the composition). In embodiments, the signaling and/or immunostimulation occurs over a period of time, e.g., minutes, hours, days e.g., by at least 8 hours, e.g., 24 hours.

In another aspect, the disclosure provides a particle, e.g., a nanoparticle, that comprises an IFM as described herein, e.g., nanoparticle that comprises a protein (e.g., a protein nanogel as described herein). In one embodiment, the particle comprises the same IFM. In other embodiments, the particle comprises one or more different types of IFM.

Compositions, e.g., pharmaceutical compositions, comprising the IFMs and/or the particles disclosed herein, are also disclosed. In embodiments, the pharmaceutical compositions further include a pharmaceutically acceptable carrier, excipient, or stabilizer.

In yet another aspect, the disclosure provides an isolated nucleic acid molecule comprising the nucleotide sequence encoding the IFM disclosed herein, or comprising a nucleotide sequences substantially identical thereto (e.g., at least 95% identical thereto), as well as a vector, e.g., an expression vector, and a host cell comprising the nucleic acid molecule disclosed herein.

Methods of making, e.g., producing, the IFM disclosed herein are also disclosed. In embodiments, the method includes culturing the host cell comprising the nucleic acid molecules disclosed herein, under suitable growth conditions.

In yet another aspect, the disclosure provides a method of treating a disorder or condition in a subject, e.g., a human. The method includes administering to the subject, in need of treatment, a composition, e.g., an IFM or a particle as described herein, in an amount effective to treat the disorder or condition. In some embodiments, the disorder is a cancer, e.g., a solid tumor or a hematological cancer. In other embodiments, the disorder is an infection, e.g., a viral, bacterial or yeast infection. In yet other embodiments, the disorder is an autoimmune disorder. The compositions disclosed herein can be used alone, or in combination with, but not limited to, cell therapy, and as a combination with chemotherapy or radiotherapy. In some embodiments, the cell therapy is chosen from an adoptive cell therapy, CAR-T cell therapy, engineered TCR T cell therapy, a tumor infiltrating lymphocyte therapy, an antigen-trained T cell therapy, or an enriched antigen-specific T cell therapy.

In a related aspect, the disclosure provides a composition, e.g., an IFM and/or a particle disclosed herein, for use in a medicament, e.g., for use in treating a disorder or condition in a subject, e.g., a mammal (e.g., a human). Alternatively, the use of a composition, e.g., an IFM, in the manufacture of a medicament for treating a disorder or condition in a subject, e.g., a mammal (e.g., a human) is disclosed. In some embodiments, the disorder is a cancer, e.g., a solid tumor or a hematological cancer. In other embodiments, the disorder is an infection, e.g., a viral (e.g., HIV), bacterial or yeast infection. In yet other embodiments, the disorder is an autoimmune disorder. The compositions disclosed herein can be used alone, or in combination with, but not limited to, cell therapy, and as a combination with chemotherapy or radiotherapy. In some embodiments, the cell therapy is chosen from an adoptive cell therapy, CAR-T cell therapy, engineered TCR T cell therapy, a tumor infiltrating lymphocyte therapy, an antigen-trained T cell therapy, or an enriched antigen-specific T cell therapy.

In another aspect, the disclosure provides a method of selectively delivering a cytokine molecule, e.g., an IL-15 molecule, to an immune cell in a subject, e.g., a mammal (e.g., a human). The method includes administering an IFM as described herein to the subject, wherein the cytokine molecule is selectively delivered to the immune cell.

In embodiments of the therapeutic and delivery methods disclosed herein, the subject herein is in need of a cell-based therapy, e.g., an immune cell therapy. For example, the subject is in need of a cell therapy chosen from an adoptive cell therapy, CAR-T cell therapy, engineered TCR T cell therapy, a tumor infiltrating lymphocyte therapy, an antigen-trained T cell therapy, or an enriched antigen-specific T cell therapy. In some embodiments, the subject is a patient, e.g., a human patient. In some embodiments, the subject has a disease chosen from cancer, diabetes, an autoimmune disease, allergies or allergic conditions, asthma or a cardiovascular disease. In an embodiment, the subject is in need of a transplant.

The IFMs described herein can be administered directly to a subject suffering from the disorder to be treated (e.g., cancer) via e.g., intravenous or subcutaneous administration. In some embodiments, the immune cell targeting moiety of the IFM delivers the cytokine molecule to the surface of an immune cell, thereby increasing the concentration of the cytokine molecule at the surface of the immune cell. In embodiments, the IFM results in one or more of: localizes the distribution and/or enhances the cell surface availability of the cytokine molecule, thereby activating and/or stimulating the immune cell.

In other embodiments, the IFMs described herein can be administered in combination with an immune cell therapy in order to activate and/or stimulate the immune cell therapy either in vivo or in vitro. For example, an IFM described herein may be co-administered with a cell based therapy to a subject suffering from the disorder to be treated (e.g., cancer) via e.g., intravenous or subcutaneous administration. In other embodiments, a cell therapy is pulsed in vitro with an IFM described herein prior to administration. In some embodiments, the cell therapy is chosen from an adoptive cell therapy, CAR-T cell therapy, engineered TCR T cell therapy, a tumor infiltrating lymphocyte therapy, an antigen-trained T cell therapy, or an enriched antigen-specific T cell therapy.

Additional features and embodiments of any of the IFMs, compositions, nanoparticles, methods, uses, nucleic acids, vectors, and host cells, disclosed herein include one or more of the following.

In some embodiments, the IFM is a bifunctional or bispecific molecule, e.g., it has at least two different kinds of members, e.g., with different functions and/or binding specificities. For example, the IFM comprises, or consists of, the immune stimulating moiety, e.g., the cytokine molecule, and the immune cell targeting moiety, wherein the immune stimulating moiety and the immune cell target moiety bind to two different cell surface targets or receptors in the same or different cells, e.g., one or more immune cells. In embodiments, the immune stimulating moiety and the immune cell target moiety bind to two different targets on the same immune cell, e.g., the same immune effector cell. A bifunctional or bispecific molecule can further comprise additional moieties, e.g., further binding and/or functional moieties. For example, the IFM can be a multifunctional or multispecific molecule, e.g., it is a trifunctional or trispecific, or a tetrafunctional or tetraspecific, fusion molecule.

In certain embodiments, the IFM can be represented with the following formula in an N to C terminal orientation: R1-(optionally L1)-R2 or R2-(optionally L1)-R1; wherein R1 comprises an immune cell targeting moiety, L1 comprises a linker (e.g., a peptide linker described herein), and R2 comprises an immune stimulating moiety, e.g., a cytokine molecule.

In some embodiments, the immune stimulating moiety, e.g., the cytokine molecule, is functionally linked, e.g., covalently linked (e.g., by chemical coupling, genetic or protein fusion, noncovalent association or otherwise) to the immune cell targeting moiety. For example, the immune stimulating moiety can be covalently coupled indirectly, e.g., via a linker to the immune cell targeting moiety. In embodiments, the linker is chosen from: a cleavable linker, a non-cleavable linker, a peptide linker, a flexible linker, a rigid linker, a helical linker, or a non-helical linker. In some embodiments, the linker is a peptide linker. The peptide linker can be 5-20, 8-18, 10-15, or about 8, 9, 10, 11, 12, 13, 14, 15-20, 20-25, or 25-30 amino acids long. In some embodiments the peptide linker can be 30 amino acids or longer; e.g., 30-35, 35-40, 40-50 50-60 amino acids long. In some embodiments, the peptide linker comprises Gly and Ser, e.g., a linker comprising the amino acid sequence $(Gly_3\text{-Ser})_n$ or $(Gly_4\text{-Ser})_n$, wherein n indicates the number of repeats of the motif, e.g., n=1, 2, 3, 4 or 5 (e.g., a $(Gly_3\text{-Ser})_2$ or $(Gly_4Ser)_2$, or a $(Gly_3\text{-Ser})_3$ or a $(Gly_4Ser)_3$ linker). In some embodiments, the linker comprises the amino acid sequence of SEQ ID NO: 36, 37, 38, or 39, or an amino acid sequence substantially identical thereto (e.g., having 1, 2, 3, 4, or 5 amino acid substitutions). In one embodiment, the linker comprises an amino acid sequence GGGSGGGS (SEQ ID NO: 37). In another embodiment, the linker comprises amino acids derived from an antibody hinge region. In certain embodiments the linker comprises amino acids derived from the hinge regions of IgG1, IgG2, IgG3, IgG4, IgGM, or IgGA antibodies. In embodiments, the linker comprises amino acids derived from an IgG hinge region, e.g., an IgG1, IgG2 or IgG4 hinge region. For example, the linker comprises a variant amino acid sequence from an IgG hinge, e.g., a variant having one or more cysteines replaced, e.g., with serines. In some embodiments, the linker comprises DKTHTCPPSCAPE (SEQ ID NO: 126), having one or both cysteines replaced with another amino acid, e.g., a serine. In some embodiments, the linker comprises amino acids DKTHTSPPSPAP (SEQ ID NO: 38), EPKSSDKTHTSPPSPAPE (SEQ ID NO: 127), or a derivative thereof. In embodiments, the linker comprises amino acids derived from an IgG2 hinge region, e.g., amino acids SVESPPSP (SEQ ID NO: 128), ERKSSVESPPSP (SEQ ID NO: 129), or a derivative thereof. In embodiments, the linker comprises amino acids derived from an IgG4 hinge region, e.g., amino acids PPSPSSP (SEQ ID NO: 130), ESKYGPPSPSSP (SEQ ID NO: 131), or a derivative thereof.

In other embodiments, the linker is a non-peptide, chemical linker. For example, the immune stimulating moiety is covalently coupled to the immune cell targeting moiety by crosslinking. Suitable crosslinkers include those that are heterobifunctional, having two distinctly reactive groups separated by an appropriate spacer (e.g., m-malcimidobenzoyl-N-hydroxysuccinimide ester) or homobifunctional (e.g., disuccinimidyl suberate). In yet other embodiments, the immune stimulating moiety is directly covalently coupled to the immune cell targeting moiety, without a linker. In yet other embodiments, the immune stimulating moiety and the immune cell targeting moiety of the IFM are not covalently linked, e.g., are non-covalently associated.

In other embodiments, the linker can be a protein or a fragment or derivative thereof, e.g., human albumin or an Fc domain, or a fragment or derivative thereof. In some embodiments, the immune cell targeting moiety is linked to the N-terminus and the immune stimulating moiety is linked to the C-terminus.

In other embodiments, the linker non-covalently associates the immune cell targeting moiety to the immune stimulating moiety. For example, the linker comprises a dimerization domain, e.g., a coiled coil or a leucine zipper.

Fusion based on other noncovalent interactions can also be used, e.g., using the high affinity of the IL-15/sushi interaction to join two other proteins.

Immune Cells

In embodiments, the immune cell is a nucleated cell, e.g., a nucleated cell as described herein below.

In some embodiments, the immune cell is a population of immune effector cells, e.g., a population of immune effector cells chosen from one or more of: T cells, e.g., CD4 T cells, CD8 T cells, alpha T cells, beta T cells, gamma T cells, and delta T cells; B cells; natural killer (NK) cells; natural killer T (NKT) cells; or dendritic cells. In embodiments, the immune cell, e.g., the immune effector cell, displays a cell surface receptor that binds the immune cell targeting moiety.

In more particular embodiments, the immune cell, e.g., an immune effector cell, (e.g., an immune cell chosen from a lymphocyte, T cell, B cell, or a Natural Killer cell), or a hematopoietic stem cell). In embodiments, the immune cell comprises a lymphocyte. In embodiments, the immune cell comprises a T cell. In embodiments, the immune cell comprises a B cell. In embodiments, the immune cell comprises a Natural Killer (NK) cell. In embodiments, the immune cell comprises a hematopoietic stem cell. In some embodiments, the immune cell is an immune cell (e.g., T cell or NK cell) that comprises, e.g., expresses, a Chimeric Antigen Receptor (CAR), e.g., a CAR that binds to a cancer antigen. In other embodiment, the immune cell expresses an exogenous high affinity Fc receptor. In some embodiments, the immune cell comprises, e.g., expresses an engineered T-cell receptor. In some embodiments, the immune cell is a tumor infiltrating lymphocyte. In some embodiments, the immune cell is a cytotoxic T cell (e.g., a CD8 T cell). In embodiments, the immune cell is a regulatory T-cell ("Treg").

In embodiments, the immune cell is an immune cell, e.g., an NK cell, acquired from a patient, e.g., a patient's blood. In other embodiments, the immune cell is an immune cell, e.g., an NK cell, acquired from a healthy donor. In some embodiments, the NK cell population is purified, e.g., depleted, of T cells, e.g., allogeneic T cells, before infusion to a patient. In embodiments, the immune cell is an immune cell. e.g., an NK cell, from an embryonic stem cell and/or an iPSC cell. In some embodiments, the immune cell is a cell line, e.g., a stable or an immortalized cell line (e.g., an NK cell immortalized cell line). In some embodiments, the immune cell is acquired from a patient, e.g., a patient with a hematological cancer, e.g., a leukemia or a lymphoma. In embodiments, the immune cell is an NK cell line, e.g., an NK cell line chosen from NK-92 (e.g., ATCC cat. no. CRL-2407), NK-YS, KHYG-1, NKL, NKG, SNK-6, IMC-1, e.g., as described in Klingemann, H. et al. (2016) *Frontiers in Immunology* Vol. 7(Art. 91): 1-7, incorporated by reference herein. In one embodiment, the immune cell is an NK92 cell line, e.g., a variant NK92 cell that expresses a high affinity Fc receptor, e.g., Fc gamma RIIIa-expressing cell (e.g., 158V). In other embodiments, the NK92 cell line comprises a CAR that binds to a cancer antigen, e.g., also as described in in Klingemann et al. supra.

Cytokine Molecules

In some embodiments, the cytokine molecule of the IFM includes an immunomodulatoiy cytokine, e.g., a pro-inflammatory cytokine or an anti-inflammatory cytokine. In some embodiments, the cytokine is a member of the common γ-chain (γc) family of cytokines. In some embodiments, the cytokine molecule comprises a cytokine chosen from one or more of interleukin-15 (IL-15), interleukin-1, e.g., interleukin-1 alpha (IL-1α) or interleukin-1 beta (IL-1β), interleukin-2 (IL-2), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin-13 (IL-13), interleukin-18 (IL-18), interleukin-21 (IL-21), interleukin-23 (IL-23), interleukin-27 (IL-27), interleukin-35 (IL-35), IFNγ, TNFα, IFNα, IFNβ, GM-CSF, or GCSF, including variant forms thereof (e.g., a cytokine derivative, a complex comprising the cytokine molecule with a polypeptide, e.g., a cytokine receptor complex, and other agonist forms thereof). In some embodiments, the cytokine molecule is a pro-inflammatory cytokine molecule chosen from an IL-1, IL-2, IL-6, IL-12, IL-15, IL-18, IL-21, IL-23, or IL-27 cytokine molecule. In some embodiments, the cytokine molecule is an anti-inflammatory cytokine molecule chosen from an IL-4, IL-10, IL-13, IL-35 cytokine molecule. In some embodiments, the cytokine molecule is chosen from IL-2, IL-6, IL-7, IL-12, IL-15, IL-21 or IL-27, including variant forms thereof (e.g., a cytokine derivative, a complex comprising the cytokine molecule with a polypeptide, e.g., a cytokine receptor complex, and other agonist forms thereof, e.g., a non-neutralizing anti-cytokine antibody molecule). In some embodiments, the cytokine molecule is a superagonist (SA), e.g., as described herein. For example, the superagonist can have increased cytokine activity, e.g., by at least 10%, 20%, or 30%, compared to the naturally-occurring cytokine. In some embodiments, the cytokine molecule is a monomer or a dimer. In embodiments, the cytokine molecule further comprises a receptor or a fragment thereof, e.g., a cytokine receptor domain.

In one embodiment, the cytokine molecule comprises a wild type cytokine, e.g., a wild type, e.g., human amino acid sequence. In other embodiments, the cytokine molecule comprises an amino acid sequence substantially identical to the wild-type cytokine sequence, e.g., the human cytokine sequence. In some embodiments, the cytokine molecule comprises an amino acid sequence at least 95% to 100% identical, or having at least 1, 2, 3, 4, 5, 6, 7, 8, 9, or 10 or more amino acid alterations (e.g., substitutions, deletions, or insertions, e.g., conservative substitutions) relative to a wild-type cytokine sequence, e.g., a human cytokine sequence. In embodiments, the cytokine molecule comprises no more than five, ten or fifteen alterations (e.g., substitutions, deletions, or insertions, e.g., conservative substitutions) relative to the wild-type cytokine sequence, e.g., the human cytokine sequence.

Exemplary cytokine amino acid sequences are disclosed herein, for example, the amino acid of IL-15 is provided as, e.g., SEQ ID NO:10 and SEQ ID NO:40; the amino acid of IL-7 is provided as, e.g., SEQ ID NO:42 and SEQ ID NO:43; the amino acid of IL-21 is provided as, e.g., SEQ ID NO:44 and SEQ ID NO:45; the amino acid of IL-12A is provided as, e.g., SEQ ID NO:46 and SEQ ID NO:47; the amino acid of IL-12B is provided as, e.g., SEQ ID NO:48 and SEQ ID NO:49; exemplary fusions of IL-12A and IL-12B are disclosed as e.g., SEQ ID NO:50 and SEQ ID NO:51. Any of the cytokine sequences disclosed herein and substantially identical sequences (e.g., at least 90%, 95% or higher sequence identity) can be used in the IFM disclosed herein.

In one embodiment, the cytokine molecule is an IL-15 molecule. In one embodiment, the IL-15 molecule (e.g., IL-15 polypeptide molecule) comprises a wild-type IL-15 amino acid sequence, e.g., a human IL-15 amino acid sequence, e.g., includes the amino acid sequence of SEQ ID NO: 10. In some embodiments, the cytokine molecule is an IL-15 molecule, e.g., a full length, a fragment or a variant of IL-15, e.g., human IL-15, that retains IL-15 activity. In other embodiments, the IL-15 molecule is a variant of human IL-5, e.g., having one or more amino acid alterations, e.g., substitutions, to the human IL-15 amino acid sequence. In some embodiments, the IL-15 variant comprises, or consists of, a mutation at position 45, 51, 52, or 72, e.g., as described in US 2016/0184399. In some embodiments, the IL-15 variant comprises, or consists of, an N, S or L to one of D, E, A Y or P substitution. In some embodiments, the mutation is chosen from L45D, L45E, S51D, L52D, N72D, N72E, N72A, N72S, N72Y, or N72P (in reference to the sequence of human IL-15, SEQ ID NO: 11).

In embodiments, the IL-15 molecule comprises an IL-15 variant, e.g., a human IL-15 polypeptide having one or more amino acid substitutions. In some embodiments, the IL-15 molecule comprises a substitution at position 72, e.g., an N to D substitution. In one embodiment, the IL-15 molecule is an IL-15N72D polypeptide of SEQ ID NO: 11 or an amino acid sequence having at least 80%, 85%, 90%, 95%, 96%, 97%, 98%, or 99% identity thereto, which has IL-15Ra binding activity.

In other embodiments, the IL-15 molecule comprises a complex of IL-15 (e.g., an IL-15 wild type or variant sequence) and an IL-15 binding fragment of an IL-15 receptor, e.g., IL-15 receptor alpha or an IL-15 binding fragment thereof. In some embodiments, the IL-15 molecule comprises a complex of the IL-15 and an IL-15 receptor fragment, e.g., an extracellular domain of an IL-15 receptor or a fragment thereof. In some embodiments, the IL-15 molecule and the IL-15 binding fragment of the IL-15 receptor are not covalently linked, e.g., are non-covalently associated.

In one embodiment, the IL-15 receptor fragment comprises, or consists of, the amino acid sequence of SEQ ID NO: 9 or SEQ ID NO: 52, or a fragment thereof, or an amino acid sequence substantially identical thereto (e.g., at least 95% identical thereto, or having at least one, two, three, four, five amino acid alterations, but not more than ten, fifteen, twenty alterations (e.g., substitutions, deletions, or insertions, e.g., conservative substitutions) to the amino acid sequence of SEQ ID NO: 9 or SEQ ID NO: 52, or a fragment thereof, and having IL-15 binding activity.

In some embodiments, the IL-15 molecule comprises a complex of the IL-15 and an IL-15 receptor fragment, e.g., a sushi domain (e.g., as described herein). In some embodiments, the sushi domain is from human or a non-human animal, e.g., mammal, e.g., non-human primate. In one embodiment, the sushi domain includes a human sequence, or a substantially identical thereto (e.g., at least 95% identical thereto). In embodiments, the extracellular domain of IL-15 Receptor alpha comprises a domain referred to as herein as "the sushi domain." which binds IL-15. In embodiments, the sushi domain is provided as a 62-amino acid referred to herein as a "minimal domain" (e.g., having the amino acid sequence of SEQ ID NO: 52), or a 65-amino acid extended domain (e.g., having the amino acid sequence of SEQ ID NO: 9), or comprises a 77-amino acid domain comprising, e.g., consisting of, amino acids 31-107 or SEQ ID NO: 63.

In some embodiments, the IL-15 receptor fragment has a wild type sequence. In other embodiments, the IL-15 receptor fragment has a mutated sequence, e.g., a substitution at position 77, e.g., an L77I substitution (with the numbering referring to the wild-type IL-15Ra of SEQ ID NO: 4). In some embodiments, the sushi domain comprises the amino acid sequence of SEQ ID NO: 9, SEQ ID NO: 52, SEQ ID NO: 65, or SEQ ID NO: 66, or an amino acid sequence substantially identical thereto (e.g., at least 95% identical thereto, or having at least one, two, three, four, five amino acid alterations, but not more than ten or fifteen alterations (e.g., substitutions, deletions, or insertions, e.g., conservative substitutions) to the amino acid sequence of SEQ ID NO: 9, SEQ ID NO: 52, SEQ ID NO: 65, or SEQ ID NO: 66, and having IL-15 binding activity.

In some embodiments, an IL-15 receptor alpha extracellular domain consists of 62-171 amino acids of SEQ ID NO: 63 or an amino acid sequence substantially identical thereto (e.g., at least 95% identical thereto 96%, 97%, 98%, or 99% identity thereto or having up to 1, 2, 3, 4, 5, 6, 7, 8, 9, 10, or 15 alterations (e.g., substitutions) relative thereto, and having IL-15 binding activity). In some embodiments, an IL-15 receptor alpha extracellular domain consists of 65-171 amino acids of SEQ ID NO: 63 or an amino acid sequence substantially identical thereto (e.g., at least 95% identical thereto 96%, 97%, 98%, or 99% identity thereto or having up to 1, 2, 3, 4, 5, 6, 7, 8, 9, 10, or 15 alterations (e.g., substitutions) relative thereto, and having IL-15 binding activity). In some embodiments, an IL-15 receptor alpha extracellular domain consists of up to 171 amino acids of SEQ ID NO: 63 or an amino acid sequence substantially identical thereto (e.g., at least 95% identical thereto 96%, 97%, 98%, or 99% identity thereto or having up to 1, 2, 3, 4, 5, 6, 7, 8, 9, 10, or 15 alterations (e.g., substitutions) relative thereto, and having IL-15 binding activity). In some embodiments, an IL-15 receptor alpha extracellular domain consists of 62-171, 62-160, 62-150, 62-140, 62-130, 62-120, 62-110, 62-100, 62-90, 62-80, 62-70, 65-171, 65-160, 65-150, 65-140, 65-130, 65-120, 65-110, 65-100, 65-90, 65-80, 65-70, or 65-77 amino acids of SEQ ID NO: 63 or a sequence having at least 95% identity thereto 96%, 97%, 98%, or 99% or having up to 1, 2, 3, 4, 5, 6, 7, 8, 9, 10, or 15 alterations (e.g., substitutions) relative thereto, and having IL-15 binding activity. In some embodiments, an IL-15 receptor alpha extracellular domain consists of 62-171, 62-160, 62-150, 62-140, 62-130, 62-120, 62-110, 62-100, 62-90, 62-80, 62-70, 65-171, 65-160, 65-150, 65-140, 65-130, 65-120, 65-110, 65-100, 65-90, 65-80, 65-70, or 65-77 amino acids of SEQ ID NO: 63.

In some embodiments, the IFM containing an IL-15 molecule can further comprise a polypeptide, e.g., a cytokine receptor, e.g., a cytokine receptor domain, and a second, heterologous domain. In one embodiment, the heterologous domain is an immunoglobulin Fc region. In other embodiments, the heterologous domain is an antibody molecule, e.g., a Fab fragment, a FAB$_2$ fragment, a scFv fragment, or an affibody fragment or derivative, e.g. a sdAb (nanobody) fragment, a heavy chain antibody fragment. In some embodiments, the polypeptide also comprises a third heterologous domain. In some embodiments, the cytokine receptor domain is N-terminal of the second domain, and in other embodiments, the cytokine receptor domain is C-terminal of the second domain.

In some embodiments, the cytokine molecule comprises a complex of a cytokine and an anti-cytokine antibody molecule. For example, the cytokine can be IL-2 and the anti-cytokine antibody can be a non-neutralizing anti-IL-2 antibody molecule (see e.g., Spangler, J. B., et al. (2015) www.dx.doi.org/10.1016/j.immuni.2015.04.015; Letourneau, S. et al. (2010) PNAS Vol 107(5): 2171-2176; Boyman, O. et al. (2006) Science 311, 1924); and Spangler, J. B. (2015) Annu Rev Immunol 33:139-167, the contents of which are entirely incorporated by reference).

Immune Cell Targeting Moieties

In some embodiments, the immune cell targeting moiety of the IFM includes an antibody molecule or a ligand that selectively binds to an immune cell surface target, e.g., an immune cell surface receptor. In some embodiments, the immune cell surface target or receptor can have one, two, three or more of the following properties: (i) is abundantly present on the surface of an immune cell (e.g., outnumbers the number of receptors for the cytokine molecule present on the immune cell surface); (ii) shows a slow downregulation, internalization, and/or cell surface turnover, e.g., relative to the receptors activated by the cytokine of the IFM; (iii) is present on the surface of the immune cell for a prolonged period of time, e.g., relative to the receptors activated by the cytokine of the IFM; or (iv) once internalized is substantially recycled back to the cell surface, e.g., at least 25%, 50%, 60%, 70%, 80%, 90% or more of the immune cell surface target is recycled back to the cell surface.

In some embodiments, the immune cell targeting moiety of the IFM binds to a recycling cell surface receptor. Without being bound by theory, it is believed that binding to the recycling cell surface receptor mediates internalization of the receptor and the IFM. For example, the IFM internalized along with the receptor may be sequestered into early endosomes and subsequently recycled back to the cell surface, instead of advancing to subsequent degradation (e.g. via either clathrin-mediated and clathrin-independent endocytosis). The return of the IFM/receptor to the cell surface can improve cytokine signaling by restoring the cytokine molecule of the IFM to the cell surface, thus increasing the time and availability of the cytokine molecule to bind its own cell-surface receptor. Additionally, signaling events that are initiated at the surface membrane by binding of a fusion protein of the disclosure may continue from endosomal compartments.

In some embodiments, the immune cell surface target or receptor is present on the surface of an immune cell, but not present on a cancer or tumor cell, e.g., a solid tumor or hematological cancer cell. In some embodiments, the immune cell surface target or receptor is predominantly present on the surface of an immune cell compared to its presence on a cancer or tumor cell, e.g., is present at least 5:1, 10:1, 15:1, 20:1 higher ratio on the immune cell relative to the cancer or tumor cell.

In some embodiments, the immune cell targeting moiety of the IFM binds to a receptor expressed on a cell (e.g., an immune cell), e.g. the surface membrane of the cell, and further the cell also expresses a cytokine receptor (e.g., a receptor to the cytokine molecule of the IFM).

In some embodiments, the immune cell targeting moiety of the IFM can be chosen from an antibody molecule or a ligand molecule that binds to an immune cell surface target, e.g., a target chosen from CD16, CD45, CD4, CD8, CD3, CD11a, CD11b, CD11c, CD18, CD25, CD127, CD56, CD19, CD20, CD22, HLA-DR, CD197, CD38, CD27, CD137, OX40, GITR, CD56, CD196, CXCR3, CXCR4, CXCR5, CD84, CD229, CCR1, CCR5, CCR4, CCR6, CCR8, or CCR10. In some embodiments, the immune cell targeting moiety binds to CD4, CD8, CD11a, CD18, CD20, CD56, or CD45. In other embodiments, the immune cell surface target is chosen from CD19, CD20, or CD22. In one embodiment, the immune cell targeting moiety comprises an antibody molecule or a ligand molecule that binds to CD45 (also interchangeably referred to herein as "CD45 receptor" or "CD45R"). In some embodiments, the target is CD45 (e.g., a CD45 isoform chosen from CD45RA, CD45RB, CD45RC or CD45RO). In embodiments, CD45 is primarily expressed on T cells. For example, CD45RA is primarily expressed on naïve T cells; CD45RO is primarily expressed on activated and memory T cells.

In some embodiments, the immune cell targeting moiety of the IFM (e.g., an antibody molecule) binds a checkpoint inhibitor such as PD-1, PD-L1, LAG-3, TIM-3, or CTLA-4. In embodiments, the checkpoint inhibitor is present on an immune effector cell, e.g., a T cell or NK cell.

In other embodiments, the immune cell targeting moiety of the IFM comprises an antibody molecule (e.g., an antigen binding domain), a receptor molecule (e.g., a receptor, a receptor fragment or functional variant thereof), or a ligand molecule (e.g., a ligand, a ligand fragment or functional variant thereof), or a combination thereof, that binds to the immune cell target or receptor.

In some embodiments, the antibody molecule of the immune cell targeting moiety of the IFM comprises a full antibody (e.g., an antibody that includes at least one, and preferably two, complete heavy chains, and at least one, and preferably two, complete light chains), or an antigen-binding fragment (e.g., a Fab, F(ab')2, Fv, a single chain Fv, a single domain antibody, a diabody (dAb), a bivalent antibody, or bispecific antibody or fragment thereof, a single domain variant thereof, or a camelid antibody)) that binds to the immune cell target or receptor.

The heavy chain constant region of the antibody molecule can be chosen from IgG1, IgG2, IgG3, or IgG4, or a fragment thereof, and more typically, IgG1, IgG2 or IgG4. In some embodiments, the Fc region of the heavy chain can include one or more alterations, e.g., substitutions, to increase or decrease one or more of: Fc receptor binding, neonatal-Fc receptor binding, antibody glycosylation, the number of cysteine residues, effector cell function, complement function, or stabilize antibody formation (e.g., stabilize IgG4). For example, the heavy chain constant region for an IgG4, e.g., a human IgG4, can include a substitution at position 228 (e.g., a Ser to Pro substitution) (see e.g., Angal, S, King, D J, et al. (1993) *Mol Immunol* 30:105-108 (initially described as S241P using a different numbering system); Owens, R, Ball, E, et al. (1997) *Immunotechnology* 3:107-116).

The light chain constant region of the antibody molecule can be chosen from the light chain constant regions of kappa or lambda, or a fragment thereof.

The antibody molecule of the immune cell targeting moiety of the IFM can bind to the target antigen with a dissociation constant of less than about 100 nM, 50 nM, 25 nM, 10 nM, e.g., less than 1 nM (e.g., about 10-100 pM). In embodiments, the antibody molecule binds to a conformational or a linear epitope on the antigen. In certain embodiments, the antigen bound by the antibody molecule of the immune cell targeting moiety is stably expressed on the surface of the immune cell. In embodiments, the antigen is a cell surface receptor that is more abundant on the cell surface relative to a receptor for the cytokine molecule of the IFM on the cell surface.

In some embodiments, the immune cell targeting moiety is chosen from an antibody molecule (e.g., a full antibody (e.g., an antibody that includes at least one, and preferably two, complete heavy chains, and at least one, and preferably two, complete light chains), or an antigen-binding fragment (e.g., a Fab, F(ab')2, Fv, a single chain Fv, a single domain antibody, a diabody (dAb), a bivalent antibody, or bispecific or multispecific antibody or fragment thereof, a single domain variant thereof, or a camelid antibody)), or a non-antibody scaffold, or a ligand that binds to an immune cell surface target or ligand. In some embodiments, the immune cell targeting moiety is an antibody molecule or a ligand that binds to CD45, CD2, CD4, CD8, CD11 (e.g., CD11a (integrin alpha-L), CD11b, or CD11c), CD18 (integrin beta-2), CD19, CD20, or CD25, or a combination thereof, e.g., a bispecific antibody that binds to two or more of the aforesaid targets.

In some embodiments, the antibody molecule (e.g., mono- or bi-specific antibodies) binds to one or more of CD45, CD8, CD18 or CD11a, e.g., it is an IgG, e.g., human IgG4, or an antigen binding domain, e.g., a Fab, a F(ab')2, Fv, a single chain Fv, that binds to CD45, CD8, CD18 or CD11a. In some embodiments, the antibody molecule is a human, a humanized or a chimeric antibody. In embodiments, the antibody molecule is a recombinant antibody.

In some embodiments, the anti-CD45 antibody is a human anti-CD45 antibody, a humanized anti-CD45 antibody, or a chimeric anti-CD45 antibody. In some embodiments, the anti-CD45 antibody is an anti-CD45 monoclonal antibody. Exemplary anti-CD45 antibodies include antibodies BC8, 4B2, GAP8.3 or 9.4. Antibodies against other immune cell surface targets are also disclosed, e.g., anti-CD8 antibodies, such as OKT8 monoclonal antibodies, anti-CD18 antibodies, such as 1B4 monoclonal antibodies, and anti-CD11a antibodies, such as MHM24 antibodies.

Also encompassed by the present disclosure are antibody molecules having the amino acid sequences disclosed herein, or an amino acid sequence substantially identical thereof), nucleic acid molecules encoding the same, host cells and vectors comprising the nucleic acid molecules.

In one embodiment, the antibody molecule that binds to CD45 is specific to one CD45 isoform or binds to more than on CD45 isoforms, e.g., is a pan-CD45 antibody. In some embodiments, the anti-CD45 antibody molecule binds to CD45RA and CD45RO. In one embodiment, the anti-CD45 antibody molecule is a BC8 antibody. In some embodiments, the BC8 antibody binds to CD45RA and CD45RO. In other embodiments, the anti-CD45 antibody molecule is CD45RO-specific or is a pan-CD45 antibody molecule, e.g., it binds to activated and memory T cells. Additional examples of anti-CD45 antibody molecules includes, but is not limited to, GAP8.3, 4B2, and 9.4.

In one embodiment, the anti-CD45 antibody molecule is a BC8 antibody, e.g., a chimeric or humanized BC8 antibody. In some embodiments, the chimeric BC8 antibody comprises:

(i) the light chain variable amino acid sequence (optionally, further including a kappa light chain sequence) corresponding to the antibody portion of the amino acid sequence shown in SEQ ID NO:1, 2, 3, 4, 7, 21, or 22, or an amino acid sequence substantially identical thereof (e.g., an amino acid sequence at least 85%, 90%, 95% or higher identical to the antibody portion of SEQ ID NO: 1, 2, 3, 4, 7, 21, or 22); and/or (ii) the heavy chain variable amino acid sequence (optionally, further including a human IgG1 heavy chain sequence or a human IgG4 sequence having an S228P substitution) of the amino acid sequence shown in SEQ ID NO:5, 6, or 8, respectively, or an amino acid sequence substantially identical thereto (e.g., an amino acid sequence at least 85%, 90%, 95% or higher identical to SEQ ID NOs: 5, 6, or 8, respectively). In embodiments, the BC8 antibody comprises one, two, or all three CDR1, CDR2 or CDR3 of the light chain variable region, and/or the heavy chain variable region, of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 1-4, 7, 21, or 22, or 5-6, or 8.

In other embodiments, the amino acid of SEQ ID NO:1-4, or an amino acid substantially identical thereto (e.g., an amino acid sequence at least 85%, 90%, 95% or higher identical to SEQ ID NO: 1-4) (optionally, further including a kappa light chain sequence), includes, optionally via a linker, an IL-15 cytokine or receptor, e.g., a sushi domain as described herein (e.g., SEQ ID NO: 9 or an amino acid substantially identical thereto (e.g., an amino acid sequence at least 85%, 90%, 95% or higher identical to SEQ ID NO: 9). In one embodiment, the IL-15 cytokine or receptor is coupled to the N-terminus of the light chain of the BC8 antibody of SEQ ID NO:1-4. In other embodiments, the IL-15 cytokine or receptor is coupled to the C-terminus of the light chain of the BC8 antibody of SEQ ID NO:1-4. In one embodiment, the linker comprises, or consists of, SEQ ID NO: 37 or 38.

In other embodiments, the amino acid of SEQ ID NO:21 or 22, or an amino acid substantially identical thereto (e.g., an amino acid sequence at least 85%, 90%, 95% or higher identical to SEQ ID NO: 21 or 22) (optionally, further including a kappa light chain sequence), includes, optionally via a linker, an IL-15 cytokine or receptor, e.g., a sushi domain as described herein (e.g., SEQ ID NO: 9 or an amino acid substantially identical thereto (e.g., an amino acid sequence at least 85%, 90%, 95% or higher identical to SEQ ID NO: 9). In one embodiment, the IL-15 cytokine or receptor is coupled to the N-terminus of the light chain of the Bc8 antibody of SEQ ID NO:21 or 22 via a linker of SEQ ID NO: 37 or 38. In other embodiments, the IL-15 cytokine or receptor is coupled to the C-terminus of the light chain of the Bc8 antibody of SEQ ID NO:21 or 22 via a linker of SEQ ID NO: 37 or 38.

In some embodiments, the amino acid of SEQ ID NO: 6 or 8, or an amino acid substantially identical thereto (e.g., an amino acid sequence at least 85%, 90%, 95% or higher identical to SEQ ID NO: 6 or 8), includes a heavy chain constant region. In some embodiments, the amino acid of SEQ ID NO 6 or 8, or an amino acid substantially identical thereto (e.g., an amino acid sequence at least 85%, 90%, 95% or higher identical to SEQ ID NO: 6 or 8), includes an IL-15 cytokine or receptor, e.g., a sushi domain as described herein (e.g., SEQ ID NO: 9 or an amino acid substantially identical thereto (e.g., an amino acid sequence at least 85%, 90%, 95% or higher identical to SEQ ID NO: 9). In one embodiment, the IL-15 cytokine or receptor is coupled to the N-terminus of the light chain of the Bc8 antibody of SEQ ID NO:6 or 8. In other embodiments, the IL-15 cytokine or receptor is coupled to the C-terminus of the light chain of the Bc8 antibody of SEQ ID NO:6 or 8.

In other embodiments, the humanized BC8 antibody comprises:

(i) the light chain variable amino acid sequence (optionally, further including a kappa light chain sequence) corresponding to the antibody portion of the amino acid sequence shown in SEQ ID NO:19, or an amino acid sequence substantially identical thereof (e.g., an amino acid sequence at least 85%, 90%, 95% or higher identical to the antibody portion of SEQ ID NO: 19); and/or (ii) the heavy chain variable amino acid sequence (optionally, further including a human IgG1 heavy chain sequence) of the amino acid sequence shown in SEQ ID NO:18, or an amino acid sequence substantially identical thereto (e.g., an amino acid sequence at least 85%, 90%, 95% or higher identical to SEQ ID NO:18). In embodiments, the BC8 antibody comprises one, two, or all three CDR1, CDR2 or CDR3 of the light chain variable region, and/or the heavy chain variable region, of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 18 or 19.

In some embodiments, the amino acid sequence of SEQ ID NO:19, or an amino acid sequence substantially identical thereof (e.g., an amino acid sequence at least 85%, 90%, 95% or higher identical to SEQ ID NO: 19) includes an IL-15 cytokine molecule, e.g., an IL-15 cytokine, coupled to the N- or C-terminus of SEQ ID NO: 19, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

Alternatively or in combination, the amino acid sequence of SEQ ID NO:18, or an amino acid sequence substantially identical thereof (e.g., an amino acid sequence at least 85%, 90%, 95% or higher identical to SEQ ID NO: 18) includes an IL-15 cytokine molecule, e.g., an IL-15 cytokine, coupled to the N- or C-terminus of SEQ ID NO: 18, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

In other embodiments, the antibody molecule that binds to CD45 is a 9.4 antibody, e.g., a chimeric or humanized 9.4 antibody. In some embodiments, the chimeric 9.4 antibody comprises:

(i) the light chain variable amino acid sequence (optionally, further including a kappa light chain sequence) corresponding to the antibody portion of the amino acid sequence shown in SEQ ID NO:15, or an amino acid sequence substantially identical thereto (e.g., an amino acid sequence at least 85%, 90%, 95% or higher identical to the antibody portion of SEQ ID NO:15); and/or (ii) the heavy chain variable amino acid sequence (optionally, further including a human IgG1 heavy chain sequence) of the amino acid sequence shown in SEQ ID NO:14, respectively, or an amino acid sequence substantially identical thereto (e.g., an amino acid sequence at least 85%, 90%, 95% or higher identical to SEQ ID NO: 14, respectively). In embodiments, the 9.4 antibody comprises one, two, or all three CDR1, CDR2 or CDR3 of the light chain variable region, and/or the heavy chain variable region, of the 9.4 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO:14 or 15.

In some embodiments, the amino acid sequence of SEQ ID NO:15, or an amino acid sequence substantially identical thereof (e.g., an amino acid sequence at least 85%, 90%, 95% or higher identical to SEQ ID NO: 15) includes an IL-15 cytokine molecule, e.g., an IL-15 cytokine, coupled to the N- or C-terminus of SEQ ID NO: 15, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

Alternatively or in combination, the amino acid sequence of SEQ ID NO:14, or an amino acid sequence substantially identical thereof (e.g., an amino acid sequence at least 85%, 90%, 95% or higher identical to SEQ ID NO: 14) includes an IL-15 cytokine molecule, e.g., an IL-15 cytokine, coupled to the N- or C-terminus of SEQ ID NO: 14, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

In other embodiments, the antibody molecule that binds to CD45 is a 4B2 antibody, e.g., a chimeric or humanized 4B2 antibody. In some embodiments, the chimeric 4B2 antibody comprises:

(i) the light chain variable amino acid sequence (optionally, further including a kappa light chain sequence) corresponding to the antibody portion of the amino acid sequence shown in SEQ ID NO:17, or an amino acid sequence substantially identical thereto (e.g., an amino acid sequence at least 85%, 90%, 95% or higher identical to the antibody portion of SEQ ID NO:17); and/or (ii) the heavy chain variable amino acid sequence (optionally, further including a human IgG1 heavy chain sequence) of the amino acid sequence shown in SEQ ID NO:16, respectively, or an amino acid sequence substantially identical thereto (e.g., an amino acid sequence at least 85%, 90%, 95% or higher identical to SEQ ID NO: 16, respectively). In embodiments, the 4B2 antibody comprises one, two, or all three CDR1, CDR2 or CDR3 of the light chain variable region, and/or the heavy chain variable region, of the 4B2 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO:16 or 17.

In some embodiments, the amino acid sequence of SEQ ID NO:17, or an amino acid sequence substantially identical thereof (e.g., an amino acid sequence at least 85%, 90%, 95% or higher identical to SEQ ID NO: 17) includes an IL-15 cytokine molecule, e.g., an IL-15 cytokine, coupled to the N- or C-terminus of SEQ ID NO: 17, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

Alternatively or in combination, the amino acid sequence of SEQ ID NO:16, or an amino acid sequence substantially identical thereof (e.g., an amino acid sequence at least 85%, 90%, 95% or higher identical to SEQ ID NO: 16) includes an IL-15 cytokine molecule, e.g., an IL-15 cytokine, coupled to the N- or C-terminus of SEQ ID NO: 16, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

In another embodiment, the antibody molecule that binds to CD8 is an OKT8 antibody, e.g., a chimeric or humanized OKT8 antibody. In some embodiments, the chimeric OKT8 antibody comprises:

(i) the light chain variable amino acid sequence (optionally, further including a kappa light chain sequence) corresponding to the antibody portion of the amino acid sequence shown in SEQ ID NO:31, or an amino acid sequence substantially identical thereof (e.g., an amino acid sequence at least 85%, 90%, 95% or higher identical to the antibody portion of SEQ ID NO:31); and/or (ii) the heavy chain variable amino acid sequence (optionally, further including a human IgG1 heavy chain sequence) of the amino acid sequence shown in SEQ ID NO:30, or an amino acid sequence substantially identical thereto (e.g., an amino acid sequence at least 85%, 90%, 95% or higher identical to SEQ ID NO:30). In embodiments, the OKT8 antibody comprises one, two, or all three CDR1, CDR2 or CDR3 of the light chain variable region, and/or the heavy chain variable region, of the OKT8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 30 or 31.

In some embodiments, the amino acid sequence of SEQ ID NO:31, or an amino acid sequence substantially identical thereof (e.g., an amino acid sequence at least 85%, 90%, 95% or higher identical to SEQ ID NO: 31) includes an IL-15 cytokine molecule, e.g., an IL-15 cytokine, coupled to the N- or C-terminus of SEQ ID NO: 31, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

Alternatively or in combination, the amino acid sequence of SEQ ID NO:30, or an amino acid sequence substantially identical thereof (e.g., an amino acid sequence at least 85%, 90%, 95% or higher identical to SEQ ID NO: 30) includes an IL-15 cytokine molecule, e.g., an IL-15 cytokine, coupled to the N- or C-terminus of SEQ ID NO: 30, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

In another embodiment, the antibody molecule that binds to CD18 is a 1B4 antibody, e.g., a chimeric or humanized 1B4 antibody. In some embodiments, the chimeric 1B4 antibody comprises:

(i) the light chain variable amino acid sequence (optionally, further including a kappa light chain sequence) corresponding to the antibody portion of the amino acid sequence shown in SEQ ID NO:29, or an amino acid sequence substantially identical thereof (e.g., an amino acid sequence at least 85%, 90%, 95% or higher identical to the antibody portion of SEQ ID NO:31); and/or (ii) the heavy chain variable amino acid sequence (optionally, further including a human IgG1 heavy chain sequence) of the amino acid sequence shown in SEQ ID NO:28, or an amino acid sequence substantially identical thereto (e.g., an amino acid sequence at least 85%, 90%, 95% or higher identical to SEQ ID NO:28). In embodiments, the 1B4 antibody comprises one, two, or all three CDR1, CDR2 or CDR3 of the light chain variable region, and/or the heavy chain variable region, of the 1B4 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 28 or 29.

In some embodiments, the amino acid sequence of SEQ ID NO:29, or an amino acid sequence substantially identical thereof (e.g., an amino acid sequence at least 85%, 90%, 95% or higher identical to SEQ ID NO: 29) includes an IL-15 cytokine molecule, e.g., an IL-15 cytokine, coupled to the N- or C-terminus of SEQ ID NO: 29, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

Alternatively or in combination, the amino acid sequence of SEQ ID NO:28, or an amino acid sequence substantially identical thereof (e.g., an amino acid sequence at least 85%, 90%, 95% or higher identical to SEQ ID NO: 28) includes an IL-15 cytokine molecule, e.g., an IL-15 cytokine, coupled to the N- or C-terminus of SEQ ID NO: 28, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

In yet another embodiment, the antibody molecule that binds to CD11a is an MHM24 antibody, e.g., a chimeric or humanized MHM24 antibody. In some embodiments, the chimeric MHM24 antibody comprises:

(i) the light chain variable amino acid sequence (optionally, further including a kappa light chain sequence) corresponding to the antibody portion of the amino acid sequence shown in SEQ ID NO:27, or an amino acid sequence substantially identical thereof (e.g., an amino acid sequence at least 85%, 90%, 95% or higher identical to the antibody portion of SEQ ID NO:27); and/or (ii) the heavy chain variable amino acid sequence (optionally, further including a human IgG1 heavy chain sequence) of the amino acid sequence shown in SEQ ID NO:26, or an amino acid sequence substantially identical thereto (e.g., an amino acid sequence at least 85%, 90%, 95% or higher identical to SEQ ID NO:26). In embodiments, the MHM24 antibody comprises one, two, or all three CDR1, CDR2 or CDR3 of the light chain variable region, and/or the heavy chain variable region, of the MHM24 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 26 or 27.

In some embodiments, the amino acid sequence of SEQ ID NO:27, or an amino acid sequence substantially identical thereof (e.g., an amino acid sequence at least 85%, 90%, 95% or higher identical to SEQ ID NO: 27) includes an IL-15 cytokine molecule, e.g., an IL-15 cytokine, coupled to the N- or C-terminus of SEQ ID NO: 27, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

Alternatively or in combination, the amino acid sequence of SEQ ID NO:26, or an amino acid sequence substantially identical thereof (e.g., an amino acid sequence at least 85%, 90%, 95% or higher identical to SEQ ID NO: 26) includes an IL-15 cytokine molecule, e.g., an IL-15 cytokine, coupled to the N- or C-terminus of SEQ ID NO: 26, optionally, via a linker (e.g., a linker comprising the amino acid sequence of SEQ ID NO: 36-39, or an amino acid sequence substantially identical thereof (e.g., an amino acid sequence at least 85%, 90%, 95% or higher identical to SEQ ID NO: 36-39).

Exemplary IFM Formats

Exemplary formats for the IFM include a cytokine molecule (e.g., one or more cytokine molecules) coupled to an antibody molecule that binds to an immune cell surface target (e.g., immunoglobulin moiety (Tg), for example an antibody (e.g., a full antibody, IgG) or antibody fragment (Fab, scFv, a half antibody, or a single domain antibody and the like). In embodiments, the IFM includes a fusion to the amino-terminus (N-terminus) or carboxy-terminus (C-terminus) of the antibody molecule, typically, the C-terminus. The cytokine molecule can be coupled to the antibody molecule, optionally, via a linker. In some embodiments, the cytokine or cytokine receptor, e.g., receptor fragment (e.g., sushi domain) is coupled to the N-terminus or the C-terminus of the antibody molecule. In embodiments, the cytokine or cytokine receptor, e.g., receptor fragment (e.g., sushi domain) is coupled to the N-terminus or the C-terminus of the light chain of the antibody molecule (e.g., a full antibody or fragment thereof, e.g., a Fab, a scFv, or a half antibody). Alternatively or in combination, the cytokine or cytokine receptor, e.g., receptor fragment (e.g., sushi domain) is coupled to the N-terminus or the C-terminus of the heavy chain of the antibody molecule (e.g., a full antibody or fragment thereof, e.g., a Fab, a scFv, a half antibody, or a single domain antibody (VH)). Examples of the formats are provided in, e.g., FIGS. 1, 2A, 3A-3D, 6A, 11A and 12A.

In some embodiments, the IFM includes a light chain of the anti-immune cell targeting antibody molecule, e.g., anti-CD45 (e.g., BC8 antibody), anti-CD8, anti-CD18, or anti-CD11a, that is coupled to, e.g., covalently linked, to a cytokine molecule, e.g., IL-15, IL-2, IL-6, IL-7, IL-12, IL-21, IL-27, or a cytokine receptor, e.g., IL-15Ralpha sushi domain, at either the N-terminal region or the C-terminal region of the light chain or heavy chain (as depicted in, e.g., FIGS. 1, 2A, 3A-3D, 6A, 11A and 12A. Any combination of orientation of light chain- or heavy chain-cytokine molecule can be present in the IFM.

For example, the IFM can include a full antibody or a tetramer of two identical half-antibodies, e.g., a first and second antibody, each having a light chain and a heavy chain of the anti-immune cell targeting antibody molecule, e.g., anti-CD45 (e.g., BC8 antibody), anti-CD8, anti-CD18, or anti-CD11a, that is coupled to, e.g., covalently linked, to a cytokine molecule, e.g., IL-15 or an IL-15 sushi domain, at the N-terminal region of the light chain (e.g., a depicted in FIGS. 3A and 3C).

In other embodiments, the IFM can include a full antibody or a tetramer of two identical half-antibodies, e.g., a first and second antibodies, each having a light chain and a heavy chain of the anti-immune cell targeting antibody molecule, e.g., anti-CD45 (e.g., BC8 antibody), anti-CD8, anti-CD18, or anti-CD11α, that is coupled to, e.g., covalently linked, to a cytokine molecule, e.g., IL-15 or an IL-15 sushi domain, at the C-terminal region of the light chain (e.g., a depicted in FIGS. 2A, 3A, 3C and 6A).

Alternatively, or in combination with the aforesaid formats, the IFM can include a full antibody or a tetramer of two identical half-antibodies, e.g., a first and second antibodies, each having a light chain and a heavy chain of the anti-immune cell targeting antibody molecule, e.g., anti-CD45 (e.g., BC8 antibody), anti-CD8, anti-CD18, or anti-CD11a, that is coupled to, e.g., covalently linked, to a cytokine molecule, e.g., IL-15 or an IL-15 sushi domain, at the C-terminal region of the heavy chain (e.g., a depicted in FIG. 6A).

Alternatively, or in combination with the aforesaid format, the IFM can include a full antibody or a tetramer of two identical half-antibodies, e.g., a first and second antibodies, each having a light chain and a heavy chain of the anti-immune cell targeting antibody molecule, e.g., anti-CD45 (e.g., BC8 antibody), anti-CD8, anti-CD18, or anti-CD 11a, that is coupled to, e.g., covalently linked, to a cytokine molecule, e.g., IL-15 or an IL-15 sushi domain, at the N-terminal region of the heavy chain.

Alternatively, or in combination with the aforesaid formats, the IFM can include an antibody fragment (e.g., a scFv, a Fab) having a light chain variable domain and a heavy chain variable domain of the anti-immune cell targeting antibody molecule, e.g., anti-CD45 (e.g., BC8 antibody), anti-CD8, anti-CD18, or anti-CD11a, that is coupled to. e.g., covalently linked, to a cytokine molecule, e.g., IL-15 or an IL-15 sushi domain, at the N- or C-terminal region of the heavy chain variable domain (e.g., a depicted in FIGS. 2A, 3B, 3D, 11A, and 12A).

Alternatively, or in combination with the aforesaid formats, the IFM can include an antibody fragment (e.g., a scFv, a Fab) having a light chain variable domain and a heavy chain variable domain of the anti-immune cell targeting antibody molecule, e.g., anti-CD45 (e.g., BC8 antibody), anti-CD8, anti-CD18, or anti-CD11a, that is coupled to, e.g., covalently linked, to a cytokine molecule, e.g., IL-15 or an IL-15 sushi domain, at the N- or C-terminal region of the light chain variable domain.

Alternatively, the IFM includes a tetramer of two different half-antibodies, e.g., a first and second antibodies, wherein the first antibody has a light chain and a heavy chain (or an fragment thereof, e.g., scFv or Fab) of the anti-immune cell targeting antibody molecule, e.g., anti-CD45 (e.g., BC8 antibody), anti-CD8, anti-CD18, or anti-CD11a, that is coupled to, e.g., covalently linked, to a cytokine molecule, e.g., IL-15 or an IL-15 sushi domain, at the N-terminal region of the light chain; and the second antibody has a light chain and a heavy chain (or an fragment thereof, e.g., scFv or Fab) of the anti-immune cell targeting antibody molecule, e.g., anti-CD45 (e.g., BC8 antibody), anti-CD8, anti-CD18, or anti-CD11a that is coupled to, e.g., covalently linked, to a cytokine molecule, e.g., IL-15 or an IL-15 sushi domain, at the C-terminal region of the light chain or the heavy chain. Any pairing of antibodies to the same or different targets can be used, e.g., CD45:CD8, CD45:CD18, CD45:CD11a, CD8:CD18, CD8:CD11a, or CD18:CD11a.

In other embodiments, the IFM includes a heavy chain of the anti-immune cell targeting antibody molecule, e.g., anti-CD45 (e.g., BC8 antibody) or anti-CD8, that is coupled to, e.g., covalently linked, to a cytokine molecule, e.g., IL-15 or an IL-15 sushi domain, at either the N-terminal region or the C-terminal region of the heavy chain (as depicted in, e.g., FIG. 6A), and the corresponding light chain. In embodiments, the cytokine molecule is covalently linked to the C-terminus of the heavy chain.

In other embodiments, the IFM includes a heavy chain of the anti-immune cell targeting antibody molecule, e.g., anti-CD45 (e.g., BC8 antibody) or anti-CD8, that is coupled to, e.g., covalently linked, to a non-cytokine immunostimulatory molecule, e.g., an agonist of an immunostimulatory molecule. In some embodiments, the immune stimulatory molecule is an agonist of CD137, OX40, GITR, CD3, or CD28. In some embodiments, the agonist of the immune stimulatory molecule is an antibody molecule or a ligand. For example, the agonist of the immune stimulatory molecule is an agonist antibody molecule against CD137, OX40, GITR, CD3, or CD28. In some embodiments, the immune stimulatory molecule is linked at either the N-terminal region or the C-terminal region of the heavy chain and the corresponding light chain. In embodiments, the immunostimulatory molecule is covalently linked to the C-terminus of the heavy chain.

In yet other embodiments, the IFM includes a heavy chain of the anti-immune cell targeting antibody molecule, e.g., anti-CD45 (e.g., BC8 antibody) or anti-CD8, that is coupled to, e.g., covalently linked, to an inhibitor of a negative immune regulator, e.g., an inhibitor of a checkpoint inhibitor. In some embodiments, the inhibitor of the negative immune regulator is an inhibitor of a checkpoint inhibitor chosen from PD-1, PD-L1, LAG-3, TIM-3, or CTLA-4. In some embodiments, the agonist of the immune stimulatory molecule is an antibody molecule or a ligand. For example, the inhibitor of the checkpoint inhibitor, e.g., the antibody molecule, binds to and/or inhibits PD-1, PD-L1, LAG-3, TIM-3, or CTLA-4.

In embodiments, the IFM described herein (LC-chBC8-sushi, sushi-LC-chBC8, LC-chBC8-L1-IL15, IL15-LC-chBC8 and HC-chBC8-Fab, HC-chBC8-IgG4S228P) can comprise:

(i) the amino acid sequence of a light chain selected from SEQ ID NO: 1, 2, 3, or 4, or an amino acid sequence substantially identical thereof (e.g., an amino acid sequence at least 85%, 90%, 95%, 96%, 97%, 98%, 99% or higher identity to SEQ ID NO: 1, or having at least 1, 2, 3, 4, 5, 6, 7, 8, 9, or 10 or more amino acid alterations (e.g., substitutions, deletions, or insertions, e.g., conservative substitutions) relative to SEQ ID NO: 1, 2, 3, or 4. In embodiments, the IFM comprises no more than five, ten or fifteen alterations (e.g., substitutions, deletions, or insertions, e.g., conservative substitutions) relative to SEQ ID NO: 1, 2, 3, or 4; and (ii) the amino acid sequence of the heavy chain selected from SEQ ID NO: 5 or 6, or an amino acid sequence substantially identical thereof (e.g., an amino acid sequence at least 85%, 90%, 95%, 96%, 97%, 98%, 99% or higher identity to SEQ ID NO: 5 or 6, or having at least 1, 2, 3, 4, 5, 6, 7, 8, 9, or 10 or more amino acid alterations (e.g., substitutions, deletions, or insertions, e.g., conservative substitutions) relative to SEQ ID NO: 5 or 6. In embodiments, the IFM comprises no more than five, ten or fifteen alterations (e.g., substitutions, deletions, or insertions, e.g., conservative substitutions) relative to SEQ ID NO: 5 or 6.

In other embodiments, the IFM described herein (e.g., HC-chBC8-IgG4S228P-IL15 and LC-chBC8) can comprise:

(i) the light chain variable amino acid sequence (optionally, further including a constant domain sequence from human kappa) shown in SEQ ID NO:7, or an amino acid sequence substantially identical thereto (e.g., an amino acid sequence at least 85%, 90%, 95% or higher identical to SEQ ID NO:7), or having at least 1, 2, 3, 4, 5, 6, 7, 8, 9, or 10 or more amino acid alterations (e.g., substitutions, deletions, or insertions. e.g., conservative substitutions) relative to SEQ ID NO: 7; and (ii) the amino acid sequence of SEQ ID NO: 8, or an amino acid sequence substantially identical thereof (e.g., an amino acid sequence at least 85%, 90%, 95%, 96%, 97%, 98%, 99% or higher identity to SEQ ID NO: 8, or having at least 1, 2, 3, 4, 5, 6, 7, 8, 9, or 10 or more amino acid alterations (e.g., substitutions, deletions, or insertions, e.g., conservative substitutions) relative to SEQ ID NO: 8. In embodiments, the IFM comprises no more than five, ten or fifteen alterations (e.g., substitutions, deletions, or insertions, e.g., conservative substitutions) relative to SEQ ID NO: 7 or 8.

In yet other embodiments, the IFM described herein (e.g., HC-ch9.4-Fab and LC-ch9.4-IL15) can comprise:

(i) the amino acid sequence shown in SEQ ID NO:15, or an amino acid sequence substantially identical thereto (e.g., an amino acid sequence at least 85%, 90%, 95% or higher identical to the antibody portion of SEQ ID NO:15), or having at least 1, 2, 3, 4, 5, 6, 7, 8, 9, or 10 or more amino acid alterations (e.g., substitutions, deletions, or insertions, e.g., conservative substitutions) relative to SEQ ID NO: 15; and (ii) the amino acid sequence shown in SEQ ID NO:14, respectively, or an amino acid sequence substantially identical thereto (e.g., an amino acid sequence at least 85%, 90%, 95% or higher identical to SEQ ID NO: 14, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 15. In embodiments, the IFM comprises no more than five, ten or fifteen alterations (e.g., substitutions, deletions, or insertions, e.g., conservative substitutions) relative to SEQ ID NO: 14 or 15.

In yet other embodiments, the IFM described herein (e.g., HC-ch4B2-Fab and LC-ch4B2-IL15) can comprise:

(i) the amino acid sequence shown in SEQ ID NO:16, or an amino acid sequence substantially identical thereto (e.g., an amino acid sequence at least 85%, 90%, 95% or higher identical to the antibody portion of SEQ ID NO:16), or having at least 1, 2, 3, 4, 5, 6, 7, 8, 9, or 10 or more amino acid alterations (e.g., substitutions, deletions, or insertions, e.g., conservative substitutions) relative to SEQ ID NO: 16; and (ii) the amino acid sequence shown in SEQ ID NO:17, respectively, or an amino acid sequence substantially identical thereto (e.g., an amino acid sequence at least 85%, 90%, 95% or higher identical to SEQ ID NO: 17, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 17. In embodiments, the IFM comprises no more than five, ten or fifteen alterations (e.g., substitutions, deletions, or insertions, e.g., conservative substitutions) relative to SEQ ID NO: 16 or 17.

In other embodiments, the IFM described herein (e.g., HC-hBC8(23)-Fab and LC-hBC8(23)-IL15) can comprise:

(i) the amino acid sequence shown in SEQ ID NO:18, or an amino acid sequence substantially identical thereto (e.g., an amino acid sequence at least 85%, 90%, 95% or higher identical to the antibody portion of SEQ ID NO:18), or having at least 1, 2, 3, 4, 5, 6, 7, 8, 9, or 10 or more amino acid alterations (e.g., substitutions, deletions, or insertions, e.g., conservative substitutions) relative to SEQ ID NO: 18; and (ii) the amino acid sequence shown in SEQ ID NO:19, respectively, or an amino acid sequence substantially identical thereto (e.g., an amino acid sequence at least 85%, 90%, 95% or higher identical to SEQ ID NO: 19, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 19. In embodiments, the IFM comprises no more than five, ten or fifteen alterations (e.g., substitutions, deletions, or insertions, e.g., conservative substitutions) relative to SEQ ID NO: 18 or 19.

In other embodiments, the IFM described herein (e.g., HC-chBC8-Fab and LC-chBC8-L2-IL15) can comprise:

(i) the amino acid sequence shown in SEQ ID NO:5, or an amino acid sequence substantially identical thereto (e.g., an amino acid sequence at least 85%, 90%, 95% or higher identical to the antibody portion of SEQ ID NO:5), or having at least 1, 2, 3, 4, 5, 6, 7, 8, 9, or 10 or more amino acid alterations (e.g., substitutions, deletions, or insertions, e.g., conservative substitutions) relative to SEQ ID NO: 5; and (ii) the amino acid sequence shown in SEQ ID NO:21, respectively, or an amino acid sequence substantially identical thereto (e.g., an amino acid sequence at least 85%, 90%, 95% or higher identical to SEQ ID NO: 21, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 21. In embodiments, the IFM comprises no more than five, ten or fifteen alterations (e.g., substitutions, deletions, or insertions, e.g., conservative substitutions) relative to SEQ ID NO: 21 or 5.

In other embodiments, the IFM described herein (e.g., HC-chBC8-Fab and LC-chBC8-L3-IL15) can comprise:

(i) the amino acid sequence shown in SEQ ID NO:5, or an amino acid sequence substantially identical thereto (e.g., an amino acid sequence at least 85%, 90%, 95% or higher identical to the antibody portion of SEQ ID NO:5), or having at least 1, 2, 3, 4, 5, 6, 7, 8, 9, or 10 or more amino acid alterations (e.g., substitutions, deletions, or insertions, e.g., conservative substitutions) relative to SEQ ID NO: 5; and (ii) the amino acid sequence shown in SEQ ID NO:22, respectively, or an amino acid sequence substantially identical thereto (e.g., an amino acid sequence at least 85%, 90%, 95% or higher identical to SEQ ID NO: 22, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 22. In embodiments, the IFM comprises no more than five, ten or fifteen alterations (e.g., substitutions, deletions, or insertions, e.g., conservative substitutions) relative to SEQ ID NO: 22 or 5.

In other embodiments, the IFM described herein (e.g., HC-chMHM24-Fab and LC-chMHM24-IL15) can comprise:

(i) the amino acid sequence shown in SEQ ID NO:26, or an amino acid sequence substantially identical thereto (e.g., an amino acid sequence at least 85%, 90%, 95% or higher identical to the antibody portion of SEQ ID NO:26), or having at least 1, 2, 3, 4, 5, 6, 7, 8, 9, or 10 or more amino acid alterations (e.g., substitutions, deletions, or insertions, e.g., conservative substitutions) relative to SEQ ID NO: 26; and (ii) the amino acid sequence shown in SEQ ID NO:27, respectively, or an amino acid sequence substantially identical thereto (e.g., an amino acid sequence at least 85%, 90%, 95% or higher identical to SEQ ID NO: 27, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 27. In embodiments, the IFM comprises no more than five, ten or fifteen alterations (e.g., substitutions, deletions, or insertions, e.g., conservative substitutions) relative to SEQ ID NO: 26 or 27.

In other embodiments, the IFM described herein (e.g., HC-chMHM24-Fab and LC-chMHM24-scIL12p70) can comprise:

(i) the amino acid sequence shown in SEQ ID NO:26, or an amino acid sequence substantially identical thereto (e.g., an amino acid sequence at least 85%, 90%, 95% or higher identical to the antibody portion of SEQ ID NO:26), or having at least 1, 2, 3, 4, 5, 6, 7, 8, 9, or 10 or more amino acid alterations (e.g., substitutions, deletions, or insertions, e.g., conservative substitutions) relative to SEQ ID NO: 26; and (ii) the amino acid sequence shown in SEQ ID NO:50 or 51, respectively, or an amino acid sequence substantially identical thereto (e.g., an amino acid sequence at least 85%, 90%, 95% or higher identical to SEQ ID NO: 50 or 51, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 50 or 51. In embodiments, the IFM comprises no more than five, ten or fifteen alterations (e.g., substitutions, deletions, or insertions, e.g., conservative substitutions) relative to SEQ ID NO: 50 or 51 or 26.

In other embodiments, the IFM described herein (e.g., HC-chMHM24-Fab and LC-chMHM24-IL7) can comprise:

(i) the amino acid sequence shown in SEQ ID NO:26, or an amino acid sequence substantially identical thereto (e.g., an amino acid sequence at least 85%, 90%, 95% or higher identical to the antibody portion of SEQ ID NO:26), or having at least 1, 2, 3, 4, 5, 6, 7, 8, 9, or 10 or more amino acid alterations (e.g., substitutions, deletions, or insertions, e.g., conservative substitutions) relative to SEQ ID NO: 26; and (ii) the amino acid sequence shown in SEQ ID NO: 42 or 43, respectively, or an amino acid sequence substantially identical thereto (e.g., an amino acid sequence at least 85%, 90%, 95% or higher identical to SEQ ID NO: 42 or 43, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 42 or 43. In embodiments, the IFM comprises no more than five, ten or fifteen alterations (e.g., substitutions, deletions, or insertions, e.g., conservative substitutions) relative to SEQ ID NO: 42 or 43 or 26.

In other embodiments, the IFM described herein (e.g., HC-chMHM24-Fab and LC-MHM24-IL15) can comprise:

(i) the amino acid sequence shown in SEQ ID NO:26, or an amino acid sequence substantially identical thereto (e.g., an amino acid sequence at least 85%, 90%, 95% or higher identical to the antibody portion of SEQ ID NO:26), or having at least 1, 2, 3, 4, 5, 6, 7, 8, 9, or 10 or more amino acid alterations (e.g., substitutions, deletions, or insertions, e.g., conservative substitutions) relative to SEQ ID NO: 26; and (ii) the amino acid sequence shown in SEQ ID NO:27, respectively, or an amino acid sequence substantially identical thereto (e.g., an amino acid sequence at least 85%, 90%, 95% or higher identical to SEQ ID NO: 27, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 27. In embodiments, the IFM comprises no more than five, ten or fifteen alterations (e.g., substitutions, deletions, or insertions, e.g., conservative substitutions) relative to SEQ ID NO: 27 or 26.

In other embodiments, the IFM described herein (e.g., HC-ch1B4-Fab and LC-ch1B4-IL15) can comprise:

(i) the amino acid sequence shown in SEQ ID NO:28, or an amino acid sequence substantially identical thereto (e.g., an amino acid sequence at least 85%, 90%, 95% or higher identical to the antibody portion of SEQ ID NO:28), or having at least 1, 2, 3, 4, 5, 6, 7, 8, 9, or 10 or more amino acid alterations (e.g., substitutions, deletions, or insertions, e.g., conservative substitutions) relative to SEQ ID NO: 28; and (ii) the amino acid sequence shown in SEQ ID NO:29, respectively, or an amino acid sequence substantially identical thereto (e.g., an amino acid sequence at least 85%, 90%, 95% or higher identical to SEQ ID NO: 29, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 29. In embodiments, the IFM comprises no more than five, ten or fifteen alterations (e.g., substitutions, deletions, or insertions, e.g., conservative substitutions) relative to SEQ ID NO: 28 or 29.

In other embodiments, the IFM described herein (e.g., HC-chOKT8-Fab and LC-chOKT8-IL15) can comprise:

(i) the amino acid sequence shown in SEQ ID NO:30, or an amino acid sequence substantially identical thereto (e.g., an amino acid sequence at least 85%, 90%, 95% or higher identical to the antibody portion of SEQ ID NO:30), or having at least 1, 2, 3, 4, 5, 6, 7, 8, 9, or 10 or more amino acid alterations (e.g., substitutions, deletions, or insertions, e.g., conservative substitutions) relative to SEQ ID NO:30; and (ii) the amino acid sequence shown in SEQ ID NO:31, respectively, or an amino acid sequence substantially identical thereto (e.g., an amino acid sequence at least 85%, 90%, 95% or higher identical to SEQ ID NO: 31, respectively), or having at least 1, 2, 3, 4, 5, 6, 7, 8, 9, or 10 or more amino acid alterations (e.g., substitutions, deletions, or insertions, e.g., conservative substitutions) relative to SEQ ID NO: 31. In embodiments, the IFM comprises no more than five, ten or fifteen alterations (e.g., substitutions, deletions, or insertions, e.g., conservative substitutions) relative to SEQ ID NO: 30 or 31.

In other embodiments, the IFM described herein (e.g., BC8scFv-IL15) can comprise the amino acid sequence shown in SEQ ID NO:32, or an amino acid sequence substantially identical thereto (e.g., an amino acid sequence at least 85%, 90%, 95% or higher identical to the antibody portion of SEQ ID NO:32), or having at least 1, 2, 3, 4, 5, 6, 7, 8, 9, or 10 or more amino acid alterations (e.g., substitutions, deletions, or insertions, e.g., conservative substitutions) relative to SEQ ID NO:32.

In other embodiments, the IFM described herein (e.g., a tetravalent CD137 agonist) can comprise an anti-CD45 humanized IgG4 (e.g. humanized BC8) covalently fused to the C-terminus of an anti-CD137 agonist single-chain variable fragment antibody. In some embodiments, the IFM further includes an additional anti-CD137 scFv on the C-terminus of the IgG4, e.g., thus yielding a molecule that is bi-valent for CD45 and tetravalent for CD137. In other embodiments, the IFM can also comprise the anti-CD45 IgG4 as stipulated above with scFv anti-CD137 agonist fused exclusively to the C-terminus of the IgG, thus yielding molecule that is bi-valent for CD45 and bi-valent for CD137.

In other embodiments, the IFM described herein (e.g., bi-valent CD137 agonist) can comprise an anti-CD45 humanized IgG1 Fab (e.g. humanized BC8) covalently fused to the N-terminus of anti-CD137 agonist single-chain variable fragment antibodies via the C-terminus of the heavy and light chains of the Fab, thus yielding a molecule that is mono-valent for CD45 and bi-valent for CD137.

In another aspect, the disclosure provides a polymeric scaffold, e.g., a polymeric hydrogel such as poly(lactic-co-glycolic acid) (PLGA), that comprises an IFM as described herein, e.g., hydrogel that comprises an IFM. The polymer can also be a polypeptide, chitosan, PVA (polyvinyl alcohol), PLA (polylactic acid), PEG (polyethylene glycol), or block copolymers. In some embodiments the polymeric scaffold comprises multiple different polypeptides or polymers. In one embodiment, the polymeric scaffold comprises one IFM. In other embodiments, the polymeric scaffold comprises one or more different IFMs. In some embodiments the polymeric scaffold is biodegradable. In embodiments, the polymeric scaffold can release the IFM over time through passive diffusion and/or through degradation of the polymeric scaffold.

In some embodiments, the polymeric scaffold is formed at least in part by chemical crosslinking, e.g., without limitation, using linkers disclosed herein. The polymer can comprise crosslinked polymer networks using covalent crosslinkers or non-covalent interactions (e.g., H-bonds, electrostatic interactions, or van der Waals interactions) between the polymer chains. In some embodiments the crosslinker is reversible, for example, without limitation, by altered redox state or altered pH of the environment, e.g. by comprising a disulfide bond or an acid-labile ester group. Other acid-labile linkers may be, for example, a cis-aconitic acid linker, acetals, ketals, activated amides such as amides of 2,3 dimethylmaleamic acid, vinyl ether, other activated ethers and esters such as enol or silyl ethers or esters, imines, iminiums, enamines, carbamates, hydrazones, and other linkages known in the art.

In embodiments the polymeric scaffold comprising one or more IFMs is administered to a subject in need thereof. In embodiments the polymeric scaffold comprising one or more IFMs is administered locally (e.g. intratumorally). In embodiments the polymeric scaffold is a liquid that solidifies upon injection or implantation into the body, e.g., with a viscosity increase of 1000 cP or more.

In another aspect, the disclosure provides a particle, e.g., a nanoparticle, that comprises an IFM as described herein, e.g., nanoparticle that comprises a protein (e.g., a protein nanogel as described herein). In one embodiment, the particle comprises the same IFM. In other embodiments, the particle comprises one or more different types of IFM.

In embodiments, a composition herein comprises a particle, e.g., a nanoparticle or a microparticle, or both of a nanoparticle and a microparticle. In embodiments, the particle, e.g., nanoparticle, has an average hydrodynamic diameter (e.g., measured by dynamic light scattering) between 30 nm and 1200 nm, between 40 nm and 1,100 nm, between 50 nm and 1,000 nm, between such as 50-500 nm, more typically, between 70 and 400 nm.

In some embodiments, the nanoparticle comprises a liposome, a protein nanogel, a nucleotide nanogel, a polymer nanoparticle, or a solid nanoparticle. In embodiments, the particle, optionally, comprises at least one polymer, cationic polymer, or cationic block co-polymer on the particle surface. In other embodiments, the nanoparticle comprises a nanogel that is cross linked by a reversible linker that is sensitive to redox (disulfide) or pH (hydrolysable groups) or enzymes (proteases).

In some embodiments, the one or more IFMs disclosed herein can be crosslinked to each other, as provided herein. In other embodiments, one or more IFMs can be formed or self-assemble into various nanostructures including, without limitation, protein-hydrophilic polymer conjugates (e.g., reversibly modified with PEG), protein-hydrophobic polymer conjugates (e.g., reversibly modified PLA or PLGA), bulk crosslinked protein hydrogels, crosslinked protein nanogel particles, protein nanocapsules with different shell materials (e.g., lipid, polymers or silica), protein-conjugated nanoparticles (e.g., micelle, polymeric nanoparticles, inorganic nanoparticles) and liposomes. Likewise, proteins crosslinked to each other, as provided herein, in some embodiments, can be formed or can self-assemble into protein nanostructures.

In embodiments, optionally, the IFM, is covalently coupled, e.g., crosslinked, to the protein-hydrophilic polymer of a nanoparticle, e.g., optionally via a degradable linker (e.g., disulfide linker), and remains biologically active, e.g., maintains its function. Thus, the compositions and methods disclosed herein can provide a significant benefit for cellular therapy, e.g., immunotherapy.

In embodiments, the particle comprising the IFM further comprises a nucleated cell, e.g., an immune cell (also referred to herein as a "nucleated cell-nanoparticle complex").

Accordingly, the disclosure provides a composition comprising an IFM and a particle, e.g., a nanoparticle. In some aspects, the present disclosure provides a composition comprising a nucleated cell and at least one IFM and/or a particle as described herein.

In embodiments, the particle is associated with the cell surface by electrostatic attraction to the nucleated cell. In embodiments, the nanoparticle comprises at least one ligand, wherein the ligand has affinity for proteins, carbohydrates or lipids on the surface of the nucleated cell.

In embodiments, the particle is covalently conjugated, e.g., to the surface, of the nucleated cell, e.g., the immune cell. In embodiments, the nanoparticle is not covalently conjugated to the nucleated cell.

In embodiments, the particle can further include one or more additional therapeutic proteins chosen from one or more (e.g., 2, 3, 4, 5 or more) therapeutic proteins, e.g., a cytokine molecule (e.g., an IL-2, IL-7, IL-12, IL-15, IL-18, IL-21, IL-23, IL-4, IL-1alpha, IL-1beta, IL-5, IFNgamma, TNFalpha (TNFa), IFNalpha, IFNbeta, GM-CSF, or GCSF, including variant forms thereof, e.g., mutant; complex comprising the cytokine molecule with a polypeptide, e.g., a cytokine receptor complex; fusion or agonist forms thereof); growth factors; and other molecules, e.g., an antibody molecule or agonist ligand against a costimulatory molecule, e.g., wherein the costimulatory molecule is chosen from CD137, OX40, CD28, GITR, VISTA, anti-CD40, or CD3.

In other aspects, the present disclosure provides a method of making the aforesaid particles.

Other features, objects, and advantages of the disclosure will be apparent from the description and drawings, and from the claims.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In addition, the materials, methods, and examples are illustrative only and not intended to be limiting.

BRIEF DESCRIPTION OF THE DRAWINGS

FIG. 2A depicts a schematic of IL-15 IFMs comprising various antibody formats. FIGS. 2B and 2C depict evaluation of IFMs on CD8 T cell expansion in pulse assay using CellTiter Blue (FIG. 2B) or flow cytometry counting beads (FIG. 2C).

FIGS. 3A and 3B depict schematics for fusion of IL-15 to the N- or C-terminus of chBC8 IgG (FIG. 3A) or chBC8 Fab (FIG. 3B) light-chain. Antibody fusions comprise a complex with IL-15Rα-sushi through a high-affinity interaction with IL-15. FIGS. 3C and 3D depict schematics for fusion of IL-15Rα-sushi to the N- or C-terminus of chBC8 IgG (FIG. 3C) or chBC8Fab (FIG. 3D) light-chain. Antibody fusions comprise a complex with IL-15$^{N72D}$ through a high-affinity interaction with IL-15Rα-sushi.

(FIGS. 4A and 4B) IFMs comprising IL-15$^{N72D}$ and chBC8 Fab (FIG. 4A) or chBC8 IgG (FIG. 4B) were evaluated for T cell expansion in pulse bioassay. CD8 T cell proliferation was analyzed using CellTiter Blue; IL15$^{N72D}$/sushi$^{L77I}$-Fc and unstimulated T-cells (neg ctrl) were included for comparison.

FIGS. 5A and 5B depict IFMs comprising wild-type IL-15 or IL-15$^{N72D}$ and chBC8 Fab (FIG. 5A) or chBC8 IgG (FIG. 5B) that were evaluated for CD8 T cell expansion in pulse assay using CellTiter Blue three days after pulse incubation with IFMs. FIGS. 5C and 5D depict the evaluation of IFMs comprising chBC8 Fab (FIG. 5C) or chBC8 IgG (FIG. 5D) on CD8 T cell expansion in a constant exposure, e.g., static, assay format using CellTiter Blue following incubation with IFMs for three days.

FIG. 6A depicts schematics of IFMs comprising IL-15 fused to the C-terminus of chBC8 IgG light- or heavy-chain and a noncovalent complex between IL-15 and IL-15Rα-sushi. FIG. 6B depicts effects of IFMs on CD8 T cell expansion in a pulse bioassay.

FIGS. 7A and 7B depict IL-15 IFMs comprising chBC8 Fab (FIG. 7A) or chBC8 IgG (FIG. 7B) in the presence or absence of soluble BC8 IgG competitor that were evaluated for expansion of CD8 T cells in pulse assay using CellTiter Blue. FIG. 7C depicts evaluation of IL-15 IFM comprising a humanized BC8 Fab fragment or a humanized BC8 Fab fragment containing a mutated CDR-H3 that ablates binding to CD45 for CD8 T cell expansion in pulse bioassay.

FIGS. 8A-8C depict cell surface loading and persistence of IFMs. FIG. 8A depicts flow cytometry histograms showing MFI after pulse of IFMs as detected by staining with fluorescently labeled anti-IL15 or anti-IgG antibodies. FIG. 8B depicts persistence of cell surface staining of IL-15 over time. FIG. 8C depicts cell density over time, measured using flow cytometry counting beads.

FIG. 9A depicts amino acid sequences of the three different linkers for fusion of IL-15 to the C-terminus of chBC8 Fab light-chain. FIG. 9B depicts evaluation of IFMs comprising different linker compositions for CD8 T cell expansion in pulse bioassay using CellTiter Blue.

FIG. 10A depicts binding affinity of various CD45 antibody clones to CD45 expressed on T cells. FIG. 10B depicts evaluation of IL-15 IFMs comprising different anti-CD45 antibody clones in pulse bioassay using CellTiter Blue.

FIG. 11A depicts a schematic of IL-15 IFMs comprising fusion of IL-15 to the light-chain C-terminus of a Fab antibody fragment targeting alternative cell surface receptors; IFMs comprise a noncovalent association between IL-15 and IL-15Rα-sushi. FIG. 11B depicts evaluation of IL-15 IFMs for CD8 T cell expansion in pulse bioassay using CellTiter Blue.

FIG. 12A depicts a schematic of IL-15 IFM comprising fusion of IL-15 to the C-terminus of an anti-CD8 Fab light-chain, and a noncovalent association with IL-15Rα-sushi. FIG. 12B depicts evaluation of potency of anti-CD8 IFM on purified CD4 or CD8 T cells in pulse bioassay using CellTiter Blue. CD4 or CD8 T cells were purified from total T cells (which naturally comprise mixtures of CD4 and CD8 T cells) using magnetic bead sorting.

FIGS. 13A and 13B depict crosslinking of IFM into protein nanogels analyzed by size-exclusion chromatography (FIG. 13A); protein nanogels comprising IL15$^{N72D}$/sushiL77I-Fc are shown for comparison (FIG. 13B). Backpacks comprising IL-15 IFM or IL15$^{N72D}$/sushiL77I-Fc were evaluated for CD8 T cell expansion in pulse bioassay (FIG. 13C). Cell density was analyzed using flow cytometry counting beads; data are presented as fold expansion.

FIGS. 22A-22D illustrate 4 exemplary constructs comprising anti-CD45 antibody and IL-12 (also referred to as "anti-CD45-IL12-TF" or "αCD45-IL12-TF" or "IL12-TF").

FIGS. 27A-27B shows STAT5 phosphorylation from combinations of IL-15 and IL-21 IFMs.

FIG. 28 shows surface loading from combinations of IL-12 and IL-15 IFMs.

DETAILED DESCRIPTION

The present disclosure provides, inter alia, compositions and related methods of use of immunostimulatory fusion molecules or IFMs. An "IFM" as described herein includes an immune stimulating moiety, e.g., a cytokine molecule (e.g., a biologically active cytokine), and an immune cell targeting moiety, e.g., an antibody molecule (e.g. an antibody or antibody fragment) capable of binding to an immune cell, e.g., an immune effector cell. In embodiments, the immune stimulating moiety and the immune cell targeting moiety are functionally linked (e.g., by chemical coupling, genetic fusion, noncovalent association or otherwise). In some embodiments, the immune cell targeting moiety is capable of binding to an immune cell surface target, thereby targeting the immune stimulating moiety, e.g., cytokine molecule, to the immune cell, e.g., an immune effector cell (e.g., a lymphocyte).

Figure 34A:
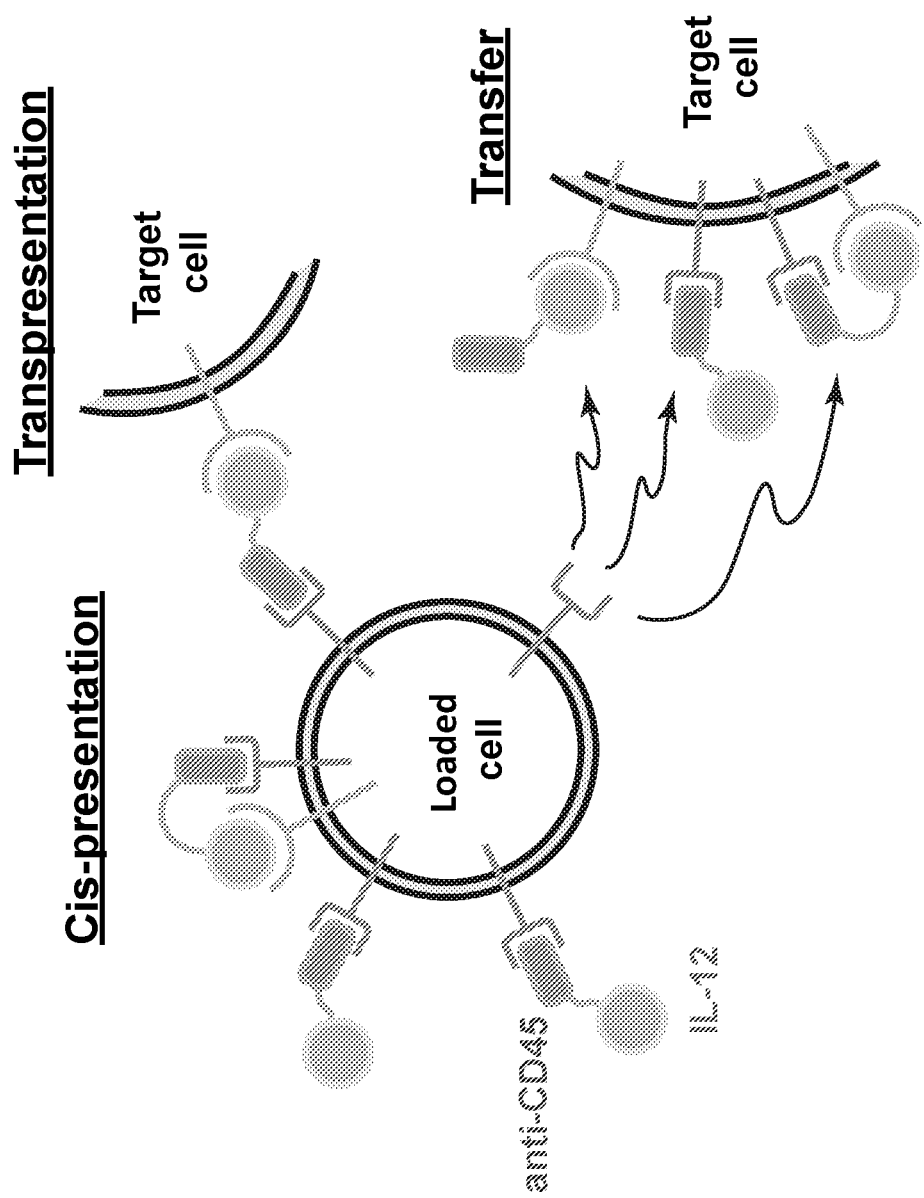
FIGS. 34A-34B shows schematic depicting tethered fusions can signal in cis, trans and by transfer to target cells, and shows activation of STAT4 phosphorylation in loaded ("cis") non-loaded target cells ("trans" and "transferred") by IL-12 tethered fusion.

Without wishing to be bound by theory, binding of the immune cell targeting moiety to the immune cell surface target is believed to increase the concentration, e.g., the concentration over time, on the surface of the immune stimulating moiety, e.g., cytokine molecule, with its corresponding receptor, e.g., a cytokine receptor, on the immune cell, e.g., relative to the association of the free cytokine molecule with its cytokine receptor. This can result in an immune effect on the immune cell itself bound by the IFMs (autocrine signaling), and/or or on another (e.g., neighboring) immune cell (paracrine signaling). Advantageously, compared to other therapeutics such as soluble cytokines, armored CAR-T (with cytokines) and nanogel backpacks (onto immune cells), the tethered fusions of the present disclosure can provide balanced, dual autocrine and paracrine activity, combining the benefits of both sufficiently high activity and low toxicity. In contrast, delivery of soluble cytokines while providing systemic activity, is known for its high toxicity. Armored CAR-T can locally secrete cytokines that provide paracrine and systemic activity, as well as systemic toxicities. Nanogel backpacks such as those described in, e.g., U.S. Publication No. 2017/0080104, U.S. Pat. No. 9,603,944, U.S. Publication No. 2014/0081012, and PCT Application No. PCT/US2017/037249 (each incorporated herein by reference in its entirety), are capable of providing highly localized autocrine activity, which may be desirable for certain cytokines (e.g., IL-15). However, for cytokines (e.g., IL-12) where paracrine activity is needed, the tethered fusions disclosed herein can be a sweet spot for balanced autocrine and paracrine activity. As shown in FIG. 34A, tethered fusions can signal in cis once tethered (or loaded) onto an immune cell, in trans to a neighboring target immune cell, and by transfer to target immune cells that are not in close proximity to the original backpack-loaded cells.

In embodiments, the immune cell targeting moiety results in an increase in one or more of: binding, availability, activation and/or signaling of the immune stimulating moiety on the immune cell, e.g., over a specified amount of time. In embodiments, the IFM does not substantially interfere with the signaling function of the cytokine molecule. Such targeting effect results in localized and prolonged stimulation of proliferation and activation of the immune cells, thus inducing the controlled expansion and activation of an immune response. The IFMs disclosed herein offer several advantages over art-known cytokines, including reduced side effects, e.g., a lower systemic toxicity, while retaining the immunostimulatory bioactivity (e.g., signaling activity and/or potency) of the cytokine molecule.

Prior disclosures of immunocytokines-antibody-cytokine fusion proteins are typically designed to target disease antigens (e.g., tumor associated antigens e.g., cell membrane antigens and extracellular matrix components) via their antibody components in order to potentiate effector functions through their cytokine components. (Clin. Pharmacol. 2013; 5(Suppl 1): 29-45. Thomas List and Dario Neri. Published online 2013 Aug. 20. doi: 10.2147/CPAA.S49231 PMCID: PMC3753206.) Exemplary barriers to the therapeutic use of cytokines relate to their short serum half-life and limited bioavailability. High doses of cytokines can overcome these barriers, but result in dose-limiting toxicities. Consequently, most cytokines require protein engineering approaches to reduce toxicity and increase half-life. Specific strategies include PEGylation, antibody complexes and fusion protein formats, and mutagenesis. (Antibodies 2013, 2, 426-451; doi:10.3390/antib2030426 Rodrigo Vazquez-Lombardi Brendan Roome and Daniel Christ.)

The present disclosure provides, inter alia, fusion proteins as a covalent conjugate of a cytokine and a targeting moiety which functions to target the fusion protein to an immune cell (e.g., healthy and/or non-malignant) with a particular composition of receptors. Fusing a pro-inflammatory cytokine to a targeting moiety, preferably an antibody or antibody fragment (e.g. single chain Fv, Fab, IgG), directs the fusion protein to a cell of interest and enhances cell surface availability of the cytokine. Cells of interest include, inter alia, immune cells, especially lymphocytes, and preferably T-cells (e.g., total CD3 T cells, CD4 T cells, or CD8 T cells), and can include other cell types. In some embodiments, the fusion proteins can activate a subset of CD8 T cells. Cells of interest, including immune cells, can be in vivo (e.g., in a subject), in vitro or ex vivo (e.g., a cell based therapy).

In some embodiments, the immune cell surface target is abundantly present on the surface of an immune cell (e.g., outnumbers the number of receptors for the cytokine molecule present on the immune cell surface). In some embodiments, the immune cell targeting moiety can be chosen from an antibody molecule or a ligand molecule that binds to an immune cell surface target, e.g., a target chosen from CD4, CD8, CD18, CD11a, CD11b, CD11c, CD19, CD20 or CD45. In one embodiment, the immune cell targeting moiety comprises an antibody molecule or a ligand molecule that binds to CD45.

CD45 is an example of an abundant receptor. CD45 is also known as leukocyte common antigen, is a type I transmembrane protein present on hematopoietic cells except erythrocytes that assists in cell activation (see e.g., Altin, J G, *Immunol Cell Biol.* 1997 October; 75(5):430-45)). Other receptors of the targeting moiety of the IFM are ideally maintained on the cell surface and are resistant to internalization by the cell (e.g. persistent receptors). An example of an abundant and persistent receptor is CD45. Alternatively, receptors of the targeting moiety may be constitutively turned over, e.g. internalized by the cell and recycled back to the surface thus allowing significant binding opportunities for the fusion protein, despite their dynamic internalization (recycling receptors). CD22 is an example of a recycling receptor.

Expression levels of cytokine receptors can vary based on a variety of factors, including the (i) cell type, and (ii) the activation state of the cell. In embodiments, the expression level can impact one or more of cytokine signal transduction, signal strength and duration. In one embodiment, the receptors expressed on the immune cell surface are present in an effective ratio whereby the number of receptors to the targeting moiety is in excess of the number of receptors to the cytokine component, on the cell surface. Such an effective ratio is realized when the targeting moiety receptors are persistent; or alternatively; when their cell surface density is effectively maintained by a recycling mechanism which restores the receptors to the cell's surface and consequently permits binding opportunities for the targeting component in excess of the cytokine component. In the case of receptors that are recycled (e.g. internalized and returned to the cell surface), antibody receptors will be present in an effective ratio to allow binding opportunities for the targeting moiety in excess of binding opportunities for the cytokine component of the protein. Such an effective ratio allows cytokine localization to the cell surface and consequently increases the time and availability of the cytokine to bind its own cell-surface receptor (despite the dynamic presence, internalization and return to the surface of the targeting receptor).

In some cases, regulation of signaling initiated by plasma membrane receptors is coupled to endocytosis. Internalization of activated receptors is a means for signal attenuation, but also regulates the duration of receptor signaling and signaling output specificity (reviewed in Barbieri, P. P. Di Fiore, S. Sigismund. Endocytic control of signaling at the plasma membrane Curr. Opin. Cell Biol., 39 (2016), pp. 21-27). Endosomes can serve as mobile signaling platforms facilitating formation of multiprotein signaling assemblies and consequently enabling efficient signal transduction in space and time. Some signaling events, e.g. cytokine-signaling events, initiated at the plasma membrane may continue from endosomal compartments.

IFMs of the disclosure can confer improved biological activity of agonistic cytokines in general, and of IL-15, IL-7, IL-21, and IL-12p70 in particular. Other agonistic cytokines include IL-2, IL-6, and IL-27. In some embodiments, the cytokine molecule includes a pro-inflammatory cytokine, e.g., includes a cytokine chosen from one or more of IL-2, IL-6, IL-7, IL-12, IL-15, IL-21 or IL-27, including variant forms thereof (e.g., a cytokine derivative, a complex comprising the cytokine molecule with a polypeptide, e.g., a cytokine receptor complex, and other agonist forms thereof). In one embodiment, the cytokine molecule includes IL-15 and/or IL-12 (in one IFM or two IFMs).

In one exemplary embodiment, the immune cell targeting moiety of the IFM is derived from an anti-CD45 antibody molecule and the cytokine molecule is interleukin-15 optionally complexed to the sushi domain of the IL-15 receptor alpha subunit (αCD45-IL15 and αCD45-IL15/sushi). In another exemplary embodiment, the immune cell targeting moiety of the IFM is derived from an anti-CD45 antibody molecule and the cytokine molecule is interleukin-12 (αCD45-IL12). The αCD45-IL15/sushi IFM and αCD45-IL12 IFM can be used together in, e.g., a combination therapy.

In another embodiment, the IFMs can be tethered to different cell surface molecules, e.g., an IFM in which the immune cell targeting moiety is derived from an antibody targeting an abundant or persistence cell surface receptor other than CD45, e.g., a target chosen from CD4, CD8, CD18, CD11a, CD11b, CD11c, CD19, or CD20. The IFMs can contain cytokines such as interleukin-15 optionally complexed to the sushi domain of the IL-15 receptor alpha subunit and/or interleukin-12. The IFMs can be used together in, e.g., a combination therapy with αCD45-IL15, αCD45-IL15/sushi, or αCD45-IL12.

In another embodiment, IFMs comprising additional cytokines tethered to the same or different cell surface receptors are used together, e.g., in a combination therapy. The immune cell targeting moiety can be chosen from an antibody molecule or a ligand molecule that binds to an immune cell surface target, e.g., a target chosen from CD4, CD8, CD18, CD11a, CD11b, CD11c, CD19, CD20 or CD45, and a pro-inflammatory cytokine, e.g., includes a cytokine chosen from one or more of IL-2, IL-6, IL-7, IL-12, IL-15, IL-21 or IL-27, including variant forms thereof. In some embodiments combinations of two different IFMs are used. In other embodiments combinations of three different IFMs are used. In other embodiments combinations of more than three IFMs are used.

Therapeutic uses for the fusion proteins of the disclosure include, inter alia, (1) as agents for specific delivery of therapeutic proteins via receptor mediated binding of receptors unique to specific cells (e.g., CD4 or CD8); (2) as ex vivo agents to induce activation and expansion of isolated autologous and allogenic cells prior to reintroduction to a patient; for example, in T cell therapies including ACT (adoptive cell transfer) and also with other important immune cell types, including for example, B cells, tumor infiltrating lymphocytes, NK cells, antigen-specific CD8 T cells, T cells genetically engineered to express chimeric antigen receptors (CARs) or CAR-T cells, T cells genetically engineered to express T-cell receptors specific to an tumor antigen, tumor infiltrating lymphocytes (TILs), and/or antigen-trained T cells (e.g., T cells that have been "trained" by antigen presenting cells (APCs) displaying antigens of interest, e.g. tumor associated antigens (TAA)); and, (3) as in vivo agents for administration to deliver cytokines used to support expansion of cells used in cell therapies, including ACT.

As such, a pharmaceutical composition comprising the IFM of the present disclosure and a pharmaceutically acceptable carrier, excipient, or stabilizer can be used to deliver therapeutic proteins to a subject in need thereof. A modified immune cell, comprising a healthy and/or non-malignant immune cell and the IFM of the present disclosure bound or targeted thereto, is also provided. Such modified immune cell can be prepared in vitro or in vivo.

The present disclosure also provides a method of in vitro preparation of modified immune cells, comprising: providing a plurality of healthy and/or non-malignant immune cells; and incubating the IFM of the present disclosure with the plurality of healthy and/or non-malignant immune cells so as to permit targeted binding of the IFM thereto, thereby producing a plurality of modified immune cells.

Also provided herein is a method of providing a cell therapy, comprising: providing a plurality of healthy and/or non-malignant immune cells; incubating the IFM of the present disclosure with the plurality of healthy and/or non-malignant immune cells so as to permit targeted binding of the IFM thereto, thereby producing a plurality of modified immune cells; and administering the plurality of modified immune cells to a subject in need thereof. In some embodiments, the cell therapy is administered in the absence of pre-conditioning of the subject, wherein said pre-conditioning comprises CPX (cyclophosphamide) or other lymphodepletion conditioning chemotherapy. The elimination of pre-conditioning is advantageous as it is well known that pre-conditioning with chemotherapy agents can cause systemic high toxicity to all cells, including healthy cells, weaken the immune system and induce many undesirable side effects.

Definitions

Certain terms are defined herein below. Additional definitions are provided throughout the application.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values. The term "substantially" means more than 50%, preferably more than 80%, and most preferably more than 90% or 95%.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

The term "autologous" refers to any material derived from the same individual to whom it is later to be re-introduced into the individual. The term "allogeneic" refers to any material derived from a different animal of the same species as the individual to whom the material is introduced.

"Antibody" or "antibody molecule" as used herein refers to a protein, e.g., an immunoglobulin chain or fragment thereof, comprising at least one immunoglobulin variable domain sequence. An antibody molecule encompasses antibodies (e.g., full-length antibodies) and antibody fragments. In an embodiment, an antibody molecule comprises an antigen binding or functional fragment of a full length antibody, or a full length immunoglobulin chain. For example, a full-length antibody is an immunoglobulin (Ig) molecule (e.g., IgG) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', F(ab')$_2$, F(ab)$_2$, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')₂ fragments, and single chain variable fragments (scFvs). The terms "Fab" and "Fab fragment" are used interchangeably and refer to a region that includes one constant and one variable domain from each heavy and light chain of the antibody, i.e., $V_L$, $C_L$, $V_H$, and $C_H1$.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

In embodiments, an antibody molecule is monospecific, e.g., it comprises binding specificity for a single epitope. In some embodiments, an antibody molecule is multispecific, e.g., it comprises a plurality of immunoglobulin variable domain sequences, where a first immunoglobulin variable domain sequence has binding specificity for a first epitope and a second immunoglobulin variable domain sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

"Antigen" (Ag) as used herein refers to a macromolecule, including all proteins or peptides. In some embodiments, an antigen is a molecule that can provoke an immune response, e.g., involving activation of certain immune cells and/or antibody generation. Antigens are not only involved in antibody generation. T cell receptors also recognized antigens (albeit antigens whose peptides or peptide fragments are complexed with an MHC molecule). Any macromolecule, including almost all proteins or peptides, can be an antigen. Antigens can also be derived from genomic recombinant or DNA. For example, any DNA comprising a nucleotide sequence or a partial nucleotide sequence that encodes a protein capable of eliciting an immune response encodes an "antigen." In embodiments, an antigen does not need to be encoded solely by a full length nucleotide sequence of a gene, nor does an antigen need to be encoded by a gene at all. In embodiments, an antigen can be synthesized or can be derived from a biological sample, e.g., a tissue sample, a tumor sample, a cell, or a fluid with other biological components. As used, herein a "tumor antigen" or interchangeably, a "cancer antigen" includes any molecule present on, or associated with, a cancer, e.g., a cancer cell or a tumor microenvironment that can provoke an immune response. As used, herein an "immune cell antigen" includes any molecule present on, or associated with, an immune cell that can provoke an immune response.

The "antigen-binding site" or "antigen-binding fragment" or "antigen-binding portion" (used interchangeably herein) of an antibody molecule refers to the part of an antibody molecule, e.g., an immunoglobulin (Ig) molecule such as IgG, that participates in antigen binding. In some embodiments, the antigen-binding site is formed by amino acid residues of the variable (V) regions of the heavy (H) and light (L) chains. Three highly divergent stretches within the variable regions of the heavy and light chains, referred to as hypervariable regions, are disposed between more conserved flanking stretches called "framework regions" (FRs). FRs are amino acid sequences that are naturally found between, and adjacent to, hypervariable regions in immunoglobulins. In embodiments, in an antibody molecule, the three hypervariable regions of a light chain and the three hypervariable regions of a heavy chain are disposed relative to each other in three dimensional space to form an antigen-binding surface, which is complementary to the three-dimensional surface of a bound antigen. The three hypervariable regions of each of the heavy and light chains are referred to as "complementarity-determining regions," or "CDRs." The framework region and CDRs have been defined and described, e.g., in Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917. Each variable chain (e.g., variable heavy chain and variable light chain) is typically made up of three CDRs and four FRs, arranged from amino-terminus to carboxy-terminus in the amino acid order: FR1, CDR1, FR2, CDR2, FR3, CDR3, and FR4. Variable light chain (VL) CDRs are generally defined to include residues at positions 27-32 (CDR1), 50-56 (CDR2), and 91-97 (CDR3). Variable heavy chain (VH) CDRs are generally defined to include residues at positions 27-33 (CDR1), 52-56 (CDR2), and 95-102 (CDR3). One of ordinary skill in the art would understand that the loops can be of different length across antibodies and the numbering systems such as the Kabat or Chotia control so that the frameworks have consistent numbering across antibodies.

In some embodiments, the antigen-binding fragment of an antibody (e.g., when included as part of the fusion molecule of the present disclosure) can lack or be free of a full Fc domain. In certain embodiments, an antibody-binding fragment does not include a full IgG or a full Fc but may include one or more constant regions (or fragments thereof) from the light and/or heavy chains. In some embodiments, the antigen-binding fragment can be completely free of any Fc domain. In some embodiments, the antigen-binding fragment can be substantially free of a full Fc domain. In some embodiments, the antigen-binding fragment can include a portion of a full Fc domain (e.g., CH2 or CH3 domain or a portion thereof). In some embodiments, the antigen-binding fragment can include a full Fc domain. In some embodiments, the Fc domain is an IgG domain, e.g., an IgG1, IgG2, IgG3, or IgG4 Fc domain. In some embodiments, the Fc domain comprises a CH2 domain and a CH3 domain.

As used herein, a "cytokine molecule" refers to full length, a fragment or a variant of a naturally-occurring, wild type cytokine (including fragments and functional variants thereof having at least 10% of the activity of the naturally-occurring cytokine molecule). In embodiments, the cytokine molecule has at least 30, 50, or 80% of the activity, e.g., the immunomodulatory activity, of the naturally-occurring molecule. In embodiments, the cytokine molecule further comprises a receptor domain, e.g., a cytokine receptor domain, optionally, coupled to an immunoglobulin Fc region. In other embodiments, the cytokine molecule is coupled to an immunoglobulin Fc region. In other embodiments, the cytokine molecule is coupled to an antibody molecule (e.g., an immunoglobulin Fab or scFv fragment, a Fab fragment, a $FAB_2$ fragment, or an affibody fragment or derivative, e.g., a sdAb (nanobody) fragment, a heavy chain antibody fragment, single-domain antibody, a bi-specific or multispecific antibody), or non-antibody scaffolds and antibody mimetics (e.g., lipocalins (e.g., anticalins), affibodies, fibronectin (e.g., monobodies or Adnectins), knottins, ankyrin repeats (e.g., DARPins), and A domains (e.g., avimers)).

"Cancer" as used herein can encompass all types of oncogenic processes and/or cancerous growths. In embodiments, cancer includes primary tumors as well as metastatic tissues or malignantly transformed cells, tissues, or organs.

In embodiments, cancer encompasses all histopathologies and stages, e.g., stages of invasiveness/severity, of a cancer. In embodiments, cancer includes relapsed and/or resistant cancer. The terms "cancer" and "tumor" can be used interchangeably. For example, both terms encompass solid and liquid tumors. As used herein, the term "cancer" or "tumor" includes premalignant, as well as malignant cancers and tumors.

As used herein, an "immune cell" refers to any of various cells that function in the immune system, e.g., to protect against agents of infection and foreign matter. In embodiments, this term includes leukocytes, e.g., neutrophils, eosinophils, basophils, lymphocytes, and monocytes. The term "immune cell" includes immune effector cells described herein. "Immune cell" also refers to modified versions of cells involved in an immune response, e.g. modified NK cells, including NK cell line NK-92 (ATCC cat. No. CRL-2407), haNK (an NK-92 variant that expresses the high-affinity Fc receptor FcγRIIIa (158V)) and taNK (targeted NK-92 cells transfected with a gene that expresses a CAR for a given tumor antigen), e.g., as described in Klingemann et al. supra.

"Immune effector cell," as that term is used herein, refers to a cell that is involved in an immune response, e.g., in the promotion of an immune effector response. Examples of immune effector cells include, but are not limited to, T cells, e.g., CD4T cells, CD8 T cells, alpha T cells, beta T cells, gamma T cells, and delta T cells; B cells; natural killer (NK) cells; natural killer T (NKT) cells; dendritic cells; and mast cells. In some embodiments, the immune cell is an immune cell (e.g., T cell or NK cell) that comprises, e.g., expresses, a Chimeric Antigen Receptor (CAR), e.g., a CAR that binds to a cancer antigen. In other embodiments, the immune cell expresses an exogenous high affinity Fc receptor. In some embodiments, the immune cell comprises, e.g., expresses, an engineered T-cell receptor. In some embodiments, the immune cell is a tumor infiltrating lymphocyte. In some embodiments the immune cells comprise a population of immune cells and comprise T cells that have been enriched for specificity for a tumor-associated antigen (TAA), e.g. enriched by sorting for T cells with specificity towards MHCs displaying a TAA of interest, e.g. MART-1. In some embodiments immune cells comprise a population of immune cells and comprise T cells that have been "trained" to possess specificity against a TAA by an antigen presenting cell (APC), e.g. a dendritic cell, displaying TAA peptides of interest. In some embodiments, the T cells are trained against a TAA chosen from one or more of MART-1, MAGE-A4, NY-ESO-1, SSX2, Survivin, or others. In some embodiments the immune cells comprise a population of T cells that have been "trained" to possess specificity against a multiple TAAs by an APC, e.g. a dendritic cell, displaying multiple TAA peptides of interest. In some embodiments, the immune cell is a cytotoxic T cell (e.g., a CD8 T cell). In some embodiments, the immune cell is a helper T cell, e.g., a CD4 T cell.

The term "effector function" or "effector response" refers to a specialized function of a cell. Effector function of a T cell, for example, may be cytolytic activity or helper activity including the secretion of cytokines.

"Cytotoxic T lymphocytes" (CTLs) as used herein refer to T cells that have the ability to kill a target cell. CTL activation can occur when two steps occur: 1) an interaction between an antigen-bound MHC molecule on the target cell and a T cell receptor on the CTL is made; and 2) a costimulatory signal is made by engagement of costimulatory molecules on the T cell and the target cell. CTLs then recognize specific antigens on target cells and induce the destruction of these target cells, e.g., by cell lysis. In some embodiments, the CTL expresses a CAR. In some embodiments, the CTL expresses an engineered T-cell receptor.

The term "subject" includes living organisms in which an immune response can be elicited (e.g., mammals, human). In one embodiment, the subject is a patient, e.g., a patient in need of immune cell therapy. In another embodiment, the subject is a donor, e.g. an allogenic donor of immune cells, e.g., intended for allogenic transplantation.

The compositions and methods of the present disclosure encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein. Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403-10. BLAST nucleotide searches can be performed with the NBLAST program, score=100, wordlength=12 to obtain nucleotide sequences homologous to a nucleic acid (e.g., SEQ ID NO: 1) molecules of the disclosure. BLAST protein searches can be performed with the XBLAST program, score=50, wordlength=3 to obtain amino acid sequences homologous to protein molecules of the disclosure. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. See http://www.ncbi.nlm.nih.gov. It is understood that the molecules of the present disclosure may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "functional variant" or "variant" or "variant form" in the context of a polypeptide refers to a polypeptide that is capable of having at least 10% of one or more activities of the naturally-occurring sequence. In some embodiments, the functional variant has substantial amino acid sequence identity to the naturally-occurring sequence, or is encoded by a substantially identical nucleotide sequence, such that the functional variant has one or more activities of the naturally-occurring sequence.

The term "molecule" as used herein can refer to a polypeptide or a nucleic acid encoding a polypeptide, as indicated by the context. This term includes full length, a fragment or a variant of a naturally-occurring, wild type polypeptide or nucleic acid encoding the same, e.g., a functional variant, thereof. In some embodiments, the variant is a derivative, e.g., a mutant, of a wild type polypeptide or nucleic acid encoding the same.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "parent polypeptide" refers to a wild-type polypeptide and the amino acid sequence or nucleotide sequence of the wild-type polypeptide is part of a publicly accessible protein database (e.g., EMBL Nucleotide Sequence Database, NCBI Entrez, ExPasy, Protein Data Bank and the like).

The term "mutant polypeptide" or "polypeptide variant" or "mutein" refers to a form of a polypeptide, wherein its amino acid sequence differs from the amino acid sequence of its corresponding wild-type (parent) form, naturally existing form or any other parent form. A mutant polypeptide can contain one or more mutations, e.g., replacement, insertion, deletion, etc. which result in the mutant polypeptide.

The term "corresponding to a parent polypeptide" (or grammatical variations of this term) is used to describe a polypeptide of the present disclosure, wherein the amino acid sequence of the polypeptide differs from the amino acid sequence of the corresponding parent polypeptide only by the presence of at least amino acid variation. Typically, the amino acid sequences of the variant polypeptide and the parent polypeptide exhibit a high percentage of identity. In one example, "corresponding to a parent polypeptide" means that the amino acid sequence of the variant polypeptide has at least about 50% identity, at least about 60%, at least about 70%, at least about 80%, at least about 90%, at least about 95% or at least about 98% identity to the amino acid sequence of the parent polypeptide. In another example, the nucleic acid sequence that encodes the variant polypeptide has at least about 50% identity, at least about 60%, at least about 70%, at least about 80%, at least about 90%, at least about 95% or at least about 98% identity to the nucleic acid sequence encoding the parent polypeptide.

The term "introducing (or adding etc.) a variation into a parent polypeptide" (or grammatical variations thereof), or "modifying a parent polypeptide" to include a variation (or grammatical variations thereof) do not necessarily mean that the parent polypeptide is a physical starting material for such conversion, but rather that the parent polypeptide provides the guiding amino acid sequence for the making of a variant polypeptide. In one example, "introducing a variant into a parent polypeptide" means that the gene for the parent polypeptide is modified through appropriate mutations to create a nucleotide sequence that encodes a variant polypeptide. In another example, "introducing a variant into a parent polypeptide" means that the resulting polypeptide is theoretically designed using the parent polypeptide sequence as a guide. The designed polypeptide may then be generated by chemical or other means.

Various aspects of the disclosure are described in further detail below. Additional definitions are set out throughout the specification.

Cytokine Molecules

Cytokines are proteinaceous signaling compounds that are mediators of the immune response. They control many different cellular functions including proliferation, differentiation and cell survival/apoptosis; cytokines are also involved in several pathophysiological processes including viral infections and autoimmune diseases. Cytokines are synthesized under various stimuli by a variety of cells, including those of both the innate (monocytes, macrophages, dendritic cells) and adaptive (T- and B-cells) immune systems. Cytokines can be classified into two groups: pro- and anti-inflammatory. Pro-inflammatory cytokines, including IFN-γ, IL-1, IL-6 and TNF-α, are predominantly derived from the innate immune cells and Th1 cells. Anti-inflammatory cytokines, including IL-10, IL-4, IL-13 and IL-5, are synthesized from Th2 immune cells.

The present disclosure provides, inter alia, IFMs (e.g., IFM polypeptides), that include, e.g., are engineered to contain, one or more cytokine molecules, e.g., immunomodulatory (e.g., proinflammatory) cytokines and variants, e.g., functional variants, thereof. Accordingly, in some embodiments, the cytokine molecule is an interleukin or a variant, e.g., a functional variant thereof. In some embodiments the interleukin is a proinflammatory interleukin.

In embodiments, the cytokine molecule is full length, a fragment or a variant of a cytokine, e.g., a cytokine comprising one or more mutations. In some embodiments the cytokine molecule comprises a cytokine chosen from interleukin-15 (IL-15), interleukin-1 alpha (IL-1 alpha), interleukin-1 beta (IL-1 beta), interleukin-2 (IL-2), interleukin-4 (IL-4), interleukin-5 (IL-5), interleukin-7 (IL-7), interleukin-12 (IL-12), interleukin-18 (IL-18), interleukin-21 (IL-21), interleukin-23 (IL-23), interferon (IFN) α, IFN-β, IFN-γ, tumor necrosis factor alpha, GM-CSF, GCSF, or a fragment or variant thereof, or a combination of any of the aforesaid cytokines. In other embodiments, the cytokine molecule is chosen from interleukin-2 (IL-2), interleukin-12 (IL-12), interleukin-15 (IL-15), interleukin-18 (IL-18), interleukin-21 (IL-21), or interferon gamma, or a fragment or variant thereof, or a combination of any of the aforesaid cytokines. The cytokine molecule can be a monomer or a dimer. In embodiments, the cytokine molecule further comprises a receptor domain, e.g., a cytokine receptor domain.

In some embodiments the cytokine or growth factor molecule can be a Treg inhibitory molecule selected from one or more of Ifn-γ, IL-1α, IL-1β, IL-6, IL-12, IL-21, IL-23, IL-27 or TNF-α. Ifn-γ promotes Treg fragility, and can reduce suppression in the tumor microenvironment. IL-1 and IL-6, IL-21 and IL-23 can induce Tregs to produce pro-inflammatory IL-17 and/or convert Tregs to Th17 T cell subset. IL-12 promotes Ifn-γ production in Tregs, leading Treg fragility and a general pro-immunogenic environment. TNF-α both impairs Treg development and reduces the function of existing Tregs. Thus, these cytokines can impair Treg development, reduce Treg function or induce Treg trans-differentiation into immune activating cells.

In the context of cancer, where it is desired to reduce Treg activity, one or more of the Treg inhibitory cytokines can be delivered systemically via Treg-specific IFMs in order to reduce Treg suppression globally. Bi-specific targeting (e.g., CD4:CD25. CD4:NRP1, CD4:CD39) can be used to direct systemically injected IFMs to the Treg cells in vivo. This concept of targeting a specific cell population is described in the Examples. These IFMs then reduce Treg numbers and/or function, and drive them to a pro-inflammatory or immunogenic state.

Additionally, Treg-specific IFMs can be loaded onto antitumor immune cells ex vivo and delivered to the Tregs via trans or paracrine signaling. In this case, the anti-tumor cells create a local anti-suppressive environment by increasing the local concentration of Treg inhibitory cytokines. This can promote local as opposed to global Treg dysfunction.

IL-15 Molecules

In some embodiments, the cytokine molecule is an IL-15 molecule, e.g., a full length, a fragment or a variant of IL-15, e.g., human IL-15. In embodiments, the IL-15 molecule is a wild-type, human IL-15, e.g., having the amino acid sequence of SEQ ID NO: 10. In other embodiments, the IL-15 molecule is a variant of human IL-5, e.g., having one or more amino acid modifications.

In some embodiments, the IL-15 variant comprises, or consists of, a mutation at position 45, 51, 52, or 72, e.g., as described in US 2016/0184399. In some embodiments, the IL-15 variant comprises, or consists of, an N, S or L to one of D, E, A Y or P substitution. In some embodiments, the mutation is chosen from L45D, L45E, S51D, L52D, N72D, N72E, N72A, N72S, N72Y, or N72P (in reference to the sequence of human IL-15, SEQ ID NO: 11). As those of skill will realize, any combination of the positions can be mutated. In some embodiments, the IL-15 variant comprises two or more mutations. In some embodiments, the IL-15 variant comprises three or more mutations. In some embodiments, the IL-15 variant comprises four, five, or six or more mutations.

In some embodiments, the IL-15 molecule comprises a mutation, e.g., an N72D point mutation as shown in SEQ ID NO: 11 herein. In some embodiments, the IL-15 molecule comprises a sequence having at least 80%, 85%, 90%, 95%, 96%, 97%, 98%, or 99% identity to SEQ ID NO: 11, wherein the sequence comprises an N72D mutation relative to wild-type human IL-15, and having IL-15Rα binding activity.

In some embodiments, the IL-15 variant comprises, or consists of, one or more mutations at amino acid position 8, 10, 61, 64, 65, 72, 101, or 108 (in reference to the sequence of human IL-15, SEQ ID NO: 11). In some embodiments the IL-15 variant possesses increased activity as compared with wild-type IL-15. In some embodiments the IL-15 variant possesses decreased activity as compared with wild-type IL-15. In some embodiments the IL-15 variant possesses approximately two-fold, four-fold, ten-fold, 20-fold, 40-fold, 60-fold, 100-fold, or more than 100-fold decreased activity as compared with wild-type IL-15. In some embodiments, the mutation is chosen from D8N. K10Q, D61N, D61H, E64H, N65H, N72A. N72H, Q101N. Q108N, or Q108H (in reference to the sequence of human IL-15, SEQ ID NO: 11). As those of ordinary skill in the art would realize, any combination of the positions can be mutated. In some embodiments, the IL-15 variant comprises two or more mutations. In some embodiments, the IL-15 variant comprises three or more mutations. In some embodiments, the IL-15 variant comprises four, five, or six or more mutations. In some embodiments the IL-15 variant comprises mutations at positions 61 and 64. In some embodiments the mutations at positions 61 and 64 are D61N or D61H and E64Q or E64H. In some embodiments the IL-15 variants comprises mutations at positions 61 and 108. In some embodiments the mutations at positions 61 and 108 are D61N or D61H and Q108N or Q108H.

In embodiments, the cytokine molecule further comprises a receptor domain, e.g., a cytokine receptor domain. In one embodiment, the cytokine molecule comprises an IL-15 receptor, or a fragment thereof (e.g., an IL-15 binding domain of an IL-15 receptor alpha) as described herein. In some embodiments, the cytokine molecule is an IL-15 molecule, e.g., IL-15 or an IL-15 superagonist as described herein. As used herein, a "superagonist" form of a cytokine molecule shows increased activity, e.g., by at least 10%, 20%, 30%, compared to the naturally-occurring cytokine. An exemplary superagonist is an IL-15 SA. In some embodiments, the IL-15 SA comprises a complex of IL-15 and an IL-15 binding fragment of an IL-15 receptor, e.g., IL-15 receptor alpha or an IL-15 binding fragment thereof, e.g., as described herein. In other embodiments, the cytokine molecule further comprises a receptor domain, e.g., an extracellular domain of an IL-15R alpha, optionally, coupled to an immunoglobulin Fc or an antibody molecule. In embodiments, the cytokine molecule is an IL-15 superagonist (IL-15SA) as described in WO 2010/059253. In some embodiments, the cytokine molecule comprises IL-15 and a soluble IL-15 receptor alpha domain fused to an Fc (e.g., a sIL-15Ra-Fc fusion protein), e.g., as described in Rubinstein et al PNAS 103:24 p. 9166-9171 (2006).

The IL-15 molecule can further comprise a polypeptide, e.g., a cytokine receptor, e.g., a cytokine receptor domain, and a second, heterologous domain. In one embodiment, the heterologous domain is an immunoglobulin Fc region. In other embodiments, the heterologous domain is an antibody molecule, e.g., a Fab fragment, a $FAB_2$ fragment, a scFv fragment, or an affibody fragment or derivative, e.g. a sdAb (nanobody) fragment, a heavy chain antibody fragment. In some embodiments, the polypeptide also comprises a third heterologous domain. In some embodiments, the cytokine receptor domain is N-terminal of the second domain, and in other embodiments, the cytokine receptor domain is C-terminal of the second domain.

The wild-type IL-15 Receptor alpha sequence and fragment and variants of this sequence are set out below.

Wild-type IL-15 Receptor alpha sequence (Genbank Acc. No. AA121141.1): SEQ ID NO: 41.

Wild-type IL-15 Receptor alpha extracellular domain (portion of accession number Q13261): SEQ ID NO: 63.

Isoform CRA_d IL-15 Receptor alpha extracellular domain (portion of accession number EAW86418): SEQ ID NO: 64.

The wild-type IL-15 Receptor alpha sequence is provided above as SEQ ID NO: 41. IL-15 receptor alpha contains an extracellular domain, a 23 amino acid transmembrane segment, and a 39 amino acid cytoplasmic tail. The extracellular domain of IL-15 Receptor alpha is provided as SEQ ID NO: 63.

In other embodiments, an IL-15 agonist can be used. For example, an agonist of an IL-15 receptor, e.g., an antibody molecule (e.g., an agonistic antibody) to an IL-15 receptor, that elicits at least one activity of a naturally-occurring cytokine. In embodiments, the IL-15 receptor or fragment thereof is from human or a non-human animal, e.g., mammal, e.g., non-human primate.

IL-15 Receptor Alpha Sushi Domain

The wild-type IL-15 Receptor alpha sequence is provided above as SEQ ID NO: 64. IL-15 receptor alpha contains an extracellular domain, a 23 amino acid transmembrane segment, and a 39 amino acid cytoplasmic tail. The sushi domain has been described in the literature including, e.g., Bergamaschi et al. (2008). JBC VOL. 283, NO. 7, pp. 4189-4199; Wei et al. (2001), Journal of Immunology 167: 277-282; Schluns et al. (2004) PNAS Vol 110 (15) 5616-5621; US 2016/0184399 (the contents of each of which is incorporated by reference herein).

The extracellular domain of IL-15 Receptor alpha is provided as SEQ ID NO: 63. The extracellular domain of IL-15 Receptor alpha comprises a domain referred to as the sushi domain, which binds IL-15. The general sushi domain, also referred to as complement control protein (CCP) modules or short consensus repeats (SCR), is a protein domain found in several proteins, including multiple members of the complement system. The sushi domain adopts a beta-sandwich fold, which is bounded by the first and fourth cysteine of four highly conserved cysteine residues, comprising to a sequence stretch of approximately 60 amino acids (Norman, Barlow, et al. J Mol Biol. 1991 Jun. 20; 219(4):717-25). The amino acid residues bounded by the first and fourth cysteines of the sushi domain in IL-15Ralpha comprise a 62 amino acid polypeptide that we refer to as the minimal domain (SEQ ID NO: 52). Including additional amino acids of IL-15Ralpha at the N- and C-terminus of the minimal sushi domain, such as inclusion of N-terminal Ile and Thr and C-terminal Ile and Arg residues result in a 65 sushi amino acid domain (SEQ ID NO: 9).

A sushi domain as described herein may comprise one or more mutations relative to a wild-type sushi domain. For instance, residue 77 of IL-15Ra is leucine in the wild-type gene (and is underlined in SEQ ID NO: 41), but can be mutated to isoleucine (L77I). Accordingly, a minimal sushi domain comprising L77I (with the numbering referring to the wild-type IL-15Ra of SEQ ID NO: 41) is provided as SEQ ID NO: 65. An extended sushi domain comprising L77I (with the numbering referring to the wild-type IL-15Ra of SEQ ID NO: 41) is provided as SEQ ID NO: 66.

```
Minimal sushi domain, wild-type:
                                          (SEQ ID NO: 52)
CPPPMSVEHADIWVKSYSLYSRERYICNSGFKRKAGTSSLTECVLNKATN

VAHWTTPSLKC

Extended sushi domain, wild-type:
                                          (SEQ ID NO: 9)
ITCPPPMSVEHADIWVKSYSLYSRERYICNSGFKRKAGTSSLTECVLNKA

TNVAHWTTPSLKCIR

Minimal sushi domain, L77I:
                                          (SEQ ID NO: 65)
CPPPMSVEHADIWVKSYSLYSRERYICNSGFKRKAGTSSLTECVINKATN

VAHWTTPSLKCI

Extended sushi domain, L77I:
                                          (SEQ ID NO: 66)
ITCPPPMSVEHADIWVKSYSLYSRERYICNSGFKRKAGTSSLTECVINKA

TNVAHWTTPSLKCIR
```

In some embodiments, a sushi domain consists of 62-171 amino acids of SEQ ID NO: 63 or a sequence having at least 80%, 85%, 90%, 95%, 96%, 97%, 98%, or 99% identity thereto, and having IL-15 binding activity. In some embodiments, a sushi domain consists of 65-171 amino acids of SEQ ID NO: 63 or a sequence having at least 80%, 85%, 90%, 95%, 96%, 97%, 98%, or 99% identity thereto, and having IL-15 binding activity. In some embodiments, a sushi domain consists of up to 171 amino acids of SEQ ID NO: 63 or a sequence having at least 80%, 85%, 90%, 95%, 96%, 97%, 98%, or 99% identity thereto, and having IL-15 binding activity. In some embodiments, a sushi domain consists of 62-171, 62-160, 62-150, 62-140, 62-130, 62-120, 62-110, 62-100, 62-90, 62-80, 62-70, 65-171, 65-160, 65-150, 65-140, 65-130, 65-120, 65-110, 65-100, 65-90, 65-80, or 65-70 amino acids of SEQ ID NO: 63 or a sequence having at least 80%, 85%, 90%, 95%, 96%, 97%, 98%, or 99% identity thereto, and having IL-15 binding activity. In some embodiments, a sushi domain consists of 62-171, 62-160, 62-150, 62-140, 62-130, 62-120, 62-110, 62-100, 62-90, 62-80, 62-70, 65-171, 65-160, 65-150, 65-140, 65-130, 65-120, 65-110, 65-100, 65-90, 65-80, or 65-70 amino acids of SEQ ID NO: 63. In some embodiments, the sushi domain comprises, or consists of, an amino acid sequence of SEQ ID NO: 9 or SEQ ID NO: 52.

In some embodiments, a sushi domain consists of 62-171 amino acids of SEQ ID NO: 63 or a sequence having up to 1, 2, 3, 4, 5, 6, 7, 8, 9, 10, 15, 20, 25, 30, 35, or 40 modifications (e.g., substitutions) relative thereto, and having IL-15 binding activity. In some embodiments, a sushi domain consists of up to 171 amino acids of SEQ ID NO: 5 or a sequence having up to 1, 2, 3, 4, 5, 6, 7, 8, 9, 10, 15, 20, 25, 30, 35, or 40 modifications (e.g., substitutions) relative thereto, and having IL-15 binding activity. In some embodiments, a sushi domain consists of 62-171, 62-160, 62-150, 62-140, 62-130, 62-120, 62-110, 62-100, 62-90, 62-80, 62-70, 65-171, 65-160, 65-150, 65-140, 65-130, 65-120, 65-110, 65-100, 65-90, 65-80, or 65-70 amino acids of SEQ ID NO: 63 or a sequence having up to 1, 2, 3, 4, 5, 6, 7, 8, 9, 10, 15, 20, 25, 30, 35, or 40 modifications (e.g., substitutions) relative thereto, and having IL-15 binding activity.

In some embodiments, a sushi domain comprises at least 62 amino acids of SEQ ID NO: 63 or a sequence having at least 80%, 85%, 90%, 95%, 96%, 97%, 98%, or 99% identity thereto, wherein the sequence comprises an L77I mutation relative to wild-type IL-15Ra, and having IL-15 binding activity. In some embodiments, a sushi domain comprises at least 65 amino acids of SEQ ID NO: 63 or a sequence having at least 80%, 85%, 90%, 95%, 96%, 97%, 98%, or 99% identity thereto, wherein the sequence comprises an L77I mutation relative to wild-type IL-15Ra. and having IL-15 binding activity. In some embodiments, a sushi domain comprises a portion of SEQ ID NO: 63 or a sequence having at least 80%, 85%, 90%, 95%, 96%, 97%, 98%, or 99% identity thereto, wherein the sequence comprises an L77I mutation relative to wild-type IL-15Ra, and having IL-15 binding activity. In some embodiments, the sushi domain comprises an amino acid sequence of SEQ ID NO: 9 or SEQ ID NO: 52.

In some embodiments, a sushi domain comprises at least 62 amino acids of SEQ ID NO: 63 or a sequence having up to 1, 2, 3, 4, 5, 6, 7, 8, 9, 10, 15, 20, 25, 30, 35, or 40 modifications (e.g., substitutions) relative thereto, wherein the sequence comprises an L77I mutation relative to wild-type IL-15Ra, and having IL-15 binding activity. In some embodiments, a sushi domain comprises a portion of SEQ ID NO: 66 or a sequence having up to 1, 2, 3, 4, 5, 6, 7, 8, 9, 10, 15, 20, 25, 30, 35, or 40 modifications (e.g., substitutions) relative thereto, wherein the sequence comprises an L77I mutation relative to wild-type IL-15Ra, and having IL-15 binding activity.

In embodiments, the sushi domain comprises at least 10, 20, 30, 40, 50, 60, 62, 65, 70, 80, 90, 100, 110, 120, 130, 140, 150, or 160 consecutive amino acids of SEQ ID NO: 63, or a sequence having an L77I mutation relative thereto. In embodiments, the sushi domain consists of 10-20, 20-30, 30-40, 40-50, 50-60, 60-70, 70-80, 80-90, 90-100, 100-110, 110-120, 120-130, 130-140, 140-150, 150-160, or 160-170 consecutive amino acids of SEQ ID NO: 63, or a sequence having an L77I mutation relative thereto.

In embodiments, the sushi domain is a sushi domain from human or a non-human animal, e.g., mammal, e.g., non-human primate.

In some embodiments, the polypeptide can have a second, heterologous domain, e.g., an Fc domain or a Fab domain.

In some embodiments, the polypeptide comprising the IL-15 receptor or fragment thereof comprises an Fc domain. In embodiments, the Fc domain is an effector-attenuated Fc domain, e.g., a human IgG2 Fc domain, e.g., a human IgG2 Fc domain of SEQ ID NO: 54 or an amino acid sequence having at least 80%, 85%, 90%, 95%, 96%, 97%, 98%, or 99% identity thereto.

In embodiments, the effector-attenuated Fc domain has reduced effector activity, e.g., compared to a wild-type IgG1 Fc domain, e.g., compared to a wild-type IgG1 Fc domain of SEQ ID NO: 67. In some embodiments, effector activity comprises antibody-dependent cellular toxicity (ADCC). In embodiments, the effector activity is reduced by 10%, 20%, 30%, 40%, 50%, 60%, 70%, 80%, 90%, 95%, or 99% in an ADCC assay, e.g., compared to a wild-type IgG1 Fc domain of SEQ ID NO: 67. In some embodiments, effector activity comprises complement dependent cytotoxicity (CDC). In embodiments, the effector activity is reduced by 10%, 20%, 30%. 40%, 50%, 60%, 70%, 80%, 90%, 95%, or 99% in a CDC assay such as a CDC assay described in Armour et al., "Recombinant human IgG molecules lacking Fc gamma receptor I binding and monocyte triggering activities." Eur J Immunol (1999) 29:2613-24" e.g., compared to a wild-type IgG1 Fc domain of SEQ ID NO: 67.

In some embodiments, the Fc domain comprises an IgG1 Fc domain of SEQ ID NO: 67 or an amino acid sequence having at least 80%, 85%, 90%, 95%, 96%, 97%, 98%, or 99% identity thereto.

In some embodiments, the Fc domain comprises an IgG2 constant region of SEQ ID NO: 68 or fragment thereof, or an amino acid sequence having at least 80%, 85%, 90%, 95%, 96%, 97%, 98%, or 99% identity thereto.

In some embodiments, the Fc domain comprises an IgG2 Da Fc domain of SEQ ID NO: 55 or an amino acid sequence having at least 80%, 85%, 90%, 95%, 96%, 97%, 98%, or 99% identity thereto. In embodiments, the Fc domain comprises one or both of A330S and P331S mutations using Kabat numbering system. In embodiments, the Fc domain is one described in Armour et al. "Recombinant human IgG molecules lacking Fc gamma receptor I binding and monocyte triggering activities." Eur J Immunol (1999) 29:2613-24.

In some embodiments, the Fc domain has dimerization activity.

In some embodiments, the Fc domain is an IgG domain, e.g., an IgG1, IgG2, IgG3, or IgG4 Fc domain. In some embodiments, the Fc domain comprises a CH2 domain and a CH3 domain.

In some embodiments, the nanoparticle comprises a protein having a sequence of SEQ ID NO: 56 (sushi-IgG2 Da-Fc) or an amino acid sequence having at least 80%, 85%, 90%, 95%, 96%, 97%, 98%, or 99% identity thereto.

In some embodiments, the IFM that comprises a sushi domain described herein (e.g., in SEQ ID NO: 9) and an Fc domain described herein, e.g., an IgG2 Fc domain (e.g., SEQ ID NO: 54 or an amino acid sequence having at least 80%, 85%, 90%, 95%, 96%, 97%, 98%, or 99% identity thereto). In some embodiments, the IFM comprises a sushi domain of SEQ ID NO: 9 and an Fc domain described herein, e.g., an IgG1 Fc domain, e.g., an Fc domain of SEQ ID NO: 67 or an amino acid sequence having at least 80%, 85%, 90%, 95%, 96%, 97%, 98%, or 99% identity thereto. In some embodiments, the IFM comprises a sushi domain of SEQ ID NO: 9 and an IgG2 Fc domain, e.g., an Fc domain of SEQ ID NO: 54 or an amino acid sequence having at least 80%, 85%, 90%, 95%, 96%, 97%, 98%, or 99% identity thereto. In some embodiments, the IFM comprises a sushi domain of SEQ ID NO: 9 and an IgG1 Fc domain, e.g., an Fc domain of SEQ ID NO: 67 or an amino acid sequence having at least 80%, 85%, 90%, 95%, 96%. 97%, 98%, or 99% identity thereto.

In some embodiments, the IFM comprises a sushi domain of SEQ ID NO: 9 and an IgG2 Da Fc domain of SEQ ID NO: 56 or an amino acid sequence having at least 80%, 85%, 90%, 95%, 96%, 97%, 98%, or 99% identity thereto. In some embodiments, the IFM comprises a sushi domain of SEQ ID NO: 9 and an IgG2 Da Fc domain of SEQ ID NO: 56 or an amino acid sequence having at least 80%, 85%, 90%, 95%, 96%, 97%, 98%, or 99% identity thereto. In some embodiments, the IFM comprises a sushi-IgG2 Da-Fc protein having a sequence of SEQ ID NO: 56 or an amino acid sequence having at least 80%, 85%, 90%, 95%, 96%, 97%, 98%, or 99% identity thereto.

In embodiments, the IL-15 molecule is a molecule described in PCT International Application Publication No. WO2017/027843, which is herein incorporated by reference in its entirety.

IL-12 Molecules

Interleukin-12 (IL-12) is a heterodimeric cytokine composed of p35 and p40 subunits which are encoded by 2 separate genes, IL-12A and IL-12B, respectively. IL-12 is involved in the differentiation of naive T cells into Th1 cells. It is known as a T cell-stimulating factor, which can stimulate the growth and function of T cells. It stimulates the production of interferon-gamma (IFN-γ) and tumor necrosis factor-alpha (TNF-α) from T cells and natural killer (NK) cells, and reduces IL-4 mediated suppression of IFN-γ. T cells that produce IL-12 have a coreceptor, CD30, which is associated with IL-12 activity.

IL-12 plays an important role in the activities of NK cells and T lymphocytes. IL-12 mediates enhancement of the cytotoxic activity of NK cells and CD8 cytotoxic T lymphocytes. There also seems to be a link between IL-2 and the signal transduction of IL-12 in NK cells. IL-2 stimulates the expression of two IL-12 receptors, IL-12R-β1 and IL-12R-β2, maintaining the expression of a critical protein involved in IL-12 signaling in NK cells. Enhanced functional response is demonstrated by IFN-γ production and killing of target cells.

IL-12 also has anti-angiogenic activity, which means it can block the formation of new blood vessels. It does this by increasing production of interferon gamma, which in turn increases the production of a chemokine called inducible protein-10 (IP-10 or CXCL10). IP-10 then mediates this anti-angiogenic effect. Because of its ability to induce immune responses and its anti-angiogenic activity, there has been an interest in testing IL-12 as a possible anti-cancer drug. There is a link that may be useful in treatment between IL-12 and the diseases psoriasis & inflammatory bowel disease.

IL-12 binds to the IL-12 receptor, which is a heterodimeric receptor formed by IL-12R-β1 and IL-12R-β2. IL-12R-β2 is considered to play a key role in IL-12 function, since it is found on activated T cells and is stimulated by cytokines that promote Th1 cells development and inhibited by those that promote Th2 cells development. Upon binding, IL-12R-β2 becomes tyrosine phosphorylated and provides binding sites for kinases, Tyk2 and Jak2. These are important in activating critical transcription factor proteins such as STAT4 that are implicated in IL-12 signaling in T cells and NK cells.

IL-12 is a potent cytokine with the potential to reshape the anti-inflammatory environment in solid tumors. However, its clinical utility has been limited by severe toxicities both from soluble administration or from adoptively transferred T cells engineered to secrete IL-12. The tethered fusion (TF) disclosed herein enables improved control of cytokine dose and biodistribution. In in vitro model systems, the IL12-TF cytokine provides persistent loading of IL-12 on the surface of T cells and sustained T cell activation and signaling downstream of the IL-12 receptors. In turn, this can activate innate and adaptive immunity.

The IL-12 in the tethered fusion can be in the form of a single chain containing both the IL-12A and IL-12B subunits. In some embodiments, the IL-12 can be present as a non single-chain (i.e., as a heterodimer of IL-12A and IL-12B, which is the natural form of IL-12). For example, the TF can be made by co-expression of three protein subunits (Fab heavy chain, Fab light-chain w/IL-12A (or IL-12B), and IL-12B (or IL-12A).

Immune Cell Targeting Moieties

In certain embodiments, the immunostimulatory fusion molecules disclosed herein include an immune cell targeting moiety. The immune cell targeting moiety can be chosen from an antibody molecule (e.g., an antigen binding domain as described herein), a receptor or a receptor fragment, or a ligand or a ligand fragment, or a combination thereof. In some embodiments, the immune cell targeting moiety associates with, e.g., binds to, an immune cell (e.g., a molecule, e.g., antigen, present on the surface of the immune cell). In certain embodiments, the immune cell targeting moiety targets, e.g., directs the immunostimulatory fusion molecules disclosed herein to an immune (e.g., a lymphocyte, e.g., a T cell).

In some embodiments, the immune cell targeting moiety is chosen from an antibody molecule (e.g., a full antibody (e.g., an antibody that includes at least one, and preferably two, complete heavy chains, and at least one, and preferably two, complete light chains), or an antigen-binding fragment (e.g., a Fab, F(ab')2, Fv, a single chain Fv, a single domain antibody, a diabody (dAb), a bivalent antibody, or bispecific antibody or fragment thereof, a single domain variant thereof, or a camelid antibody)), non-antibody scaffold, or ligand that binds to the CD45 receptor.

In some embodiments, the immune cell targeting moiety targets the IFM to persistent, abundant, and/or recycling cell surface receptors and molecules expressed on the surface of the immune cell. These receptors/molecules include, e.g., CD45 (via, e.g., BC8 (ACCT: HB-10507), 9.4 (ATTC: HB-10508), GAP8.3 (ATTC: HB-12), monoclonal antibodies), CD8 (via OKT8 monoclonal antibody), the transmembrane integrin molecules CD11a (via MHM24 monoclonal antibody) or CD18 (via chimeric1B4 monoclonal antibody). In other preferred embodiments, the targeting moiety is directed to a marker selected from the group consisting of CD4, CD8, CD11a, CD18, CD19, CD20, and CD22. In some embodiments, the immune cell targeting moiety is chosen from an antibody molecule, e.g., an antigen binding domain, non-antibody scaffold, or ligand that binds to CD45, CD4, CD8, CD3, CD11a, CD11b, CD11c, CD25, CD127, CD137, CD19, CD20, CD22, HLA-DR, CD197, CD38, CD27, CD196, CXCR3, CXCR4, CXCR5, CD84, CD229, CCR1, CCR5, CCR4, CCR6, CCR8, or CCR10.

"CD45," also known as leukocyte common antigen, refers to human CD45 protein and species, isoforms, and other sequence variants thereof. Thus, CD45 can be the native, full-length protein or can be a truncated fragment or a sequence variant (e.g., a naturally occurring isoform, or recombinant variant) that retains at least one biological activity of the native protein. CD45 is a receptor-linked protein tyrosine phosphatase that is expressed on leukocytes, and which plays an important role in the function of these cells (reviewed in Altin, J G (1997) Immunol Cell Biol. 75(5):430-45, incorporated herein by reference). For example, the extracellular domain of CD45 is expressed in several different isoforms on T cells, and the particular isoform(s) expressed depends on the particular subpopulation of cell, their state of maturation, and antigen exposure. Expression of CD45 is important for the activation of T cells via the TCR, and that different CD45 isoforms display a different ability to support T cell activation.

"CD4" is a co-receptor for MHC Class II (with TCR, T-cell receptor); found on the surface of immune cells such as T helper cells, monocytes, macrophages, and dendritic cells. CD4 T cells are crucial in achieving a regulated effective immune response to pathogens. Naive CD4 T cells are activated after interaction with antigen-MHC complex and differentiate into specific subtypes depending mainly on the cytokine milieu of the microenvironment. Besides the classical T-helper 1 and T-helper 2, other subsets have been identified, including T-helper 17, regulatory T cell (Treg), follicular helper T cell, and T-helper 9, each with a characteristic cytokine profile. CD4 T cells carry out multiple functions, ranging from activation of the cells of the innate immune system, B-lymphocytes, cytotoxic T cells, as well as nonimmune cells, and also play critical role in the suppression of immune reaction. See e.g., Rishi Vishal et al. "CD4+ T Cells: Differentiation and Functions," Clinical and Developmental Immunology, vol. 2012, Article ID 925135, 12 pages, 2012. doi:10.1155/2012/925135.

"CD8" is a transmembrane glycoprotein that serves as a co-receptor for the T cell receptor (TCR). Like the TCR, CD8 binds to a major histocompatibility complex (MHC) molecule, but is specific for the class I MHC protein. There are two isoforms of the protein, alpha and beta, each encoded by a different gene. In humans, both genes are located on chromosome 2 in position 2p12. The CD8 co-receptor is predominantly expressed on the surface of cytotoxic T cells, but can also be found on natural killer cells, cortical thymocytes, and dendritic cells. It is expressed in T cell lymphoblastic lymphoma and hypo-pigmented mycosis fungoides. To function, CD8 forms a dimer, consisting of a pair of CD8 chains. The most common form of CD8 is composed of a CD8-α and CD8-β chain, both members of the immunoglobulin superfamily with an immunoglobulin variable (IgV)-like extracellular domain connected to the membrane by a thin stalk, and an intracellular tail. Less-common homodimers of the CD8-α chain are also expressed on some cells. The extracellular IgV-like domain of CD8-α interacts with the α3 portion of the Class I MHC molecule. This affinity keeps the T cell receptor of the cytotoxic T cell and the target cell bound closely together during antigen-specific activation. Cytotoxic T cells with CD8 surface protein are called CD8 T cells. See e.g., Leahy D J et al. (March 1992). "Crystal structure of a soluble form of the human T cell coreceptor CD8 at 2.6 A resolution". Cell. 68 (6): 1145-62; Gao G et al. (2000). "Molecular interactions of coreceptor CD8 and MHC class I: the molecular basis for functional coordination with the T-cell receptor". Immunol Today. 21 (12): 630-6; and Devine L et al. (1999). "Orientation of the Ig domains of CD8 alpha beta relative to MHC class I". J Immunol. 162 (2): 846-51.

"CD11a" also known as "Integrin Alpha L (ITGAL)" and "the alpha subunit of LFA-1" is a membrane glycoprotein that provides cell-cell adhesion by interaction with ICAM-1. The gene ITGAL encodes the integrin alpha L chain. Integrins are heterodimeric integral membrane proteins composed of an alpha chain and a beta chain. This I-domain containing alpha integrin combines with the beta 2 chain (ITGB2) to form the integrin lymphocyte function-associated antigen-1 (LFA-1), which is expressed on all leukocytes. LFA-1 plays an important role in leukocyte intercellular adhesion through interactions with its ligands, ICAMs 1-3 (intercellular adhesion molecules 1 through 3), and also functions in lymphocyte costimulatory signaling. Two transcript variants encoding different isoforms have been found for this gene. See e.g, Cornwell R D et al. Description of the leukocyte function-associated antigen 1 (LFA-1 or CD11a) promoter. Proceedings of the National Academy of Sciences of the United States of America. 1993; 90(9):4221-4225; and Bose T O et al. CD11a Regulates Effector CD8 T Cell Differentiation and Central Memory Development in Response to Infection with *Listeria monocytogenes*. Flynn J L, ed. Infection and Immunity. 2013; 81(4):1140-1151. doi:10.1128/IAI.00749-12.

"CD18" also known as Integrin Beta 2 chain (ITGB2) is the beta subunit of four different structures: LFA-1 (paired with CD11a); Macrophage-1 antigen (paired with CD11b);

Integrin alphaXbeta2 (paired with CD11c); and Integrin alphaDbeta2 (paired with CD11d). n humans lack of CD18 causes Leukocyte Adhesion Deficiency, a disease defined by a lack of leukocyte extravasation from blood into tissues. The beta 2 integrins have also been found in a soluble form. The soluble beta 2 integrins are ligand binding and plasma levels are inversely associated with disease activity in the autoimmune disease spondyloarthritis. See e.g., Mazzone Al et al. Leukocyte CD11/CD18 integrins: biological and clinical relevance. Haematologica. 1995 March-April; 80(2): 161-75; and Gjelstrup et al (8 Sep. 2010). "Shedding of Large Functionally Active CD11/CD18 Integrin Complexes from Leukocyte Membranes during Synovial Inflammation Distinguishes Three Types of Arthritis through Differential Epitope Exposure". The Journal of Immunology. 185 (7): 4154-4168.

"CD20" is a type III transmembrane protein found on B cells that forms a calcium channel in the cell membrane allowing for the influx of calcium required for cell activation; expressed in B-cell lymphomas, hairy cell leukemia, and B-cell chronic lymphocytic leukemia. Important for therapy of those diseases, as antibodies against CD20 exist: e.g. Rituximab and Ofatumumab, with several more in development. Similarly, anti-CD20 monoclonal antibody Ocrelizumab is in trials for multiple sclerosis. See e.g., Cragg M S et al (2005). "The biology of CD20 and its potential as a target for mAb therapy". Current Directions in Autoimmunity. Current Directions in Autoimmunity. 8: 140-74; and Kuijpers T W et al (January 2010). "CD20 deficiency in humans results in impaired T cell-independent antibody responses". The Journal of Clinical Investigation. 120 (1): 214-22.

Moieties Targeting Checkpoint Inhibitors

In some embodiments, the immunostimulatory moiety or the targeting moiety (e.g., an antibody molecule) binds an inhibitor of an immunosuppressor, e.g., an inhibitor of a checkpoint inhibitor, such as PD-1, PD-L1, LAG-3, TIM-3, CTLA-4, inhibitory KIR, CD276, VTCN1, BTLA/HVEM, HAVCR2 and ADORA2A, e.g., as described in US 2016/0184399 incorporated herein by reference. In embodiments, the checkpoint inhibitor is present on an immune effector cell, e.g., a T cell or NK cell.

In some embodiments, the immunostimulatory or the targeting moiety binds PD-1. For instance, Pidilizumab and other anti-PD-1 antibodies are disclosed in Rosenblatt, J. et al. (2011) J Immunotherapy 34(5): 409-18, U.S. Pat. Nos. 7,695,715, 7,332,582, and 8,686,119, incorporated by reference in their entireties. MEDI0680 and other anti-PD-1 antibodies are disclosed in U.S. Pat. No. 9,205,148 and WO 2012/145493, incorporated by reference in their entireties. Further anti-PD-1 antibodies include those described, e.g., in WO 2010/027827 WO 2011/066342, WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entireties.

In some embodiments, the immunostimulatory or the targeting moiety binds PD-L1. For instance, Atezolizumab and other anti-PD-L1 antibodies are disclosed in U.S. Pat. No. 8,217,149, incorporated by reference in its entirety. Avelumab and other anti-PD-L1 antibodies are disclosed in WO 2013/079174, incorporated by reference in its entirety. Durvalumab and other anti-PD-L1 antibodies are disclosed in U.S. Pat. No. 8,779,108, incorporated by reference in its entirety. BMS-936559 and other anti-PD-L1 antibodies are disclosed in U.S. Pat. No. 7,943,743 and WO 2015/081158, incorporated by reference in their entireties. Further anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entireties.

In some embodiments, the immunostimulatory or the targeting moiety binds LAG-3. LAG-3 antibodies have been reported in the art, e.g., BMS-986016 (Bristol-Myers Squibb), TSR-033 (Tesaro), MK-4280 (Merck & Co), or REGN3767 (Regeneron). IMP731 and other anti-LAG-3 antibodies are disclosed in WO 2008/132601 and U.S. Pat. No. 9,244,059, incorporated by reference in their entireties. Further anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entireties.

In some embodiments, the immunostimulatory or the targeting moiety binds TIM-3. In some embodiments, the TIM-3 targeting moiety is chosen from TSR-022 (Tesaro), or LY3321367 (Eli Lilly). APE5137, APE5121, and other anti-TIM-3 antibodies are disclosed in WO 2016/161270, incorporated by reference in its entireties. Further anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entireties.

In some embodiments, the immunostimulatory or the targeting moiety binds CTLA-4. The antibody Ipilimumab and other anti-CTLA-4 antibodies are disclosed in U.S. Pat. No. 6,984,720, herein incorporated by reference. The antibody Tremelimumab and other anti-CTLA-4 antibodies are disclosed in U.S. Pat. No. 7,411,057, herein incorporated by reference.

Antibody Molecules

The immunostimulatory fusion molecules described herein may comprise one or more antibody molecule. For example, the immune cell engager may comprise an antibody molecule. In one embodiment, the antibody molecule binds to a cancer antigen, e.g., a tumor antigen or a stromal antigen. In some embodiments, the cancer antigen is, e.g., a mammalian, e.g., a human, cancer antigen. In other embodiments, the antibody molecule binds to an immune cell antigen, e.g., a mammalian, e.g., a human, immune cell antigen. For example, the antibody molecule binds specifically to an epitope, e.g., linear or conformational epitope, on the cancer antigen or the immune cell antigen.

In an embodiment, an antibody molecule is a monospecific antibody molecule and binds a single epitope. E.g., a monospecific antibody molecule having a plurality of immunoglobulin variable domain sequences, each of which binds the same epitope.

In another embodiment, an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or a tetraspecific antibody molecule.

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv or a Fab, or fragment thereof, have binding specificity for a first epitope and a scFv or a Fab, or fragment thereof, have binding specificity for a second epitope.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and mono or bispecific), triabodies (trivalent and mono or multispecific), and chimeric or humanized antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. A preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

Antibody molecules include intact molecules as well as functional fragments thereof. Constant regions of the antibody molecules can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the disclosure, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the disclosure.

Antibody molecules can include non-antibody scaffolds and antibody mimetics. Exemplary non-antibody scaffolds include: lipocalins (e.g. anticalins), affibodies, fibronectin (e.g. monobodies or Adnectins), knottins, ankyrin repeats (e.g. DARPins), and A domains (e.g. avimers).

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia, the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3).

Each VH and VL typically includes three CDRs and four FRs, arranged from amino-terminus to carboxy-terminus in the following order: FR1, CDR1, FR2, CDR2, FR3, CDR3, FR4.

The antibody molecule can be a polyclonal or a monoclonal antibody.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

The antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay el al. (1992) *Hum Antibod Hybridomas* 3:81-85; Huse el al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. el al. 1994 *Proc. Natl. Acad. Sci. USA* 81:6851-6855; Bruggeman el al. 1993 *Year Immunol* 7:33-40; Tuaillon et al. 1993 *PNAS* 90:3720-3724; Bruggeman et al. 1991 *Eur J Immunol* 21:1323-1326).

An antibody molecule can be one in which the variable region, or a portion thereof, e.g., the CDRs, are generated in a non-human organism, e.g., a rat or mouse. Chimeric, CDR-grafted, and humanized antibodies are within the disclosure. Antibody molecules generated in a non-human organism, e.g., a rat or mouse, and then modified, e.g., in the variable framework or constant region, to decrease antigenicity in a human are within the disclosure. For example, anti-human CD45 antibodies such as 9.4, 4B2 and BC8 can be humanized using techniques known in the art, for making the tethered fusions disclosed herein.

An "effectively human" protein is a protein that does substantially not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Inmunol. Immunother.*, 32:180-190 (1990)) and also because of potential allergic reactions (see, e.g., LoBuglio et al., *Hybridoma*, 5:5117-5123 (1986)).

Chimeric antibodies (e.g. antibodies containing mouse variable domains and human constant domains) can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu el al., 1987, *J. Immunol.* 139:3521-3526; Sun el al. (1987) *PNAS* 84:214-218; Nishimura el al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding to the antigen. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody molecule can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibody molecules can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239: 1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present disclosure (UK Patent Application GB 2188638A, filed on Mar. 26, 1987; Winter U.S. Pat. No. 5,225,539), the contents of which is expressly incorporated by reference.

Also within the scope of the disclosure are humanized antibody molecules in which specific amino acids have been substituted, deleted or added. Criteria for selecting amino acids from the donor are described in U.S. Pat. No. 5,585, 089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFv) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., a cytokine molecule as described herein or other chemical or proteinaceous groups). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the disclosure are intended to include derivatized and otherwise modified forms of the antibodies described herein, including immunoadhesion molecules. For example, an antibody molecule can be functionally linked (e.g., by chemical coupling, genetic fusion, noncovalent association or otherwise) to one or more other molecular entities, such as a cytokine molecule, another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking an antibody molecule to one or more proteins, e.g., a cytokine molecule, another antibody molecule (of the same type or of different types, e.g., to create bispecific antibodies). Suitable crosslinkers include those that are heterobifunctional, having two distinctly reactive groups separated by an appropriate spacer (e.g., m-malcimidobenzoyl-N-hydroxysuccinimide ester) or homobifunctional (e.g., disuccinimidyl suberate). Such linkers are available from Pierce Chemical Company, Rockford, Ill.

Exemplary Immunostimulatory Fusion Molecules and Linkers

In certain embodiments, the IFM can be represented with the following formula in an N to C terminal orientation: R1-(optionally L1)-R2 or R2-(optionally L1)-R1; wherein R1 comprises an immune cell targeting moiety, L1 comprises a linker (e.g., a peptide linker described herein), and R2 comprises an immune stimulating moiety, e.g., a cytokine molecule.

In some embodiments, the immune stimulating moiety, e.g., the cytokine molecule, is connected to, e.g., covalently linked to, the immune cell targeting moiety.

In some embodiments, the immune stimulating moiety, e.g., the cytokine molecule, is functionally linked, e.g., covalently linked (e.g., by chemical coupling, fusion, non-covalent association or otherwise) to the immune cell targeting moiety. For example, the immune stimulating moiety can be covalently coupled indirectly, e.g., via a linker to the immune cell targeting moiety.

In embodiments, the linker is chosen from: a cleavable linker, a non-cleavable linker, a peptide linker, a flexible linker, a rigid linker, a helical linker, or a non-helical linker. In some embodiments, the linker is a peptide linker. The peptide linker can be 5-20, 8-18, 10-15, or about 8, 9, 10, 11, 12, 13, 14, or 15 amino acids long. In some embodiments, the peptide linker comprises Gly and Ser, e.g., a linker comprising the amino acid sequence (Gly$_4$-Ser)n, wherein n indicates the number of repeats of the motif, e.g., n=1, 2, 3, 4 or 5 (e.g., a (Gly$_4$Ser)$_2$ or a (Gly$_4$Ser)$_3$ linker). In some embodiments, the linker comprises the amino acid sequence of SEQ ID NO: 36, 37, 38, or 39, or an amino acid sequence substantially identical thereto (e.g., having 1, 2, 3, 4, or 5 amino acid substitutions). In one embodiment, the linker comprises an amino acid sequence GGGSGGGS (SEQ ID NO: 37). In another embodiment, the linker comprises amino acids from an IgG4 hinge region, e.g., amino acids DKTHTSPPSPAP (SEQ ID NO: 38).

In other embodiments, the linker is a non-peptide, chemical linker. For example, the immune stimulating moiety is covalently coupled to the immune cell targeting moiety by crosslinking. Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate).

In some embodiments, the linker can be a biodegradable or cleavable linker. A cleavable linker allows for cleavage of the IFM such that the immune stimulating moiety, e.g., the cytokine molecule, can be released from the immune targeting moiety. The cleavage of the linker may be caused by biological activation within the relevant tissue or, alternatively, by external stimuli such as, e.g., electromagnetic radiation e.g., UV-radiation.

In one embodiment, the cleavable linker is configured for cleavage exterior to a cell, e.g., to be cleaved in conditions associated with cell or tissue damage or disease. Such conditions include, for example, acidosis; the presence of intracellular enzymes (that are normally confined within cells), including necrotic conditions (e.g., cleaved by calpains or other proteases that spill out of necrotic cells); hypoxic conditions such as a reducing environment; thrombosis (e.g., a linker may be cleavable by thrombin or by another enzyme associated with the blood clotting cascade); immune system activation (e.g., a linker may be cleavable by action of an activated complement protein); or other condition associated with disease or injury.

In one embodiment, a cleavable linker may include an S—S linkage (disulfide bond), or may include a transition metal complex that falls apart when the metal is reduced. One embodiment of the S—S linker may have the following structure (as disclosed in U.S. Pat. No. 9,603,944, incorporated herein by reference in its entirety:

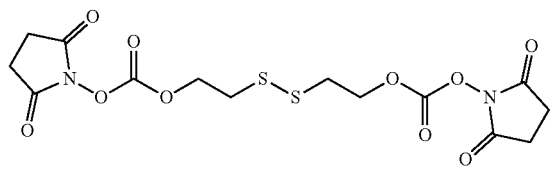 [SMILES: O=C(OCCSSCCOC(=O)ON1C(=O)CCC1=O)ON1C(=O)CCC1=O]

Another example pH sensitive linkers which are cleaved upon a change in pH, e.g., at low pH, which will facilitate hydrolysis of acid (or base) labile moieties, e.g. acid labile ester groups etc. Such conditions may be found in the extracellular environment, such as acidic conditions which may be found near cancerous cells and tissues or a reducing environment, as may be found near hypoxic or ischemic cells and tissues; by proteases or other enzymes found on the surface of cells or released near cells having a condition to be treated, such as diseased, apoptotic or necrotic cells and tissues; or by other conditions or factors. An acid-labile linker may be, for example, a cis-aconitic acid linker. Other examples of pH-sensitive linkages include acetals, ketals, activated amides such as amides of 2,3 dimethylmaleamic acid, vinyl ether, other activated ethers and esters such as enol or silyl ethers or esters, imines, iminiums, orthoesters, enamines, carbamates, hydrazones, and other linkages known in the art (see, e.g., PCT Publication No. WO 2012/155920 and Franco et al. AIMS Materials Science, 3(1): 289-323, incorporated herein by reference). The linkers disclosed in U.S. Provisional Application Nos. 62/554,067 filed Sep. 5, 2017 and 62/616,221 filed Jan. 11, 2018 can also used and are incorporated herein by reference. The expression "pH sensitive" refers to the fact that the cleavable linker in question is substantially cleaved at an acidic pH (e.g., a pH below 6.0, such as in the range of 4.0-6.0).

In still another embodiment, the cleavable linker is configured for cleavage by an enzyme, such as a protease (e.g., pepsin, trypsin, thermolysine, matrix metalloproteinase (MMP), a disintegrin and metalloprotease (ADAM; e.g. ADAM-10 or ADAM-17)), a glycosidase (e.g., α-, β-, γ-amylase, α-, β-glucosidase or lactase) or an esterase (e.g. acetyl cholinesterase, pseudo cholinesterase or acetyl esterase). Other enzymes which may cleave the cleavable linker include urokinase plasminogen activator (uPA), tissue plasminogen activator (tPA), granzyme A, granzyme B, lysosomal enzymes, cathepsins, prostate-specific antigen, Herpes simplex virus protease, cytomegalovirus protease, thrombin, caspase, and interleukin 1 beta converting enzyme.

Still another example is over-expression of an enzyme, e.g., proteases (e.g., pepsin, trypsin), in the tissue of interest, whereby a specifically designed peptide linker will be cleaved in upon arrival at the tissue of interest. Illustrative examples of suitable linkers in this respect are Gly-Phe-Ser-Gly (SEQ ID NO: 105), Gly-Lys-Val-Ser (SEQ ID NO: 106), Gly-Trp-Ile-Gly (SEQ ID NO: 107), Gly-Lys-Lys-Trp (SEQ ID NO: 108), Gly-Ala-Tyr-Met (SEQ ID NO: 109).

In still another example, over-expression of an enzyme, e.g. of glycosidases (e.g. α-amylase), in the tissue of interest, causes a specifically designed carbohydrate linker to be cleaved upon arrival at the tissue of interest. Illustrative examples of suitable linkers in this respect are -(α-1-4-D-Glucose)n- where n≥4.

In still another example, the cleavable linker is configured for cleavage by electromagnetic radiation, e.g., UV-radiation. UV-exposure of the tissue of interest resulting in cleavage of the linker B can facilitate drug release or facilitate nanoparticles uptake in the desired tissue.

The cleavable linker may include a total of from 2 to 60 atoms, such as from 2 to 20 atoms. The cleavable linker may include amino acid residues, and may be a peptide linkage, e.g., of from 1 to 30, or 2 to 10, amino acid residues. In one variant, the cleavable linker B consists of from 1 to 30, such as from 2 to 10, or from 2 to 8, or from 3 to 9, or from 4-10, amino acids. For pH sensitive linkers, the number of atoms is typically from 2 to 50, such as from 2-30.

In some embodiments of the invention, the linker includes an aminocaproic acid (also termed aminohexanoic acid) linkage or a linkage composed of from 1 to 30, or from 2 to 10 carbohydrate residues.

In one embodiment, the linker includes a peptide that can serve as a substrate of a matrix metalloproteinase. As the matrix metalloproteinase, for example, MMP-1 (interstitial collagenase), MMP-2 (gelatinase A), MMP-3, MMP-7, MMP-9 (gelatinase B), and the like are known, and a substrate peptide that can serve as a substrate of one or more kinds of matrix metalloproteinases among those mentioned above can be used. For matrix metalloproteinases, see for example, "Molecular mechanism of cancer metastasis", Ed. by Tsuruo T., pp. 92-107, Medical View Co., Ltd., published in 1993. As for the substrate peptide that can serve as a substrate of a matrix metalloproteinase, for example, the matrix metalloproteinases of particular types and substrate peptides specifically recognized thereby are explained in Nature Biotechnology, 19, pp. 661-667, 2001. Therefore, by referring to this publication, a substrate peptide specifically cleaved by a particular type of matrix metalloproteinase can be chosen. For example, Val-Pro-Leu-Ser-Leu-Tyr-Ser-Gly (SEQ ID NO: 110) is known as a specific substrate for MMP-9, and it is preferable to use the aforementioned octapeptide as a substrate peptide that can serve as a substrate of MMP-9. Illustrative examples of the substrate peptide that can serve as a substrate of a matrix metalloproteinase include Gly-Pro-Gln-Gly-Ile-Ala-Gly-Gln (SEQ ID NO: 111), Val-Pro-Met-Ser-Met-Arg-Gly-Gly (SEQ ID NO: 112), Ile-Pro-Val-Ser-Leu-Arg-Ser-Gly (SEQ ID NO: 113), Arg-Pro-Phe-Ser-Met-Ile-Met-Gly (SEQ ID NO: 114), Val-Pro-Leu-Ser-Leu-Thr-Met-Gly (SEQ ID NO: 115), Ile-Pro-Glu-Ser-Leu-Arg-Ala-Gly (SEQ ID NO: 116), Arg-His-Asp, Arg-Pro-Lys-Pro-Val-Glu-Nva-Trp-Arg-Lys (SEQ ID NO: 117). Arg-Pro-Lys-Pro-Tyr-Ala-Nva-Trp-Met-Lys (SEQ ID NO: 118), Pro-Gln-Gly-Ile-Ala-Gly-Gln-Arg (SEQ ID NO: 119), Pro-Leu-Gly-Ile-Ala-Gly-Arg (SEQ ID NO: 120), Gly-Pro-Leu-Gly-Pro (SEQ ID NO: 121), Gly-Pro-Ile-Gly-Pro (SEQ ID NO: 122), and the like.

In another embodiment, the linker includes a peptide that can serve as a substrate of a disintegrate and metalloprotease (ADAM), an MMP, or a granzyme. For example, without limitation the linker could comprise a peptide substrate of ADAM-8, ADAM-10, ADAM-12, ADAM-17, MMP-1, MMP-2, MMP-3, MMP-7, MMP-9, MMP-13, granzyme A, or granzyme B. Substrates of ADAMs, MMPs, and granzymes have been well-described (e.g. in Miller, M A, et al. Integrative Biology (2011) 3:422-438, Van Damme et al. Biol Chem (2010) 391:983-997, and Casciola-Rosen, L, et al. J Biol Chem (2007) 282:4545-4552) and one skilled in the art would readily be able to incorporate such peptides, or variants thereof, into a linker of interest.

The linker may, besides the substrate peptide, contain connectors, involved in the bond or bonds with the therapeutic protein. Such connectors may each consist of one amino acid residue or of an oligopeptide containing from 2 to 10, such as from 3 to 9, or from 4 to 8, or from 2 to 8, amino acid residues. The amino acid residue or oligopeptide as the connectors may, if present, bind to both ends of the substrate peptide, or may bind only to one end of the substrate peptide so as to represent one of the structures. Types of one amino acid usable as the connector(s), and amino acid residues constituting an oligopeptide usable as the connector(s) are not particularly limited, and one amino acid residue of an arbitrary type, or an arbitrary oligopeptide containing, e.g., from 2 to 8 of the same or different amino acid residues of arbitrary types can be used. Examples of the oligopeptide usable as the connector(s) include, for example, connectors that are rich in Gly amino acids. Other organic moieties can also be used as connectors.

In yet other embodiments, the immune stimulating moiety is directly covalently coupled to the immune cell targeting moiety, without a linker.

In yet other embodiments, the immune stimulating moiety and the immune cell targeting moiety of the IFM are not covalently linked, e.g., are non-covalently associated.

Exemplary formats for fusion of a cytokine molecule to an antibody molecule, e.g., an immunoglobulin moiety (Ig), for example an antibody (IgG) or antibody fragment (Fab, scFv and the like) can include a fusion to the amino-terminus (N-terminus) or carboxy-terminus (C-terminus) of the antibody molecule, typically, the C-terminus of the antibody molecule. In one embodiment, a cytokine-Ig moiety fusion molecule comprising a cytokine polypeptide, cytokine-receptor complex, or a cytokine-receptor Fc complex joined to an Ig polypeptide, a suitable junction between the cytokine polypeptide chain and an Ig polypeptide chain includes a direct polypeptide bond, a junction having a polypeptide linker between the two chains; and, a chemical linkage between the chains. A typical junction is a flexible linker composed of small Gly4Ser linker $(GGGGS)_N$, where $N$ indicates the number of repeats of the motif. $(GGGGS)_2$ and $(GGGGS)_3$ are preferred embodiments of linkers for use in the fusion constructs of the disclosure.

Exemplary immunostimulatory fusion molecules described herein can comprise the amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO: 70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO:87, SEQ ID NO:88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO:97, SEQ ID NO:98, SEQ ID NO: 99, SEQ ID NO: 100, SEQ ID NO: 101, SEQ ID NO: 102, SEQ ID NO: 103, SEQ ID NO: 104, or an amino acid sequence substantially identical thereto (e.g., an amino acid sequence at least 85%, 90%, 95%, 96%, 97%, 98%, 99% or higher identity to any of the aforesaid amino acid sequences).

Described herein are exemplary immunostimulatory fusion molecules (or portion thereof) of the present disclosure. It should be noted that in certain scFv the arrangement is VH-linker-VL. However, the VL-linker-VH arrangement can also be used without affecting functionality. In addition, while specific linkers (Linker-1, Linker-2, etc.) were used in various constructs, other linkers disclosed herein can also be used interchangeably.

SEQ ID NO: 1
Name: LC-chBC8-sushi

Light-chain of chimeric BC8 anti-CD45 antibody; contains variable domain from parental BC8 mouse monoclonal antibody and human constant kappa domain; contains wild-type IL-15Rα-sushi domain genetically fused to antibody light-chain C-terminus using a flexible linker.

DIVLTQSPASLAVSLGQRATISCRASKSVSTSGYSYLHWYQQKPGQPPKL

LIYLASNLESGVPARFSGSGSGTDFTLNIHPVEEEDAATYYCQHSRELPF

TFGSGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC*GGGGSGGGGSGGGGS*ITCPPPMSVEHADIWVK

SYSLYSRERYICNSGFKRKAGTSSLTECVLNKATNVAHWTTPSLKCIR

From N-to C-terminus, a light chain portion of a chimeric BC8 Fab is shown fused via a peptide linker to an IL-15-binding sushi domain. The sequence of the light chain is shown in normal font; the location of the peptide linker is shown by italics and single underline; and the sushi domain is shown by the double underline. The kappa constant region is shown as SEQ ID NO: 74.

In some embodiments, the chimeric BC8 antibody comprises the light chain variable amino acid sequence (optionally, further including a kappa light chain sequence) shown in SEQ ID NO:1, or an amino acid sequence substantially identical thereto (e.g., an amino acid sequence at least 95% or higher identical to SEQ ID NO:1). In embodiments, the chimeric BC8 antibody comprises one, two, or all three CDR1, CDR2 or CDR3 of the light chain variable region of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 1.

In embodiments, the IFMs described herein can comprise the amino acid sequence selected from SEQ ID NO: 1, or an amino acid sequence substantially identical thereto (e.g., an amino acid sequence at least 85%, 90%, 95%, 96%, 97%, 98%, 99% or higher identity to SEQ ID NO: 1, or having at least 1, 2, 3, 4, 5, 6, 7, 8, 9, or 10 or more amino acid alterations (e.g., substitutions, deletions, or insertions, e.g., conservative substitutions) relative to SEQ ID NO: 1. In embodiments, the IFM comprises no more than five, ten or fifteen alterations (e.g., substitutions, deletions, or insertions, e.g., conservative substitutions) relative to SEQ ID NO: 1.

SEQ ID NO: 2
Name: sushi-LC-chBC8

Light-chain of chimeric BC8 anti-CD45 antibody; contains variable domain from parental BC8 mouse monoclonal antibody and human constant kappa domain; contains wild-type IL-15Rα-sushi domain genetically fused to antibody light-chain N-terminus using a flexible linker.

ITCPPPMSVEHADIWVKSYSLYSRERYICNSGFKRKAGTSSLTECVLNKA

TNVAHWTTPSLKCIR*GGGGSGGGGSGGGGS*DIVLTQSPASLAVSLGQRAT

ISCRASKSVSTSGYSYLHWYQQKPGQPPKLLIYLASNLESGVPARFSGSG

SGTDFTLNIHPVEEEDAATYYCQHSRELPFTFGSGTKLEIKRTVAAPSVF

IFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC

From N- to C-terminus, an IL-15-binding wild type sushi domain is fused via a peptide linker to a light chain portion of a chimeric BC8 Fab is shown. The sequence of the light chain is shown in normal font; the location of the peptide linker is shown by italics and single underline; and the sushi domain is shown by the double underline. The kappa constant region is shown as SEQ ID NO: 74.

In some embodiments, the chimeric BC8 antibody comprises the light chain variable amino acid sequence (optionally, further including a kappa light chain sequence) shown in SEQ ID NO:2, or an amino acid sequence substantially identical thereof (e.g., an amino acid sequence at least 85%, 90%, 95% or higher identical to SEQ ID NO:2). In embodiments, the BC8 antibody comprises one, two, or all three CDR1, CDR2 or CDR3 of the light chain variable region of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 2.

In embodiments, the IFMs described herein can comprise the amino acid sequence selected from SEQ ID NO: 2, or an amino acid sequence substantially identical thereto (e.g., an amino acid sequence at least 85%, 90%, 95%, 96%, 97%, 98%, 99% or higher identity to SEQ ID NO: 2, or having at least 1, 2, 3, 4, 5, 6, 7, 8, 9, or 10 or more amino acid alterations (e.g., substitutions, deletions, or insertions, e.g., conservative substitutions) relative to SEQ ID NO: 2. In embodiments, the IFM comprises no more than five, ten or fifteen alterations (e.g., substitutions, deletions, or insertions, e.g., conservative substitutions) relative to SEQ ID NO: 2.

SEQ ID NO: 3
Name: LC-chBC8-IL15 (Also Referred to as LC-chBC8-L1-IL15)

Light-chain of chimeric BC8 anti-CD45 antibody; contains variable domain from parental mouse monoclonal antibody and human constant kappa domain; contains wild-type IL-15 genetically fused to antibody light-chain C-terminus using a flexible linker.

DIVLTQSPASLAVSLGQRATISCRASKSVSTSGYSYLHWYQQKPGQPPKL

LIYLASNLESGVPARFSGSGSGTDFTLNIHPVEEEDAATYYCQHSRELPF

TFGSGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC*GGGGSGGGGSGGGGS*NWVNVISDLKKIEDLIQ

SMHIDATLYTESDVHPSCKVTAMKCFLLELQVISLESGDASIHDTVENLI

ILANNSLSSNGNVTESGCKECEELEEKNIKEFLQSFVHIVQMFINTS

From N- to C-terminus, a light chain portion of a chimeric BC8 Fab is shown fused via a peptide linker to an IL-15 cytokine. The sequence of the light chain is shown in normal font; the location of the peptide linker is shown by italics and single underline; and the cytokine molecule is shown by the double underline. The kappa constant region is shown as SEQ ID NO: 74.

In some embodiments, the chimeric BC8 antibody comprises the light chain variable amino acid sequence (optionally, further including a kappa light chain sequence) shown in SEQ ID NO:3, or an amino acid sequence substantially identical thereof (e.g., an amino acid sequence at least 85%, 90%, 95% or higher identical to SEQ ID NO:3). In embodiments, the BC8 antibody comprises one, two, or all three CDR1, CDR2 or CDR3 of the light chain variable domain of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 3.

In embodiments, the IFMs described herein can comprise the amino acid sequence selected from SEQ ID NO: 3, or an amino acid sequence substantially identical thereto (e.g., an amino acid sequence at least 85%, 90%, 95%, 96%, 97%, 98%, 99% or higher identity to SEQ ID NO: 3, or having at least 1, 2, 3, 4, 5, 6, 7, 8, 9, or 10 or more amino acid alterations (e.g., substitutions, deletions, or insertions, e.g., conservative substitutions) relative to SEQ ID NO: 3. In embodiments, the IFM comprises no more than five, ten or fifteen alterations (e.g., substitutions, deletions, or insertions, e.g., conservative substitutions) relative to SEQ ID NO: 3.

SEQ ID NO: 4
Name: IL15-LC-chBC8
Light-chain of chimeric BC8 anti-CD45 antibody; contains variable domain from parental mouse monoclonal antibody and human constant kappa domain; contains wild-type IL-15 genetically fused to antibody light-chain N-terminus using a flexible linker.

NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS*GGGGSGGGGSGGGGS*DIVLTQSPASLAVSLGQRATI

SCRASKSVSTSGYSYLHWYQQKPGQPPKLLIYLASNLESGVPARFSGSGS

GTDFTLNIHPVEEEDAATYYCQHSRELPFTFGSGTKLEIKRTVAAPSVFI

FPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC

From N- to C-terminus, an IL-15 cytokine fused via a peptide linker to a light chain portion of a chimeric BC8 Fab is shown. The sequence of the light chain is shown in normal font; the location of the peptide linker is shown by italics and underline; and the cytokine molecule is shown by the double underline. The kappa constant region is shown as SEQ ID NO: 74.

In some embodiments, the chimeric BC8 antibody comprises the light chain variable amino acid sequence (optionally, further including a kappa light chain sequence) shown in SEQ ID NO:4, or an amino acid sequence substantially identical thereto (e.g., an amino acid sequence at least 95% or higher identical to SEQ ID NO:4). In embodiments, the BC8 antibody comprises one, two, or all three CDR1, CDR2 or CDR3 of the light chain variable domain of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the any of the CDR sequences of SEQ ID NO: 4.

In embodiments, the IFMs described herein can comprise the amino acid sequence selected from SEQ ID NO: 4, or an amino acid sequence substantially identical thereto (e.g., an amino acid sequence at least 85%, 90%, 95%, 96%, 97%, 98%, 99% or higher identity to SEQ ID NO: 2, or having at least 1, 2, 3, 4, 5, 6, 7, 8, 9, or 10 or more amino acid alterations (e.g., substitutions, deletions, or insertions, e.g., conservative substitutions) relative to SEQ ID NO: 4. In embodiments, the IFM comprises no more than five, ten or fifteen alterations (e.g., substitutions, deletions, or insertions, e.g., conservative substitutions) relative to SEQ ID NO: 4.

An exemplary corresponding heavy chain of the chimeric BC8 antibody molecule, e.g., a Fab or IgG, is shown below as SEQ ID NO:5 or SEQ ID NO:6, respectively.

SEQ ID NO: 5
Name: HC-chBC8-Fab
Fab heavy-chain of chimeric BC8 anti-CD45 antibody; contains variable domain from parental BC8 mouse monoclonal antibody and CH1 domain from human IgG1.

In some embodiments, the chimeric BC8 antibody comprises the heavy chain variable amino acid sequence (optionally, further including a CH1 domain sequence from human IgG1) shown in SEQ ID NO:5, or an amino acid sequence substantially identical thereto (e.g., an amino acid sequence at least 85%, 90%, 95% or higher identical to SEQ ID NO:5). In embodiments, the BC8 antibody comprises one, two, or all three CDR1, CDR2 or CDR3 of the heavy chain variable domain of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 5.

SEQ ID NO: 6
Name: HC-chBC8-IgG4S228P
Heavy-chain of chimeric BC8 anti-CD45 antibody; contains variable domain from parental BC8 mouse monoclonal antibody and constant region from human IgG4 containing S228P mutation (IgG4-S228P).

In some embodiments, the chimeric BC8 antibody comprises the heavy chain variable amino acid sequence (optionally, further including a constant domain sequence from human IgG4 containing S228P mutation (IgG4-S228P)) shown in SEQ ID NO:6, or an amino acid sequence substantially identical thereto (e.g., an amino acid sequence at least 85%, 90%, 95% or higher identical to SEQ ID NO:6). In embodiments, the chimeric BC8 antibody comprises one, two, or all three CDR1, CDR2 or CDR3 of the heavy chain variable domain of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 6.

SEQ ID NO: 7
Name: LC-chBC8
Light-chain of chimeric BC8 anti-CD45 antibody; contains variable domain from parental BC8 mouse monoclonal antibody and human constant kappa domain.

In some embodiments, the BC8 antibody comprises the light chain variable amino acid sequence (optionally, further including a constant domain sequence from human kappa) shown in SEQ ID NO:7, or an amino acid sequence substantially identical thereto (e.g., an amino acid sequence at least 85%, 90%, 95% or higher identical to SEQ ID NO:7). In embodiments, the BC8 antibody comprises one, two, or all three CDR1, CDR2 or CDR3 of the light chain variable domain of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 7.
SEQ ID NO: 8
Name: HC-chBC8-IgG4S228P-IL15

Heavy-chain of chimeric BC8 anti-CD45 antibody; contains variable domain from parental BC8 mouse monoclonal antibody and constant region from human IgG4 containing S228P mutation (IgG4-S228P); contains wild-type IL-15 genetically fused to antibody heavy-chain C-terminus using a flexible linker.

QVQLVESGGGLVQPGGSLKLSCAASGFDFSRYWMSWVRQAPGKGLEWIGE

INPTSSTINFTPSLKDKVFISRDNAKNTLYLQMSKVRSEDTALYYCARGN

YYRYGDAMDYWGQGTSVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK*GG*

*GGSGGGGSGGGGS*NWVNVISDLKKIEDLIQSMHIDATLYTESDVHPSCKV

TAMKCFLLELQVISLESGDASIHDTVENLIILANNSLSSNGNVTESGCKE

CEELEEKNIKEFLQSFVHIVQMFINTS

From N- to C-terminus, a heavy chain portion of a chimeric BC8 IgG4 fused to an IL-15 cytokine fused via a peptide linker is shown. The sequence of the heavy chain is shown in normal font; the location of the peptide linker is shown by italics and underline; and the cytokine molecule is shown by the double underline.

In some embodiments, the BC8 antibody comprises the heavy chain variable amino acid sequence (optionally, further including human IgG4 constant sequence) shown in SEQ ID NO:8, or an amino acid sequence substantially identical thereto (e.g., an amino acid sequence at least 95% or higher identical to SEQ ID NO:8). In embodiments, the BC8 antibody comprises one, two, or all three CDR1, CDR2 or CDR3 of the heavy chain variable domain of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the any of the CDR sequences of SEQ ID NO: 8.

In embodiments, the IFMs described herein can comprise the amino acid sequence of SEQ ID NO: 8, or an amino acid sequence substantially identical thereto (e.g., an amino acid sequence at least 85%, 90%, 95%, 96%, 97%, 98%, 99% or higher identity to SEQ ID NO: 8, or having at least 1, 2, 3, 4, 5, 6, 7, 8, 9, or 10 or more amino acid alterations (e.g., substitutions, deletions, or insertions, e.g., conservative substitutions) relative to SEQ ID NO: 8. In embodiments, the IFM comprises no more than five, ten or fifteen alterations (e.g., substitutions, deletions, or insertions, e.g., conservative substitutions) relative to SEQ ID NO: 8.

SEQ ID NO: 14
Name: HC-ch9.4-Fab

Fab heavy-chain of chimeric 9.4 anti-CD45 antibody; contains variable domain from parental 9.4 mouse monoclonal antibody and CH1 domain from human IgG1.

In some embodiments, the chimeric 9.4 antibody comprises the heavy chain variable amino acid sequence (optionally, further including a human IgG1 heavy chain sequence) shown in SEQ ID NO:14, or an amino acid sequence substantially identical thereto (e.g., an amino acid sequence at least 95% or higher identical to SEQ ID NO:14). In embodiments, the 9.4 antibody comprises one, two, or all three CDR1, CDR2 or CDR3 of the heavy chain variable domain of the 9.4 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO:14.
SEQ ID NO: 15
Name: LC-ch9.4-IL15

Light-chain of chimeric 9.4 anti-CD45 antibody; contains variable domain from parental 9.4 mouse monoclonal antibody and human constant kappa domain; contains wild-type IL-15 genetically fused to antibody light-chain C-terminus using a flexible linker.

DIVMTQAAPSVPVTPGESLSISCRSSKSLLHSSGITYLYWFLQRPGQSPQ

LLIYRMSNLASGVPDRFSGSGSGTAFTLRISRVEAEDVGVYYCMQHLEYP

FTFGGGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC*GGGGSGGGGSGGGGS*NWVNVISDLKKIEDLI

QSMHIDATLYTESDVHPSCKVTAMKCFLLELQVISLESGDASIHDTVENL

IILANNSLSSNGNVTESGCKECEELEEKNIKEFLQSFVHIVQMFINTS

From N- to C-terminus, a light chain portion of a chimeric 9.4 IgG1 fused to an IL-15 cytokine fused via a peptide linker is shown. The sequence of the light-chain is shown in normal font; the location of the peptide linker is shown by italics and underline; and the cytokine molecule is shown by the double underline. The kappa constant region is shown as SEQ ID NO: 74.

In some embodiments, the light chain variable amino acid sequence of the chimeric 9.4 antibody (optionally, further including a kappa light chain sequence) corresponding to the antibody portion of the amino acid sequence shown in SEQ ID NO:15, or an amino acid sequence substantially identical thereto (e.g., an amino acid sequence at least 85%, 90%, 95% or higher identical to the antibody portion of SEQ ID NO:15). In embodiments, the 9.4 antibody comprises one, two, or all three CDR1, CDR2 or CDR3 of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the any of the CDR sequences of SEQ ID NO: 15.

In embodiments, the IFMs described herein can comprise the amino acid sequence of SEQ ID NO: 15, or an amino acid sequence substantially identical thereto (e.g., an amino acid sequence at least 85%, 90%, 95%, 96%, 97%, 98%, 99% or higher identity to SEQ ID NO: 15, or having at least 1, 2, 3, 4, 5, 6, 7, 8, 9, or 10 or more amino acid alterations (e.g., substitutions, deletions, or insertions, e.g., conservative substitutions) relative to SEQ ID NO: 15. In embodiments, the IFM comprises no more than five, ten or fifteen alterations (e.g., substitutions, deletions, or insertions, e.g., conservative substitutions) relative to SEQ ID NO: 15.

SEQ ID NO: 16
Name: HC-ch4B2-Fab

Fab heavy-chain of chimeric 4B2 anti-CD45 antibody; contains variable domain from parental 4B2 mouse monoclonal antibody and CH1 domain from human IgG1.

In some embodiments, the chimeric 4B2 antibody comprises the heavy chain variable amino acid sequence (optionally, further including a human IgG1 heavy chain sequence) shown in SEQ ID NO:16, or an amino acid sequence substantially identical thereto (e.g., an amino acid sequence at least 95% or higher identical to SEQ ID NO:16). In embodiments, the 4B2 antibody comprises one, two, or all three CDR1, CDR2 or CDR3 of the heavy chain variable domain of the 4B2 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO:16.

SEQ ID NO: 17
Name: LC-ch4B2-IL15

Light-chain of chimeric 4B2 anti-CD45 antibody; contains variable domain from parental 4B2 mouse monoclonal antibody and human constant kappa domain; contains wild-type IL-15 genetically fused to antibody light-chain C-terminus using a flexible linker.

DIVITQDELSNPVTSGESVSISCRSSKSLLYKDGKTYLNWFLQRPGQSPQ

LLIYLMSTRASGVSDRFSGSGSGTDFTLEISRVKAEDVGVYYCQQLVEYP

FTFGGGTKLEVKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC*GGGGSGGGGSGGGGS*NWVNVISDLKKIEDLI

QSMHIDATLYTESDVHPSCKVTAMKCFLLELQVISLESGDASIHDTVENL

IILANNSLSSNGNVTESGCKECEELEEKNIKEFLQSFVHIVQMFINTS

From N- to C-terminus, a light chain portion of a chimeric 4B2 IgG1 fused to an IL-15 cytokine via a peptide linker is shown. The sequence of the light chain is shown in normal font: the location of the peptide linker is shown by italics and underline; and the cytokine molecule is shown by the double underline. The kappa constant region is shown as SEQ ID NO: 74.

In some embodiments, the light chain variable amino acid sequence of the chimeric 4B2 antibody (optionally, further including a kappa light chain sequence) corresponding to the antibody portion of the amino acid sequence shown in SEQ ID NO:17, or an amino acid sequence substantially identical thereto (e.g., an amino acid sequence at least 85%, 90%, 95% or higher identical to the antibody portion of SEQ ID NO:17). In embodiments, the 4B2 antibody comprises one, two, or all three CDR1, CDR2 or CDR3 of the 4B2 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the any of the CDR sequences of SEQ ID NO: 17.

In embodiments, the IFMs described herein can comprise the amino acid sequence of SEQ ID NO: 17, or an amino acid sequence substantially identical thereto (e.g., an amino acid sequence at least 85%, 90%, 95%, 96%, 97%, 98%, 99% or higher identity to SEQ ID NO: 17, or having at least 1, 2, 3, 4, 5, 6, 7, 8, 9, or 10 or more amino acid alterations (e.g., substitutions, deletions, or insertions, e.g., conservative substitutions) relative to SEQ ID NO: 17. In embodiments, the IFM comprises no more than five, ten or fifteen alterations (e.g., substitutions, deletions, or insertions, e.g., conservative substitutions) relative to SEQ ID NO: 17.

SEQ ID NO: 18
Name: HC-hBC8(23)-Fab

Fab heavy-chain of humanized BC8 anti-CD45 antibody; contains humanized variable domain and CH1 domain from human IgG1.

In some embodiments, the heavy chain variable amino acid sequence of a humanized BC8 antibody (optionally, further including a CH1 domain sequence from human IgG1) has the amino acid sequence shown in SEQ ID NO:18, or an amino acid sequence substantially identical thereto (e.g., an amino acid sequence at least 85%, 90%, 95% or higher identical to the antibody portion of SEQ ID NO:18). In embodiments, the BC8 antibody comprises one, two, or all three CDR1, CDR2 or CDR3 of the heavy chain variable domain of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 18.

SEQ ID NO: 19
Name: LC-hBC8(23)-1L15

Light-chain of humanized BC8 anti-CD45 antibody; contains humanized variable domain and human constant kappa domain; contains wild-type IL-15 genetically fused to antibody light-chain C-terminus using a flexible linker.

EIVLTQSPATLSLSLGERATISCRASKSVSTSGYSYLHWYQQKPGQAPKL

LIYLASNRATGVPARFSGSGPGTDFTLTISSLEPEDFATYYCQHSRELPF

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC*GGGGSGGGGSGGGGS*NWVNVISDLKKIEDLIQ

SMHIDATLYTESDVHPSCKVTAMKCFLLELQVISLESGDASIHDTVENLI

ILANNSLSSNGNVTESGCKECEELEEKNIKEFLQSFVHIVQMFINTS

From N- to C-terminus, a light chain portion of a humanized BC8 IgG1 fused to an IL-15 cytokine via a peptide linker is shown. The sequence of the light chain is shown in normal font: the location of the peptide linker is shown by italics and underline; and the cytokine molecule is shown by the double underline. The kappa constant region is shown as SEQ ID NO: 74.

In some embodiments, the light chain variable amino acid sequence of the humanized BC8 antibody (optionally, further including a kappa light chain sequence) corresponding to the antibody portion of the amino acid sequence shown in SEQ ID NO:19, or an amino acid sequence substantially identical thereto (e.g., an amino acid sequence at least 85%, 90%, 95% or higher identical to the antibody portion of SEQ ID NO:19). In embodiments, the BC8 antibody comprises one, two, or all three CDR1, CDR2 or CDR3 of the light chain variable domain of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any the CDR sequences of SEQ ID NO: 19.

In embodiments, the IFMs described herein can comprise the amino acid sequence of SEQ ID NO: 19, or an amino acid sequence substantially identical thereto (e.g., an amino acid sequence at least 85%, 90%, 95%, 96%, 97%, 98%, 99% or higher identity to SEQ ID NO: 19, or having at least 1, 2, 3, 4, 5, 6, 7, 8, 9, or 10 or more amino acid alterations (e.g., substitutions, deletions, or insertions, e.g., conservative substitutions) relative to SEQ ID NO: 19. In embodiments, the IFM comprises no more than five, ten or fifteen alterations (e.g., substitutions, deletions, or insertions, e.g., conservative substitutions) relative to SEQ ID NO: 19.

SEQ ID NO: 20
Name: HC-hBC8(23)-null-Fab

Fab heavy-chain of humanized BC8 anti-CD45 antibody; contains humanized variable domain, an SGGGS (SEQ ID NO: 123) substitution in CDR-H3, and CH1 domain from human IgG1.

SEQ ID NO: 21
Name: LC-chBC8-L2-IL15

Light-chain of chimeric BC8 anti-CD45 antibody; contains variable domain from parental mouse monoclonal antibody and human constant kappa domain; contains wild-type IL-15 genetically fused to antibody light-chain C-terminus using a flexible linker with sequence

GGGSGGGS (SEQ ID NO: 37)

DIVLTQSPASLAVSLGQRATISCRASKSVSTSGYSYLHWYQQKPGQPPKL

LIYLASNLESGVPARFSGSGSGTDFTLNIHPVEEEDAATYYCQHSRELPF

TFGSGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC*GGGSGGGS*NWVNVISDLKKIEDLIQSMHIDAT

LYTESDVHPSCKVTAMKCFLLELQVISLESGDASIHDTVENLIILANNSL

SSNGNVTESGCKECEELEEKNIKEFLQSFVHIVQMFINTS.

From N- to C-terminus, a light chain portion of a chimeric BC8 IgG1 fused to an IL-15 cytokine via a peptide linker (L2) is shown. The sequence of the light chain is shown in normal font; the location of the peptide linker is shown by italics and underline; and the cytokine molecule is shown by the double underline. The kappa constant region is shown as SEQ ID NO: 74.

In some embodiments, the light chain variable amino acid sequence of the chimeric BC8 antibody (optionally, further including a kappa light chain sequence) corresponding to the antibody portion of the amino acid sequence shown in SEQ ID NO:21, or an amino acid sequence substantially identical thereto (e.g., an amino acid sequence at least 85%, 90%, 95% or higher identical to the antibody portion of SEQ ID NO:21). In embodiments, the BC8 antibody comprises one, two, or all three CDR1, CDR2 or CDR3 of the light chain variable domain of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any the CDR sequences of SEQ ID NO: 21.

In embodiments, the IFMs described herein can comprise the amino acid sequence of SEQ ID NO: 21, or an amino acid sequence substantially identical thereto (e.g., an amino acid sequence at least 85%, 90%, 95%, 96%, 97%, 98%, 99% or higher identity to SEQ ID NO:21, or having at least 1, 2, 3, 4, 5, 6, 7, 8, 9, or 10 or more amino acid alterations (e.g., substitutions, deletions, or insertions, e.g., conservative substitutions) relative to SEQ ID NO: 21. In embodiments, the IFM comprises no more than five, ten or fifteen alterations (e.g., substitutions, deletions, or insertions, e.g., conservative substitutions) relative to SEQ ID NO: 21.

SEQ ID NO: 22
Name: LC-chBC8-L3-IL15

Light-chain of chimeric BC8 anti-CD45 antibody; contains variable domain from parental mouse monoclonal antibody and human constant kappa domain; contains wild-type IL-15 genetically fused to antibody light-chain C-terminus using a linker related to the human IgG1 hinge (SEQ ID NO: 38).

DIVLTQSPASLAVSLGQRATISCRASKSVSTSGYSYLHWYQQKPGQPPKL

LIYLASNLESGVPARFSGSGSGTDFTLNIHPVEEEDAATYYCQHSRELPF

TFGSGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC*DKTHTSPPSPAP*NWVNVISDLKKIEDLIQSMH

IDATLYTESDVHPSCKVTAMKCFLLELQVISLESGDASIHDTVENLIILA

NNSLSSNGNVTESGCKECEELEEKNIKEFLQSFVHIVQMFINTS

From N- to C-terminus, a light chain portion of a chimeric BC8 IgG1 fused to an IL-15 cytokine via a peptide linker (L3) is shown. The sequence of the light chain is shown in normal font; the location of the peptide linker is shown by italics and underline; and the cytokine molecule is shown by the double underline. The kappa constant region is shown as SEQ ID NO: 74.

In some embodiments, the light chain variable amino acid sequence of the chimeric BC8 antibody (optionally, further including a kappa light chain sequence) corresponding to the antibody portion of the amino acid sequence shown in SEQ ID NO:22, or an amino acid sequence substantially identical thereto (e.g., an amino acid sequence at least 85%, 90%, 95% or higher identical to the antibody portion of SEQ ID NO:22). In embodiments, the BC8 antibody comprises one, two, or all three CDR1, CDR2 or CDR3 of the light chain variable domain of the BC8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 22.

In embodiments, the IFMs described herein can comprise the amino acid sequence of SEQ ID NO: 22, or an amino acid sequence substantially identical thereto (e.g., an amino acid sequence at least 85%, 90%, 95%, 96%, 97%, 98%, 99% or higher identity to SEQ ID NO:22, or having at least 1, 2, 3, 4, 5, 6, 7, 8, 9, or 10 or more amino acid alterations (e.g., substitutions, deletions, or insertions, e.g., conservative substitutions) relative to SEQ ID NO: 22. In embodiments, the IFM comprises no more than five, ten or fifteen alterations (e.g., substitutions, deletions, or insertions, e.g., conservative substitutions) relative to SEQ ID NO: 22.

SEQ ID NO: 25
Name: hBC8(23)-null heavy-chain variable domain
Heavy-chain variable domain of humanized BC8 anti-CD45 antibody; contains an SGGGS substitution in CDR-H3.

In embodiments, the IFMs described herein can comprise the amino acid sequence of SEQ ID NO: 25, or an amino acid sequence substantially identical thereto (e.g., an amino acid sequence at least 85%, 90%, 95%, 96%, 97%, 98%, 99% or higher identity to SEQ ID NO:25, or having at least 1, 2, 3, 4, 5, 6, 7, 8, 9, or 10 or more amino acid alterations (e.g., substitutions, deletions, or insertions, e.g., conservative substitutions) relative to SEQ ID NO: 25. In embodiments, the IFM comprises no more than five, ten or fifteen alterations (e.g., substitutions, deletions, or insertions, e.g., conservative substitutions) relative to SEQ ID NO: 25.

SEQ ID NO: 26
Name: HC-chMHM24-Fab
Fab heavy-chain of chimeric MHM24 anti-CD11a antibody; contains variable domain from parental mouse monoclonal antibody and CH1 domain from human IgG1.

In some embodiments, the heavy chain variable amino acid sequence of a chimeric MHM24 antibody (optionally, further including a CH1 domain sequence from human IgG1) has the amino acid sequence shown in SEQ ID NO:26, or an amino acid sequence substantially identical thereto (e.g., an amino acid sequence at least 85%, 90%, 95% or higher identical to the antibody portion of SEQ ID NO:26). In embodiments, the MHM24 antibody comprises one, two, or all three CDR1, CDR2 or CDR3 of the heavy chain variable domain of the MHM24 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 26.

SEQ ID NO: 69
Name: HC-hMHM24-Fab
Fab heavy-chain of humanized MHM24 anti-CD11a antibody; contains variable domain from a humanized MHM24 heavy-chain variable domain and CH1 domain from human IgG1.

In some embodiments, the heavy chain variable amino acid sequence of a humanized MHM24 antibody (optionally, further including a CH1 domain sequence from human IgG1) has the amino acid sequence shown in SEQ ID NO: 27, or an amino acid sequence substantially identical thereto (e.g., an amino acid sequence at least 85%, 90%, 95% or higher identical to the antibody portion of SEQ ID NO: 27). In embodiments, the MHM24 antibody comprises one, two, or all three CDR1, CDR2 or CDR3 of the heavy chain variable domain of the MHM24 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 27.

SEQ ID NO: 27
Name: LC-chMHM24-IL15
Light-chain of chimeric MHM24 anti-CD11a antibody; contains variable domain from parental mouse monoclonal antibody and human constant kappa domain; contains wild-type IL-genetically fused to antibody light-chain C-terminus using a flexible linker.

DVQITQSPSYLAASPGETISINCRASKTISKYLAWYQEKPGKTNKLLIYS

GSTLQSGIPSRFSGSGSGTDFTLTISSLEPEDFAMYYCQQHNEYPLTFGT

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC*GGGGSGGGGSGGGGS*<u>NWVNVISDLKKIEDLIQSMHI</u>

<u>DATLYTESDVHPSCKVTAMKCFLLELQVISLESGDASIHDTVENLIILAN</u>

<u>NSLSSNGNVTESGCKECEELEEKNIKEFLQSFVHIVQMFINTS</u>

From N- to C-terminus, a light chain portion of a chimeric MHM24 IgG1 fused to an IL-15 cytokine via a peptide linker is shown. The sequence of the light chain is shown in normal font; the location of the peptide linker is shown by italics and underline; and the cytokine molecule is shown by the double underline. The kappa constant region is shown as SEQ ID NO: 74.

In some embodiments, the light chain variable amino acid sequence of the chimeric MHM24 antibody (optionally, further including a kappa light chain sequence) corresponding to the antibody portion of the amino acid sequence shown in SEQ ID NO:27, or an amino acid sequence substantially identical thereto (e.g., an amino acid sequence at least 85%, 90%, 95% or higher identical to the antibody portion of SEQ ID NO:27). In embodiments, the chimeric MHM24 antibody comprises one, two, or all three CDR1, CDR2 or CDR3 of the light chain variable domain of the antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 27.

In embodiments, the IFMs described herein can comprise the amino acid sequence of SEQ ID NO: 27, or an amino acid sequence substantially identical thereto (e.g., an amino acid sequence at least 85%, 90%, 95%, 96%, 97%, 98%, 99% or higher identity to SEQ ID NO:27, or having at least 1, 2, 3, 4, 5, 6, 7, 8, 9, or 10 or more amino acid alterations (e.g., substitutions, deletions, or insertions, e.g., conservative substitutions) relative to SEQ ID NO: 27. In embodiments, the IFM comprises no more than five, ten or fifteen alterations (e.g., substitutions, deletions, or insertions, e.g., conservative substitutions) relative to SEQ ID NO: 27.

SEQ ID NO: 28
Name: HC-ch1B4-Fab
Fab heavy-chain of chimeric 1B4 anti-CD18 antibody; contains variable domain from parental mouse monoclonal antibody and CH1 domain from human IgG1.

In some embodiments, the heavy chain variable amino acid sequence of a chimeric 1B4 antibody (optionally, further including a CH1 domain sequence from human IgG1) has the amino acid sequence shown in SEQ ID NO:28, or an amino acid sequence substantially identical thereto (e.g., an amino acid sequence at least 85%, 90%, 95% or higher identical to the antibody portion of SEQ ID NO:28). In embodiments, the chimeric 1B4 antibody comprises one, two, or all three CDR1, CDR2 or CDR3 of the heavy chain variable domain of the 1B4 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 28.

SEQ ID NO: 29
Name: LC-ch1B4-IL15
Light-chain of chimeric 1B4 anti-CD18 antibody; contains variable domain from parental mouse monoclonal antibody and human constant kappa domain; contains wild-type IL-15 genetically fused to antibody light-chain C-terminus using a flexible linker.

DIVLTQSPASLAVSLGQRATISCRASESVDSYGNSFMHWYQQKPGQPPKL

LIYRASNLESGIPARFSGSGSRTDFTLTINPVEADDVATYYCQQSNEDPL

TFGAGTKLELKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC*GGGGSGGGGSGGGGS*NWVNVISDLKKIEDLIQ

SMHIDATLYTESDVHPSCKVTAMKCFLLELQVISLESGDASIHDTVENLI

ILANNSLSSNGNVTESGCKECEELEEKNIKEFLQSFVHIVQMFINTS

From N- to C-terminus, a light chain portion of a chimeric 1B4 IgG1 fused to an IL-15 cytokine via a peptide linker is shown. The sequence of the light chain is shown in normal font; the location of the peptide linker is shown by italics and underline; and the cytokine molecule is shown by the double underline. The kappa constant region is shown as SEQ ID NO: 74.

In some embodiments, the light chain variable amino acid sequence of the chimeric 1B4 antibody (optionally, further including a kappa light chain sequence) corresponding to the antibody portion of the amino acid sequence shown in SEQ ID NO:29, or an amino acid sequence substantially identical thereto (e.g., an amino acid sequence at least 85%, 90%, 95% or higher identical to the antibody portion of SEQ ID NO:29). In embodiments, the chimeric 1B4 antibody comprises one, two, or all three CDR1, CDR2 or CDR3 of the light chain variable domain of the antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 29.

In embodiments, the IFMs described herein can comprise the amino acid sequence of SEQ ID NO: 29, or an amino acid sequence substantially identical thereto (e.g., an amino acid sequence at least 85%, 90%, 95%, 96%, 97%, 98%, 99% or higher identity to SEQ ID NO:29, or having at least 1, 2, 3, 4, 5, 6, 7, 8, 9, or 10 or more amino acid alterations (e.g., substitutions, deletions, or insertions, e.g., conservative substitutions) relative to SEQ ID NO: 29. In embodiments, the IFM comprises no more than five, ten or fifteen alterations (e.g., substitutions, deletions, or insertions, e.g., conservative substitutions) relative to SEQ ID NO: 29.

SEQ ID NO: 30
Name: HC-chOKT8-Fab
Fab heavy-chain of chimeric OKT8 anti-CD8 antibody; contains variable domain from parental mouse monoclonal antibody and CH1 domain from human IgG1.

In some embodiments, the heavy chain variable amino acid sequence of a chimeric OKT8 anti-CD8 antibody (optionally, further including a CH1 domain sequence from human IgG1) has the amino acid sequence shown in SEQ ID NO:30, or an amino acid sequence substantially identical thereto (e.g., an amino acid sequence at least 85%, 90%, 95% or higher identical to the antibody portion of SEQ ID NO:30). In embodiments, the chimeric OKT8 anti-CD8 antibody comprises one, two, or all three CDR1, CDR2 or CDR3 of the heavy chain variable domain of the OKT8 anti-CD8 antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 30.

SEQ ID NO: 31
Name: LC-chOKT8-IL15
Light-chain of chimeric OKT8 anti-CD8 antibody; contains variable domain from parental mouse monoclonal antibody and human constant kappa domain; contains wild-type IL-15 genetically fused to antibody light-chain C-terminus using a flexible linker.

DVQINQSPSFLAASPGETITINCRTSRSISQYLAWYQEKPGKTNKLLIYS

GSTLQSGIPSRFSGSGSGTDFTLTISGLEPEDFAMYYCQQHNENPLTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC*GGGGSGGGGSGGGGS*NWVNVISDLKKIEDLIQSMHI

DATLYTESDVHPSCKVTAMKCFLLELQVISLESGDASIHDTVENLIILAN

NSLSSNGNVTESGCKECEELEEKNIKEFLQSFVHIVQMFINTS

From N- to C-terminus, a light chain portion of a chimeric OKT8 IgG1 fused to an IL-15 cytokine via a peptide linker is shown. The sequence of the light chain is shown in normal font; the location of the peptide linker is shown by italics and underline; and the cytokine molecule is shown by the double underline. The kappa constant region is shown as SEQ ID NO: 74.

In some embodiments, the light chain variable amino acid sequence of the chimeric OKT8 antibody (optionally, further including a kappa light chain sequence) corresponding to the antibody portion of the amino acid sequence shown in SEQ ID NO:31, or an amino acid sequence substantially identical thereto (e.g., an amino acid sequence at least 85%, 90%, 95% or higher identical to the antibody portion of SEQ ID NO:31). In embodiments, the chimeric OKT8 antibody comprises one, two, or all three CDR1, CDR2 or CDR3 of the light chain variable domain of the antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences of SEQ ID NO: 31.

In embodiments, the IFMs described herein can comprise the amino acid sequence of SEQ ID NO: 31, or an amino acid sequence substantially identical thereto (e.g., an amino acid sequence at least 85%, 90%, 95%, 96%, 97%, 98%, 99% or higher identity to SEQ ID NO:31, or having at least 1, 2, 3, 4, 5, 6, 7, 8, 9, or 10 or more amino acid alterations (e.g., substitutions, deletions, or insertions, e.g., conservative substitutions) relative to SEQ ID NO: 31. In embodiments, the IFM comprises no more than five, ten or fifteen alterations (e.g., substitutions, deletions, or insertions, e.g., conservative substitutions) relative to SEQ ID NO: 31.

SEQ ID NO: 32
Name: BC8scFv-IL15
IL-15 fused to the C-terminus of BC8-scFv using a short flexible linker and a hexahistidine tag.

QVQLVESGGGLVQPGGSLKLSCAASGFDFSRYWMSWVRQAPGKGLEWIGE

INPTSSTINFTPSLKDKVFISRDNAKNTLYLQMSKVRSEDTALYYCARGN

YYRYGDAMDYWGQGTSVTVSGGGGSGGGGSGGGTGDIVLTQSPASLAVSL

GQRATISCRASKSVSTSGYSYLHWYQQKPGQPPKLLIYLASNLESGVPAR

FSGSGSGTDFTLNIHPVEEEDAATYYCQHSRELPFTFGSGTKLEIK*RSGS*

*GGGGSLQ*NWVNVISDLKKIEDLIQSMHIDATLYTESDVHPSCKVTAMKCF

LLELQVISLESGDASIHDTVENLIILANNSLSSNGNVTESGCKECEELEE

KNIKEFLQSFVHIVQMFINTSAAAHHHHHH

From N- to C-terminus, a light chain portion of a BC8 scFv fused to an IL-15 cytokine via a peptide linker is shown. The scFv sequence is shown in normal font; the location of the peptide linker is shown by italics and underline; and the cytokine molecule is shown by the double underline.

In some embodiments, the light chain variable amino acid sequence of the BC8 scFv antibody corresponding to the antibody portion of the amino acid sequence shown in SEQ ID NO:31, or an amino acid sequence substantially identical thereto (e.g., an amino acid sequence at least 85%, 90%, 95% or higher identical to the antibody portion of SEQ ID NO:32). In embodiments, the BC8 antibody comprises one, two, or all three CDR1, CDR2 or CDR3 of the light chain variable domain of the antibody, e.g., according to the Kabat definition, or a closely related CDR, e.g., CDRs which have at least one amino acid alteration, but not more than two, three or four alterations (e.g., substitutions, deletions, or insertions, e.g., conservative substitutions) from any of the CDR sequences within SEQ ID NO: 32.

In embodiments, the IFMs described herein can comprise the amino acid sequence of SEQ ID NO: 32, or an amino acid sequence substantially identical thereto (e.g., an amino acid sequence at least 85%, 90%, 95%, 96%, 97%, 98%, 99% or higher identity to SEQ ID NO:32, or having at least 1, 2, 3, 4, 5, 6, 7, 8, 9, or 10 or more amino acid alterations (e.g., substitutions, deletions, or insertions, e.g., conservative substitutions) relative to SEQ ID NO: 32. In embodiments, the IFM comprises no more than five, ten or fifteen alterations (e.g., substitutions, deletions, or insertions, e.g., conservative substitutions) relative to SEQ ID NO: 32.

Additional sequences that can be included in the IFM of the present disclosure are shown in Table 1 below. In some embodiments, the IFM comprises a constant lamba or lamda region. Exemplary constant lamba or lamda regions include SEQ ID NOS: 74-78. In various embodiments, the IFMs described herein can comprise one or more of the amino acid sequences of SEQ ID NOS: 1-104, or an amino acid sequence substantially identical thereto (e.g., an amino acid sequence at least 70%, 75%, 80%, 85%, 90%, 95%, 96%, 97%, 98%, 99% or higher identity to any one of SEQ ID NOS: 1-104, or having at least 1, 2, 3, 4, 5, 6, 7, 8, 9, or 10 or more amino acid alterations (e.g., substitutions, deletions, or insertions, e.g., conservative substitutions) relative to any one of SEQ ID NOS: 1-104. In embodiments, the IFM comprises no more than five, ten or fifteen alterations (e.g., substitutions, deletions, or insertions, e.g., conservative substitutions) relative to any one of SEQ ID NOS: 1-104.

TABLE 1

Additional Sequences

| SEQ ID NO: | Name | Description/Comments |
|---|---|---|
| 9 | IL-15Rα-sushi (also referred as sushi) | Sushi domain from wild-type IL-15Rα. |
| 10 | IL15-WT | Wild-type IL-15, corresponds to mature polypeptide from full IL-15 sequence described in SEQ ID NO: 40. |
| 11 | IL15-N72D | IL-15 containing N72D mutation |
| 12 | sushiL77I-Fc | Sushi domain from IL-15Rα fused to IgG1-Fc; sushi domain contains L77I mutation |
| 13 | sushi-Fc | Sushi domain from IL-15Rα fused to IgG1-Fc |
| 23 | hBC8(23) heavy-chain variable domain | Humanized BC8(23) heavy-chain variable domain. |
| 24 | hBC8(23) light-chain variable domain | Humanized BC8(23) light-chain variable domain. |
| 33 | Leader-1 | Leader sequence (e.g. signal sequence, signal peptide) used for antibody light-chain, IL-15, N-terminal IL-15 fusions, and N-terminal fusion of sushi to Fab-light-chain. |
| 34 | Leader-2 | Leader sequence (e.g. signal sequence, signal peptide) used for antibody heavy-chain. |
| 35 | IL-15Rα leader sequence | Leader sequence used for sushi and sushi-Fc constructs. |
| 36 | Linker-1 (L1) | (G4S)3 linker |
| 37 | Linker-2 (L2) | (G3S)2 linker |
| 38 | Linker-3 (L3) | Linker derived from IgG1 hinge |
| 39 | Linker-4 (L4) | Linker for fusing IL-15 to C-terminus of BC8-scFv |
| 40 | Human IL-15 full sequence | Genbank Accession No. CAA62616.1 |
| 41 | Human IL-15Rα full sequence | Genbank Accession No. AAI21141.1 |
| 42 | IL-7 full sequence | Genbank Accession No. AAA59156, AAC63047, and NP_000871, and UniProtKB/Swiss-Prot-P13232 |
| 43 | IL-7 mature sequence | |
| 44 | IL-21 full sequence | Genbank Accession No. AAG29348, AAH66262, AAH69124, and EAX05226 |

TABLE 1-continued

Additional Sequences

| SEQ ID NO: | Name | Description/Comments |
|---|---|---|
| 45 | IL-21 mature sequence | |
| 46 | IL-12A full sequence (also referred to as IL-12p35) | Genbank Accession No. P29459 |
| 47 | IL-12A mature sequence | |
| 48 | IL-12B full sequence (also referred to as IL-12p40) | Genbank Accession No. P29460 |
| 49 | IL-12B mature sequence | |
| 50 | scIL-12p70-BA | Synthetic sequence; IL-12B and IL-12A joined by flexible linker |
| 51 | scIL-12p70-AB | Synthetic sequence; IL-12A and IL-12B joined by flexible linker |
| 52 | Minimal sushi domain | |
| 53 | IgG1-Fc | Fc domain (CH2 and CH3 domains) from human IgG1 |
| 54 | IgG2-Fc | Fc domain (CH2 and CH3 domains) from human IgG2 |
| 55 | IgG2Da-Fc | Fc domain from human IgG2 containing two point mutations |
| 56 | sushi-IgG2Da-Fc (also referred to as sushi-Fc2Da) | Sushi domain from IL-15Rα fused to IgG2Da-Fc |
| 57 | BC8 heavy-chain variable domain | |
| 58 | BC8 light-chain variable domain | |
| 59 | 9.4 heavy-chain variable domain | |
| 60 | 9.4 light-chain variable domain | |
| 61 | 4B2 heavy-chain variable domain | |
| 62 | 4B2 light-chain variable domain | |
| 70 | Linker-5 (L5) | $(G_3S)_4$ linker, e.g., as described above in SEQ ID NOs: 50 and 51 |
| 71 | Linker-6 (L6) | $(G_4S)_4$ linker |
| 72 | scIL-12p70-BA-L6 | Synthetic sequence; IL-12B and IL-12A joined by linker L5. |
| 73 | scIL-12p70-AB-L5 | Synthetic sequence; IL-12A and IL-12B joined by linker L5. |
| 74 | human immunoglobulin kappa constant domain | |
| 75 | human immunoglobulin lambda constant 1 | |
| 76 | human immunoglobulin lambda constant 2 | |
| 77 | human immunoglobulin lambda constant 3 | |
| 78 | human immunoglobulin lambda constant 7 | |
| 79 | HC-h9.4Fab | Heavy-chain of a humanized anti-CD45 antibody; contains humanized 9.4 (h9.4) heavy-chain variable domain and the CH1 domain from human IgG1 |
| 80 | HC-h9.4Fab-h9.4scFv | Heavy-chain of a humanized anti-CD45 antibody linked to a humanized anti-CD45 scFv; contains variable domain from h9.4 heavy-chain and the CH1 domain from human IgG1. An h9.4 scFv is genetically fused to the Fab heavy chain C-terminus using a flexible linker (Linker-1, SEQ ID NO: 36). |
| 81 | HC-h9.4Fab-hBC8scFv | Heavy-chain of a humanized anti-CD45 antibody linked to a humanized anti-CD45 scFv; contains variable domain from h9.4 heavy-chain and the CH1 domain from human IgG1. A humanized BC8 (hBC8) scFv is genetically fused to the Fab heavy chain C-terminus using a flexible linker (Linker-1, SEQ ID NO: 36). |
| 82 | LC-h9.4Fab-scIL-12p70 | Light-chain of a humanized anti-CD45 antibody; contains variable domain from h9.4 light-chain and human constant kappa domain, a wild-type single-chain human IL-12p70 (SEQ ID NO: 50) genetically fused to antibody light-chain C-terminus using a flexible linker (Linker-1, SEQ ID NO: 36); single-chain human IL-12p70 comprises a genetic fusion of human IL-12A and IL-12B using a flexible linker (Linker-5; SEQ ID NO: 70). |

TABLE 1-continued

Additional Sequences

| SEQ ID NO: | Name | Description/Comments |
|---|---|---|
| 83 | HC-chM1Fab | Heavy-chain of chimeric M1 (chM1) anti-CD45 antibody; contains variable domain from rat monoclonal antibody clone M1/0.3.4.HL.2 (M1) heavy-chain and the CH1 domain from human IgG1. |
| 84 | LC-chM1Fab-scIL-12p70 | Light-chain of chM1 anti-CD45 antibody; contains variable domain from rat monoclonal antibody clone M1/0.3.4.HL.2 (M1), light-chain and human constant kappa domain, and a wild-type single-chain mouse IL-12p70 genetically fused to antibody light-chain C-terminus using a flexible linker (Linker-1, SEQ ID NO: 36); single-chain mouse IL-12p70 comprises a genetic fusion of mouse IL-12A(p40) and IL-12B(p35) using a flexible linker (Linker-6, SEQ ID NO: 71). |
| 85 | LC-chM1Fab-IL-15 | Light-chain of chM1 anti-CD45 antibody; contains variable domain from rat monoclonal antibody clone M1/0.3.4.HL.2 (M1) light-chain and human constant kappa domain; contains wild-type human IL-15 genetically fused to antibody light-chain C-terminus using a flexible linker (Linker-1, SEQ ID NO: 36). |
| 86 | HC-chM1Fab-M1scFv | Heavy-chain of chM1 anti-CD45 antibody; contains variable domain from rat monoclonal antibody clone M1/0.3.4.HL.2 heavy-chain and the CH1 domain from human IgG1. An M1 scFv is genetically fused to the Fab heavy chain C-terminus using a flexible linker (Linker-1, SEQ ID NO: 36). |
| 87 | HC-chY169Fab | Heavy-chain of chimeric YTS 169.4.2.1 anti-CD8 antibody; contains variable domain from rat monoclonal antibody clone YTS 169.4.2.1 (Y169) heavy-chain and the CH1 domain from human IgG1. |
| 88 | LC-chY169Fab-IL-15 | Light-chain of chimeric YTS 169.4.2.1 anti-CD8 antibody; contains variable domain from rat monoclonal antibody Y169 light-chain and human constant kappa domain; contains wild-type human IL-15 genetically fused to antibody light-chain C-terminus using a flexible linker (Linker-1, SEQ ID NO: 36). |
| 89 | HC-chY169Fab-M1scFv | Heavy-chain of chimeric YTS 169.4.2.1 anti-CD8 antibody; contains variable domain from rat monoclonal antibody Y169 heavy-chain and the CH1 domain from human IgG1. An M1/0.3.4.HL.2 scFv is genetically fused to the Fab heavy chain C-terminus using a flexible linker (Linker-1, SEQ ID NO: 36). |
| 90 | LC-chY169Fab-scIL-12p70 | Light-chain of chimeric YTS 169.4.2.1 anti-CD8 antibody; contains variable domain from rat monoclonal antibody Y169 light-chain and human constant kappa domain; contains a single-chain mouse IL-12 genetically fused to antibody light-chain C-terminus using a flexible linker (Linker-1, SEQ ID NO: 36). |
| 91 | h9.4 scFv | An scFv comprising a humanized 9.4 antibody; heavy-chain and light-chain variable domains are genetically fused using a flexible linker (Linker-6; SEQ ID NO: 71). |
| 92 | hBC8 scFv | An scFv comprising a humanized BC8 antibody; heavy-chain and light-chain variable domains are genetically fused using a flexible linker (Linker-6; SEQ ID NO: 71). |
| 93 | M1 scFv | An scFv comprising M1 variable domains; heavy-chain and light-chain variable domains are genetically fused using a flexible linker (Linker-6; SEQ ID NO: 71). |
| 94 | VH-h9.4 | Heavy-chain variable domain of a humanized 9.4 variant. |
| 95 | VL-h9.4 | Light-chain variable domain of a humanized 9.4 variant. |
| 96 | VH-hBC8 | Heavy-chain variable domain of a humanized BC8 variant. |
| 97 | VL-hBC8 | Light-chain variable domain of a humanized BC8 variant. |
| 98 | VH-M1 | Heavy-chain variable domain of antibody clone M1. |
| 99 | VL-M1 | Light-chain variable domain of antibody clone M1. |
| 100 | VH-Y169 | Heavy-chain variable domain of antibody clone YTS 169.4.2.1. |
| 101 | VL-Y169 | Light-chain variable domain of antibody clone YTS 169.4.2.1. |

TABLE 1-continued

Additional Sequences

| SEQ ID NO: | Name | Description/Comments |
| --- | --- | --- |
| 102 | LC-h9.4Fab-scIL-12p70AB | Light-chain of a humanized anti-CD45 antibody; contains variable domain from h9.4 light-chain and human constant kappa domain; contains a single-chain human IL-12p70 (SEQ ID NO: 51) genetically fused to antibody light-chain C-terminus using a flexible linker (Linker-1, SEQ ID NO: 36); single-chain human IL-12p70 comprises a genetic fusion of human IL-12A and IL-12B using a flexible linker (Linker-5; SEQ ID NO: 70). |
| 103 | LC-h9.4Fab-IL-12A | Light-chain of a humanized anti-CD45 antibody; contains variable domain from h9.4 light-chain and human constant kappa domain; contains a human IL-12A (SEQ ID NO: 47) genetically fused to antibody light-chain C-terminus using a flexible linker (Linker-1, SEQ ID NO: 36). |
| 104 | LC-h9.4Fab-IL-12B | Light-chain of a humanized anti-CD45 antibody; contains variable domain from h9.4 light-chain and human constant kappa domain; contains a human IL-12B (SEQ ID NO: 49) genetically fused to antibody light-chain C-terminus using a flexible linker (Linker-1, SEQ ID NO: 36). |

Protein Variants

Full length polypeptides and variants thereof are described below. Full-length IL-15 sequence (SEQ ID NO: 40) is taken from Genbank Accession No. CAA62616.1; mature IL-15 is devoid of the signal sequence and is defined in SEQ ID NO: 10. Full-length IL-15Rα (SEQ ID NO: 41) is taken from Genbank Accession No. AAI21141.1. The sushi domain of IL-15Rα (IL-15Rα-sushi) is given by SEQ ID NO: 9. A minimal sushi domain encompassing the first and fourth cysteines and the intervening amino acids (SEQ ID NO: 52) have also been described elsewhere and are plausible substitutes. Similarly, optional N-terminal additions to the minimal sushi domain comprising the native Thr or Ile-Thr and/or optional C-terminal additions to the minimal sushi domain comprising Ile or Ile-Arg residues are also plausible.

Protein variants described below specify protein subunit names and SEQ ID NOs corresponding to the mature proteins. Each protein subunit was recombinantly expressed with an N-terminal signal peptide to facilitate secretion from the expressing cell. The native IL-15Rα signal peptide (SEQ ID NO: 35) was used for sushi, sushi-L77I-Fc, and sushi-Fc. The leader sequence in SEQ ID NO: 33 was used to support secretion of antibody light-chains, IL15-WT, N-terminal IL-15 fusions, IL15-N72D, and N-terminal fusion of sushi to Fab-light-chain. The leader sequence in SEQ ID NO: 34 was used to support secretion of antibody heavy chains.

For "heavy-chain" and "light-chain" nomenclature we use the standard naming system for antibodies. For example, in an antibody Fab fragment both chains have approximately the same molecular mass, but we refer to the heavy-chain as the chain of the Fab fragment corresponding to the heavy-chain in the full-length antibody (e.g. containing the variable heavy-chain and CH1 domains). Further, in the case of cytokine fusions to the light-chain of a Fab fragment, the light-chain would actually have a larger molecular mass than the heavy-chain due to the cytokine fusion; for consistency, however, we maintain the standard naming convention in which the variable light-chain domain and constant kappa domain and cytokine fusion comprise the "light-chain" while the variable heavy-chain domain and CH1 domain comprises the "heavy-chain".

Protein Name: chBC8-IL15/sushi Fab (Also Referred to as chBC8-L1-IL15/sushi Fab).

This protein was made by coexpression of three subunits: HC-chBC8-Fab (SEQ ID NO: 5), LC-chBC8-IL15 (SEQ ID NO: 3), and IL-15Rα-sushi (SEQ ID NO: 9). The resulting protein comprises a fusion of wild-type IL-15 to the C-terminus of the chimeric BC8 Fab fragment light-chain using linker-L1 (SEQ ID NO: 36), and a noncovalent association with TL-15Rα-sushi (via interaction with IL-15). The chimeric BC8 Fab is an anti-human CD45R antibody Fab fragment comprising variable-heavy and variable-light chain domains (VH and VL) from the parental mouse monoclonal antibody (mAb) and constant domains from human (human constant kappa domain and human IgG1-CH1 domain).

Protein Name: IL15-chBC8/sushi Fab

This protein was made by coexpression of three subunits: HC-chBC8-Fab (SEQ ID NO: 5), IL15-LC-chBC8 (SEQ ID NO: 4), and IL-15Rα-sushi (SEQ ID NO: 9). The resulting protein comprises a fusion of IL-15 to the N-terminus of the chimeric BC8 Fab fragment light-chain using linker-L1 (SEQ ID NO: 36), and a noncovalent association between IL-15 and IL-15Rα-sushi.

Protein Name: chBC8-sushi/IL15-N72D Fab

This protein was made by coexpression of three subunits: HC-chBC8-Fab (SEQ ID NO: 5), LC-chBC8-sushi (SEQ ID NO: 1), and IL15-N72D (SEQ ID NO: 11). The resulting protein comprises a fusion of IL-15Rα-sushi to the C-terminus of the chimeric BC8 Fab fragment light-chain using linker-L1 (SEQ ID NO: 36), and a noncovalent association between IL15-N72D and IL-15Rα-sushi.

Protein Name: sushi-chBC8/IL15-N72D Fab

This protein was made by coexpression of three subunits: HC-chBC8-Fab (SEQ ID NO: 5), sushi-LC-chBC8 (SEQ ID NO: 2), and IL15-N72D (SEQ ID NO: 11). The resulting protein comprises a fusion of IL-15Rα-sushi to the N-terminus of the chimeric BC8 Fab fragment light-chain using linker-L1 (SEQ ID NO: 36), and a noncovalent association between IL15-N72D and IL-15Rα-sushi.

Protein Name: chBC8-IL15/sushi IgG

This protein was made by coexpression of three subunits: HC-chBC8-IgG4S228P (SEQ ID NO: 6), LC-chBC8-IL15

(SEQ ID NO: 3), and IL-15Rα-sushi (SEQ ID NO: 9). The resulting protein comprises a fusion of wild-type IL-15 to the C-terminus of the chimeric BC8 IgG-S228P light-chain using linker-L1 (SEQ ID NO: 36), and a noncovalent association with IL-15Rα-sushi (via interaction with IL-15). The chimeric BC8 IgG4-S228P is an anti-human CD45R antibody comprising variable-heavy and variable-light chain domains (VH and VL) from the parental mouse mAb and constant domains from human (human constant kappa domain and human IgG4 containing an S228P point mutation, which reduces susceptibility of Fab-arm-exchange of IgG4).

Protein Name: IL15-chBC8/sushi IgG
This protein was made by coexpression of three subunits: HC-chBC8-IgG4S228P (SEQ ID NO: 6), IL15-LC-chBC8 (SEQ ID NO: 4), and IL-15Rα-sushi (SEQ ID NO: 9). The resulting protein comprises a fusion of wild-type IL-15 to the N-terminus of the chimeric BC8 IgG4-S228P light-chain using linker-L1 (SEQ ID NO: 36), and a noncovalent association between IL-15 and IL-15Rα-sushi.

Protein Name: chBC8-sushi/1L15-N72D IgG
This protein was made by coexpression of three subunits: HC-chBC8-IgG4S228P (SEQ ID NO: 6), LC-chBC8-sushi (SEQ ID NO: 1), and IL15-N72D (SEQ ID NO: 11). The resulting protein comprises a fusion of IL-15Rα-sushi to the C-terminus of the chimeric BC8 IgG4-S228P light-chain using linker-L1 (SEQ ID NO: 36), and a noncovalent association with between IL-15Ra-sushi and IL-15.

Protein Name: sushi-chBC8/IL15-N72D IgG
This protein was made by coexpression of three subunits: HC-chBC8-IgG4S228P (SEQ ID NO: 6), sushi-LC-chBC8 (SEQ ID NO: 2), and IL15-N72D (SEQ ID NO: 11). The resulting protein comprises a fusion of IL-15Rα-sushi to the N-terminus of the chimeric BC8 IgG4-S228P light-chain using linker-L1 (SEQ ID NO: 36), and a noncovalent association with between IL-15Ra-sushi and IL-15.

Protein Name: chBC8-(HC)-IL15/sushi IgG
This protein was made by coexpression of three subunits: HC-chBC8-IgG4S228P-IL15 (SEQ ID NO: 8), LC-chBC8 (SEQ ID NO: 7), and IL-15Rα-sushi (SEQ ID NO: 9). The resulting protein comprises a fusion of IL-15 to the C-terminus of the chimeric BC8 IgG4-S228P heavy-chain using linker-L1 (SEQ ID NO: 36), and a noncovalent association with between IL-15 and IL-15Rα-sushi.

Protein Name: chBC8-IL15/sushi scFv
This protein was made by coexpression of two subunits: BC8scFv-IL15 (SEQ ID NO: 32) and IL-15Rα-sushi (SEQ ID NO: 9). The resulting protein comprises a fusion of IL-15 to the C-terminus of BC8-scFv using linker-L1 (SEQ ID NO: 36), and a noncovalent association with between IL-15 and IL-15Rα-sushi. BC8-scFv comprises the variable domains from the parental mouse mAb joined by a flexible linker.

Protein Name: IL15-N72D/sushiL77I-Fc
This protein was made by coexpression of two subunits: IL15-N72D (SEQ ID NO: 11) and sushi-L77I-Fc (SEQ ID NO: 12). The resulting protein comprises IL-15Rα-sushi containing an L77I mutation fused to the N-terminus of human IgG1-Fc region, and a noncovalent association with between IL15-N72D and IL-15Rα-sushi.

Protein Name: IL15-WT/sushi-Fc
This protein was made by coexpression of two subunits: IL15-WT (SEQ ID NO: 10) and sushi-Fc (SEQ ID NO: 13). The resulting protein comprises a fusion of IL-15Rα-sushi to the N-terminus of human IgG1-Fc region, and a noncovalent association with between IL15-WT and IL-15Rα-sushi.

Protein Name: IL15-WT/sushi-IgG2 Da-Fc
This protein was made by coexpression of two subunits: IL15-WT (SEQ ID NO: 10) and sushi-IgG2 Da-Fc (SEQ ID NO: 56). The resulting protein comprises a fusion of IL-15Rα-sushi to the N-terminus of human IgG2 Da-Fc region, and a noncovalent association with IL15-WT (via interaction with IL-15Rα-sushi).

Protein Name: ch9.4-IL15/sushi Fab
This protein was made by coexpression of three subunits: HC-ch9.4-Fab (SEQ ID NO: 14), LC-ch9.4-IL15 (SEQ ID NO: 15), and IL-15Rα-sushi (SEQ ID NO: 9). The resulting protein comprises a fusion of wild-type IL-15 to the C-terminus of the chimeric 9.4 Fab fragment light-chain using linker-L1 (SEQ ID NO: 36), and a noncovalent association between IL-15 and IL-15Rα-sushi. The chimeric 9.4 Fab is an anti-CD45R antibody Fab fragment comprising variable-heavy and variable-light chain domains (VH and VL) from the parental mouse mAb (corresponding to ATCC hybridoma HB-10508) and constant domains from human (human constant kappa domain and human IgG1-$C_H1$ domain).

Protein Name: ch4B2-IL15/sushi Fab
This protein was made by coexpression of three subunits: HC-ch4B2-IL15 (SEQ ID NO: 16), LC-ch4B2-1L15 (SEQ ID NO: 17), and IL-15Rα-sushi (SEQ ID NO: 9). The resulting protein comprises a fusion of wild-type IL-15 to the C-terminus of the chimeric 4B2 Fab fragment light-chain using linker-L1 (SEQ ID NO: 36), and a noncovalent association between IL-15 and IL-15Rα-sushi. The chimeric 4B2 Fab is an anti-CD45R antibody Fab fragment comprising variable-heavy and variable-light chain domains (VH and VL) from the parental mouse mAb (corresponding to ATCC hybridoma HB-11186) and constant domains from human (human constant kappa domain and human IgG1-CH1 domain).

Protein Name: hBC8(23)-IL15/sushi Fab
This protein was made by coexpression of three subunits: HC-hBC8(23)-Fab (SEQ ID NO: 18), LC-hBC8(23)-IL15 (SEQ ID NO: 19), and IL-15Rα-sushi (SEQ ID NO: 9). The resulting protein comprises a fusion of wild-type IL-15 to the C-terminus of the humanized BC8 Fab fragment light-chain using linker-L1 (SEQ ID NO: 36), and a noncovalent association between IL-15 and IL-15Rα-sushi. The humanized BC8(23) Fab is an anti-CD45R antibody Fab fragment comprising variable-heavy and variable-light chain domains (VH and VL) humanized from the parental mouse mAb and constant domains from human (human constant kappa domain and human IgG1-$C_H1$ domain).

Protein Name: hBC8-null-IL15/sushi Fab
This protein was made by coexpression of three subunits: HC-chBC8(23)-null-Fab (SEQ ID NO: 20), LC-hBC8(23)-1L15 (SEQ ID NO: 19), and IL-15Rα-sushi (SEQ ID NO: 9). The resulting protein comprises a fusion of wild-type IL-15 to the C-terminus of the humanized BC8 Fab fragment light-chain using linker-L1 (SEQ ID NO: 36), and a noncovalent association between IL-15 and IL-15Rα-sushi. This protein differs from hBC8(23)-IL15/sushi Fab in that its heavy chain contains a GGGS substitution within the CDR-H3 loop, which results in ablated binding affinity towards CD45R (hence, the designation as "null" binding variant). This IL15 fusion protein thus serves as a negative control for the effect of CD45R engagement.

Protein Name: chBC8-L2-IL15/sushi Fab
This protein was made by coexpression of three subunits: HC-chBC8-Fab (SEQ ID NO: 5), LC-chBC8-L2-IL15 (SEQ ID NO: 21), and IL-15Rα-sushi (SEQ ID NO: 9). The resulting protein comprises a fusion of IL-15 to the N-terminus of the chimeric BC8 Fab fragment light-chain using linker-L2 (SEQ ID NO: 37), and a noncovalent association between IL-15 and IL-15RC-sushi.

Protein Name: chBC8-L3-IL15/sushi Fab

This protein was made by coexpression of three subunits: HC-chBC8-Fab (SEQ ID NO: 5), LC-chBC8-L3-IL15 (SEQ ID NO: 22), and IL-15Rα-sushi (SEQ ID NO: 9). The resulting protein comprises a fusion of IL-15 to the N-terminus of the chimeric BC8 Fab fragment light-chain using linker-L3 (SEQ ID NO: 38), and a noncovalent association between IL-15 and IL-15Ra-sushi.

Protein Name: chMHM24-IL15/sushi Fab

This protein was made by coexpression of three subunits: HC-chMHM24-Fab (SEQ ID NO: 26), LC-MHM24-IL15 (SEQ ID NO: 27), and IL-15Rα-sushi (SEQ ID NO: 9). The resulting protein comprises a fusion of wild-type IL-15 to the C-terminus of the chimeric MHM24 Fab fragment light-chain using linker-L1 (SEQ ID NO: 36), and a noncovalent association with IL-15Rα-sushi (via interaction with IL-15). The chimeric MHM24 Fab is an anti-human CD11a antibody Fab fragment comprising variable-heavy and variable-light chain domains (VH and $V_L$) from the parental mouse mAb and constant domains from human (human constant kappa domain and human IgG1-$C_H1$ domain).

Protein Name: ch1B4-IL15/sushi Fab

This protein was made by coexpression of three subunits: HC-ch1B4-Fab (SEQ ID NO: 28), LC-ch1B4-IL15 (SEQ ID NO: 29), and IL-15Rα-sushi (SEQ ID NO: 9). The resulting protein comprises a fusion of wild-type IL-15 to the C-terminus of the chimeric 1B4 Fab fragment light-chain using linker-L1 (SEQ ID NO: 36), and a noncovalent association with IL-15Rα-sushi (via interaction with IL-15). The chimeric 1B4 Fab is an anti-human CD18 antibody Fab fragment comprising variable-heavy and variable-light chain domains (VH and VL) from the parental mouse mAb and constant domains from human (human constant kappa domain and human IgG1-$C_H1$ domain).

Protein Name: chOKT8-IL15/sushi Fab

This protein was made by coexpression of three subunits: HC-chOKT8-Fab (SEQ ID NO: 30), LC-chOKT8-IL15 (SEQ ID NO: 31), and IL-15Rα-sushi (SEQ ID NO: 9). The resulting protein comprises a fusion of wild-type IL-15 to the C-terminus of the chimeric OKT8 Fab fragment light-chain using linker-L1 (SEQ ID NO: 36), and a noncovalent association with IL-15Rα-sushi (via interaction with IL-15). The chimeric OKT8 Fab is an anti-human CD8 antibody Fab fragment comprising variable-heavy and variable-light chain domains (VH and VL) from the parental mouse mAb and constant domains from human (human constant kappa domain and human IgG1-CH1 domain).

Protein Name: h9.4Fab-scIL-12p70

This protein was made by coexpression of two subunits: HC-h9.4Fab (SEQ ID NO: 79) and LC-h9.4Fab-scIL-12p70 (SEQ ID NO: 82). The resulting protein comprises a fusion of a single-chain human IL-12p70 to the C-terminus of h9.4 Fab fragment light-chain using Linker-1 (SEQ ID NO: 36). The h9.4 Fab is an anti-human CD45R antibody Fab fragment comprising variable-heavy and variable-light chain domains (VH and VL) from h9.4 and constant domains from human (human constant kappa domain and human IgG1-$C_H1$ domain).

Protein Name: h9.4Fab-h9.4scFv-scIL-12p70

This protein was made by coexpression of two subunits: HC-h9.4Fab-h9.4scFv (SEQ ID NO: 80) and LC-h9.4Fab-scIL-12p70 (SEQ ID NO: 82). The resulting protein comprises a fusion of a single-chain human IL-12p70 to the C-terminus of h9.4 Fab fragment light-chain using Linker-1 (SEQ ID NO: 36) and a fusion of an h9.4 scFv to the h9.4 Fab fragment heavy-chain using Linker-1.

Protein Name: h9.4Fab-hBC8scFv-scIL-12-p70

This protein was made by coexpression of two subunits: HC-h9.4Fab-hBC8scFv (SEQ ID NO: 81) and LC-h9.4Fab-scIL-12p70 (SEQ ID NO: 82). The resulting protein comprises a fusion of a single-chain human IL-12p70 to the C-terminus of h9.4 Fab fragment light-chain using Linker-1 (SEQ ID NO: 36) and a fusion of an hBC8 scFv to the h9.4 Fab fragment heavy-chain using Linker-1 (SEQ ID NO: 36).

Protein Name: h9.4Fab-scIL-12p70AB

This protein is made by coexpression of two subunits: HC-h9.4Fab (SEQ ID NO: 79) and LC-h9.4Fab-scIL-12p70AB (SEQ ID NO: 102). The resulting protein comprises a fusion of a single-chain human IL-12p70 to the C-terminus of h9.4 Fab fragment light-chain using Linker-1 (SEQ ID NO: 36).

Protein Name: h9.4Fab-h9.4scFv-scIL-12p70AB

This protein is made by coexpression of two subunits: HC-h9.4Fab-h9.4scFv (SEQ ID NO: 80) and LC-h9.4Fab-scIL-12p70AB (SEQ ID NO: 102). The resulting protein comprises a fusion of a single-chain human IL-12p70 to the C-terminus of h9.4 Fab fragment light-chain using Linker-1 (SEQ ID NO: 36) and a fusion of an h9.4 scFv to the h9.4 Fab fragment heavy-chain using Linker-1.

Protein Name: h9.4Fab-hBC8scFv-scIL-12-p70AB

This protein is made by coexpression of two subunits: HC-h9.4Fab-hBC8scFv (SEQ ID NO: 81) and LC-h9.4Fab-scIL-12p70AB (SEQ ID NO: 102). The resulting protein comprises a fusion of a single-chain human IL-12p70 to the C-terminus of h9.4 Fab fragment light-chain using Linker-1 (SEQ ID NO: 36) and a fusion of an hBC8 scFv to the h9.4 Fab fragment heavy-chain using Linker-1 (SEQ ID NO: 36).

Protein Name: h9.4Fab-IL-12p70AB

This protein is made by coexpression of three subunits: HC-h9.4Fab (SEQ ID NO: 79), LC-h9.4Fab-IL-12A (SEQ ID NO: 103), and IL-12B (SEQ ID NO: 49). The resulting protein comprises a fusion of a human IL-12A to the C-terminus of h9.4 Fab fragment light-chain using Linker-1 (SEQ ID NO: 36). The full IL-12p70 is formed by association between IL-12A and IL-12B.

Protein Name: h9.4Fab-h9.4scFv-IL-12p70AB

This protein is made by coexpression of three subunits: HC-h9.4Fab-h9.4scFv (SEQ ID NO: 80), LC-h9.4Fab-IL-12A (SEQ ID NO: 103), and IL-12B (SEQ ID NO: 49). The resulting protein comprises a fusion of a human IL-12A to the C-terminus of h9.4 Fab fragment light-chain using Linker-1 (SEQ ID NO: 36) and a fusion of an h9.4 scFv to the h9.4 Fab fragment heavy-chain using Linker-1. The full IL-12p70 is formed by association between IL-12A and IL-12B.

Protein Name: h9.4Fab-hBC8scFv-IL-12-p70AB

This protein is made by coexpression of three subunits: HC-h9.4Fab-hBC8scFv (SEQ ID NO: 81), LC-h9.4Fab-IL-12A (SEQ ID NO: 103), and IL-12B (SEQ ID NO: 49). The resulting protein comprises a fusion of a human IL-12A to the C-terminus of h9.4 Fab fragment light-chain using Linker-1 (SEQ ID NO: 36) and a fusion of an hBC8 scFv to the h9.4 Fab fragment heavy-chain using Linker-1 (SEQ ID NO: 36). The full IL-12p70 is formed by association between IL-12A and IL-12B.

Protein Name: h9.4Fab-IL-12p70BA

This protein is made by coexpression of three subunits: HC-h9.4Fab (SEQ ID NO: 79), LC-h9.4Fab-IL-12B (SEQ ID NO: 104), and IL-12A (SEQ ID NO: 47). The resulting protein comprises a fusion of a human IL-12B to the C-terminus of h9.4 Fab fragment light-chain using Linker-1 (SEQ ID NO: 36). The full IL-12p70 is formed by association between IL-12B and IL-12A.

Protein Name: h9.4Fab-h9.4scFv-IL-12p70BA

This protein is made by coexpression of three subunits: HC-h9.4Fab-h9.4scFv (SEQ ID NO: 80), LC-h9.4Fab-IL-12B (SEQ ID NO: 104), and IL-12A (SEQ ID NO: 47). The resulting protein comprises a fusion of a human IL-12B to the C-terminus of h9.4 Fab fragment light-chain using Linker-1 (SEQ ID NO: 36) and a fusion of an h9.4 scFv to the h9.4 Fab fragment heavy-chain using Linker-1. The full IL-12p70 is formed by association between IL-12B and IL-12A.

Protein Name: h9.4Fab-hBC8scFv-IL-12-p70BA

This protein is made by coexpression of three subunits: HC-h9.4Fab-hBC8scFv (SEQ ID NO: 81), LC-h9.4Fab-IL-12B (SEQ ID NO: 104), and IL-12A (SEQ ID NO: 47). The resulting protein comprises a fusion of a human IL-12B to the C-terminus of h9.4 Fab fragment light-chain using Linker-1 (SEQ ID NO: 36) and a fusion of an hBC8 scFv to the h9.4 Fab fragment heavy-chain using Linker-1 (SEQ ID NO: 36). The full IL-12p70 is formed by association between IL-12B and IL-12A.

Protein Name: chM1Fab-scIL-12p70

This protein was made by coexpression of two subunits: HC-chM1Fab (SEQ ID NO: 83) and LC-chM1Fab-scIL-12p70 (SEQ ID NO: 84). The resulting protein comprises a fusion of a single-chain mouse IL-12p70 to the C-terminus of chM1 Fab fragment light-chain using Linker-1 (SEQ ID NO: 36).

Protein Name: chM1Fab-M1scFv-scIL-12p70

This protein was made by coexpression of two subunits: HC-chM1Fab-M1scFv (SEQ ID NO: 86) and LC-chM1Fab-scIL-12p70 (SEQ ID NO: 84). The resulting protein comprises a fusion of a single-chain mouse IL-12p70 to the C-terminus of chM1 Fab fragment light-chain using Linker-1 (SEQ ID NO: 36) and a fusion of an M1 scFv to the chM1 Fab fragment heavy-chain using Linker-1 (SEQ ID NO: 36).

Protein Name: chM1Fab-IL-15/sushi

This protein was made by co-expression of three subunits: HC-chM1Fab (SEQ ID NO: 83), LC-chM1Fab-IL-15 (SEQ ID NO: 85), and IL-15Rα-sushi (SEQ ID NO: 9). The resulting protein comprises a fusion of wild-type human IL-15 to the C-terminus of chM1 Fab fragment light-chain using Linker-1 (SEQ ID NO: 36), and a noncovalent association with IL-15Rα-sushi (via interaction with IL-15).

Protein Name: chM1Fab-M1scFv-IL-15/sushi

This protein was made by coexpression of three subunits: HC-chM1Fab-M1scFv (SEQ ID NO: 86) and LC-chM1Fab-IL-15 (SEQ ID NO: 85), and IL-15Rα-sushi (SEQ ID NO: 9). The resulting protein comprises a fusion of wild-type human IL-15 to the C-terminus of chM1 Fab fragment light-chain using Linker-1 (SEQ ID NO: 36), a fusion of an M1 scFv to the chM1 Fab fragment heavy-chain using Linker-1 (SEQ ID NO: 36), and a noncovalent association with IL-15Rα-sushi (via interaction with IL-15).

Protein Name: chY169Fab-IL-15/sushi

This protein was made by coexpression of three subunits: HC-chY169Fab (SEQ ID NO: 87), LC-chY169Fab-IL-15 (SEQ ID NO: 88), and IL-15Rα-sushi (SEQ ID NO: 9). The resulting protein comprises a fusion of wild-type IL-15 to the C-terminus of the chimeric Y169 Fab fragment light-chain using Linker-1 (SEQ ID NO: 36), and a noncovalent association with IL-15Rα-sushi (via interaction with IL-15).

Protein Name: chY169Fab-M1scFv-IL-15/sushi

This protein was made by coexpression of three subunits: HC-chY169Fab-M1scFv (SEQ ID NO: 89), LC-chY169Fab-IL-15 (SEQ ID NO: 88), and IL-15Rα-sushi (SEQ ID NO: 9). The resulting protein comprises a fusion of wild-type IL-15 to the C-terminus of the chimeric Y169 Fab fragment light-chain using Linker-1 (SEQ ID NO: 36), a fusion of M1 scFv to the chY169 Fab fragment heavy-chain using Linker-1 (SEQ ID NO: 36), and a non-covalent association with IL-15Rα-sushi (via interaction with IL-15).

Protein Name: chY169Fab-M1scFv-scIL-12p70

This protein was made by coexpression of two subunits: HC-chY169Fab-M1scFv (SEQ ID NO: 89) and LC-chY169Fab-scIL-12p70 (SEQ ID NO: 90). The resulting protein comprises a fusion of a single-chain mouse IL-12p70 to the C-terminus of the chimeric Y 169 Fab fragment light-chain using Linker-1 (SEQ ID NO: 36), and a fusion of M1 scFv to the chY169 Fab fragment heavy-chain using Linker-1 (SEQ ID NO: 36).

Protein Name: chY169Fab-scIL-12p70

This protein was made by coexpression of two subunits: HC-chY169Fab-(SEQ ID NO: 87) and LC-chY169Fab-scIL-12p70 (SEQ ID NO: 90). The resulting protein comprises a fusion of a single-chain mouse IL-12p70 to the C-terminus of the chimeric Y169 Fab fragment light-chain using Linker-1 (SEQ ID NO: 36).

Nucleic Acids/Vectors/Cells

The disclosure also features nucleic acids comprising nucleotide sequences that encode the immunostimulatory fusion molecules described herein. Further provided herein are vectors comprising the nucleotide sequences encoding an IFMs and the antibody molecule described herein. In one embodiment, the vectors comprise nucleotides encoding the IFMs and the antibody molecules described herein. In one embodiment, the vectors comprise the nucleotide sequences described herein. The vectors include, but are not limited to, a virus, plasmid, cosmid, lambda phage or a yeast artificial chromosome (YAC). Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., $E.$ $coli$. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

The disclosure also provides host cells comprising a nucleic acid encoding an antibody molecule as described herein. In one embodiment, the host cells are genetically engineered to comprise nucleic acids encoding the antibody molecule. In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter. The disclosure also provides host cells comprising the vectors described herein. The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Compositions

Compositions, including pharmaceutical compositions, comprising the immunostimulatory fusion molecules are provided herein. A composition can be formulated in pharmaceutically-acceptable amounts and in pharmaceutically-acceptable compositions. The term "pharmaceutically acceptable" means a non-toxic material that does not interfere with the effectiveness of the biological activity of the active ingredients (e.g., biologically-active proteins of the nanoparticles). Such compositions may, in some embodiments, contain salts, buffering agents, preservatives, and optionally other therapeutic agents. Pharmaceutical compositions also may contain, in some embodiments, suitable preservatives. Pharmaceutical compositions may, in some embodiments, be presented in unit dosage form and may be prepared by any of the methods well-known in the art of pharmacy. Pharmaceutical compositions suitable for parenteral administration, in some embodiments, comprise a sterile aqueous or non-aqueous preparation of the nanoparticles, which is, in some embodiments, isotonic with the blood of the recipient subject. This preparation may be formulated according to known methods. A sterile injectable preparation also may be a sterile injectable solution or suspension in a non-toxic parenterally-acceptable diluent or solvent.

Additional compositions include modified cells, such as modified immune cells further comprising one or more tethered fusions proteins on their cell surface. This can be useful for ex vivo preparation of a cell therapy such as an adoptive cell therapy, CAR-T cell therapy, engineered TCR T cell therapy, a tumor infiltrating lymphocyte therapy, an antigen-trained T cell therapy, an enriched antigen-specific T cell therapy, or an NK cell therapy.

In some embodiments, the IFM of the present disclosure can be administered directly to a patient in need thereof, e.g., in the form of a nanogel or hydrogel or biogel, as agents for specific delivery of therapeutic proteins via receptor mediated binding of receptors unique to specific cells (e.g., CD4 or CD8). Such direct administration can be systemic (e.g., parenteral such as intravenous injection or infusion) or local (e.g., intratumoral, e.g., injection into the tumor microenvironment). The phrases "parenteral administration" and "administered parenterally" as used herein refer to modes of administration other than enteral (i.e, via the digestive tract) and topical administration, usually by injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection, and infusion.

In some embodiments, the IFM of the present disclosure can be used as ex vivo agents to induce activation and expansion of isolated autologous and allogenic cells prior to administration or reintroduction to a patient, via systemic or local administration. For example, the expanded cells can be used in T cell therapies including ACT (adoptive cell transfer) and also with other important immune cell types, including for example, B cells, tumor infiltrating lymphocytes, NK cells, antigen-specific CD8 T cells, T cells genetically engineered to express chimeric antigen receptors (CARs) or CAR-T cells, T cells genetically engineered to express T-cell receptors specific to an tumor antigen, tumor infiltrating lymphocytes (ILs), and/or antigen-trained T cells (e.g., T cells that have been "trained" by antigen presenting cells (APCs) displaying antigens of interest, e.g. tumor associated antigens (TAA)).

Therapeutic Uses and Methods

The immunostimulatory fusion molecules and compositions containing such have numerous therapeutic utilities, including, e.g., the treatment of cancers and infectious diseases. The present disclosure provides, inter alia, methods for inducing an immune response in a subject with a cancer in order to treat the subject having cancer. Exemplary methods comprise administering to the subject a therapeutically effective amount of any of the immunostimulatory fusion molecules described herein, wherein the IFM has been selected and designed to increase the cell surface availability of a cytokine and consequently potentiate its signaling.

Methods described herein include treating a cancer in a subject by using an IFM, e.g., an IFM or a nanoparticle comprising the IFM as described herein, e.g., using a pharmaceutical composition described herein. Also provided are methods for reducing or ameliorating a symptom of a cancer in a subject, as well as methods for inhibiting the growth of a cancer and/or killing one or more cancer cells. In embodiments, the methods described herein decrease the size of a tumor and/or decrease the number of cancer cells in a subject administered with a described herein or a pharmaceutical composition described herein.

In embodiments, the cancer is a hematological cancer. In embodiments, the hematological cancer is a leukemia or a lymphoma. As used herein, a "hematologic cancer" refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sézary syndrome, Waldenström macroglobulinemia), chronic mycloproliferative neoplasm, Langerhans cell histiocytosis, multiple myeloma/plasma cell neoplasm, myelodysplastic syndrome, or myelodysplastic/myeloproliferative neoplasm.

In embodiments, the cancer is a solid cancer. Exemplary solid cancers include, but are not limited to, ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof.

In embodiments, the immunostimulatory fusion molecules (or pharmaceutical composition) are administered in a manner appropriate to the disease to be treated or prevented. The quantity and frequency of administration will be determined by such factors as the condition of the patient, and the type and severity of the patient's disease. Appropriate dosages may be determined by clinical trials. For example, when "an effective amount" or "a therapeutic amount" is indicated, the precise amount of the pharmaceutical composition (or immunostimulatory fusion molecules) to be administered can be determined by a physician with consideration of individual differences in tumor size, extent of infection or metastasis, age, weight, and condition of the subject. In embodiments, the pharmaceutical composition described herein can be administered at a dosage of $10^4$ to $10^9$ cells/kg body weight, e.g., $10^5$ to $10^6$ cells/kg body weight, including all integer values within those ranges. In embodiments, the pharmaceutical composition described herein can be administered multiple times at these dosages. In embodiments, the pharmaceutical composition described herein can be administered using infusion techniques described in immunotherapy (see, e.g., Rosenberg et al., New Eng. J. of Med. 319:1676, 1988).

In embodiments, the immunostimulatory fusion molecules or pharmaceutical composition is administered to the subject parenterally. In embodiments, the cells are administered to the subject intravenously, subcutaneously, intratumorally, intranodally, intramuscularly, intradermally, or intraperitoncally. In embodiments, the cells are administered, e.g., injected, directly into a tumor or lymph node. In embodiments, the cells are administered as an infusion (e.g., as described in Rosenberg et al., New Eng. J. of Med. 319:1676, 1988) or an intravenous push. In embodiments, the cells are administered as an injectable depot formulation.

In embodiments, the subject is a mammal. In embodiments, the subject is a human, monkey, pig, dog, cat, cow, sheep, goat, rabbit, rat, or mouse. In embodiments, the subject is a human. In embodiments, the subject is a pediatric subject, e.g., less than 18 years of age, e.g., less than 17, 16, 15, 14, 13, 12, 11, 10, 9, 8, 7, 6, 5, 4, 3, 2, 1 or less years of age. In embodiments, the subject is an adult, e.g., at least 18 years of age, e.g., at least 19, 20, 21, 22, 23, 24, 25, 25-30, 30-35, 35-40, 40-50, 50-60, 60-70, 70-80, or 80-90 years of age.

Combination Therapies

The immunostimulatory fusion molecules disclosed herein can be used in combination with a second therapeutic agent or procedure.

In some embodiments, the immunostimulatory fusion molecule is administered in combination with radiotherapy.

In some embodiments, the immunostimulatory fusion molecule is administered in conjunction with a cell therapy, e.g., a cell therapy chosen from an adoptive cell therapy, CAR-T cell therapy, engineered TCR T cell therapy, a tumor infiltrating lymphocyte therapy, an antigen-trained T cell therapy, or an enriched antigen-specific T cell therapy.

In embodiments, the immunostimulatory fusion molecule and the second therapeutic agent or procedure are administered/performed after a subject has been diagnosed with a cancer, e.g., before the cancer has been eliminated from the subject. In embodiments, the immunostimulatory fusion molecule and the second therapeutic agent or procedure are administered/performed simultaneously or concurrently. For example, the delivery of one treatment is still occurring when the delivery of the second commences, e.g., there is an overlap in administration of the treatments. In other embodiments, the immunostimulatory fusion molecule and the second therapeutic agent or procedure are administered/performed sequentially. For example, the delivery of one treatment ceases before the delivery of the other treatment begins.

In embodiments, combination therapy can lead to more effective treatment than monotherapy with either agent alone. In embodiments, the combination of the first and second treatment is more effective (e.g., leads to a greater reduction in symptoms and/or cancer cells) than the first or second treatment alone. In embodiments, the combination therapy permits use of a lower dose of the first or the second treatment compared to the dose of the first or second treatment normally required to achieve similar effects when administered as a monotherapy. In embodiments, the combination therapy has a partially additive effect, wholly additive effect, or greater than additive effect.

In one embodiment, the immunostimulatory fusion molecule is administered in combination with a therapy, e.g., a cancer therapy (e.g., one or more of anti-cancer agents, immunotherapy, photodynamic therapy (PDT), surgery and/or radiation). The terms "chemotherapeutic," "chemotherapeutic agent," and "anti-cancer agent" are used interchangeably herein. The administration of the immunostimulatory fusion molecule and the therapy, e.g., the cancer therapy, can be sequential (with or without overlap) or simultaneous. Administration of the immunostimulatory fusion molecule can be continuous or intermittent during the course of therapy (e.g., cancer therapy). Certain therapies described herein can be used to treat cancers and non-cancerous diseases. For example, PDT efficacy can be enhanced in cancerous and non-cancerous conditions (e.g., tuberculosis) using the methods and compositions described herein (reviewed in, e.g., Agostinis, P. et al. (2011) CA Cancer J. Clin. 61:250-281).

Anti-Cancer Therapies

In other embodiments, the immunostimulatory fusion molecule is administered in combination with a low or small molecular weight chemotherapeutic agent. Exemplary low or small molecular weight chemotherapeutic agents include, but not limited to, 13-cis-retinoic acid (isotretinoin, ACCUTANE®), 2-CdA (2-chlorodeoxyadenosine, cladribine, LEUSTATIN™), 5-azacitidine (azacitidine, VIDAZA®), 5-fluorouracil (5-FU, fluorouracil, ADRUCIL®), 6-mercaptopurine (6-MP, mercaptopurine, PURINETHOL®), 6-TG (6-thioguanine, thioguanine, THIOGUANINE TABLOID®), abraxane (paclitaxel protein-bound), actinomycin-D (dactinomycin, COSMEGEN®), alitretinoin (PANRETIN®), all-transretinoic acid (ATRA, tretinoin, VESANOID®), altretamine (hexamethylmelamine, HMM, HEXALEN®), amethopterin (methotrexate, methotrexate sodium, MTX, TREXALL™, RHEUMATREX®), amifostine (ETHYOL®), arabinosylcytosine (Ara-C, cytarabine, CYTOSAR-U®), arsenic trioxide (TRISENOX®), asparaginase (Erwinia L-asparaginase, L-asparaginase, ELSPAR®, KIDROLASE®), BCNU (carmustine, BiCNU®), bendamustine (TREANDA®), bexarotene (TARGRETIN®), bleomycin (BLENOXANE®), busulfan (BUSULFEX®, MYLERAN®), calcium leucovorin (Citrovorum Factor, folinic acid, leucovorin), camptothecin-11 (CPT-11, irinotecan, CAMPTOSAR®), capecitabine (XELODA®), carboplatin (PARAPLATIN®), carmustine wafer (prolifeprospan 20 with carmustine implant, GLIADEL® wafer), CC1-779 (temsirolimus, TORISEL®), CCNU (lomustine, CeeNU), CDDP (cisplatin, PLATINOL®, PLATINOL-AQ®), chlorambucil (leukeran), cyclophosphamide (CYTOXAN®, NEOSAR®), dacarbazine (DIC, DTIC, imidazole carboxamide, DTIC-DOME®), daunomycin (daunorubicin, daunorubicin hydrochloride, rubidomycin hydrochloride, CERUBIDINE®), decitabine (DACOGEN®), dexrazoxane (ZINECARD®), DHAD (mitoxantrone, NOVANTRONE®), docetaxel (TAXOTERE®), doxorubicin (ADRIAMYCIN®, RUBEX®), epirubicin (ELLENCE™), estramustine (EMCYT®), etoposide (VP-16, etoposide phosphate, TOPOSAR®, VEPESID®, ETOPOPHOS®), floxuridine (FUDR®), fludarabine (FLUDARA®), fluorouracil (cream) (CARAC™. EFUDEX®, FLUOROPLEX®), gemcitabine (GEMZAR®), hydroxyurea (HYDREA®, DROXIA™, MYLOCEL™), idarubicin (IDAMYCIN®), ifosfamide (IFEX®), ixabepilone (IXEMPRA™), LCR (leurocristine, vincristine, VCR, ONCOVIN®, VINCASAR PFS®), L-PAM (L-sarcolysin, melphalan, phenylalanine mustard, ALKERAN®), mechlorethamine (mechlorethamine hydrochloride, mustine, nitrogen mustard, MUSTARGEN®), mesna (MESNEX™), mitomycin (mitomycin-C, MTC, MUTAMYCIN®), nelarabine (ARRANON®), oxaliplatin (ELOXATIN™), paclitaxel (TAXOL®, ONXAL™), pegaspargase (PEG-L-asparaginase, ONCOSPAR®), PEMETREXED (ALIMTA®), pentostatin (NIPENT®), procarbazine (MATULANE®), streptozocin (ZANOSAR®), temozolomide (TEMODAR®), teniposide (VM-26, VUMON®), TESPA (thiophosphoamide, thiotepa, TSPA, THIOPLEX®), topotecan (HYCAMTIN®), vinblastine (vinblastine sulfate, vincaleukoblastine, VLB, ALKABAN-AQ®, VELBAN®), vinorelbine (vinorelbine tartrate, NAVELBINE®), and vorinostat (ZOLINZA®).

In another embodiment, the immunostimulatory fusion molecule is administered in conjunction with a biologic. Exemplary biologics include, e.g., HERCEPTIN® (trastuzumab); FASLODEX® (fulvestrant); ARIMIDEX® (anastrozole); Aromasin® (exemestane); FEMARA® (letrozole); NOLVADEX® (tamoxifen), AVASTIN® (bevacizumab); and ZEVALIN® (ibritumomab tiuxetan).

EXAMPLES

Example 1. Constructing Antibody/IL-15 Fusion Molecules with Increased Biological Persistence To demonstrate the ability to generate IFMs with improved properties we constructed a series of IFMs comprising multiple formats: (i) IFMs comprising an IgG, Fab fragment, or scFv fragment, (ii) fusion to the N- or C-terminus of the antibody or antibody fragment; (iii) fusion of either IL-15 or the IL-15Rα sushi domain to the antibody or antibody fragment (e.g., FIG. 1 and FIGS. 2A-2C); and (iv) IFMs comprising varied linker composition between the antibody and cytokine.

A. IL-15 IFMs Comprising Multiple Different Antibody Formats

To explore the potential for fusion molecules of IL-15 and an immune-targeted antibody to improve IL-15 biological activity we constructed IFMs comprising IL-15 and mAb clone BC8, which targets human CD45, an abundant receptor on the surface of immune cells (Cyster et al., EMBO Journal, Vol 10, no 4, 893-902, 1991). The IFMs comprised three different antibody formats: scFv, Fab, and full-length IgG. Briefly, wild-type IL-15 was genetically fused to the C-terminus of the Fab or IgG light-chain using an amino acid linker consisting of (GGGGS)3 (SEQ ID NO: 36) or to the C-terminus of the scFv using the amino acid linker RSGSGGGSLQ (SEQ ID NO: 39). The Fab and IgG antibody formats comprised human constant regions and variable domains from the mouse monoclonal antibody BC8 (e.g. chBC8 Fab or chBC8 IgG). The scFv comprised BC8 heavy- and light-chain variable domains genetically fused with a (GGGGS)3 linker. The IL-15/antibody fusions were co-expressed with IL-15Rα-sushi; the high-affinity interaction between IL-15 and sushi resulted in an IL-15-antibody complex comprising a noncovalent association with IL-15Rα-sushi. Together, this resulted in three IFM variants: chBC8-IL15/sushi scFv, chBC8-IL15/sushi Fab, and chBC8-IL15/sushi IgG (FIG. 2A; see Protein Variants section for more details).

Figure 1:
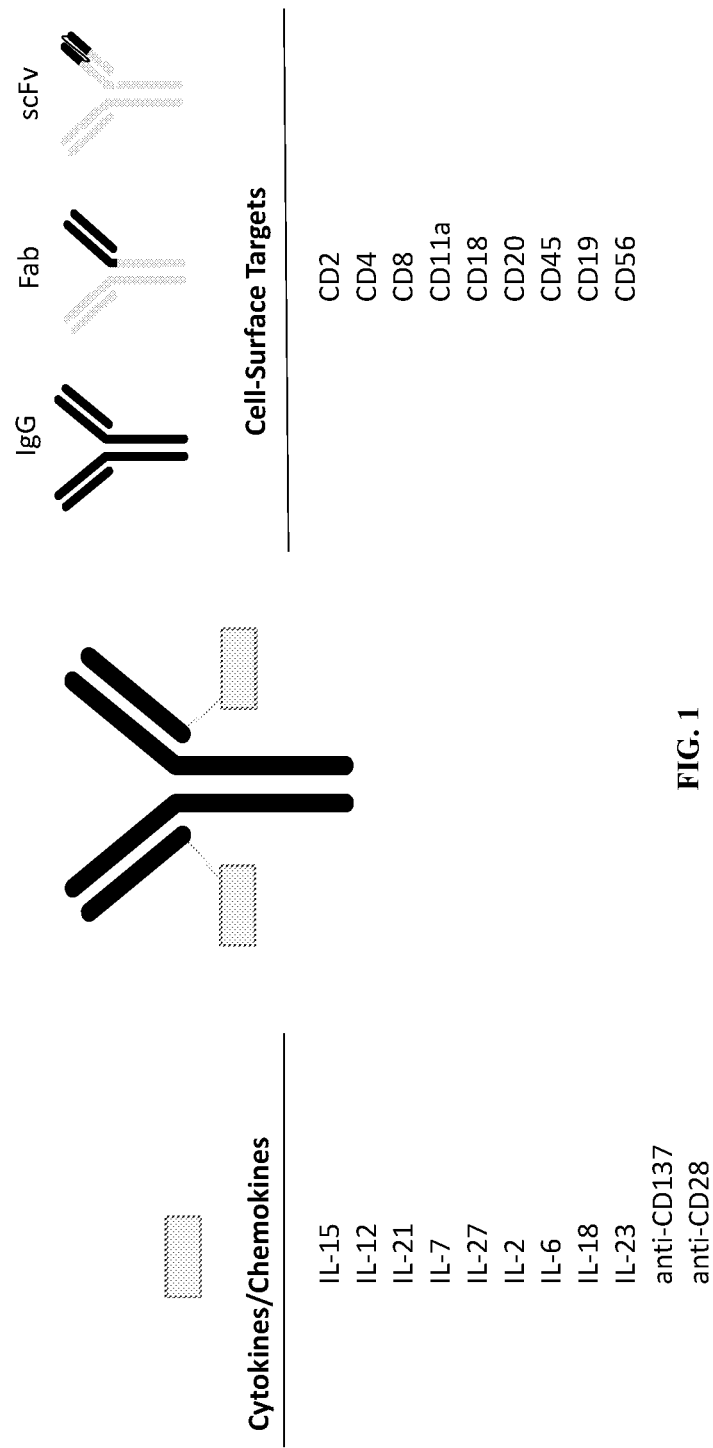
FIG. 1 depicts exemplary fusion proteins of the present disclosure combining a cytokine and an immunoglobulin moiety for cell-surface targeting and stimulation.
Figure 2A:
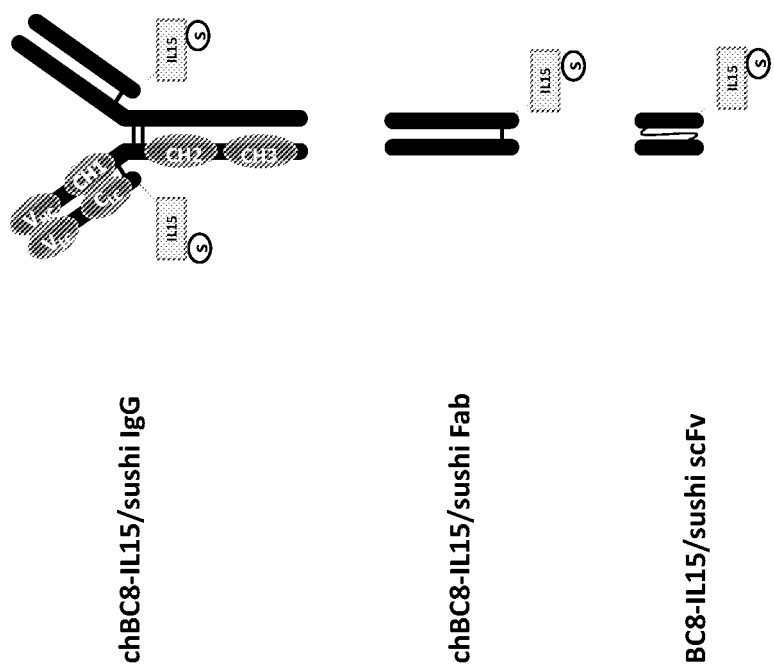
FIGS. 2A-2C depict IFMs comprising various antibody formats.
Figures 2B, 2C:
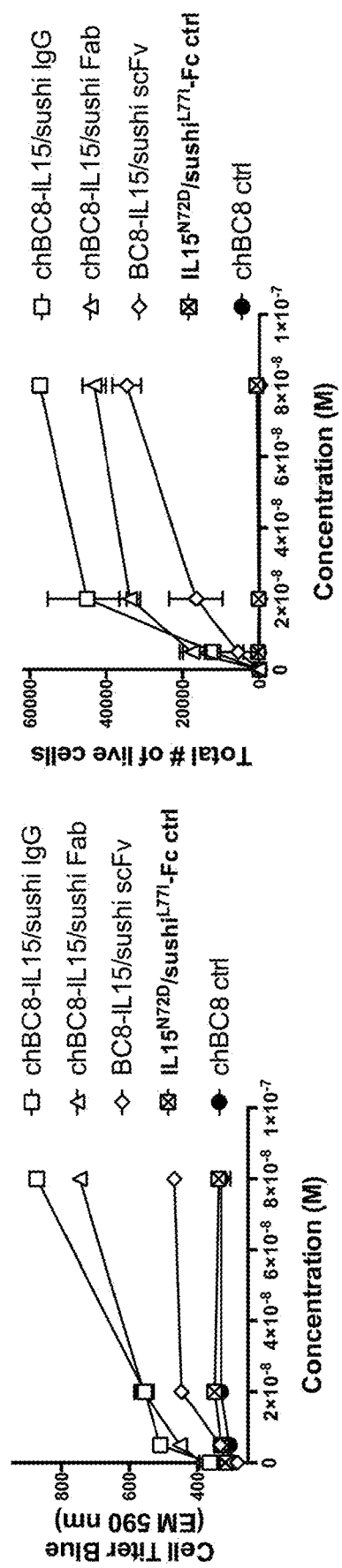

The effects of the IFMs on CD8 T cell expansion were evaluated using a pulse bioassay in which the cytokine is incubated with cells for a fixed amount of time followed by removal of unbound cytokine by washing. As compared with a "static" stimulation assay, in which the cytokine is not washed away, the pulse bioassay provides better characterization of the persistence of a biological effect. It also accommodates confounding factors associated with ligand-depletion, which is a well-appreciated challenge for quantitative analysis of high-affinity receptor/ligand interactions (Hulme, Tevethick, Ligand binding assays at equilibrium:

validation and interpretation Br J Pharm 2010, 161:1219-1237). The same principles apply to quantitative cell-based assays of cytokines and growth factors that mediate their effects by binding to cellular receptors. We compared the effects of the IFMs to an IL15/sushi-Fc protein comprising a sushi domain containing a conservative L77I mutation fused to a human IgG1-Fc domain, and noncovalently associated (via interaction with the sushi domain) with an IL-15 variant containing an N72D mutation: IL15$^{N72D}$/sushiL77I-Fc. The N72D mutation is purported to improve agonistic properties of IL-15 (Zhu, Marcus, Xu, Lee, et al. Novel Human Interleukin-15 Agonists. Journal of Immunology 2009). As a negative control we also evaluated chBC8 alone (without fusion to IL-15). IFMs and controls were incubated with CD8 T cells for 1 hr at 37° C., followed by three washes to remove unbound protein. Cells were then plated in full media, allowed to grow for three days, and then were assessed for proliferation using both CellTiter Blue (FIG. 2B) and flow cytometry counting beads (FIG. 2C). Both of these methods yielded consistent results, and demonstrated that all three antibody formats were capable of producing IFMs with greater persistence than the IL-15$^{N72D}$/sushiL77I-Fc protein. There was a trend of increasing potency of IFMs containing scFv, Fab, or IgG (i.e. potency: IgG IFM>Fab IFM>scFv IFM). The negative control of the chBC8 antibody alone did not induce T cell expansion indicating the presence of IL-15 is necessary for the proliferative effects of the IFMs. The foregoing provides a non-limiting example of a fusion of IL-15 to an anti-CD45 antibody or antibody fragment that improves biological persistence of IL-15. Multiple antibody formats, e.g., as described herein, are capable of producing such IFMs with improved potency.

B. IFMs Comprising Varied Fusion Strategies of IL-15 to Anti-CD45

To explore alternative fusion strategies between the cytokine and the antibody of the IFM we constructed six additional IFMs comprising fusion of IL-15 to the N- or C-terminus of chimeric BC8 Fab or IgG antibodies. The first two IFMs were constructed by genetically fusing IL-15 to the N-terminus of chBC8 Fab or chBC8 IgG light-chains and the antibody fusions were co-expressed with IL-15Rα to result in the IFMs: IL15-chBC8/sushi Fab and IL15-chBC8/sushi IgG (FIGS. 3A-3B; see "Protein Variants" section for more details). We use a naming convention of chBC8-IL15 in Example 1A above and IL15-chBC8 here to refer to fusion of IL-15 to the antibody C- or N-terminus, respectively. The four additional IFMs were constructed by fusing wild-type IL-15Rα-sushi to the N- or C-terminus of the chBC8 Fab or IgG light-chain, and co-expressed these antibody fusions with IL-15$^{N72D}$ (FIGS. 3C-3D): chBC8-sushi/IL15$^{N72D}$ Fab, sushi-chBC8/IL15$^{N72D}$ Fab, chBC8-sushi/IL15$^{N72D}$ IgG, sushi-chBC8/IL15$^{N72D}$ IgG (see Protein Variants section for more details). Along with the two Fab and IgG IFMs in Example 1A (chBC8-IL15/sushi Fab and chBC8-IL15/sushi IgG) these eight IFMs allowed us to test a variety of antibody fusion strategies, genetic fusion of IL-15 vs. genetic fusion of sushi to the immune-targeting moiety, and IFMs comprising either wild-type or mutated IL-15 variants.

Figures 3A, 3B:
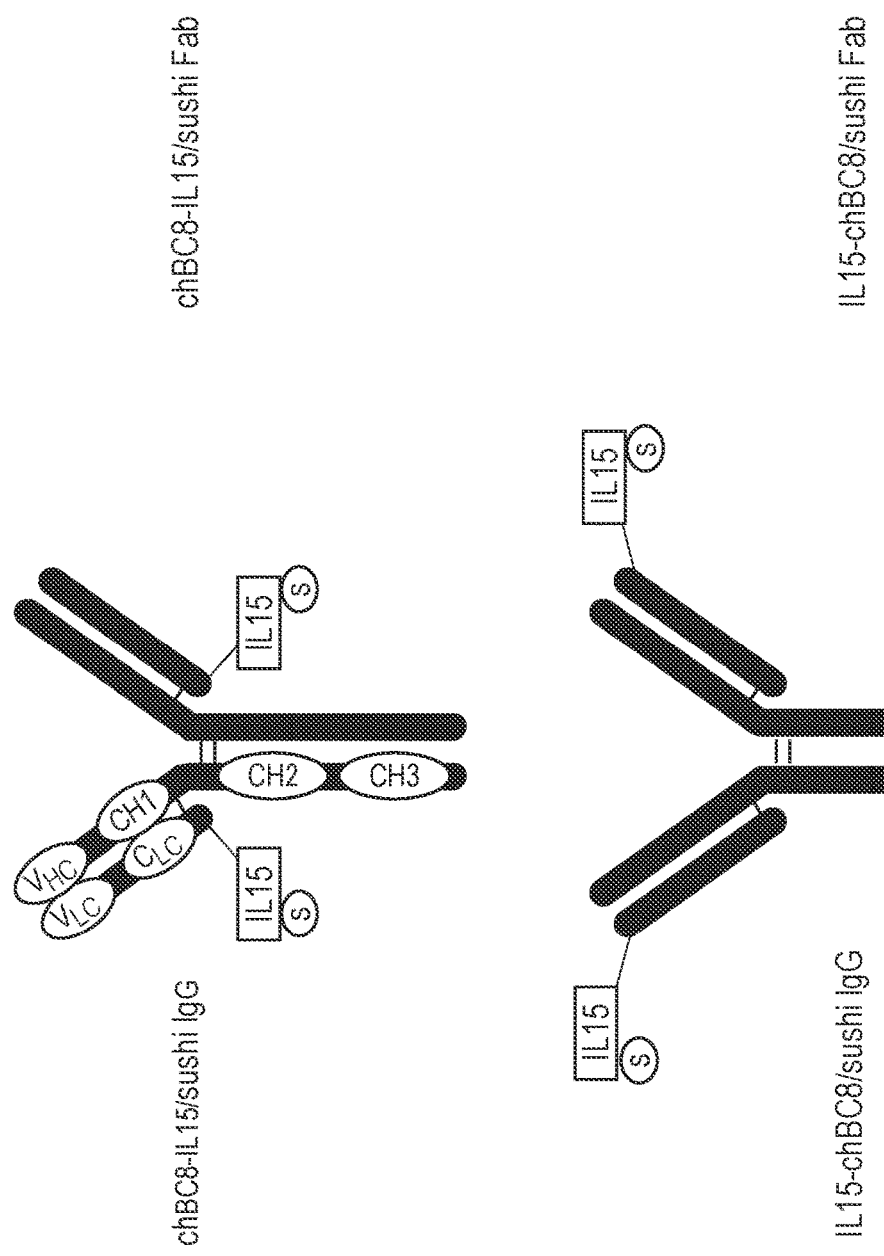
FIGS. 3A-3D depict a schematic for various fusion strategies between the IL-15/sushi complex and an anti-CD45 antibody.
Figures 3C, 3D:
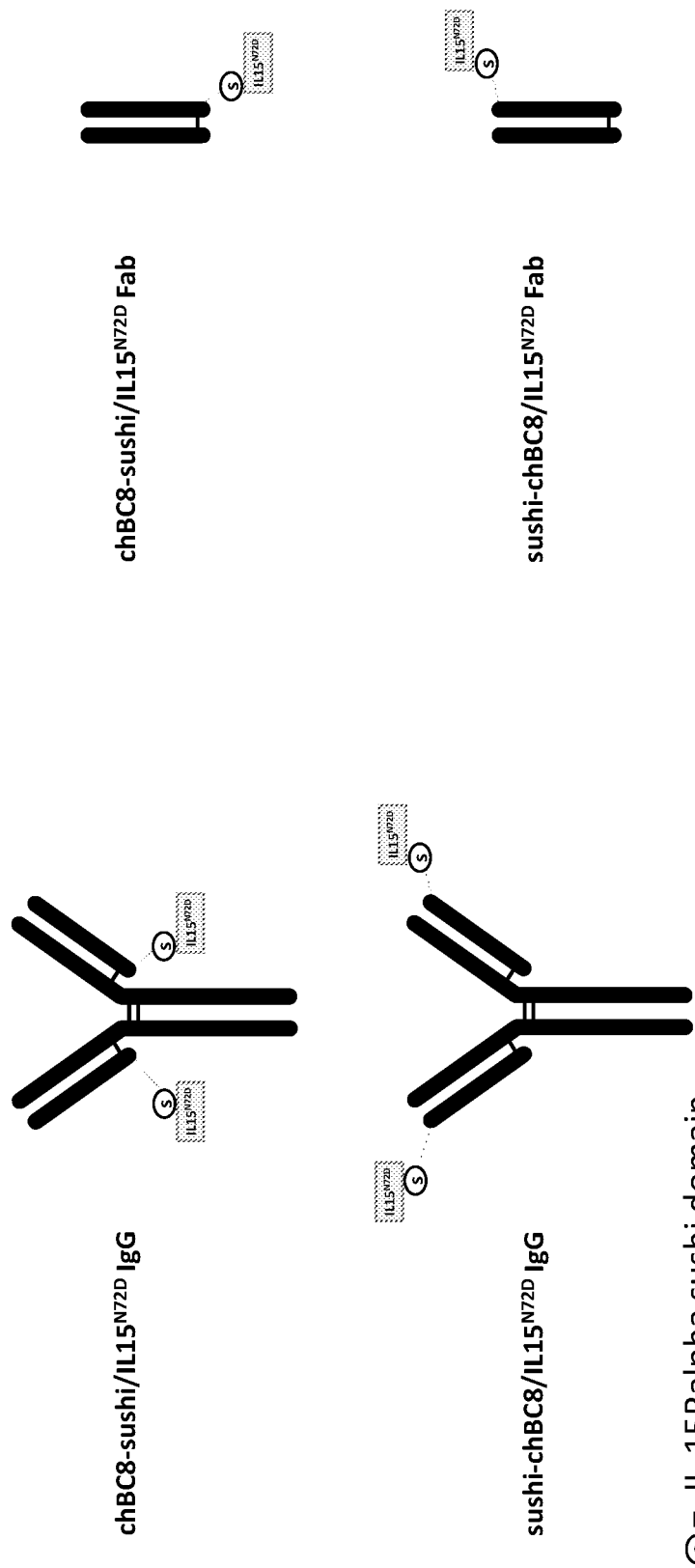
Figure 4B:
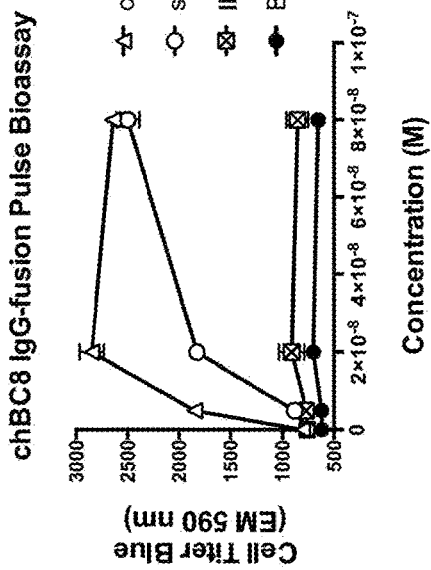
FIGS. 4A-4B depict the effect of IFMs comprising various fusion strategies on CD8 T cell expansion.
Figure 4A:
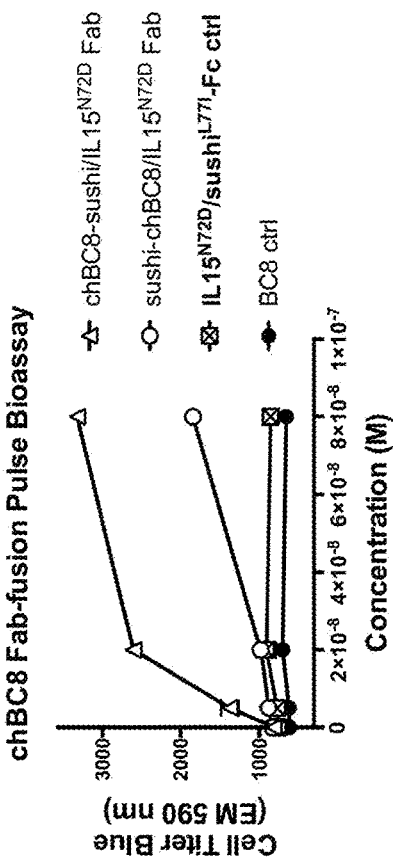
Figures 5A, 5B:
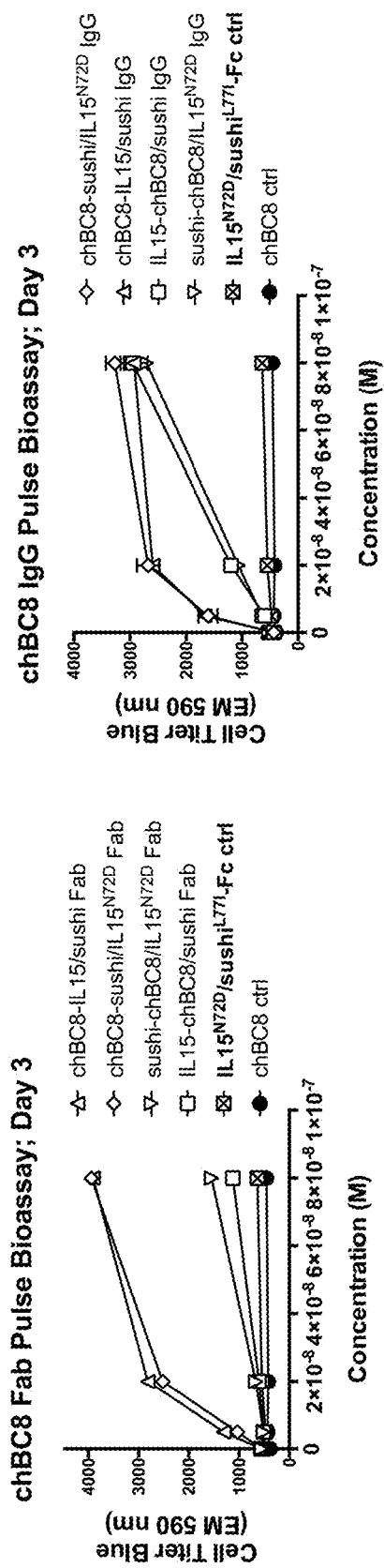
FIGS. 5A-5D depict biological activity of IFMs comprising wild-type or mutated IL-15 and various fusion strategies of IL-15/sushi complex to anti-CD45 antibody.
Figures 5C, 5D:
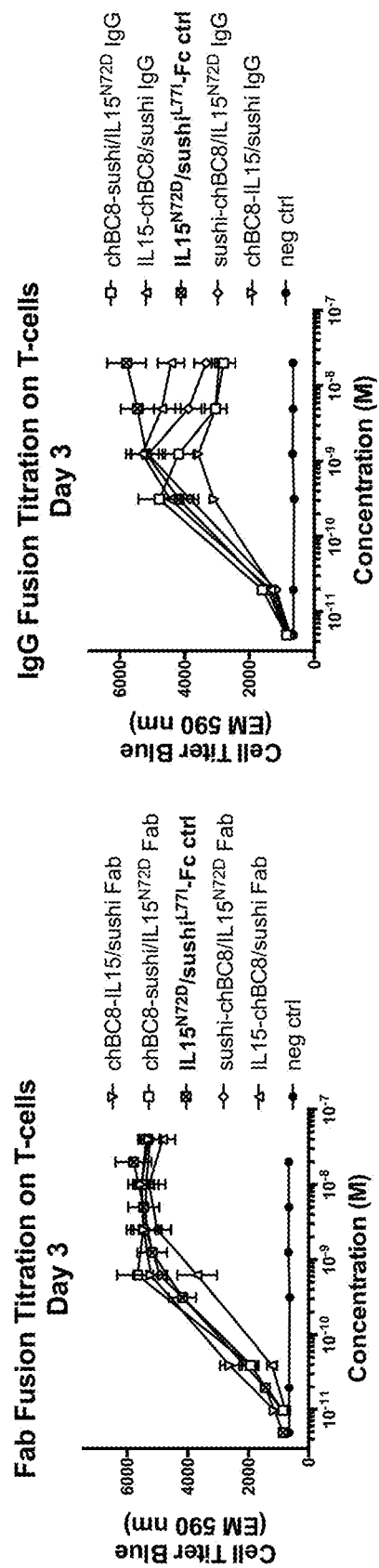

In a first experiment we evaluated the IFMs comprising IL-15$^{N72D}$ in the pulse bioassay format and found that for both the Fab and IgG fusions, as well as the N- and C-terminal fusions, the IFMs exhibited improved activity as compared to the IL-15 format comprising a complex between IL-15$^{N72D}$ and a sushi-Fc variant (FIGS. 4A-4B). In an additional experiment comparing all eight IFM variants we observed similar potencies for either IL-15 or sushi fusion to the antibody, and also observed similar potencies for protein variants containing wild-type IL-15 and IL15-N72D (FIGS. 5A-5B). We observed a trend in which fusion of IL-15 or sushi to the C-terminus of the chBC8 IgG or Fab resulted in greater CD8 T cell expansion than fusion to the antibody N-terminus (FIGS. 4A-4B and FIGS. 5A-5B). However, each of the IFM variants (including N-terminal fusion to the IgG or Fab) displayed greater potency than the control protein, IL15-N72D/sushiL77I-Fc, which does not contain CD45 receptor binding functionality (FIGS. 3C-3D and FIGS. 4A-4B). As a control, chimeric BC8 or the parental BC8 mouse mAb antibodies alone did not induce T cell expansion (FIGS. 4A-4B and FIGS. 5A-5B), consistent with our observations above. We also evaluated the eight IFMs on CD8 T cell proliferation in a "static" assay format. After three days of incubation (without washing) each of the IFMs resulted in similar activity as IL15$^{N72D}$/sushiL77I-Fc, with the exception of the IFM comprising N-terminal fusion of IL-15 to the Fab fragment (IL15-chBC8/sushi Fab), which resulted in slightly weaker potency in this assay format (FIGS. 5C-5D). The IgG fusions displayed similar potency to the IL-15 Fab fusions (FIG. 3B). We conclude that multiple fusions strategies of the IL-15/sushi complex to an antibody targeting the CD45 receptor result in IFMs with increased biological persistence, and that the IFM fusion strategy improves activity of both wild-type and mutated forms of IL-15.

Figure 6B:
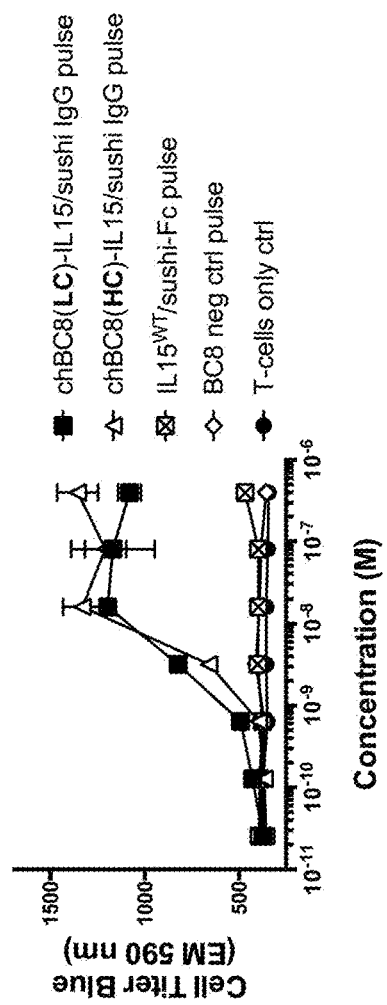
FIGS. 6A-6B depict IFMs comprising C-terminal fusion to chBC8 IgG light- or heavy-chain.
Figure 6A:
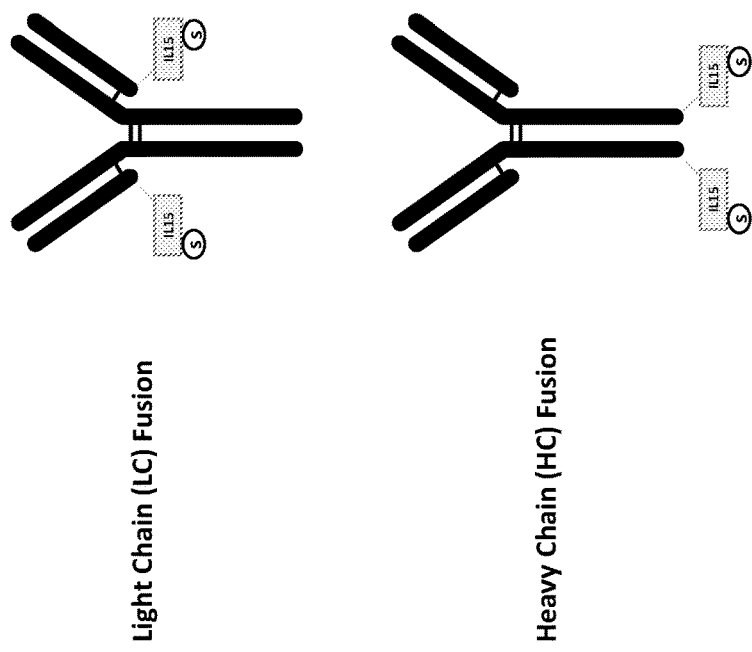

C. IFMs Comprising IL-15 Fused to the C-Terminus of an Antibody Heavy Chain or Light Chain We constructed an additional chBC8-cytokine fusion to evaluate the ability to fuse the cytokine to the antibody heavy- or light-chain C-terminus. Wild-type IL-15 was genetically fused to the C-terminus of the chBC8 heavy-chain (HC) and this construct was co-expressed with IL15Rα-sushi to yield the IFM variant chBC8(HC)-IL15/sushi IgG (FIG. 6A). We compared chBC8(HC)-IL15/sushi IgG to the chBC8-IL15/sushi IgG described in the previous example, which comprises IL-15 fused to the light-chain C-terminus; for clarity we refer to this latter protein here as chBC8(LC)-IL15/sushi IgG in order to differentiate from the IFM comprising fusion to the heavy-chain C-terminus. Activated human CD8 T cells were pulsed with seven serial five-fold dilutions spanning 400 nM to 25.6 pM of chBC8 (HC)-IL15/sushi IgG or chBC8-IL15(LC)/sushi IgG for 1 hr at 37° C., and then washed three times will full media and plated at 500,000 cells/mL. Serial dilution of media only, the parental BC8 antibody (which does not contain a fusion with IL-15), or IL-15$^{WT}$/sushi-Fc (which is devoid of immune-targeting function) were used as controls. Following 5 days of culture we measured CD8 T cell expansion using CellTiter Blue. The chBC8(HC)-IL15/sushi IgG and chBC8-IL15(LC)/sushi IgG IFMs, but not IL15$^{WT}$/sushi-Fc or the parental BC8 antibody, each induced T cell expansion and exhibited similar dose-response characteristics (FIG. 6B). We conclude that fusion of IL-15 to the C-terminus of the antibody light- or heavy-chain are each capable of producing IFMs with increased persistence.

D. Functional Antibody Binding is Required for Improved Potency of IFMs.

Figures 7A, 7B:
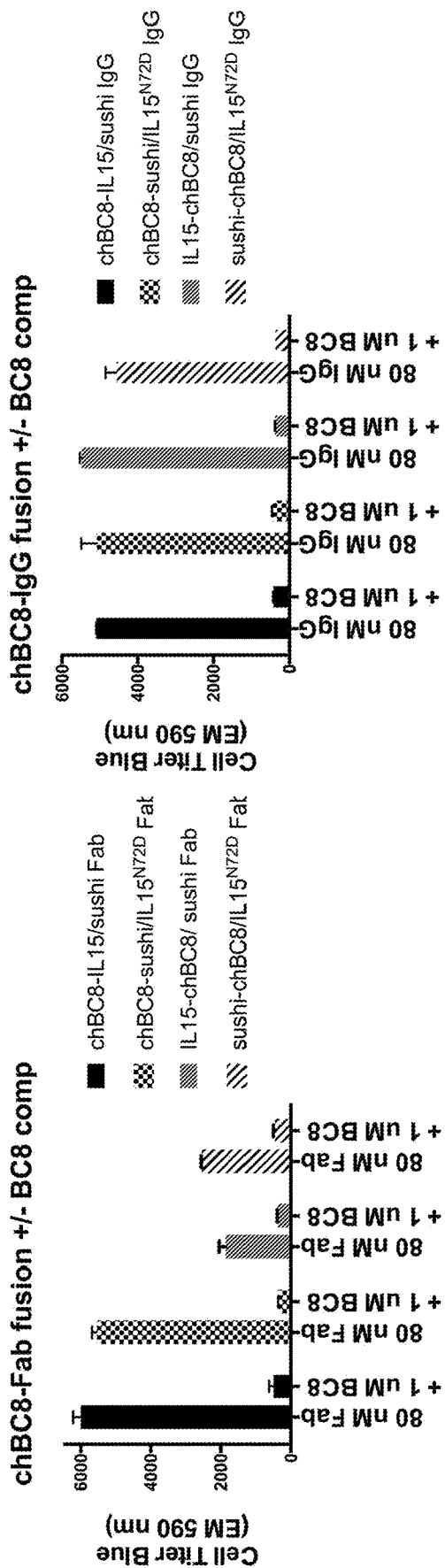
FIGS. 7A-7C depict IFMs require functional binding of the antibody fragment for improved activity.

We have demonstrated above that binding to CD45 alone (e.g. with a BC8 antibody that does not comprise a fusion with IL-15) does not explain the increased activity of the IFMs (FIGS. 3C-3D, FIGS. 4A-4B, and FIGS. 5A-5D). This supports the requirement of the cytokine for the potency of the IFM. We conducted two additional controls to demonstrate the functional requirement of the antibody binding to its cognate cell surface receptor. In the first experiment we conducted a pulse assay on activated primary human CD8 T cells for each of the eight IFMs described in Example 1A in the presence or absence of 1 µM BC8 as a soluble competitor to the CD45 cell surface receptor. Following a 1 hr pulse incubation at 37° C. cells were washed three times and then plated in full RPMI medium at a density of 300,000 cells/mL. Following 5 days at 37° C. cell expansion was measured using CellTiter Blue; the presence of the BC8 competitor ablated the activity of all eight IFMs in the pulse bioassay (FIGS. 7A-7B).

Figure 7C:
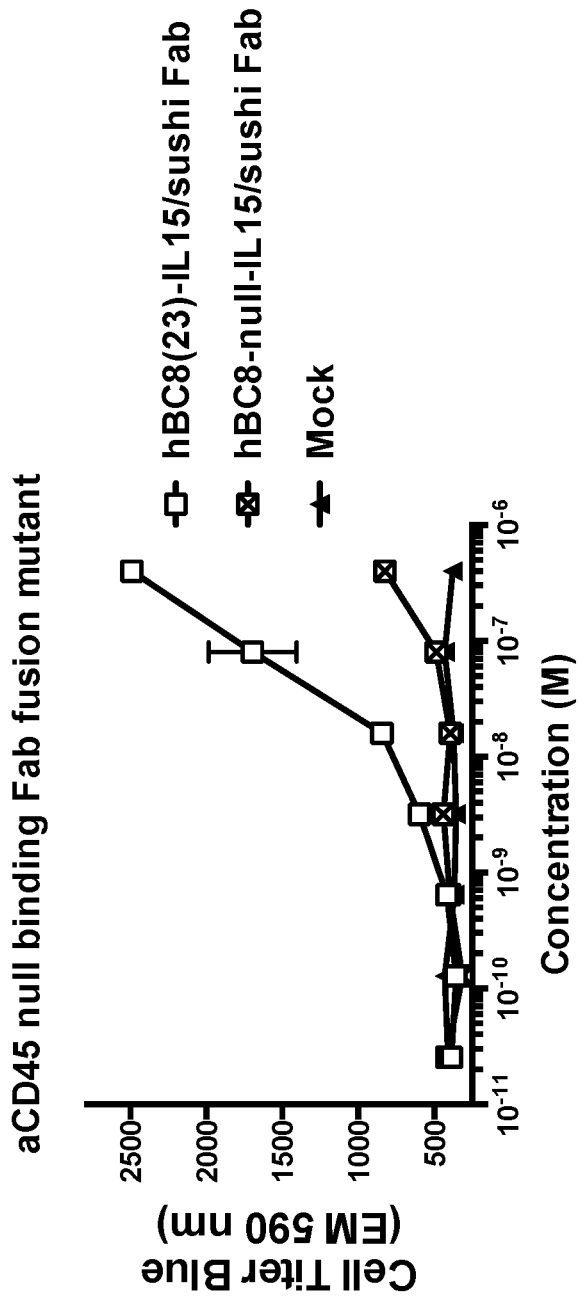
Figures 10A, 10B:
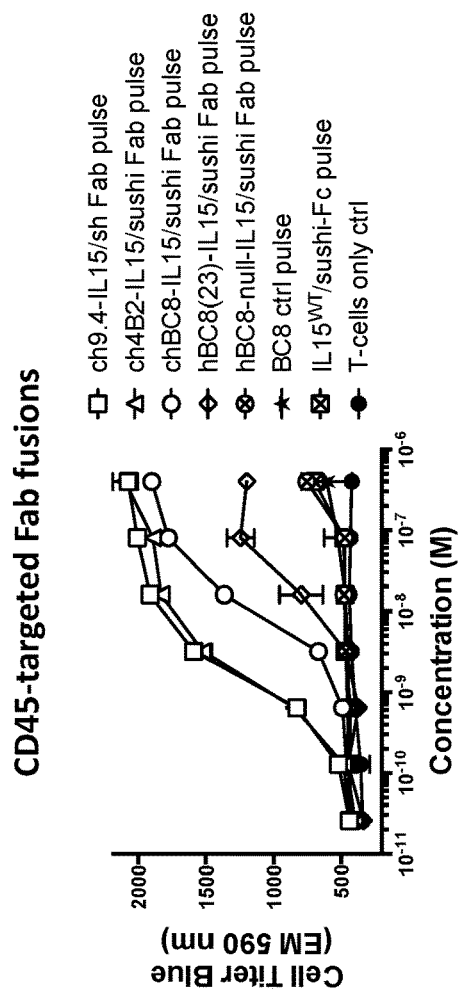
FIGS. 10A-10B depict evaluation of IFMs comprising alternative CD45 antibody clones.

In a second experiment we generated two IFMs comprising either a functional or nonfunctional BC8 binding region. The IFM with the functional BC8 region comprised a Fab antibody fragment with humanized BC8 variable domain, in which CDRs from the parental BC8 antibody were grafted onto human variable domains, and a fusion of IL-15$^{WT}$ to the humanized BC8 Fab light-chain. This complex was co-expressed with IL-15Rα-sushi to result in the IFM variant hBC8(23)-IL15/sushi Fab (see "Protein Variants" section for more details). The humanized BC8 antibody (hBC8(23)) possesses similar binding affinity as the chimeric BC8 antibody (FIG. 10A). The IFM with the nonfunctional BC8 region (hBC8-null-IL15/sushi Fab) comprised the same Fab fragment, with the exception of five amino acids of CDR3 in the antibody heavy-chain, which were replaced with the residues SGGGS. These amino acid substitutions resulted in a humanized BC8 antibody that did not exhibit detectable binding to cellular CD45 for the concentrations tested (FIG. 10A). Each of these proteins were pulsed with activated human CD8 T cells (seven serial five-fold dilutions spanning a concentration range of 400 nM to 25.6 pM), cells were then washed and plated at 500,000 cells/mL in 96-well plates. Following three days at 37° C. hBC8(23)-IL15/sushi Fab, but not hBC8-null-IL15/sushi Fab, supported CD8 T cell expansion (FIG. 7C). Taken together, these data demonstrate functional cell surface receptor binding is required for the improved potency of the IFMs.

E. Fusion to Anti-CD45 Increases Loading and Cell Surface Persistence of IL-15

To explore whether the improved biological persistence of the IFMs correlates to increased loading and persistence of IL-15 onto cells we analyzed cell surface IFM levels over time. CD8 T cells at a density of 5×10$^7$ cells/mL were pulsed with 0.75 mg/mL hBC8(23)-IL15/sushi Fab, IL-15/sushi-Fc2 Da, or IL-15$^{N72D}$/sushiL77I-Fc for 1 hr in a 1:1 mixture of PBS and HBSS, and then washed three times with full media. Sushi-Fc2 Da is a fusion of wild-type IL-15Rα-sushi to a variant of the human IgG2-Fc domain. A mock pulse control in which cells were incubated in a 1:1 mixture of PBS and HBSS was used as a negative control. Cells were then stained for IL-15 using a fluorescently-labeled anti-IL-15 antibody or for IgG domains (Fab or Fc fragments) using a fluorescently-labeled polyclonal antibody that recognizes human IgG light and heavy chains. These antibodies provided detection of both IL-15 or the associated Fab or Fc fragments on the T cell surface. The hBC8(23)-IL15/sushi Fab protein yielded substantially higher levels of IL-15 staining than the IL15/sushi-Fc2 Da or IL15-N72D/sushiL77I-Fc proteins indicating a greater abundance of IL-15 on the cell surface (FIG. 8A). We observed consistent results for IgG staining in which the IFMs resulted in a higher levels of staining than the IL15/sushi-Fc constructs (FIG. 8A). As a positive control for proliferative effects of IL-15 we added approximately 10 nM of IL15/sushi-Fc2 Da to a mock pulse control (a "mock then saturating" condition); this corresponds to a concentration above the EC90 for IL-15/sushi-containing variants (see FIGS. 3A-3D) and thus serves as a positive control for a maximal proliferative effect by IL-15. The cells were propagated in culture and monitored for IL-15 surface levels for three days following the pulse incubation. IL-15 detection remained above background for hBC8(23)-IL15/sushi Fab, while both of the IL15/sushi-Fc variants were indistinguishable from background one day after the pulse incubation (FIG. 8B). The pulse of hBC8(23)-IL15/sushi Fab further resulted in similar cell expansion to the saturating amount of the IL15/sushi-Fc variant (FIG. 8C).

We reason that the IL-15 antibody that we used (clone no. 34559, R&D Systems) likely binds to an epitope on IL-15 that at least partially overlaps with IL-15R3, and thus may detect IL-15 that is not already productively engaged with IL-15 signaling receptors. This antibody has been described as a blocking/neutralizing antibody by several groups (see e.g., Neely, G G, Robbins, Amankwah, et al. (2001) J Imm 167:5011-5017; Krutzik, Hewison, Liu, Robles, et al (2008) J Imm 181:7115-7120; Schlaepfer, Speck (2008) PLoS ONE 3:e1999; and Correia, Cardoso, Pereira, Neves, et al., J Imm (2009) 182: 6149-6159). However, it does not appear to mediate its neutralizing effects through competitive IL-15 binding with IL-15Rα: IL-15 is presented on the dendritic cell surface via its interaction with IL-15Rα, and this antibody has been used previously to detect such a presentation of IL-15 on dendritic cells (Ferlazzo, Pack, Thomas, Paludan, et al PNAS 2004). Consistent with these observations, we are able to detect hBC8(23)-1L15/sushi Fab and IL15/sushi-Fc variants on the T cell surface using this antibody (FIGS. 8A-8B; each protein variant comprises an association between IL-15Rα-sushi and IL-15). The antibody's neutralizing activity may therefore derive from competitive binding with one of the other two cell surface receptors for IL-15, IL-2/IL-15Rβ or the common γ chain. As such, detection of IL-15 with this antibody may reflect an excess loading of IL-15 onto the T cell surface beyond the levels that saturate its cell surface receptors, e.g. IL-2/IL-15Rβ or the common γ chain. This may also explain the low levels of cell surface IL-15 detected for the IL-15/sushi-Fc constructs (FIGS. 8A-8B), which would only interact with T cells through the IL-15 receptors, though the dimeric IL-15 that results from association with the sushi-Fc fusion could result in a slight abundance of the cytokine. Overall, we conclude that IFMs both facilitate greater initial loading of IL-15 on the T cell surface and support elevated levels of biologically available IL-15 on the cell surface over time.

F. Multiple Linker Compositions Support Enhanced IFM Potency

Figures 9A, 9B:
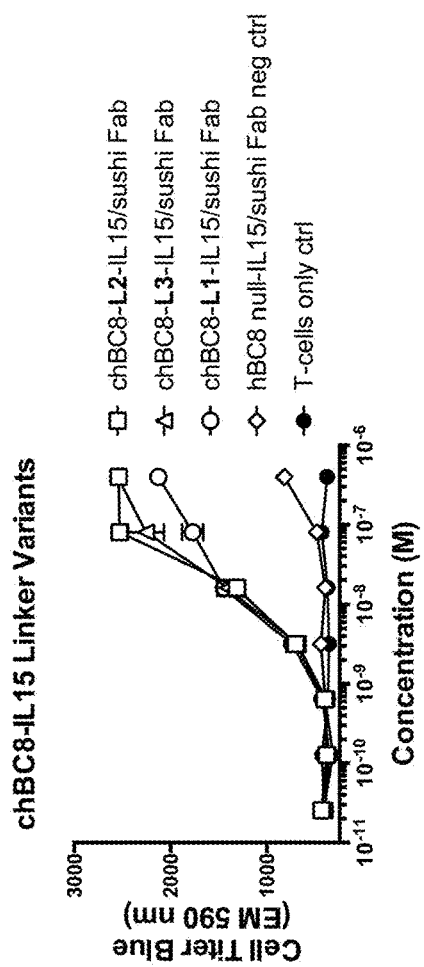
FIG. 9A-9B depict evaluation of IFMs comprising varied linker composition between IL-15 and chBC8.

To evaluate flexibility around linkage between IL-15 and the antibody of the IFM we explored multiple different polypeptide linker compositions. The IFMs explored in Example 1 each comprised a flexible 15 amino acid linker between IL-15 or sushi and the antibody consisting of three tandem repeats of (GGGGS)3; Linker-1, SEQ ID NO: 36). Here, we explored two additional linker compositions including a flexible eight amino acid linker ((GGGS)2; Linker-2, SEQ ID NO: 37) and a moderately flexible 12 amino acid linker derived from the human IgG1 hinge region (DKTHTSPPSPAP; Linker-3, SEQ ID NO: 38, underlined positions denote residues of the IgG1 hinge region that were mutated from cysteine to serine for this linker). IL-15$^{WT}$ was fused to the C-terminus of the chBC8 Fab fragment light-chain using Linker-2 or Linker-3 and was co-expressed with IL-15Rα-sushi to generate chBC8-L2-IL15/sushi Fab and chBC8-L3-IL15/sushi Fab, respectively (FIG. 9A). We previously described chBC8-IL15/sushi Fab in Example 1; this IFM variant comprises a (GGGGS)3 linker (Linker-1, SEQ ID NO: 36) between IL-15 and the chBC8 light-chain; for consistency we refer to this construct here as chBC8-L1-IL15/sushi Fab (FIG. 9A). These protein constructs were evaluated in the pulse bioassay with CD8 T cells as described in Example 1. Incubation with a mock serial dilution comprising media only or hBC8-null-IL15/sushi Fab, which comprises a BC8 binding domain mutated to ablate affinity to CD45 (FIG. 10A), were used as negative controls. Three days after the pulse incubation we analyzed cell proliferation using CellTiter Blue and found all three linker compositions were capable of inducing T cell expansion (FIG. 9B). We conclude that multiple linker compositions between the cytokine and the antibody are capable of generating IFMs with improved potency.

Methods

Protein expression. Proteins were produced from suspension adapted HEK 293 cells in serum-free media. An exception was the parental mouse monoclonal antibody BC8, which was purified from the BC8 hybridoma culture obtained from American Type Cell Culture (ATCC, cat. no. HB-10507). Proteins were then purified by either protein A resin (for Fc fusions and full-length (IgG) antibodies), KappaSelect resin (GE Healthcare; for fusions to antibody Fab fragments), or histidine affinity resin (e.g. nickel-nitrilotriacetic acid, Ni-NTA; for 6-His-tagged scFv fusions) as appropriate. Purified proteins were buffer exchanged into phosphate buffered saline (PBS). Approximate molecular weights were confirmed by reducing and non-reducing SDS-PAGE and aggregation and multimeric status was determined by size-exclusion chromatography (SEC). Based on aggregation or multimeric status, proteins were optionally purified by SEC using a HiLoad Superdex 200 prep-grade columns (GE Life Sciences) on an AKTA Pure chromatography system (GE Life Sciences).

Static bioassay. CD8 T-cells isolated from human blood (from Biospecialty Corp.) were activated with CD3/CD28 beads (Dynabeads cat. No. 11132D, ThermoFisher Scientific, Inc.) according to the manufacturer's instructions and in the presence of 10 ng/mL human IL-2 (cat. no. 202-IL-050/CF, R&D Systems) according to the manufacturer's instructions, plated in 6 well 9.5 cm2 plates in full RPMI media containing RPMI 1640 (cat. No. 30-2001, American Type Cell Culture), supplemented with 10% heat inactivated fetal bovine serum (FBS-HI, ThermoFisher Scientific, Inc.), penicillin/streptomycin, and 1% Glutamax (cat. no. 35050-061, ThermoFisher Scientific, Inc.), and cultured at 37° C. and 5% $CO_2$. After 3 days of stimulation, the CD3/CD28 beads were removed, and cells were allowed to rest in full RPMI media for 24 hours. The T-cells were then seeded into 96-well plates at $0.5 \times 10^6$ cells/mL in the presence of six serial four-fold dilution of IFMs or control proteins spanning a concentration range of 20 nM to 4.9 pM, unless otherwise indicated, or with media only as a negative control. Following three days at 37° C. and 5% $CO_2$ cell expansion was analyzed via CellTiter-Blue (cat. no. G8081, Promega).

Pulse Bioassay. Human CD8 T-cells (from Biospecialty Corp.) were stimulated with CD3/CD28 beads (Dynabeads, ThermoFisher Scientific, Inc.) in the presence of 10 ng/mL IL-2 as described for the static bioassay. After 3 days of stimulation, the CD3/CD28 beads were removed, and cells allowed to rest in full RPMI media for 24 hours. Unless otherwise indicated, the activated T-cells were incubated at a cell density of 500,000 cells/mL with IFMs or control proteins at concentration range of 80 nM to 5 nM (three serial four-fold dilutions), unless otherwise indicated, or with media only (0 nM) as a negative control. Following 1 hour at 37° C. and 5% $CO_2$ cells were washed three times with full RPMI media to remove unbound cytokine and then plated in full RPMI media (in the absence of additional cytokines) at $0.5 \times 10^6$ cells/mL in 96-well plates unless otherwise indicated. Additional controls optionally included either the parental BC8 antibody or chBC8 IgG antibody. Following three days at 37° C. and 5% $CO_2$ T cell expansion was analyzed via CellTiter-Blue or Flow cytometry. For flow cytometry, 7-AAD (cat. no. A9400-5MG, Sigma) was used to stain for (and subsequently exclude dead cells during the analysis) and CountBright Absolute Counting Beads (cat. no. C36950, Thermo Fisher Scientific, Inc.) were used to quantify viable cell densities according the manufacturer's instructions.

Measurement of IFM on cell surface. Cells were analyzed by immunofluorescent staining to detect cell surface IFMs following 0, 1, and 3 days in culture following pulse incubation and washes. Briefly, cells were washed with 1× phosphate buffered saline (PBS) containing 1 mg/mL bovine serum albumin (PBS/BSA) and then stained with a 1:100 dilution of PE-conjugated anti-IL15 antibody (clone no. 34559; R&D Systems cat. no. IC2471P) and a 1:100 dilution of DyLight650-conjugated anti-human IgG H+L polyclonal antibody (ThermoFisher cat. no. Sa5-10129) in PBS/BSA. Following 20-30 min incubation at 4° C., cells were washed one time with PBS/BSA, and then resuspended in PBS/BSA for analysis on a FACSCelesta using Diva software (BD Biosciences). Data were analyzed using Cytobank (Cytobank, Inc) and GraphPad Prism (GraphPad Software, Inc).

Example 2. Fusion of IL15 to Alternative Anti-CD45 Antibodies

To evaluate whether anti-CD45 antibodies other than BC8 are capable of generating IFMs with improved potency, we evaluated two additional anti-CD45 monoclonal antibodies (mAb clones 9.4 and 4B2). We first evaluated the binding affinities of chimeric IgG forms of these antibodies to CD45 expressed on the surface of activated CD8 T cells. The chimeric antibodies each comprise mouse variable domains and human constant region (human constant kappa domain and human IgG4 containing an S228P mutation to stabilize the IgG4 hinge region). For comparison with previous results we evaluated these antibodies alongside chBC8, hBC8(23), and a non-binding variant hBC8-null. The humanized BC8 antibody consists of variable domains containing CDR regions grafted from BC8, and the hBC8-null variant contains an SGGGS substitution in the heavy-chain CDR3, which ablates binding to CD45 (FIG. 10A). The ch4B2 and ch9.4 antibodies exhibited the highest affinity to cellular CD45, with apparent dissociation constants ($K_{D,app}$) of 0.44 and 0.84 nM, respectively, while the chBC8 and hBC8(23) antibodies exhibited $K_{D,app}$ of 6.68 and 7.8 nM, respectively (FIG. 10A). The hBC8-null antibody did not exhibit significant binding at the highest concentration examined (500 nM; FIG. 10A). We use the term apparent dissociation constant ($K_{D,app}$) to distinguish from a true equilibrium dissociation constant: the bivalent nature of the IgG antibody introduces an avidity effect that complicates the calculation of a true equilibrium dissociation constant for these type of assays. Nevertheless, the $K_{D,app}$ is a useful metric for scoring relative affinities of the antibodies to the cellular receptor in its native context.

We next evaluated the potency of IFMs comprising each of these antibodies. Briefly, IL-15 was fused to the C-terminus of ch9.4 or ch4B2 Fab fragment light-chain and co-expressed with IL-15Rα-sushi to generate ch9.4-IL15/ sushi Fab and ch4B2-IL15/sushi Fab, respectively. Construction of chBC8-IL15/sushi Fab, hBC8(23)-IL15/sushi Fab, and hBC8-null-IL15/sushi Fab were described in Example 1. We compared the potency of these IFMs in the pulse bioassay, and included a series of negative controls: hBC8-null-IL15/sushi Fab (an IFM with ablated CD45 binding), IL-15$^{WT}$/sushi-Fc, BC8 antibody, and media only. Each of the IFMs induced greater T cell expansion than the negative controls as measured three days after the pulse incubation (FIG. 10B). The IFMs comprising 4B2 or 9.4 possessed increased potency compared to IFMs comprising chBC8 or hBC8(23). This is consistent with the increased affinity of 4B2 and 9.4 compared to chBC8 and hBC8(23), and is consistent with the idea that increased affinity of the antibody to the cell surface receptor results in increased potency of the IFM. Overall, we conclude that generation of IFMs with improved biological persistence is not restricted to the BC8 antibody, and that increased affinity to the cell surface receptor can improve the potency of the IFM.

Methods

Cell binding assay. Primary human CD8 T-cells were activated with CD3/CD28 beads and 10 ng/mL IL-2 as described in Example 1. Following activation and an overnight rest in full RPMI media (see Example 1 methods) the T-cells were incubated with seven serial five-fold dilutions of antibodies spanning 500 nM to 6.4 pM, or with media only control at 4° C. for 1 hr. Cells were washed with MACS buffer (PBS, 2% FBS, 1 mM EDTA) three times, and antibody binding was detected using a PE-conjugated anti-human IgG-Fc antibody (BioLegend, cat. no. HP6017) for 20 min. at 4° C. Cells were washed two times with MACS buffer, and the resuspended in MACS buffer with live-dead stain (7-AAD). Antibody binding was quantified using the median fluorescence intensity (MFI) of the live cell population (via 7-AAD exclusion) within the PE signal. Curves were generated by plotting mean fluorescent units against antibody concentration, and apparent dissociation constants ($K_{D,app}$) were determined by non-linear regression using a four-parameter logistic equation using GraphPad Prism (GraphPad Software, Inc.).

Pulse bioassay. The pulse bioassay was conducted as described in Example 1.

Protein expression. Proteins were produced as described in Example 1.

Example 3. IFMs Targeting Additional Cell Surface Receptors Facilitate Improved Potency and Specificity A. Additional Cell Surface Receptors Other than CD45 Facilitate Improved Cytokine Potency.

To explore whether IFMs targeting cell surface receptors other than CD45 are capable of resulting in increased biological potency we constructed IFMs comprising antibodies targeting additional cell surface receptors. The alternative receptors can either be abundant receptors on the cell surface or exhibit persistence at the protein level (e.g. display slow receptor internalization or strong recycling back to the cell surface upon receptor internalization). Ideally the receptor is both abundant and persistent. Based on these considerations we selected IFMs targeting CD8, CD11a, or CD18 for evaluation. CD8 is a co-receptor for the T cell receptor that is expressed on cytotoxic T cells. CD8 can also be expressed in cortical thymocytes, dendritic cells, and natural killer cells. In cytotoxic T cells, CD8 helps maintain the activated T cell receptor/MHC complex on the cell surface (Wooldridge, van den berg, Glick, et al. JBC 2005), and once the T cell receptor is internalized the CD8 co-receptor is preferentially maintained on the cell surface in comparison to the T cell receptor (1989 J Imm Boyer, Auphan, Gabert, Schmitt-Verhulst et al Comparison of phosphorylation and internalization of the antigen receptor/CD3 complex, CD8, and Class I MHC-encoded proteins on T cells). Lymphocyte function-associated antigen 1 (LFA-1) is a heterodimeric cell surface receptor composed of integrin alpha-L (CD11a) and integrin beta-2 (CD18) and is involved in intercellular adhesion and lymphocyte costimulation. Integrins generally display persistence at the protein level: they typically either exhibit slow internalization from the cell surface or are recycled back to the cell surface upon internalization (2012 J Cell Sci Integrins at a Glance and 1989 EMBO J Endocytosis and recycling of the Fn receptor in CHO). LFA-1 is present at high levels on several different types of leukocytes and has been shown to exhibit slow internalization in multiple different cell types, including monocytic U937 cells, the promyelocytic leukemia cell line HL-60, and the lymphoblastoid cell line JY (1992 EMBO J Circulating Integrins Bretscher). In addition, preclinical studies of the CD11a antibody efalizumab demonstrated that CD11a exhibits persistence at the protein level in human and mouse T cells isolated from blood; efalizumab can, however, induce receptor internalization and degradation in the presence of a secondary cross-linking antibody (2004 Coffey, Pippig et al J Pharm Exp Ther).

Figure 11B:
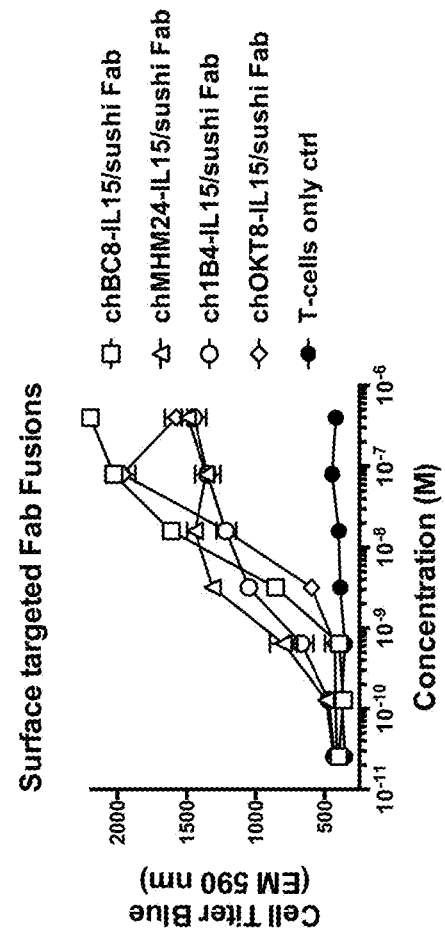
FIGS. 11A-11B depict IFMs comprising antibodies targeting CD8, CD11a, or CD18.
Figure 11A:
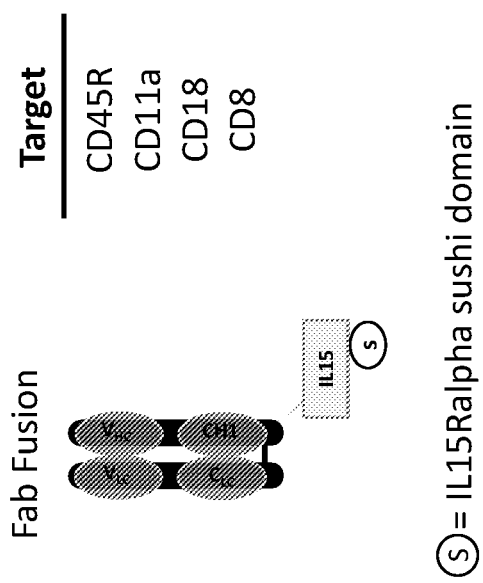

We constructed IFMs targeting CD8 (antibody clone OKT8), CD11a (antibody clone MHM24), or CD18 (antibody clone 1B4) by genetically fusing IL-15 to the C-terminus of the respective antibody fragment light-chain. The IL-15-antibody fusions were co-expressed with IL-15Rα-sushi to generate three IFMs: chMHM24-IL15/sushi Fab, ch1B4-IL15/sushi Fab, and chOKT8-IL15/sushi Fab (FIG. 11A). Each Fab fragment was composed of chimeric human and mouse regions with mouse variable region and human constant domains (kappa and CH1). The potency of the IFMs on CD8 T cells was analyzed in the pulse bioassay as described in Example 1; after three days in culture following the pulse incubation cells were analyzed for proliferation using CellTiter Blue. The three IFMs each supported similar levels of T cell proliferation to that of chBC8-IL15/sushi Fab (FIG. 11B). We have demonstrated above that forms of IL-15 that do not contain an immune-targeting functionality exhibit minimal effects in the pulse bioassay (FIGS. 2A-2C, 4A-4B, 5A-5D, 6A-6B, and 8A-8C). Together this demonstrates that additional cell surface receptors are capable of generating IFMs with improved biological persistence.

B. IFMs that Facilitate Improve Potency Towards CD8 T Cells

Figures 12A, 12B:
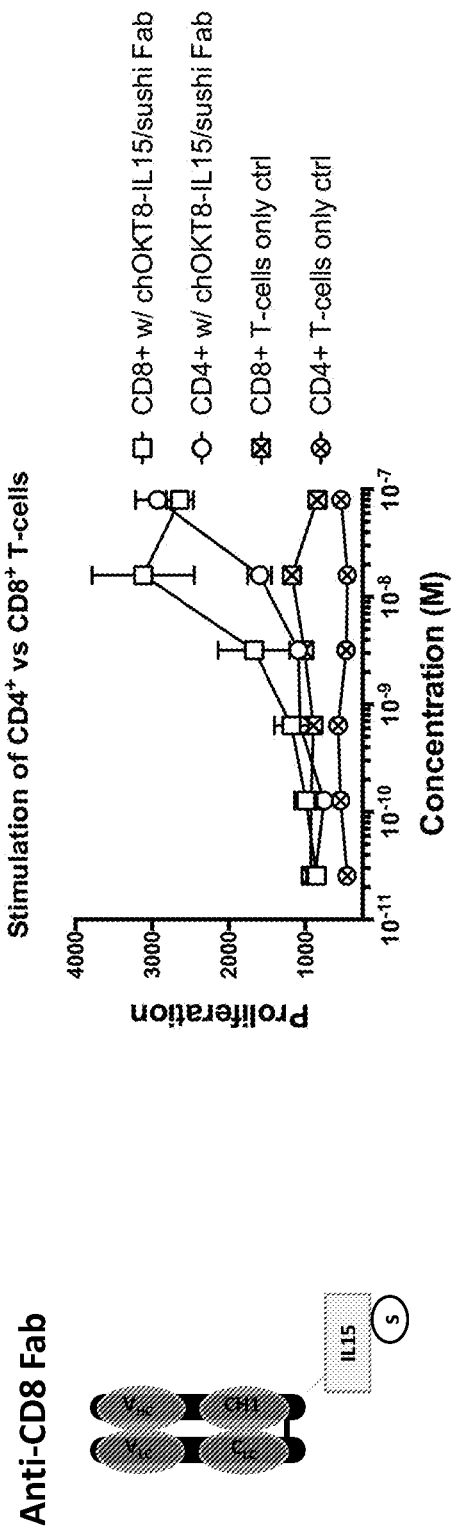
FIGS. 12A-12B depict evaluation of IFM potency comprising anti-CD8 on CD4 or CD8 T cells.

To evaluate whether cell surface receptor targeting can facilitate improved potency towards individual cell types we compared the potency of CD8-targeted IFM on CD4 and CD8 T cells. CD4 or CD8 cells were treated with chOKT8-IL15/sushi Fab in the pulse bioassay format, and cell proliferation was measured three days after the pulse incubation. The CD8-targeted IFM more potently stimulated CD8 T cells compared to CD4 T cells (FIGS. 12A-12B), supporting the ability to target specific cell types based on the antibody of the IFM.

Methods

Pulse bioassay on CD4 or CD8 T cells. Primary human CD3 T cells, which contain a mixture of cells expressing CD4, CD8, or CD4 and CD8 coreceptors, were activated using CD3/CD28 activation beads in the presence of 10 ng/mL IL-2 as described in Example 1. Following three days of activation the beads were removed and cells were rested overnight in full RPMI media. We then purified individual populations of CD4 and CD8 T cells using magnetic activated cell sorting (MACS) using (cat. no. 130-045-101, and no. 130-045-201, Miltenyi Biotec, Inc.) according the manufacturer's protocol. CD4 or CD8 T cells were then analyzed in the pulse bioassay as described in Example 1.

Figures 13A, 13B:
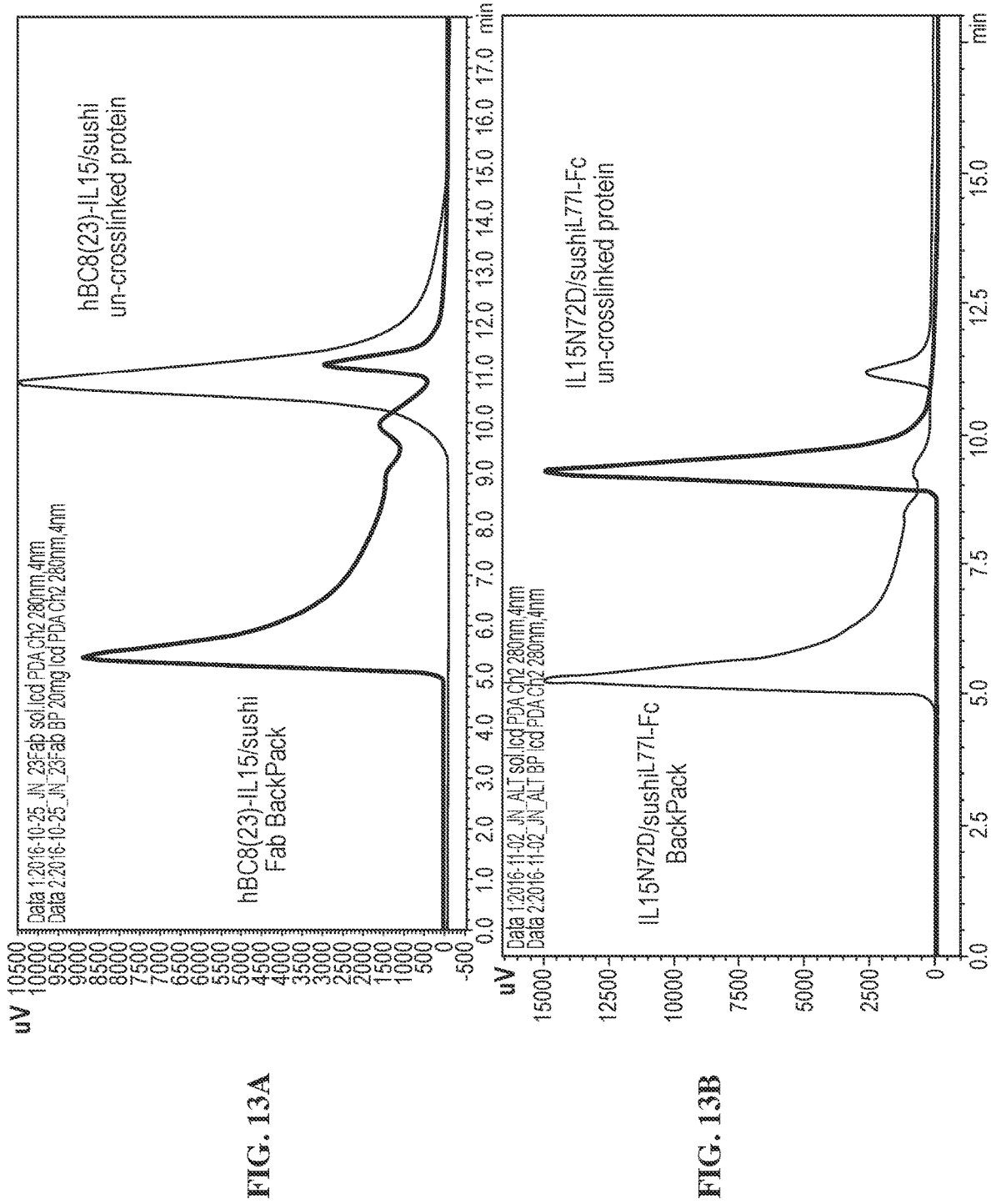
FIGS. 13A-13C depict graphs showing that nanoparticles comprising IL-15 IFMs support T cell expansion.
Figure 13C:
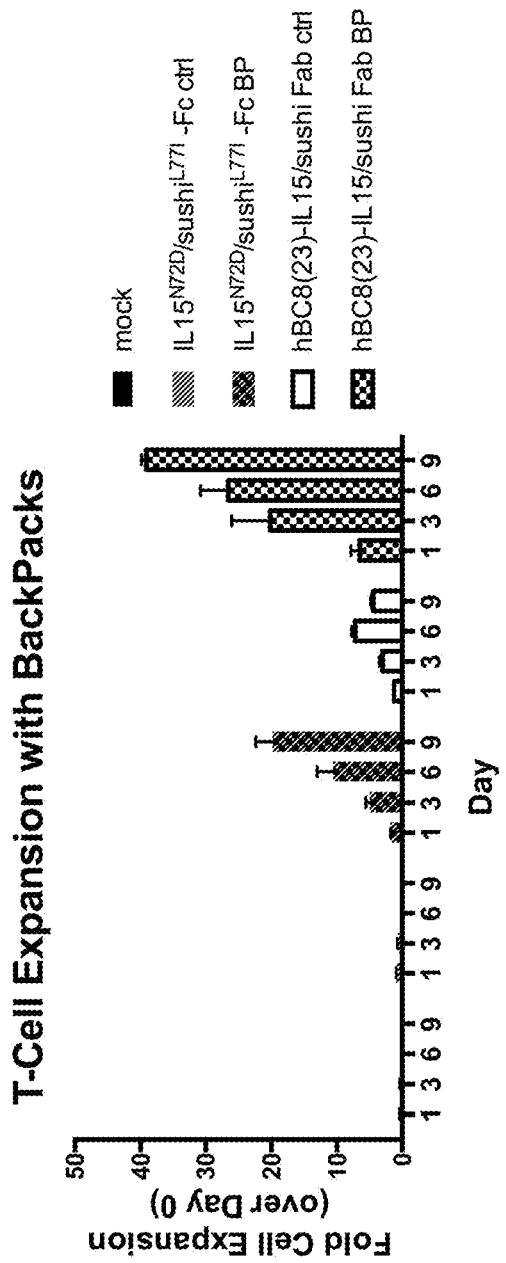

Example 4. Protein Nanogels Comprising IL-15 IFMs Support Long-Term Cell Expansion Drug-loaded nanoparticles (also referred to herein as "backpacks") hold potential for supporting cell viability and function. We therefore explored the ability to form nanoparticles comprising an IFM and the effect of these nanoparticles on T cell viability and expansion. We crosslinked hBC8(23)-IL15/sushi Fab into a protein nanogel using a reversible, amine-reactive, homobifunctional cross-linker. Protein nanogels comprising IL15$^{N72D}$/sushi$^{L77I}$-Fc were used as a comparator. Both of these proteins efficiently crosslinked into protein nanogels: by SEC analysis the protein nanogels traveled with a faster elution time than the free protein, consistent with a larger species (FIGS. 13A and 13B). Comparison of HPLC traces of the protein nanogel with the free (noncrosslinked) protein (FIGS. 13A-13B) revealed a minimal amount of free protein remaining in the cross-linked nanogels, suggesting high conversion of the proteins into nanogels. The protein nanogels were coated with a co-block polymer of polyethylene glycol and polylysine and incubated with CD8 T cells. Both protein nanogels supported long term cell expansion in comparison to non-crosslinked protein and unstimulated controls (FIG. 13C).
Methods Protein nanogel synthesis. Protein nanogels comprising a crosslinked protein nanoparticle were formed as follows. The chBC8-IL15/sushi Fab fusion protein was crosslinked into protein nanogels by incubating the protein at a concentration of 17 mg/mL with a 27-fold molar excess of a degradable crosslinker (Formula I) in the presence of a final concentration of 2.5% polyethylene glycol with an average molecular weight of 400 Dalton (PEG-400, Spectrum Chemical Mfg. Corp.) and 10% glycerol (Sigma). The IL15$^{N72D}$/sushiL77I-Fc protein was crosslinked into protein nanogels by incubating the protein at a concentration of 17 mg/mL with a 27-fold molar excess of a degradable crosslinker (Formula T). The cross-linker used in this study, Bis[2-(N-succinimidyl-oxycarbonyloxy)ethyl] disulfide, contains two N-hydroxysuccinimide (NHS) ester groups joined together by a flexible disulfide-containing linker as shown in Formula I.

Formula I

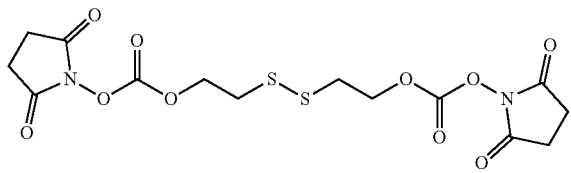

After 30 minutes incubation at room temperature, the reactions were diluted with Dulbecco's phosphate buffered saline (DPBS) to a final cytokine concentration of 1.5 mg/mL. Protein nanogels were then purified from linker leaving groups (which comprise molecular fragments of the linker that are removed as part of the cross-linking reaction) and unreacted linker by buffer exchange into DPBS using a Zeba column (40,000 MW cut-off, ThermoFisher). Zeba columns were used according to the manufacturer's instructions, including equilibrating the column in DPBS by three consecutive washes with DPBS to facilitate buffer exchange, followed by application of the reaction products. Buffer-exchanged protein nanogels were analyzed by size exclusion chromatography (SEC) using a BioSep™ SEC-s4000 column (Phenomenex Inc.) with PBS (pH 7.2) as eluent (flow rate 0.5 mL/min) on a Prominence HPLC system equipped with a photodiode array (Shimadzu Corp.).

Protein nanogels at a cytokine concentration of approximately 1-1.5 mg/mL were conjugated with a polyethylene glycol-polylysine (PEG-polyK) block co-polymer: PEG5k-polyK30 (Alamanda Polymers cat. no. 050-KC030), which is a block co-polymer comprising a polyethylene glycol polymer of 5 kiloDalton (kD) average molecular weight and a 30 amino acid polylysine polymer (polylysine30 or polyK30). PEG5k-polyK30 or were reconstituted to 1 mg/mL in DPBS and added to 1-1.5 mg/mL of protein nanogels at a final block copolymer concentration of 50 ug/mL and incubated at room temperature for 30 min.

T cell expansion analysis. Protein nanogels comprising PEG5k-polyK30 at a protein concentration of 1-1.5 mg/mL were mixed in equal volume with 1×10$^6$ CD8 T-cells in HBSS at a cell concentration of 100×10$^6$ cells/mL and incubated at 37° C. for 1 hr. T-cells were then washed three times with RPMI media containing 10% FBS, penicillin/streptomycin, and Glutamax (all from ThermoFisher Scientific, Inc.), seeded at a cell density of approximately 1×10$^6$ cells/mL, and cultured for 9 days in 24-well tissue culture plates. Cells were split into fresh medium at a ratio of 1:5 on three days after cell attachment of backpacks. Cell proliferation was measured by live-dead cell stain (7-AAD) and counting beads (CountBright Absolute Counting Beads, Thermo Fisher Scientific, Inc.) by flow cytometry on Days 0, 1, 2, 3, 6, and 9.

Example 5: Exemplary IFMs Comprising Fusions to Immune Regulators

In addition to fusions to cytokines, immune-cell targeted antibodies can be coupled to non-cytokine immune regulators, e.g., an antibody or a ligand against a costimulatory molecule or a checkpoint inhibitor.

In one embodiment, a construct comprising the chBC8 anti-CD45 Fab or IgG can be coupled to an antibody molecule, e.g., a Fab or a scFv, targeting a co-stimulatory receptor such as 4-1BB (CD137). In some embodiments, the antibody molecule to CD137 is an agonist antibody. In some embodiments, the antibody molecule to CD137 is chosen from an scFv, Fab, or IgG. In embodiments, the fusion comprises the antibody molecule to the co-stimulatory receptor fused to the N-terminal or C-terminal domain of the anti-CD45 (or CD11, CD8, CD4, etc.) part of the fusion. In short, all of the fusions described above and in the figures could be modified such that the cytokine is replaced by a Fab or scFv agonist to 4-1BB (or agonist of any other cell surface receptor).

In other embodiments, a construct comprising the chBC8 anti-CD45 Fab or IgG can be coupled to an antibody molecule, e.g., a Fab or a scFv, targeting a negative immune regulator, e.g., an inhibitor of a checkpoint inhibitor, e.g., an inhibitor of a checkpoint inhibitor chosen from PD-1, PD-L1, LAG-3, TIM-3, or CTLA-4. For example, an antagonist such as an IgG, Fab, or scFv antibody to CTLA-4 or PD-1 can be substituted for the cytokine which would result in sustained antagonism of a cell surface receptor via the fusion's interaction with CD45, CD11, etc.

Example 6: Priming can Improve ACT Efficacy

In some embodiments, it has been shown that priming (or pre-conditioning) cell therapeutic, tumor microenvironment, and/or the host can deliver extended benefits for adoptive cell therapy (ACT). In certain embodiments, even short (e.g., about 1-3 days, about 1 day, or less than 1 day) priming events can surprisingly have a dramatic effect on the efficacy of cell therapy.

Figure 14B:
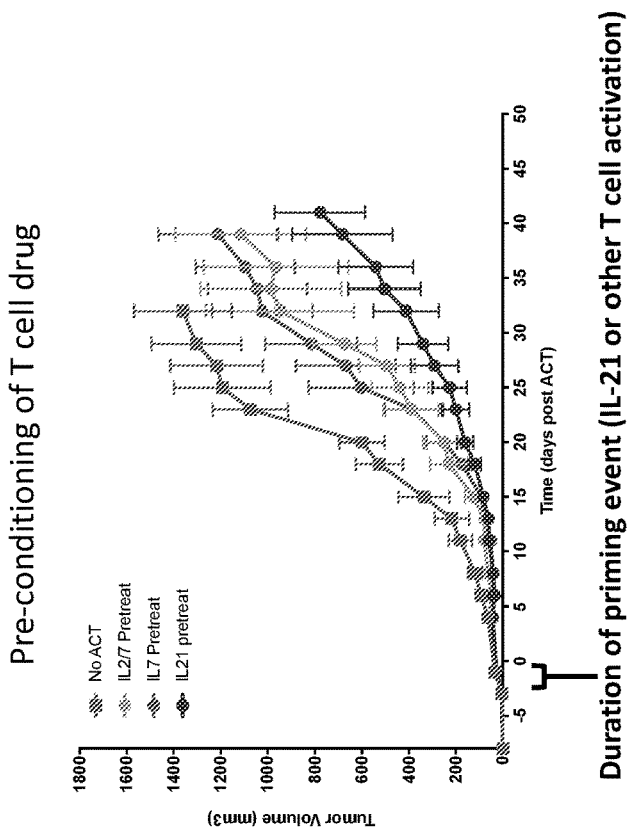
FIGS. 14A-14B show priming can improve ACT efficacy.
Figure 14A:
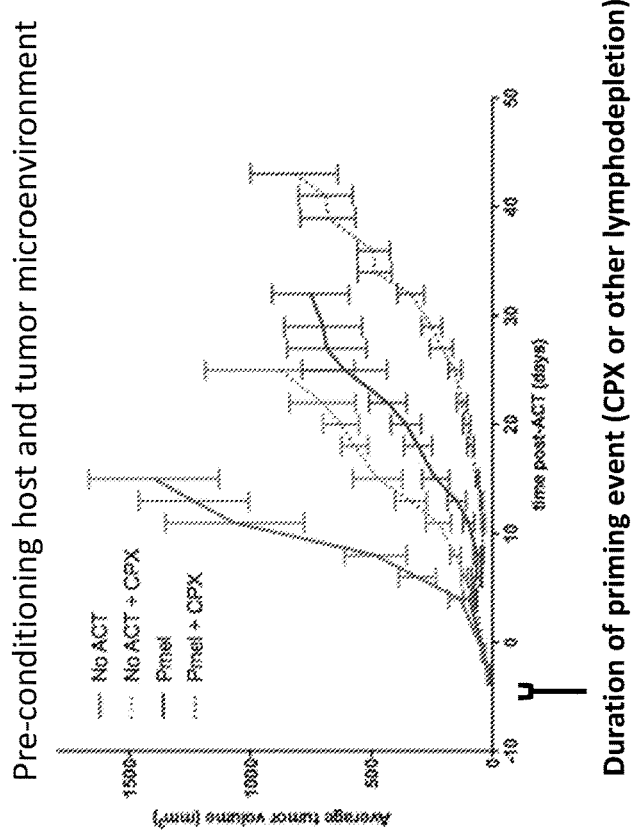

As shown in FIG. 14A, priming the host and tumor microenvironment with, for example, CPX (cyclophosphamide) or other lymphodepletion conditioning chemotherapy significantly suppressed tumor growth and thus, improves ACT efficacy. Pmel transgenic mouse strain was from Finkelstein et al., J Leukoc Biol. 2004 August; 76(2): 333-337.

In some embodiments, the cell therapeutic (e.g., T cell ACT) can also be primed to improve or optimize T cell activation. As shown in FIG. 14B, pretreatment with IL-21 showed the most improvement in ACT efficacy, followed by IL-2/IL-7 and IL-7.

In certain embodiments, the immunostimulatory fusion molecules disclosed herein can be used to extend such priming to in vivo environments.

Example 7: Versatility of Immunotargeted Surface Receptor

Figure 15:
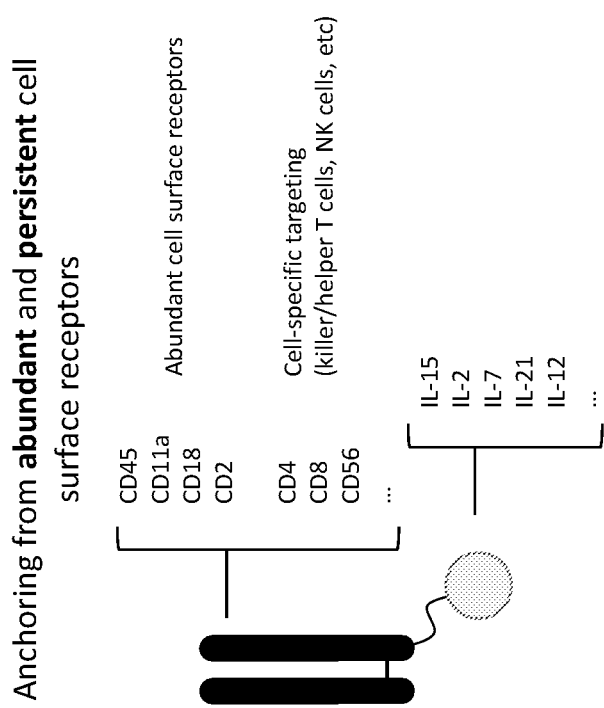
FIG. 15 shows example immunotargeted surface receptors and cytokines, illustrating versatility of the platform.

FIG. 15 illustrates various combinations of immunotargeting moieties (e.g., antibodies against various cell surface receptors) and cytokine molecules. Multiple receptors can facilitate cytokine immunotargeting. For example, tethered fusions can be made with various cytokines tethered to antibodies against "abundant" cell surface receptors such as CD11a, CD18, CD45 and/or CD2 which may be present on multiple cell types. Cytokines can also be immunotargeted to specific cells via cell type-specific surface receptors such as CD4, CD8 or CD56.

Example 8: IL-15 Tethered Fusions Improve T Cell Therapy in Solid Tumors

We evaluated the ability of IL-15 IFMs to augment the efficacy of anti-cancer therapy using two different tumor-specific cell therapy models. Collectively, these studies demonstrate the ability of IL-15 IFMs to augment tumor-specific cell therapy across tumor models comprising human or mouse T cells, CAR-T cells or tumor-specific TCRs, and immune-deficient or immunocompetent animal models. Pre-loading immunotargeted IL-15 on tumor-specific T cells supports anti-tumor activity in vivo, as shown in FIGS. 16A-16C (immune-competent, C57BL/6J mice bearing B16-F10 tumors) and FIGS. 16D-16E (xenogeneic tumor model, NSG mice bearing H1299 tumors), IL-15 tethered fusion augments efficacy of tumor-specific cell therapy over time.

IL-15 IFMs were first examined in the Pmel/B16-F10 model. For this model, CD8 T cells specific to a melanoma antigen (gp100) are expanded ex vivo and then injected into syngeneic mice carrying the gp100-expressing B16-F10 tumor cell line. Nine days prior to ACT 200,000 B16-F10 murine melanoma cells were injected intradermally into right flank of C57BL/6J mice. Melanoma antigen gp100-specific mouse CD8 T cells were isolated from Pmel mice, activated for two days using plate-coated antibodies against mouse CD3 and CD28 receptors, and then expanded in the presence of IL-21 for two days. Following ex vivo expansion, cells were loaded with chM1Fab-IL15/sushi at a concentration of 0.75 mg/mL. Cells were washed three times in HBSS to remove excess cytokine, and then injected as a single dose of $6.0 \times 10^6$ cells/mouse. Additional groups included vehicle alone (no cells), and a single dose of $6.0 \times 10^6$ cells that were mock-loaded with HBSS in the absence of IL-15 IFM (Pmel alone). All animals were also given cyclophosphamide lymphodepletion (4 mg/mouse) one day prior to ACT.

Figures 16A, 16B:
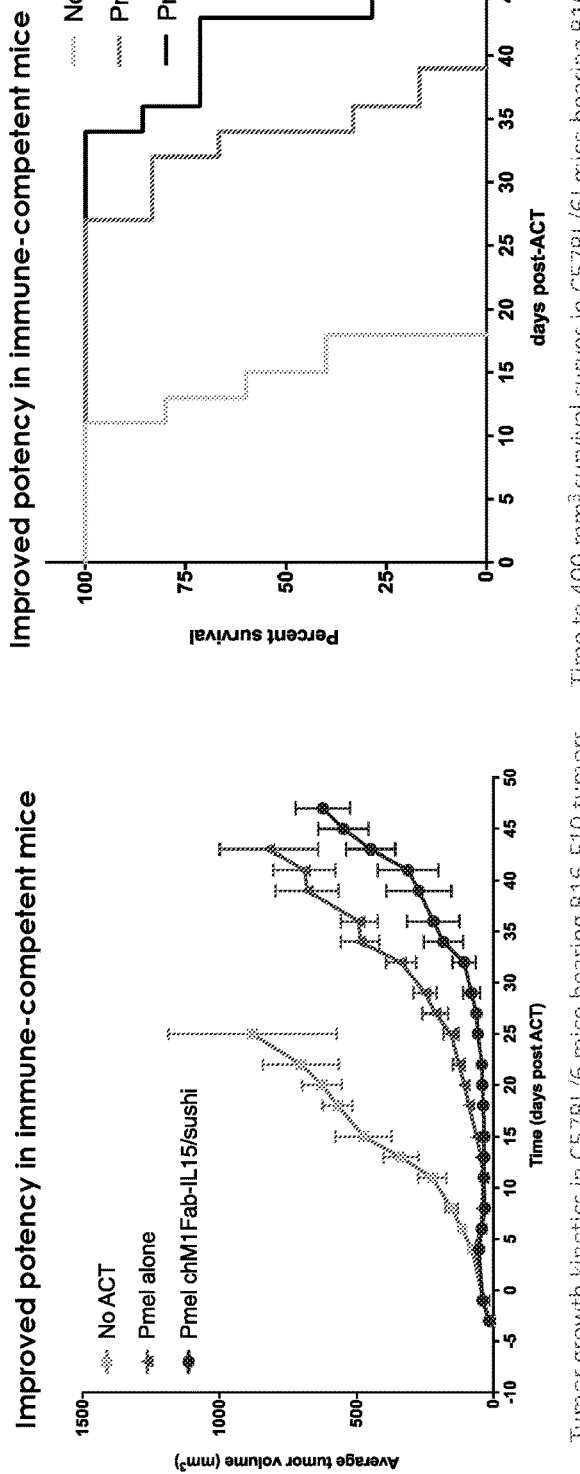
FIGS. 16A-16E show IL-15 tethered fusions improve tumor-specific T cell therapies in solid tumor models.
Figure 16C:
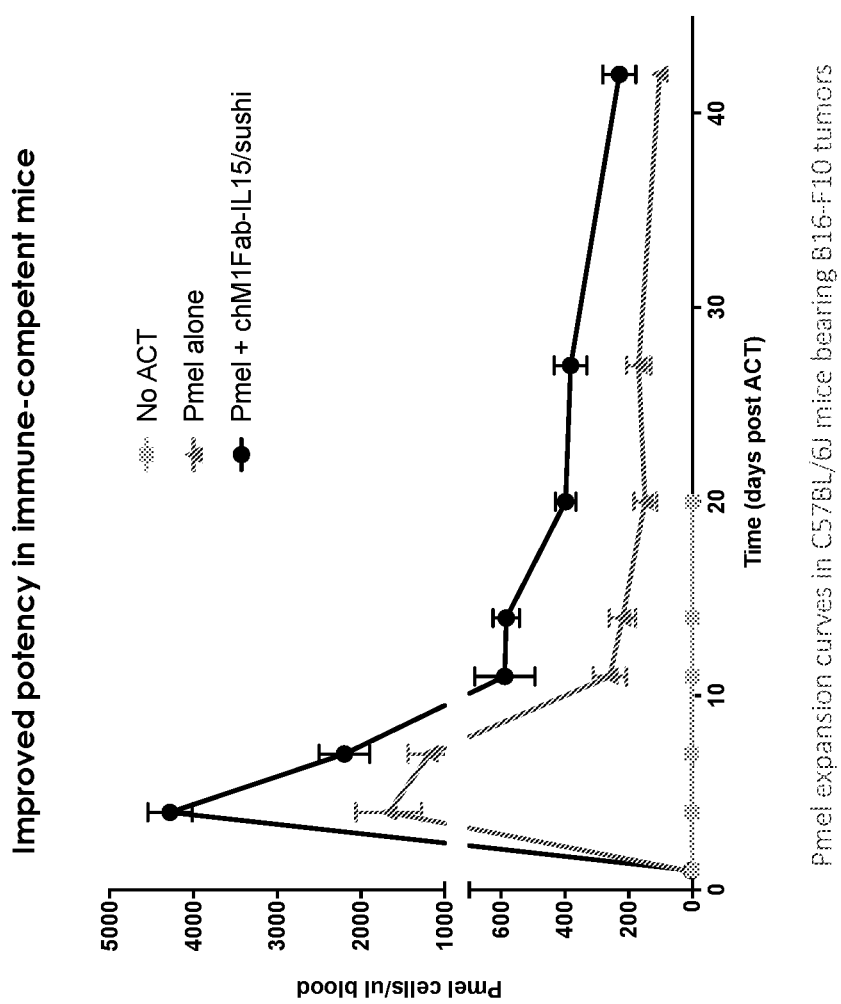

FIGS. 16A-16C shows tumor growth curves, mouse survival curves, and Pmel expansion curves from the above described study. Pmel cells alone reduced tumor volume over the course of the study, and this effect was enhanced by pre-loading the cells with chM1Fab-IL15/sushi (FIG. 16A). This reduced tumor volume translated to improved survival outcomes, as measured by time to tumor volume of 400 mm³ (FIG. 16B). Vehicle control mice had a median survival of 13 days, whereas treatment with Pmel cells alone increased this median survival to 34 days. Pmel with pre-loaded chM1Fab-IL15/sushi extended the median survival time to 43 days, and led to two complete remissions (28.6%). Neither the vehicle control, nor the Pmel alone groups had any mice survive past 39 days. This increased tumor control and survival was correlated with increased numbers of circulating Pmel cells (FIG. 16C). At peak expansion, the chM1Fab-IL15/sushi-loaded Pmel had a 2.6-fold higher blood concentration than the Pmel alone and this increased concentration was maintained long past peak expansion: for the chM1Fab-IL15/sushi-loaded group, there were still more than 200 Pmel cells/µl of blood as far as 42 days post-ACT, which was substantially more than the mock-loaded Pmel group (FIG. 16C). We conclude that pre-loading tumor-targeting T cells with the IL-15 tethered fusion molecule enhances cell expansion in a syngeneic host, and leads to better tumor control and overall survival.

An additional mouse model comprising a human xenograft tumor and chimeric antigen receptor T (CAR-T) cell therapy, was used to test the ability of IL-15 IFMs to enhance tumor-specific cell therapy. Briefly, CAR-T cells were generated according to protocols similar to those used for ex vivo expansion of clinical CAR-T cells. After transduction and expansion of CD3 human T cells with an EGFR-targeted CAR construct (which will recognize EGFR expressed on the tumor cells), the cells were loaded with a human CD45-targeted IL-15 IFM (h9.4Fab-IL15/sushi), injected into tumor xenograft-bearing mice, and assessed for in vivo expansion and therapeutic efficacy. In this study, H1299 human lung cancer cell line was acquired from the American Type Culture Collection (ATCC, Manassas, Va.) and $1.0 \times 10^7$ tumor cells were injected subcutaneously (SC) into the shaved right flank of NOD.Cg-Prkdc$^{scid}$ Il2rg$^{tm1Wjl}$/ SzJ mice (NSG, Jackson Laboratories, Bar Harbor, Me.). Human CD3 T cells were activated with Dynabeads, T cell Expander beads, at a 1:1 bead:cell ratio and a cell density of $1 \times 10^6$ cells/mL. T cell medium (TCM, RPMI 1640 supplemented with 10% fetal bovine serums, 25 mM HEPES buffer, and 2 mM L-glutamine) was supplemented with IL-7 (10 ng/mL) and IL-21 (100 ng/mL), and cells were cultured at 37° C. with 5% $CO_2$. After 2 days of culture, beads were removed from the culture by magnet, and cells were washed with media. T cells were resuspended in fresh media at $2.0 \times 10^7$ cells/mL and transduced for 30 min under 500 g centrifugation with CAR-T expressing lentivral vectors at a multiplicity of infection of 5 with 10 ng/mL protamine sulfate. After 30 min of centrifugation, cells were diluted to 5.0×10⁶ cells/mL with fresh TCM that was further supplemented with IL-7 and IL-21 at concentrations of 10 ng/mL and 100 ng/mL, respectively. Cells were transduced for an additional 12 hr at 37° C. with 5% $CO_2$. After 12 hr transduction, cells were pelleted to remove virus-containing media and resuspended at 1.0×10⁶ cells/mL in fresh T cell media supplemented with IL-15 (50 ng/mL) and IL-21 (100 ng/mL). Cells were cultured at 37° C. with 5% $CO_2$ for an additional 3 days and then loaded with an IL-15 IFM at a concentration of 0.75 mg/mL. Cells were washed three times in HBSS to remove excess cytokine, and then injected as a single dose into H1299 tumor-bearing mice with 5.0×10⁶ CAR-T cells/mouse. Other groups included vehicle alone (no cells), and a single dose of 5.0×10⁶ cells that were mock-loaded with HBSS (CAR-T alone). The CAR-T generation was repeated (using the same human donor) and animals were injected with a second dose of 5×10⁶ CAR-T cells (with or without the IL-15 IFM) on Day 37.

Figures 16D, 16E:
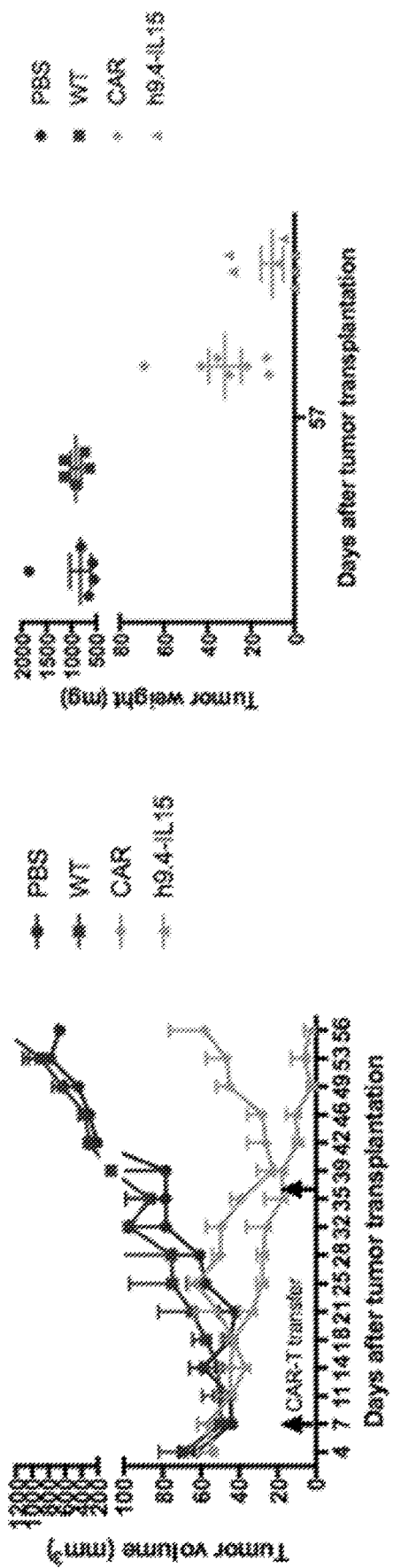

FIG. 16D shows tumor growth curves from the above described study. CAR-T cells alone reduced tumor volume over the course of the study, compared to control groups (HBSS: no T cells; WT: activated and expanded, but non-CAR-transduced T cells), and this effect was enhanced by pre-loading the cells with h9.4Fab-IL15/sushi. Only the mice treated with the IL-15 IFM-loaded CAR-T cells showed continue tumor regression, the h9.4Fab-IL15/sushi tethered fusion molecule enhances CAR-T anti-tumor activity. After 8 weeks post-ACT, tumors were harvested and weighed; FIG. 16E shows that the IL-15 IFM decreased tumor weight compared to CAR-T cells alone, and also resulted in three out of seven mice with complete response (tumor-free).

Example 9: Tethered Fusion Platform Enables Selective Cell Targeting

Figure 17B:
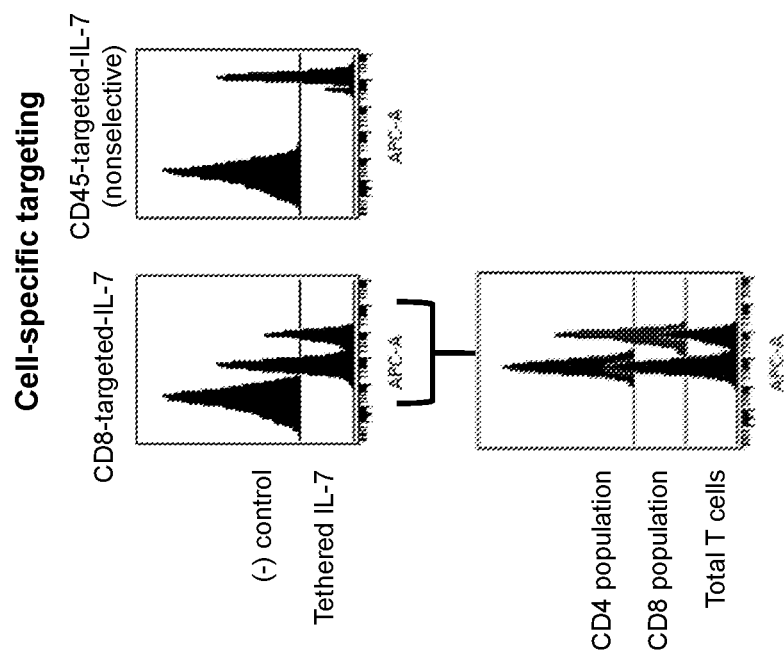
FIGS. 17A-17G show tethered fusion platform enables selective cell targeting and improved expansion of CD8 T cells in cultures of activated total CD3 human T cells by pulse incubation with CD8-targeted IFMs.
Figure 17A:
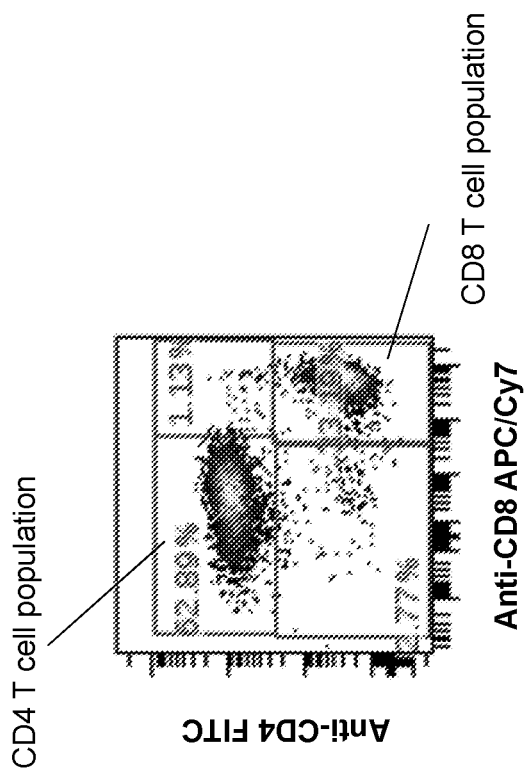
Figure 17C:
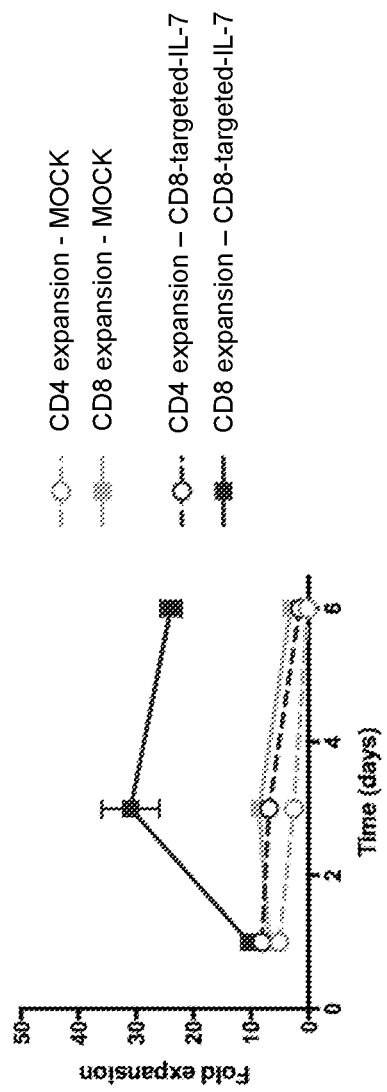

CD8-targeted IL-7 delivers selective loading and expansion of CD8 T cells. FIGS. 17A-17B shows cell-specific targeting, in which CD8-targeted-IL-7 selectively targets CD8 T cells. FIG. 17C shows selective expansion of CD8 T cells, but not CD4 T cells, in cultures of activated total CD3 human T cells by pulse incubation with CD8-targeted IL-7. Briefly, activated human T cells were prepared by stimulating total CD3 human T cells (comprising both CD4 and CD8 T cells) for three days using CD3/CD28 Dynabead Activator beads (Thermo) according to the manufacturer's instructions and in the presence of in the presence of 20 ng/mL IL-7 and 100 ng/mL IL-21. The CD3/CD28 beads were then removed and cells were incubated in full medium (RPMI 1640 containing 10% FBS) overnight in the presence of 20 ng/mL IL-7 and 100 ng/mL IL-21 at 37 C and 5% CO2. Cells were then washed and incubated with 500 nM of a CD8-targeted IL-7 construct (chOKT8Fab-IL7). After 1 hr at 37 C cells were washed two times with full medium, plated at a density of 200,000 cells/mL, and incubated at 37 C and 5% CO2. Separately, cells were analyzed for loading onto CD8 and CD4 T cells by staining the T cells with DyLight 650-conjugated anti-human IgG polyclonal antibody (Thermo cat. no. SA5-10129; DyLight 650 fluorophore can be read on the APC channel for flow cytometry, see FIG. 17B), FITC-conjugated anti-CD4 antibody (BioLegend cat. no. 344604), and APC/Cy7-conjugated anti-CD8 antibody (BioLegend cat. no. 344715). The anti-human IgG polyclonal antibody detects the Fab region of the CD8-targeted IFM. The anti-CD4 and anti-CD8 antibodies can differentiate the CD4 and CD8 T cell populations (FIG. 17A). FIG. 17B shows that the CD8-targeted IL-7 construct selectively loaded to greater levels on CD8 T cells when incubated with a mixed population of CD4 and CD8 T cells. FIG. 17C shows selective expansion of the CD8 T cells by the CD8-targeted IL-7 construct.

Figure 17D:
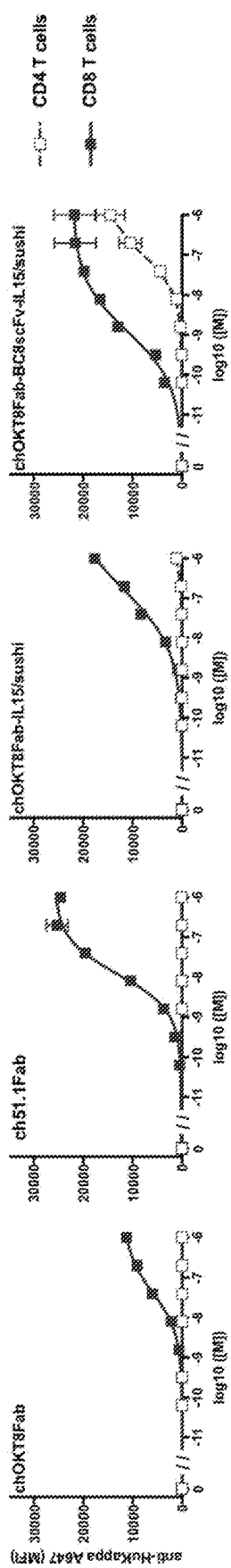
Figure 17E:
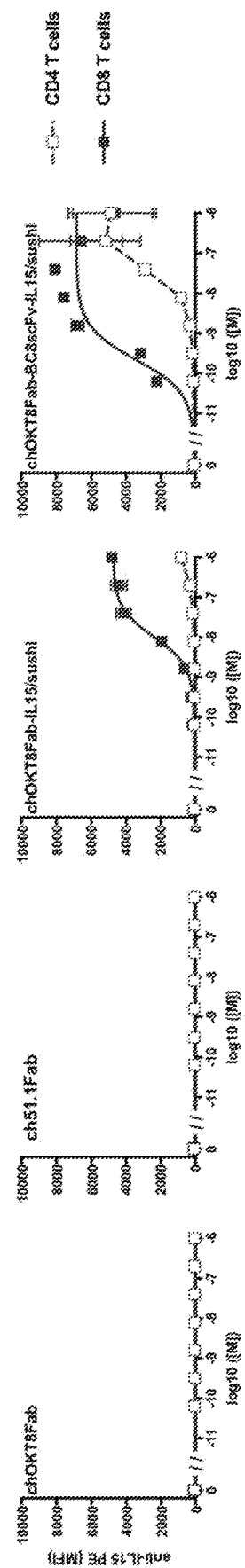

To further explore selective cell loading by different antibody clones and antibody configurations we compared the loading onto CD4 and CD8 T cells by two different anti-CD8 monoclonal antibodies. Briefly, we recombinantly produced anti-human CD8 antibody clones OKT8 and 51.1 as Fab fragments (chOKT8Fab and ch51.1Fab). We additionally constructed two IL-15 IFMs: one comprising the chOKT8Fab (chOKT8Fab-IL15/sushi) and a second comprising the chOKT8Fab and an anti-CD45 scFv (chOKT8Fab-BC8scFv-IL15/sushi). This latter construct contains antibody fragments against two different cell surface receptors, CD8 and CD45, and we reasoned it may give stronger cell loading of CD8 T cells through an avidity effect. We evaluated the ability of these four antibody and IFM constructs to load onto CD4 and CD8 T cells using total CD3 T cells (comprising mixtures of CD4 and CD8 T cells). FIG. 17D shows strong selective loading onto CD8 T cells for each construct. In FIG. 17E we similarly show selective loading of IL-15 onto CD8 T cells using anti-IL15 staining (Fab constructs that do not contain IL-15, chOKT8Fab and ch51.1Fab, are of course negative in this assay).

Figures 17F, 17G:
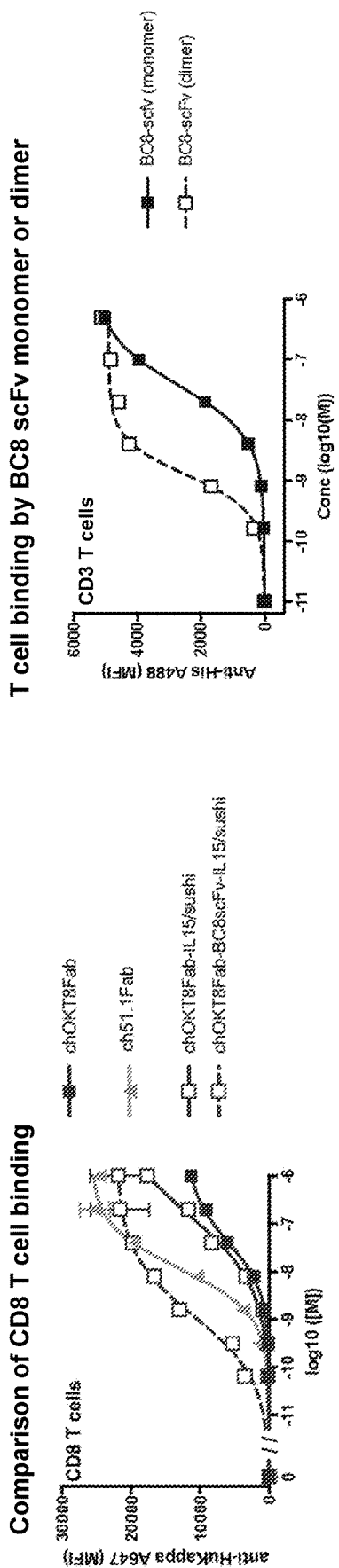
Figures 18A, 18B:
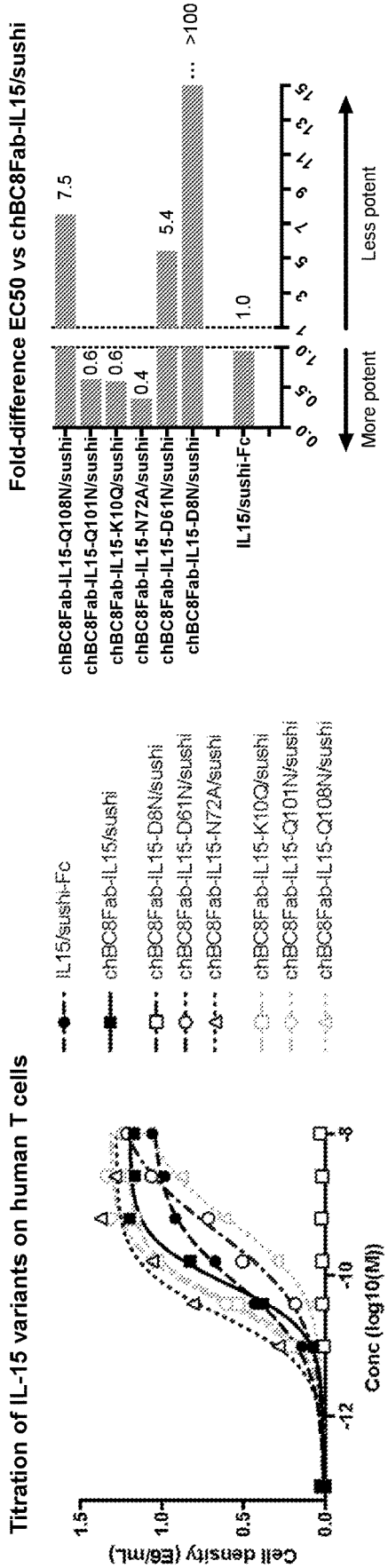
FIGS. 18A-18E shows cellular activities of various mutated forms of IL-15 and surface persistence of IFMs comprising IL-15 mutants.
Figure 18C:
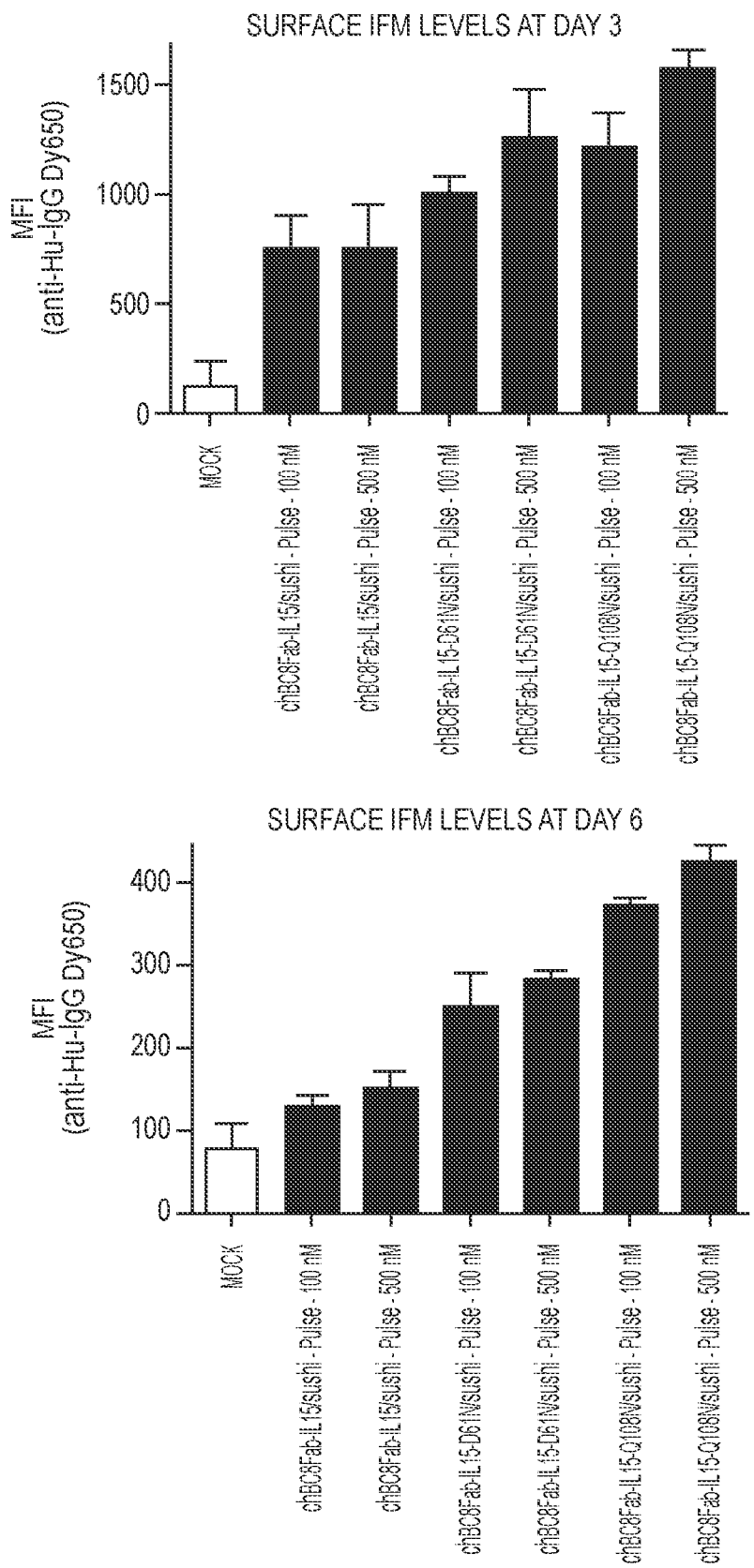
Figure 18D:
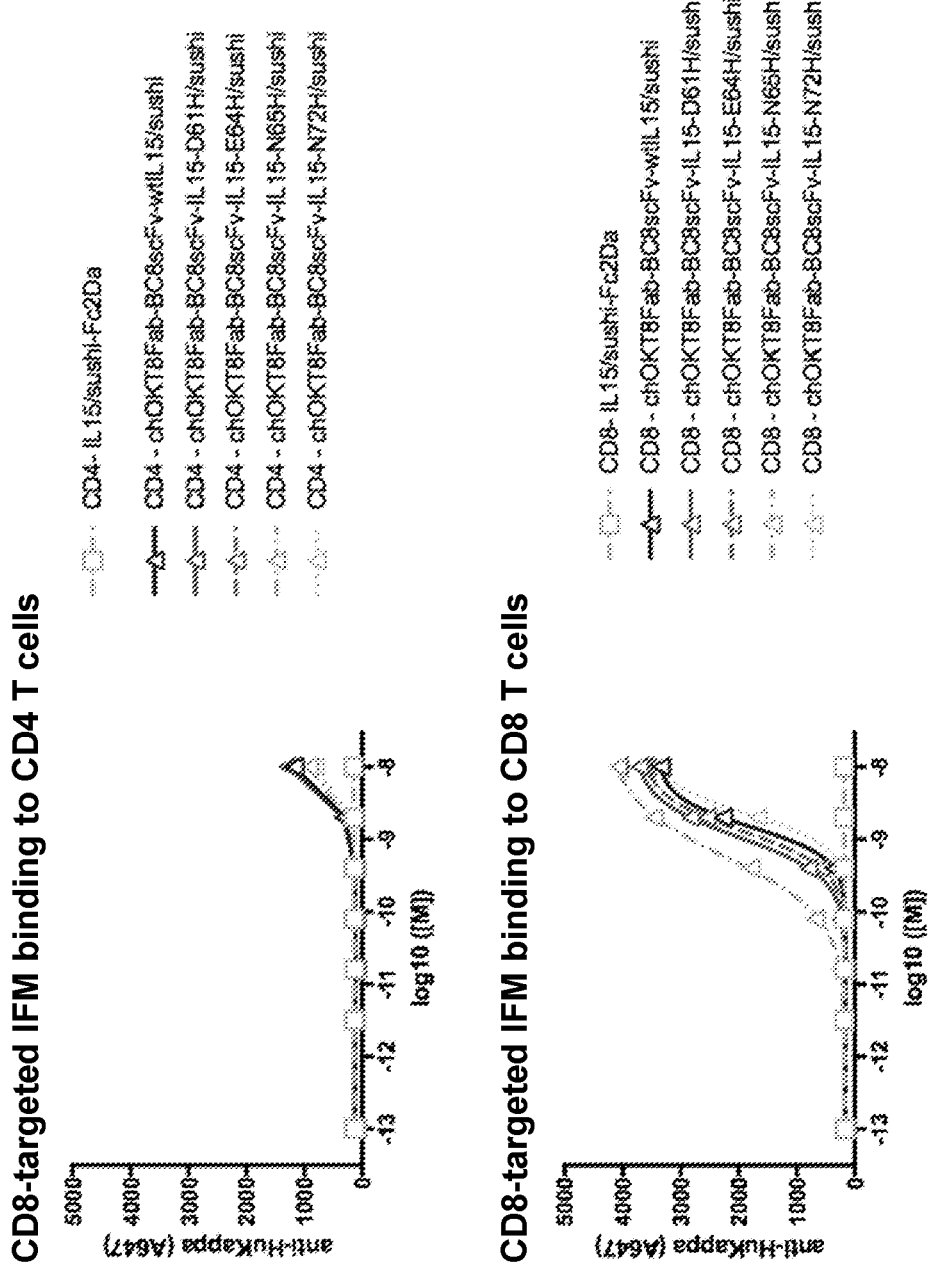
Figure 18E:
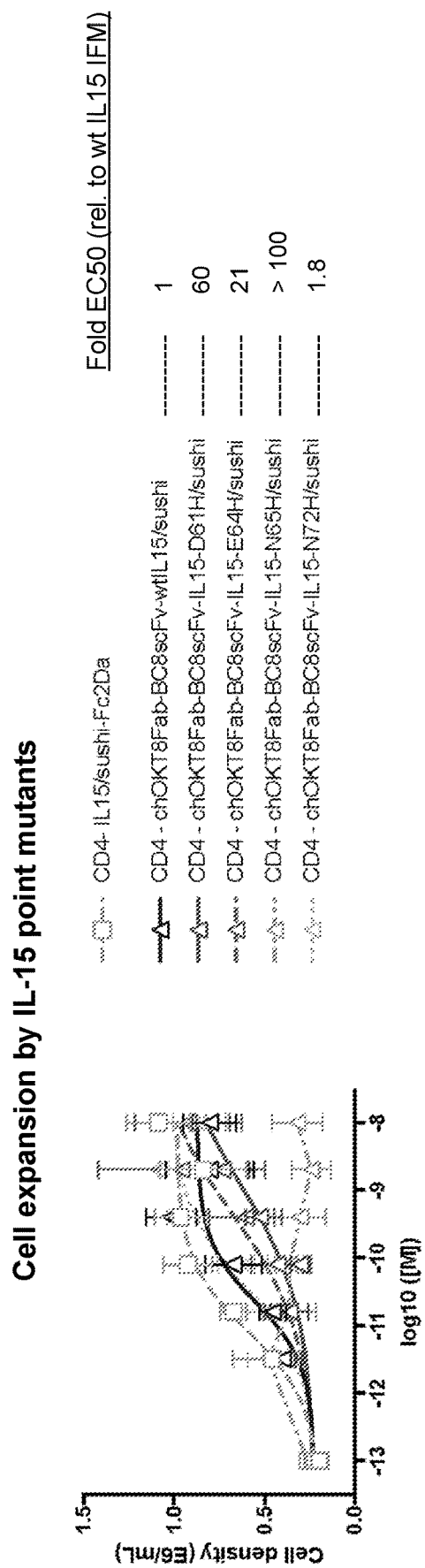
Figure 19A:
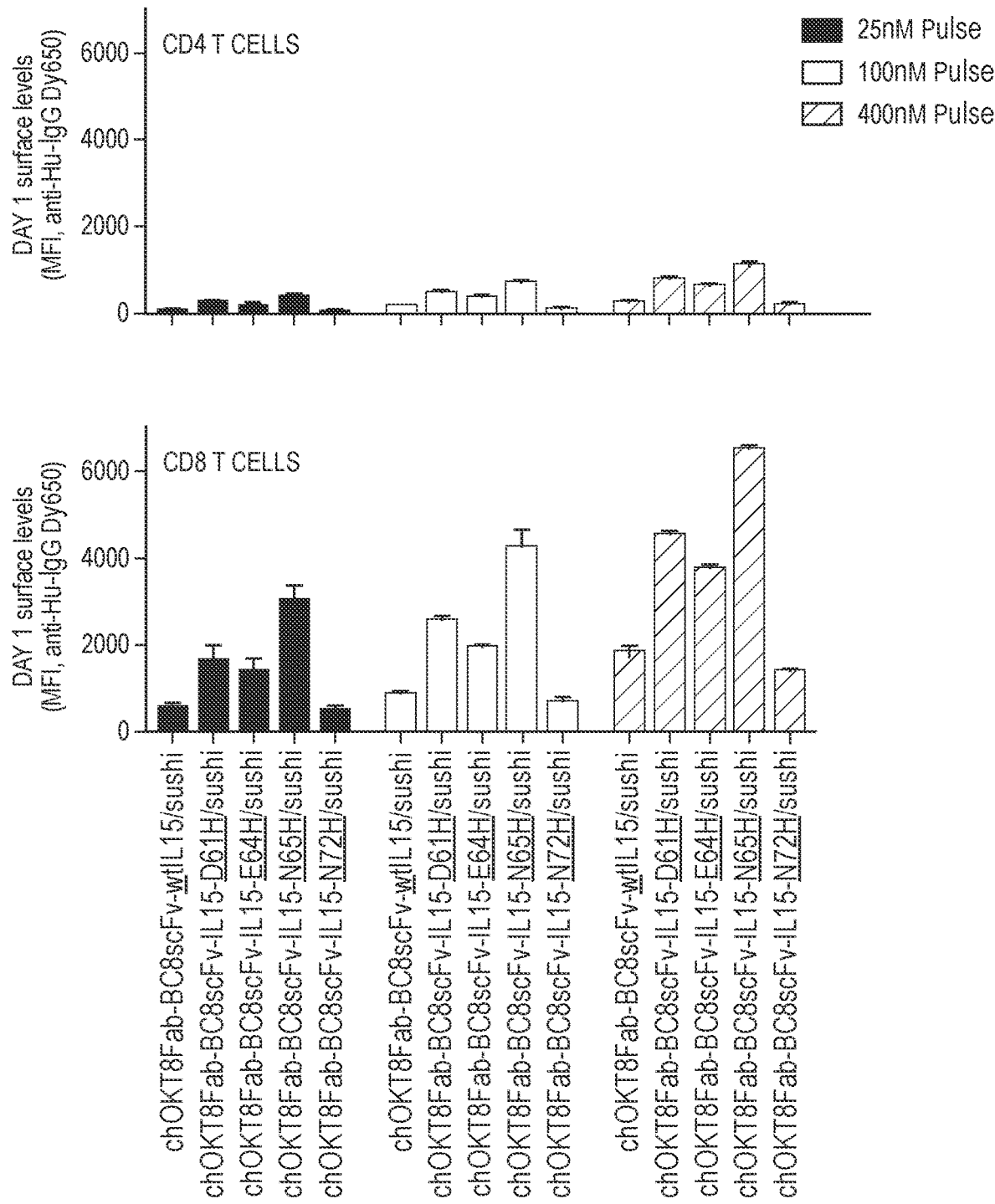
FIGS. 19A-19C shows selective cell targeting and CD8 T cell expansion by CD8-targeted IFMs comprising wild-type or mutated IL-15.
Figure 19B:
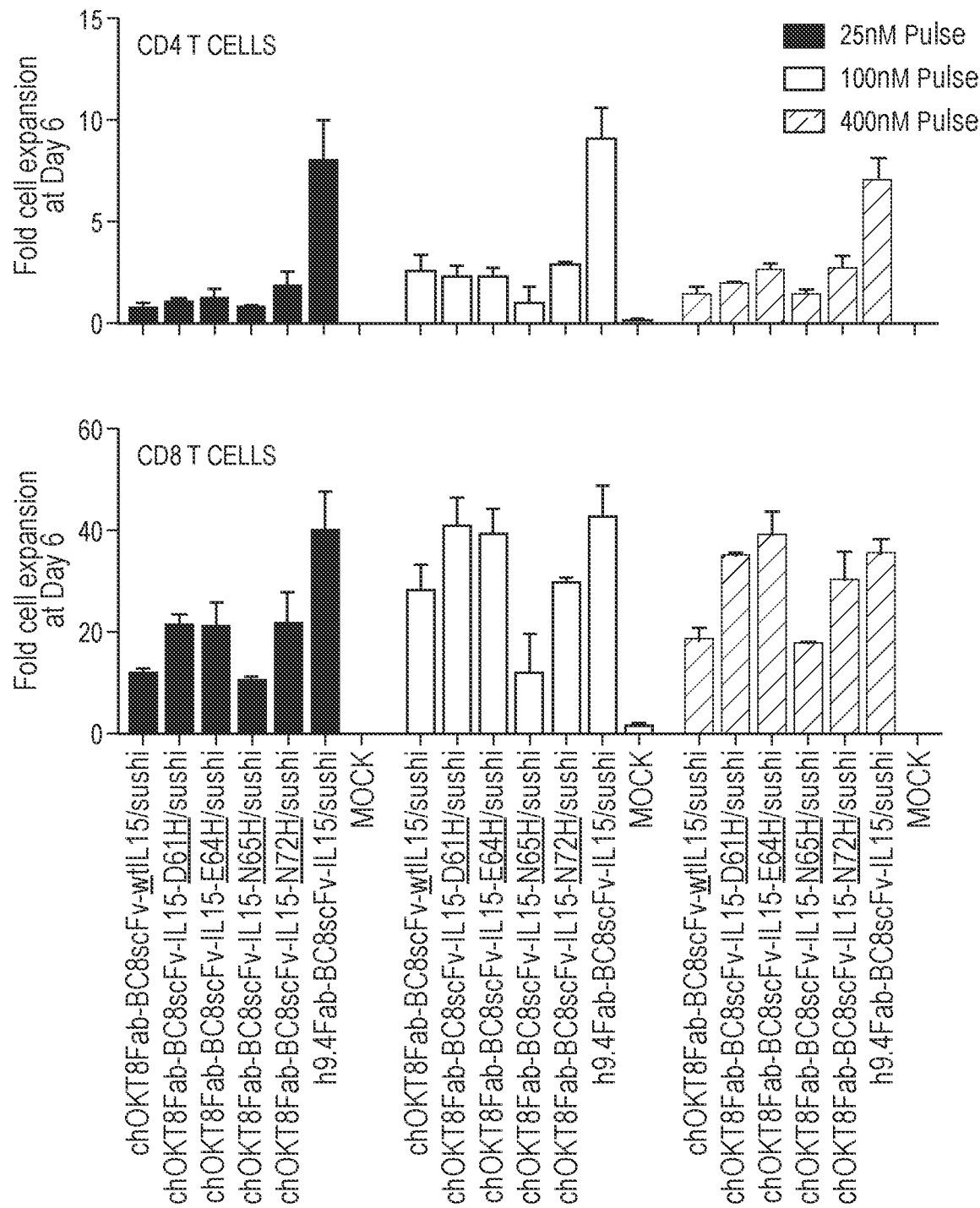
Figure 19C:
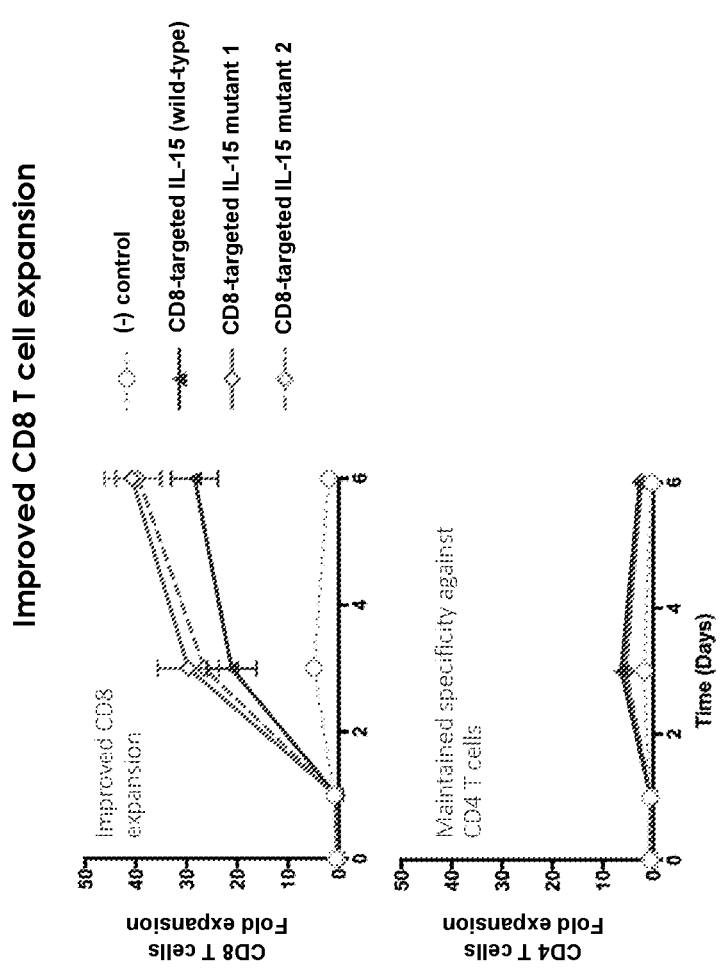
Figure 20:
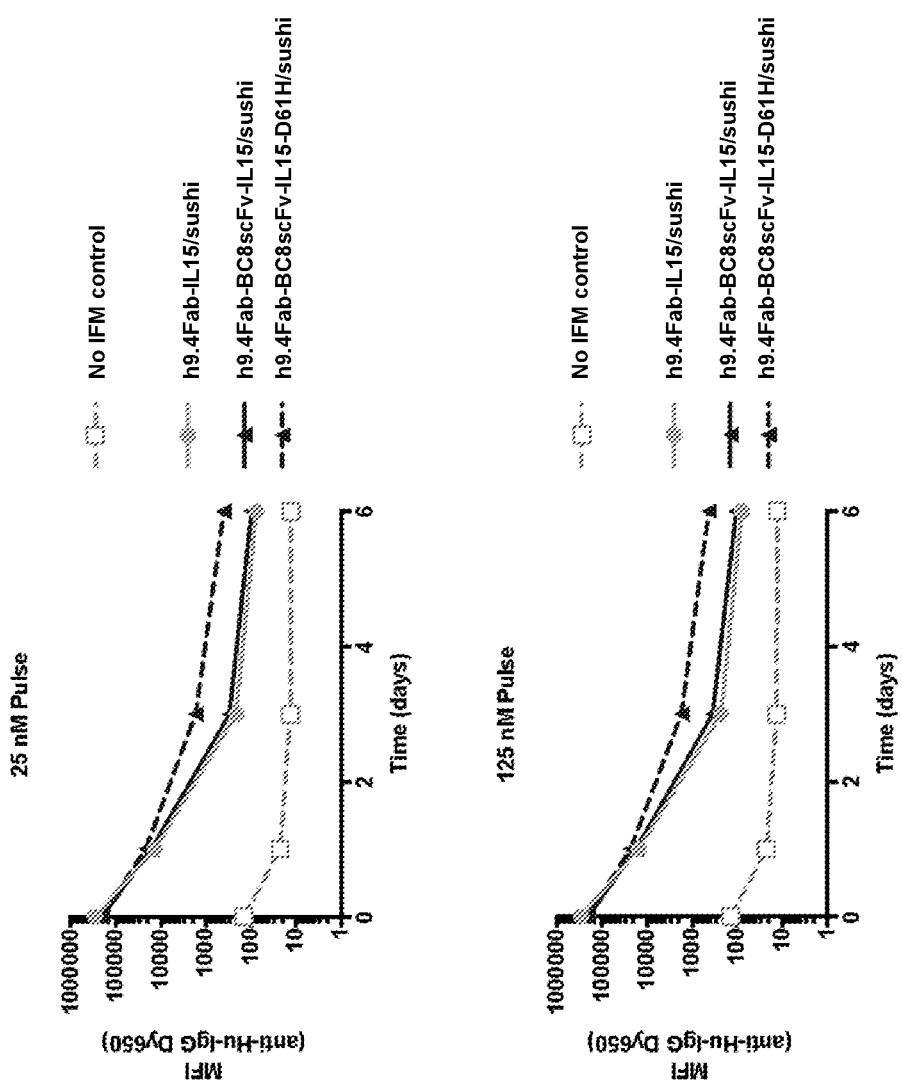
FIG. 20 shows surface persistence of CD45-targeted IFM comprising wild-type or mutated IL-15.

To compare relative affinities against CD8 T cells, we compiled the binding titrations against CD8 T cells from FIG. 17D into a single plot in FIG. 17F. The chOKT8Fab-BC8scFv antibody configuration delivered the tightest binding to the CD8 T cells. This IFM also resulted in loading onto CD4 T cells when used at higher concentrations (FIG. 17D and FIG. 17E). We reason that this is due to the BC8scFv, which binds to the CD45 receptor, which is present on both CD4 and CD8 T cells. The relative affinity of chOKT8Fab-BC8scFv-IL15/sushi for CD4 T cells observed in FIG. 17D is similar to the affinity of monomeric BC8scFv against T cells (FIG. 17G, the BC8scFv was constructed using a hexahistidine tag, which is used here as a handle for detection by flow cytometry); together with the minimal binding of chOKT8Fab and chOKT8Fab-I115/sushi to CD4 T cells, we conclude that binding of chOKT8Fab-BC8scFv-IL15/sushi to CD4 T cells is driven by the BC8scFv. A dimeric form of BC8scFv results in higher affinity to T cells, likely due to the avidity affect from bivalent binding. We further reason that the higher binding affinity of chOKT8Fab-BC8scFv-IL15/sushi to CD8 vs CD4 T cells—as well as the higher binding to CD8 T cells as compared with the monovalent chOKT8Fab-IL15/sushi—is similarly due an avidity effects that results from bivalent binding to CD8 T cells. We thus conclude that IFMs can be constructed using antibody clones that are specific for different cell surface receptors to improve cellular affinity and loading. Furthermore, one or more of the selected antibodies can be specific for a particular cell type in order to enable improved affinity while still retaining cell-selective loading. Using such a method, we show that it is further feasible to construct heterospecific antibodies with varied loading efficiencies on different cell types (e.g. in this case, stronger loading onto CD8 T cells and weaker—but nonzero—loading onto CD4 T cells).

Example 10: Cytokine Engineering Improves Tethered Fusion Potency

Figure 21:
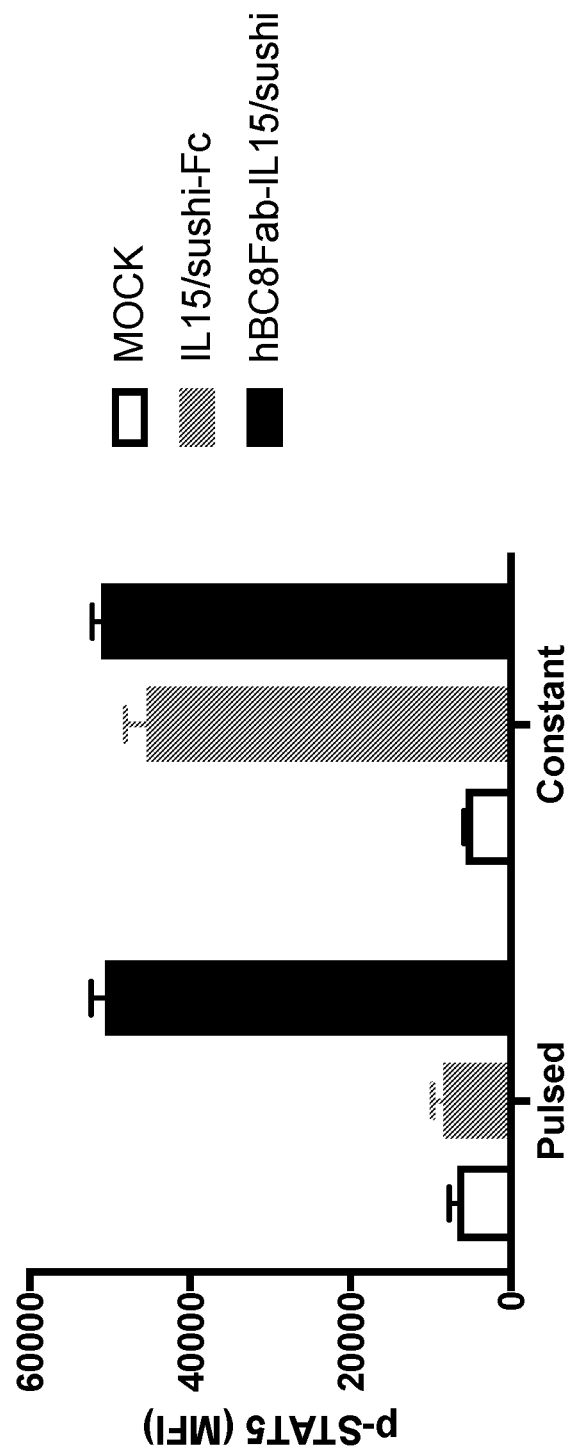
FIG. 21 shows IL-15 tethered fusion supports persistent signaling downstream of IL-15 receptors.

We evaluated the ability to further augment IFM potency by engineering cytokine mutants with modulated biological activity. Based on the structure-function understanding of the interaction between IL-15 and its cellular signaling receptors (Chirifu et al. Nat Immunol. 2007 September; 8(9):1001-7; Ring et al. Nat Immunol. 2012 December; 13(12):1187-95), we constructed three IL-15 variants comprising mutations to amino acid side-chains believed to interact with the IL-15/IL-2 receptor beta (specifically, IL-15-D8N, IL-15-D61N, and IL-15N72A), and three additional IL-15 variants comprising mutations to amino acid side-chains believed to interact with the gamma chain (IL-15-K10Q, IL-15-Q101N, and IL-15-Q108N). We constructed the IL-15 mutants as fusions to the chBC8Fab antibody fragment and evaluated their binding and activity on human T cells. Briefly, primary human T cells were activated as described in Example 1, and then incubated with five-fold serial dilutions of IFMs comprising the IL-15 variants (without washing after IFM incubation, e.g. a 'constant' incubation assay format). An IFM comprising wild-type IL-15 an IL-15/sushi-Fc construct were used as controls for comparison. After incubation with the IL-15 constructs for three days at 37 C and 5% CO2 cell density was analyzed using CountBright Absolute Counting Beads (Thermo) by flow cytometry following the manufacturer's instructions. The IFM containing wild-type IL-15 (chBC8Fab-IL15/sushi) exhibited similar cellular potency as the IL-15/sushi-Fc construct (FIG. 18A and FIG. 18B). In addition, FIG. 18A and FIG. 18B shows that three different IL-15 variants result in stronger cellular potency than wild-type IL-15 (IL-15-K10Q, IL-15-Q101N, and IL-15-N72A), two IL-15 variants resulted in reduced cellular potency (IL-15-D61N and IL-15-Q108N), and a single IL-15 variant did not display cellular activity under the range of concentrations evaluated (IL-15-D8N). In a separate experiment we evaluated the surface persistence of the two attenuated IL-15 variants (IL-15-D61N and IL-15-Q108N) in the pulse assay format as described in Example 1. We found that the IFMs comprising the attenuated variants exhibited stronger persistence on the cell surface (FIG. 18C). Activation of growth factor and cytokine signaling receptors induces negative regulatory feedback mechanisms within the cell. One such mechanism involves internalization and degradation of activated cytokine and growth factor receptors (reviewed in Jones et al. Trends Biotechnol. 2008 September; 26(9):498-505). Without wishing to be bound by theory, we reason that the elevated surface persistence from cytokine variants having attenuated activity may be due to weaker induction of such negative regulatory feedback mechanisms within the cell.

To further explore the relationship between cytokine activity and IFM surface persistence and potency, we designed four additional IL-15 variants comprising mutations at the interface with IL-15 and its IL-15/IL-2 receptor beta. In particular, we constructed CD8-targeted IFMs comprising the IL-15 variants IL-15-D61H, IL-15E64H, IL-15-D65H, or IL-15-N72H. Activated human T cells were prepared by stimulating CD3 human T cells for three days using CD3/CD28 Dynabead Activator beads (Thermo) according to the manufacturer's instructions, beads were then removed and cells were incubated in full medium (RPMI 1640 containing 10% FBS) overnight in the presence of 20 ng/mL IL-7 and 100 ng/mL IL-21 at 37 C and 5% CO2. The activated T cells were then incubated with a serial five-fold dilution of IFMs spanning a concentration range of 10-0.0032 nM and plated at a density of 200,000 cells/mL into 96-well plates (without washing after IFM incubation, e.g. a 'constant' incubation assay format). After three days at 37 C and 5% CO2 cells were harvested and evaluated for cell expansion and IFM surface levels. For analysis of IFM surface levels, cells were stained with BV421-conjugated anti-CD4 antibody (BioLegend cat. no. 344632), BV786-conjugated anti-CD8 antibody (BioLegend cat. no. 344740), and Alexa-Fluor-647-conjugated anti-human kappa (light-chain) antibody. FIG. 18D demonstrates high loading of the CD8-targeted IL-15 constructs onto CD8 T cells, and minimal loading onto CD4 T cells. The limited loading of the CD8-targeted IFMs onto CD4 T cells enabled a controlled evaluation of the effects of IL-15 mutations on cellular responses. Expansion of CD4 T cells in response to incubation with CD8-targeted IL-15 constructs comprising D61H, E64H, N65H, or N72H point mutations demonstrated attenuating activity of D61H, E64H, and N65H mutations (FIG. 18E).

We further evaluated activity of these constructs on CD8 and CD4 T cells in the pulse assay format. Briefly, activated total CD3 human T cells were incubated with the CD8-targeted IL-15 variants for 1 hr at 37 C, washed to remove unbound IFM, plated at a density of 200,000 cells/mL, and incubated at 37 C and 5% $CO_2$. To control for effects of induced cytokine secretion or tethered fusion unbinding and rebinding, each of which may support further T cell survival or expansion, we refreshed the cell culture medium one and three days after pulse incubation; cells were additionally split using a five-fold dilution ratio into fresh medium three days after pulse incubation to allow for further cell expansion. Each CD8-targeted construct selectively loaded to higher degrees onto CD8 T cells as compared with CD4 T cells (FIG. 19A). In addition, each of the histidine mutants comprising attenuated cellular activity (D61H, E64H, and N65H) exhibited higher surface persistence one day following the pulse incubation onto mixed CD4 and CD8 T cells (FIG. 19A). To evaluate the ability of the CD8-targeted constructs to selectively expand CD8 vs CD4 T cells we compared their activity with a nonselectively-loaded, CD45-targeted IL-15 IFM constructed with the same antibody configuration as the CD8-targeted IL-15 IFMs (h9.4Fab-BC8scFv-IL15/sushi, which contains a Fab-scFv format consistent with the antibody format for the CD8-targeted constructs). Each CD8-targeted IL-15 construct delivered selective expansion of CD8 T cells, and the CD8-targeted IL-15 constructs comprising the D61H and E64H mutations supported greater CD8 T cell expansion than the CD8-targeted construct comprising wild-type IL-15 (FIG. 19B). Notably, in this pulse assay format each of the CD8-targeted IL-15 constructs only weakly expanded the CD4 T cells (FIG. 19B), consistent with their design for CD8-specificity and consistent with their specificity for loading onto CD8 T cells. For comparison, a full expansion time course is shown for the CD8-targeted constructs comprising wild-type IL-15, IL-15-D61H, or IL-15-E64H (FIG. 19C).

We additionally evaluated the attenuated IL-15 variant IL-15-D61H within the context of a CD45-targeted IFM (h9.4Fab-BC8scFv-IL15-D61H). Consistent with the data observed for the CD8-targeted IL-15-D61H IFM, the CD45-tethered construct delivered stronger cell surface persistence as compared both with a monovalent and bivalent CD45-tethered IL-15 IFMs (FIG. 20). Collectively, we conclude that IFMs comprising attenuated IL-15 variants can result in higher cell surface persistence and induce stronger cell proliferation over time.

Example 11: IL-15 Tethered Fusion Supports Persistent Signaling Downstream of IL-15 Receptors We evaluated the ability for an IL-15 tethered fusion to support activation of intracellular signaling one day after pulse incubation with the tethered fusion. Briefly, human T cells were activated with CD3/CD28 Dynabeads for three days as described in the manufacturers instructions. Beads were removed and cells were incubated with IL-2 for 1 day prior to pulse or constant incubation with IL-15 constructs. Cells were incubated in biological duplicate with PBS (Mock condition), and IL-15/sushi-Fc construct, or hBC8Fab-IL15/sushi for 1 hr at 37° C. and then washed three times will full media (RPMI 1640 with 10% FBS). Cells were then plated in full medium at a cell density of approximately 400,000 cells/mL and incubated at 37° C., 5% CO2. For "constant" incubation conditions cells were supplemented with the indicated IL-15 construct at a concentration of approximately 1 µg/mL. The following day cells were recovered, fixed with approximately 1.5% paraformaldehyde for 10 min at room temperature, and permeabilized with 100% methanol for 10 min at 4° C. Cells were then immunostained using an antibody specific to phosphorylated STAT5 (a transcription factor activated by signaling molecules downstream from the IL-15 receptors) and analyzed on a FACSCelesta using Diva Software; data was analyzed using Cytobank. While both IL-15 constructs induced phosphorylation of STAT5 when incubated with the T cells in the "constant" format, only the tethered fusion maintained STAT5 phosphorylation one day following the pulse incubation (FIG. 21).

Example 12a: Exemplary Immunostimulatory Fusion Proteins Comprising IL-12

Figure 22A:
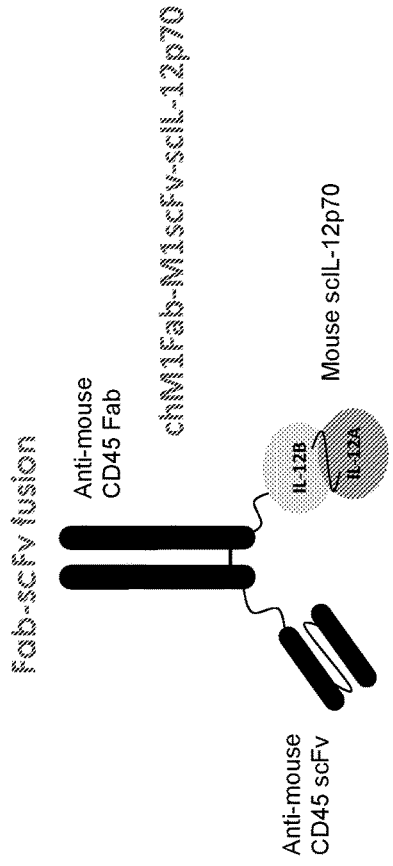
Figure 22B:
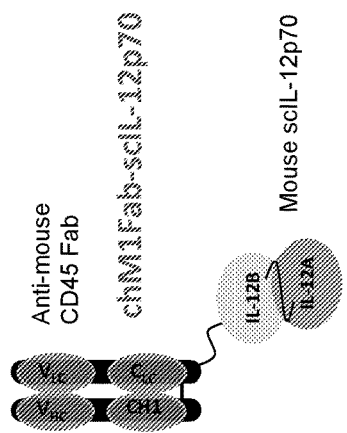

Tethered fusions (also referred to as IFMs) comprising IL-12 can be constructed in a similar manner to those described for IL-15. Exemplary IL-12 tethered fusions (IL12-TFs) are depicted in FIGS. 22A-22D. IL12-TFs for use on both human or mouse cells have been constructed using either human or mouse IL-12 and antibody fragments specific to either human or mouse CD45. The IL12-TF chM1Fab-sc-IL12p70 comprises an anti-mouse CD45 Fab fragment fused to the mouse single-chain IL-12p70 (FIG. 22A). Mouse single-chain IL-12p70 comprises a genetic fusion between mouse IL-12A and IL-12B. Another IL12-TF for use in mouse cells, chM1Fab-M1scFv-scIL-12p70, comprises a Fab-scFv fusion of anti-mouse CD45 Fab and scFv antibody fragments and a mouse single-chain IL-12p70 (FIG. 22B). Corresponding IL12-TFs for use with human cells have also been constructed: h9.4Fab-scIL-12p70 (FIG. 22C) and h9.4Fab-h9.4scFv-scIL-12p70 (FIG. 22D) comprise a Fab or Fab-scFv fusion specific for human CD45 and a single-chain human IL-12p70. The respective IL-12p70 subunits IL-12A and IL-12B for all four constructs are expressed as a single-chain molecule with the orientation IL-12B-IL-12A, although the converse expression orientation is also possible (e.g. IL-12A-IL-12B). Multiple different flexible linkers joining the IL-12A and IL-12B subunits are possible. IL-12p70 can also be expressed as a heterodimer of IL-12A and IL-12B, which is the natural form of the protein. Various linkers disclosed herein can be used to operably link the anti-CD45 antibody and IL-12, which act to add space therebetween.

Example 12b: Antibody-Mediated Tethering of IL-12 to CD45 Supports Cell Loading of IL-12 and Prolonged Surface Persistence We evaluated the ability of IL12-TFs to support the loading of IL-12 onto T cells. Briefly, human total CD3 T cells were activated with CD3/CD28 Dynabeads for three days. Beads were removed and cells were incubated with IL-2 for 1 day prior to pulse incubation with h9.4Fab-scIL-12p70 diluted in full medium (RPMI 1640 with 10% FBS). Cells were incubated in biological duplicate with full media (Mock condition) or h9.4Fab-scIL-12p70 for 1 hr at 37° C. and then washed three times will full media (RPMI 1640 with 10% FBS) to remove unbound IL12-TF. Cells were then plated in full medium at a cell density of approximately 200,000 cells/mL and incubated at 37° C., 5% CO2. Surface tethered IL-12 was detected using flow cytometry by immunostaining with a polyclonal anti-human IgG antibody. Cells were counted using CountBright Absolute flow cytometry counting beads. In each case cells were analyzed on a FACSCelesta using Diva Software; data was analyzed using Cytobank.

Figure 23:
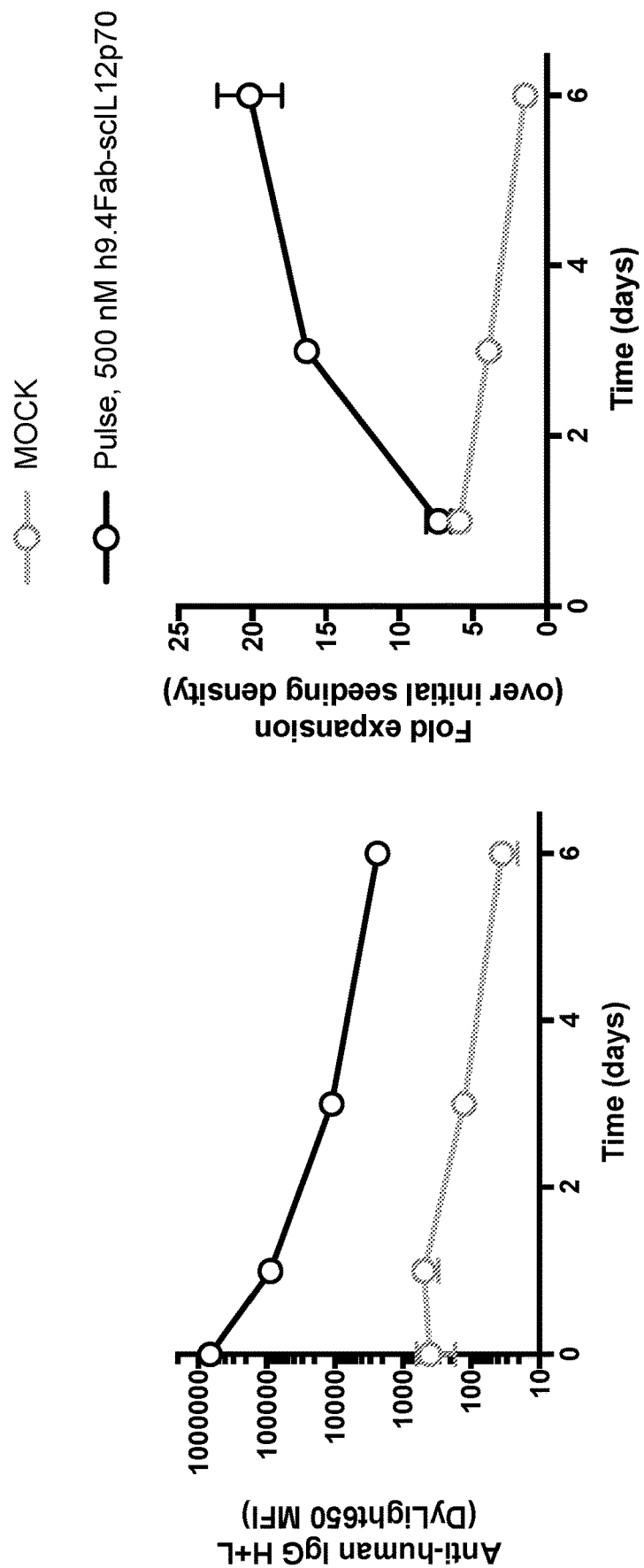
FIG. 23 show anti-CD45-IL12-TF supports strong cell loading of IL-12 and strong surface persistence.

As shown in FIG. 23, pulse incubation of IL-12 fused to an anti-CD45 antibody supports not only significant loading and prolonged persistence of IL-12 on the T cell surface, but also significant T cell expansion.

Example 13: IL-12 Tethered Fusions Induce Persistent STAT4 Phosphorylation

Human total CD3 T cells were activated with CD3/CD28 Dynabeads for three days. Beads were removed and cells were incubated with IL-2 for 1 day prior to pulse incubation with IL-12 and IL-15 tethered fusion constructs diluted in full medium (RPMI 1640 with 10% FBS). Cells were incubated in biological duplicate with full medium (Mock condition), an IL-15/sushi-Fc, h9.4Fab-scIL-12p70, h9.4Fab-IL-15/sushi, or a combination of h9.4Fab-scIL-12p70 and h9.4Fab-IL-15/sushi constructs (each at 500 nM) for 1 hr at 37° C. and then washed two times will full media. Cells were then plated in full medium at a cell density of approximately 200,000 cells/mL and incubated at 37° C., 5% CO2. For a control condition of constant IL-15 incubation cells were supplemented with the IL-15/sushi-Fc construct at a concentration of approximately 25 nM. The following day cells were recovered, fixed with approximately 2% paraformaldehyde for 10 min at room temperature and permeabilized with 100% methanol for 10 min at 4° C. Cells were then immunostained using antibodies specific to phosphorylated STAT4 or phosphorylated STAT5 and analyzed on a FACSCelesta using Diva Software; data was analyzed using Cytobank.

Figure 24:
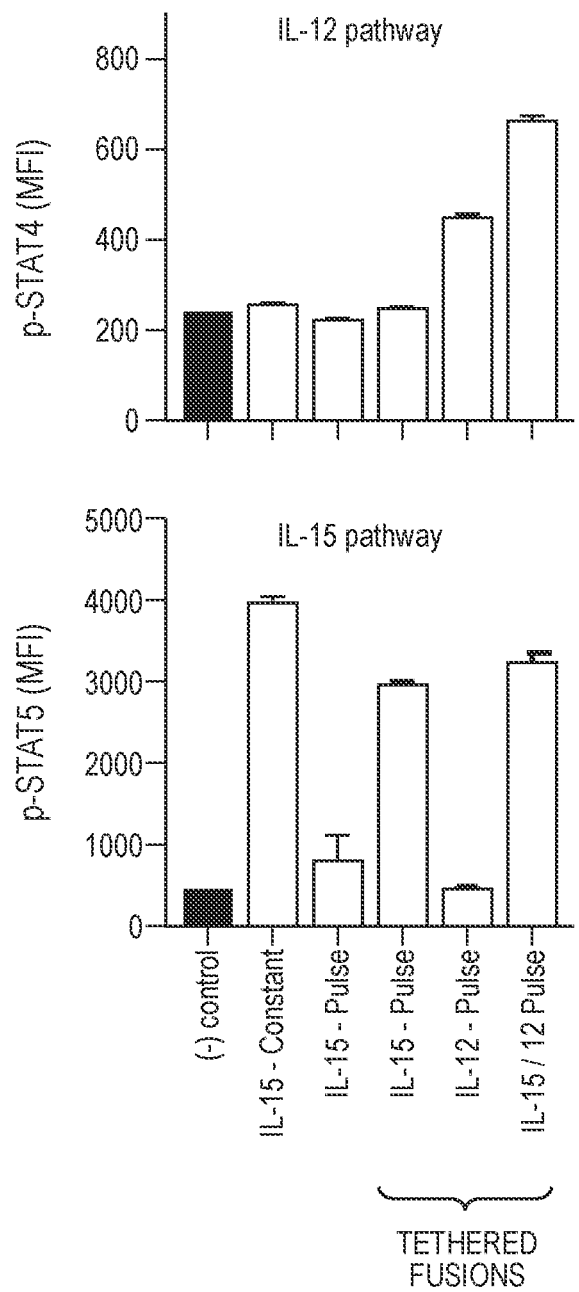
FIG. 24 shows that IL-12 tethered fusions induce persistent STAT4 phosphorylation and STAT4 phosphorylation is augmented by combined treatment with IL-12 and IL-15 tethered fusions.

As shown in FIG. 24, pulse incubation of the IL-15 tethered fusion induces STAT5 phosphorylation to similar levels as constant incubation with 25 nM IL-15/sushi-Fc, while pulse incubation with IL-15/sushi-Fc does not induce STAT5 phosphorylation above background levels. The IL-12 tethered fusion induces phosphorylation of STAT4; this activity is augmented by combined pulsed incubation with an IL-15 tethered fusion. We conclude that tethered fusions can induce sustained intracellular signaling activity when used both individually and in combination, and that combinations of IFMs with different cytokines can deliver increased activity beyond that observed by a single IFM.

Example 14: Tethering Multiple Cytokines to the Immune Cell Surface

Immune cells often sense and integrate signals from multiple different inputs. Indeed, many examples in the art demonstrate the ability for multiple cytokines to elicit broader or more potent immune responses than the individual cytokines alone. We therefore evaluated the ability to simultaneously tether multiple cytokines to the immune cell surface using the IFM platform. We examined this possibility using multiple different combinations of cytokines and also by tethering stimuli from multiple different cell surface receptors.

Figure 25:
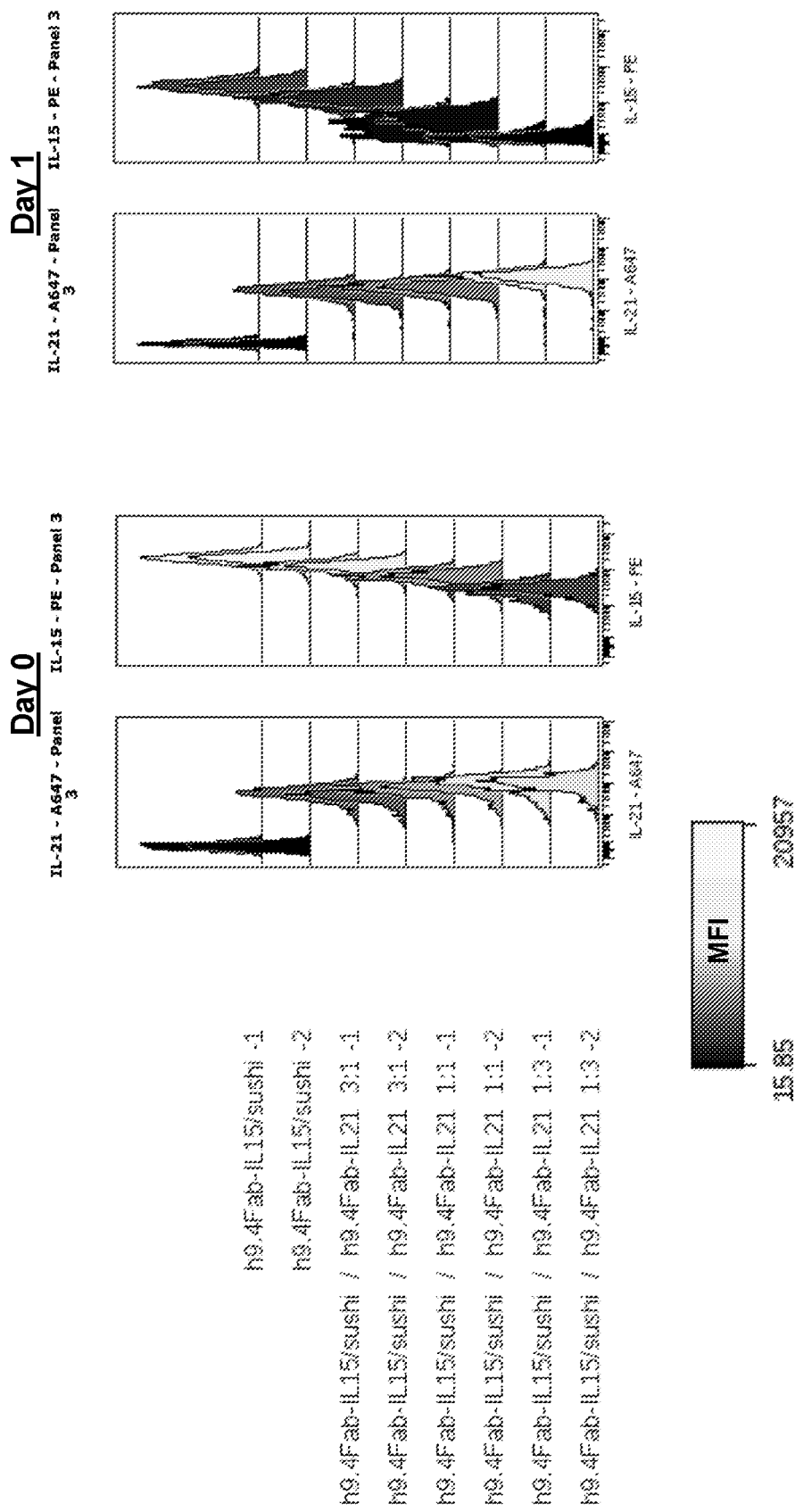
FIG. 25 shows surface loading and persistence of combinations of IL-15 and IL-21 IFMs.

We first demonstrated the ability to simulataneously tether two cytokines onto the immune cell surface by tethering IL-15 and IL-21 from a single cell surface receptor. Briefly, total CD3 human T cells were activated using CD3/CD28 stimulation as described in Example 13. Cells were then incubated with CD45-tethered IL-15 and IL-21 (h9.4Fab-IL15/sushi and h9.4Fab-IL21) at a range of molar ratios in order to examine the effects of the relative concentrations on cell surface cytokine loading. IL-15:IL-21 tethered fusion (TF) ratios of 1:0, 3:1, 1:1, and 1:3 were evaluated by mixing IL-15 and IL-21 TFs at concentrations of 500 nM:0 nM, 1500 nM:500 nM, 500 nM:1500 nM, and 500 nM:1500 nM, respectively. After 1 hr incubation at 37° C. cells were washed two times in full media, followed by staining with PE-conjugated anti-IL-15 and Alexa-Fluor-647-conjugated anti-IL-21 antibodies (R&D Systems cat. no. IC2471P and BioLegend cat. no. 513006). Cells were analyzed on a FACSCelesta flow cytometer using DiVa software, and data were analyzed using Cytobank. FIG. 25 demonstrates that both IL-15 and IL-21 can be simultaneously loaded onto the T cell surface via tethering to the CD45 receptor. We additionally observed, however, that increasing the molar ratio of IL-21:IL-15 TF resulted in increasing amounts of IL-21 on the cell surface at the expense of decreasing amounts of IL-15; FIG. 25 shows this effect was observed both on the day of loading (Day 0) and one day following the pulse incubation (Day 1), indicating initial differences in loading impacts surface levels observed over time.

Figure 26:
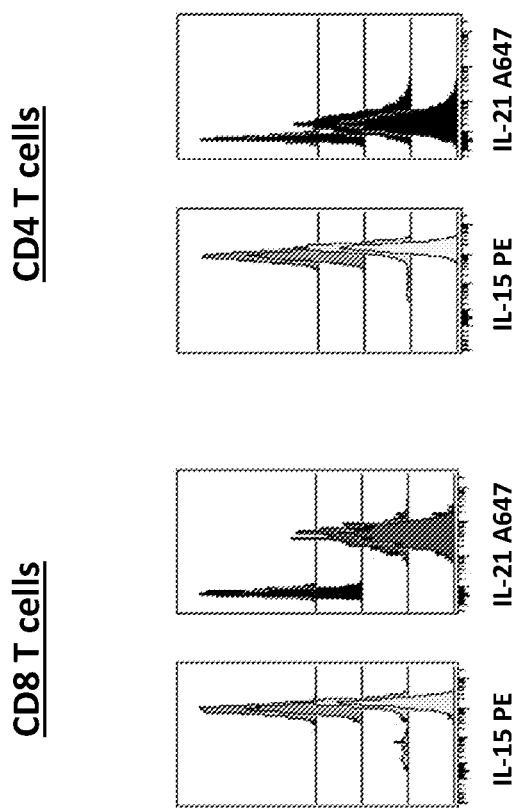
FIG. 26 shows surface loading of combinations of CD45-targeted IL-15 and CD8-targeted IL-21 IFMs.

We next evaluated the ability to 'additively' load multiple cytokines on the cell surface by tethering them to different cell surface receptors. We additionally evaluated the potential to couple cell selective cytokine loading with TF combinations by using a CD8-targeted IL-21 construct. IL-21 has been reported to confer a desirable stem-cell memory phenotype on CD8 T cells, but can undesirably repress differentiation of CD4 T cells into the IFNg-producing Th1 phenotype while promoting differentiation of CD4 T cells to a Th2 helper phenotype (Tian et al. Trends Immunol. 2016 August; 37(8): 557-568). Hence, an IL-21 tethered fusion specific for CD8 T cells would be desirable for anti-cancer therapy. Briefly, total human CD3 T cells were activated as described in Example 13. Cells were then incubated with a combination of CD45-tethered IL-15 (h9.4Fab-IL15/sushi) or CD8-tethered IL-21 (chOKT8Fab-BC8scFv-IL21), each at concentrations of 500 nM. After 1 hr incubation at 37 C cells were washed two times and then stained with PE-conjugated anti-IL-15 and Alexa-fluor-647 conjugated anti-IL-21 antibodies. To enable independent quantification of cytokine loading onto CD4 or CD8 T cells, cells were additionally stained with PE/Cy7-conjugated anti-CD4 and BV785-conjugated anti-CD8 antibodies (BioLegend cat. nos. 344612 and 344740). Cells were analyzed on a FACSCelesta flow cytometer using DiVa software, and data were analyzed using Cytobank. FIG. 26 demonstrates that the CD45-tethered IL-15 loaded to similarly high levels on both CD4 and CD8 T cells. By comparison, the CD8-targeted IL-21 selectively loaded to high levels on the CD8 T cells. Critically, addition of the CD8-targeted IL-21 did not reduce the levels of the CD45-targeted IL-15 (FIG. 26), demonstrating additive cytokine loading via tethering from different cell surface receptors.

To explore the ability of IFM combinations to augment biological activity we evaluated the activation of STAT5 (via phosphorylation), a transcription factor downstream of both the IL-15 and IL-21 signaling receptors, following pulse incubation with IL-15 and IL-21 TFs. Briefly, following the pulse incubation and washing described above, cells were plated into full medium at a density of approximately 200,000 cells/mL, incubated overnight at 37 C and 5% CO2. Intracellular signaling is a dynamic process, in which signal is reduced over time by negative regulatory feedback mechanisms within the cell; we therefore included a control condition comprising constant incubation with saturating amounts (25 nM) of an IL15/sushi-Fc construct to reflect an upper limit for STAT5 signaling activity. We additionally evaluated combinations of CD45-tethered IL-15 and IL-21 or CD45-tethered IL-15 and CD8-tethered IL-21 (each TF incubated at 500 nM). After one or three days incubation at 37 C and 5% CO2 wells were fixed, permeabilized, and immunostained for STAT5 phosphorylation as described in Example 11. Notably, one day after pulse incubation the CD45-targeted IL-15 induced STAT5 phosphorylation to levels approaching those of constant incubation with IL15/sushi-Fc (FIG. 27A). Combination of IL-15 and IL-21 tethered fusions—both by tethering each cytokine to the same receptor or by tethering the cytokines to separate receptors—resulted in further increased STAT5 phosphorylation as compared with the IL-15 TF alone, and reach similar levels as the constant IL15/sushi-Fc control condition (FIG. 27A). The additively loaded tethered fusions—i.e. combination of the CD45-targeted IL-15 with the CD8-targeted IL-21—further maintained STAT5 phosphorylation to similar levels as the saturating IL15/sushi-Fc condition at the Day 3 time point (FIG. 27B). We conclude that tethering multiple cytokines to the cell surface, both by tethering to the same receptor or to different receptors, can augment cellular responses. Tethering from different cell surface receptors can additionally enable additive cytokine loading and deliver further improve cellular activity.

Figure 29:
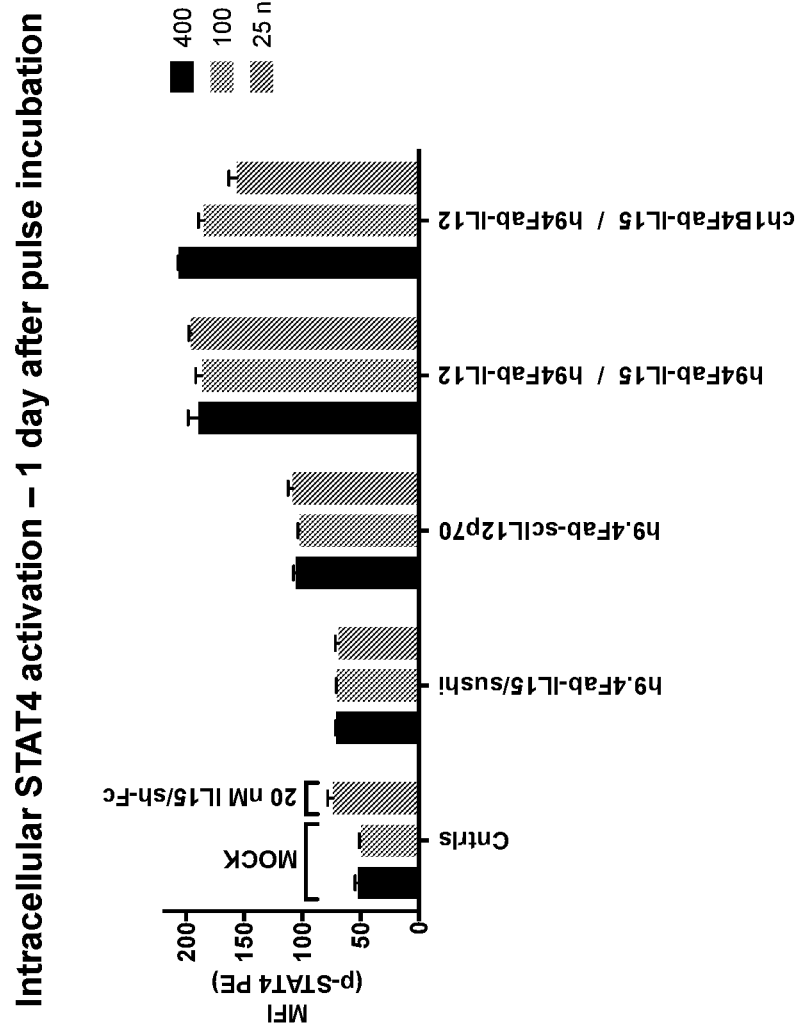
FIG. 29 shows STAT4 phosphorylation from combinations of IL-12 and IL-15 IFMs.

To further explore the modularity of cytokines and cell surface receptors for IFM combinations, we examined cell surface loading and cellular responses from combinations of IFMs comprising IL-15 and IL-12. Improved anti-tumor activity from IL-15 and IL-12 combination has been well described in the art (Di Carlo et al. J Immunol. 2000 Sep. 15; 165(6):3111-8; Lasek et al. Eur Cytokine Netw. 1999 September; 10(3):345-56). This is likely due at least in part from elevated expression of IL-12 receptor levels induced by IL-15 (Wu et al. Eur J Immunol. 1997 January; 27(1):147-54). Hence, combinations of IFMs comprising IL-15 and IL-12 may deliver further improved therapeutic activity. We evaluated IFM combinations in which IL-15 and IL-12 were both tethered from the CD45 receptor as well as a combination in which IL-12 was tethered from CD45 while IL-15 was tethered from CD18. Briefly, total CD3 human T cells were activated as described in Example 13. Cells were then incubated with a combination of CD45-tethered IL-15 or IL-12 (h9.4Fab-IL15/sushi and h9.4Fab-scIL12p70) or a combination of CD45-tethered IL-12 with CD18-tethered IL-15 (ch1B4Fab-IL15/sushi). Both combinations were evaluated at concentrations of 25, 100, and 400 nM for each IFM. After 1 hr incubation at 37 C cells were washed and then plated in full media at a density of 200,000 cells/mL and incubated overnight at 37 C and 5% CO2. Cell surface levels of IL-12 (using Alexa-fluor-647-conjugated anti-IL-12 antibody, BioLegend cat. no. 501818) were evaluated on Days 0 and 1 and activation of STAT4 (using PE-conjugated anti-p-STAT4 antibody, BD Biosciences cat. no. 558249), a transcription factor downstream of IL-12 receptors, was analyzed on Day 1. Staining for cell surface cytokines and intracellular signaling was performed as described above. Consistent with the data observed above for combination IL-15 and IL-21 loading, we observed lower overall loading of CD45-targeted-IL-12 when combined with CD45-targeted IL-15 (h9.4Fab-scIL12p70 and h9.4Fab-IL15/sushi combination; FIG. 28). Combination of CD45-targeted IL-12 with CD18-targeted IL-15, however, did not reduce the levels of IL-12 on the cell surface (h9.4Fab-scIL12p70 and ch1B4Fab-1L15/sushi combination, FIG. 28). The IL-12 tethered fusion—but not the IL-15 tethered fusion nor constant incubation with 20 nM IL15/sushi-Fc—induced STAT4 phosphorylation (FIG. 29). This is consistent with the understanding of intracellular signaling by IL-15 and IL-12 and suggests pulse incubation from IFMs is capable of delivering cytokine activities typically only observed by constant incubation of native cytokines. Notably, STAT4 phosphorylation was augmented by combination of IL-12 TF with the IL-15 TFs, even though the IL-15 TF did not induce STAT4 activity on its own (FIG. 29). We conclude that combining IFMs comprising IL-15 and IL-12 can further augment signaling beyond that induced by IL-12 alone. This may result from induction of IL-12 receptor expression by IL-15, IL-2 and IL-7 have been additionally described as elevating IL-12 receptor expression (Wu et al., Eur J Immunol. 1997 January; 27(1):147-54), and combinations of IFMs comprising IL-2 or IL-7 with an IL-12 IFM would also likely augment IL-12 or IL-12 IFM activity.

Figure 30:
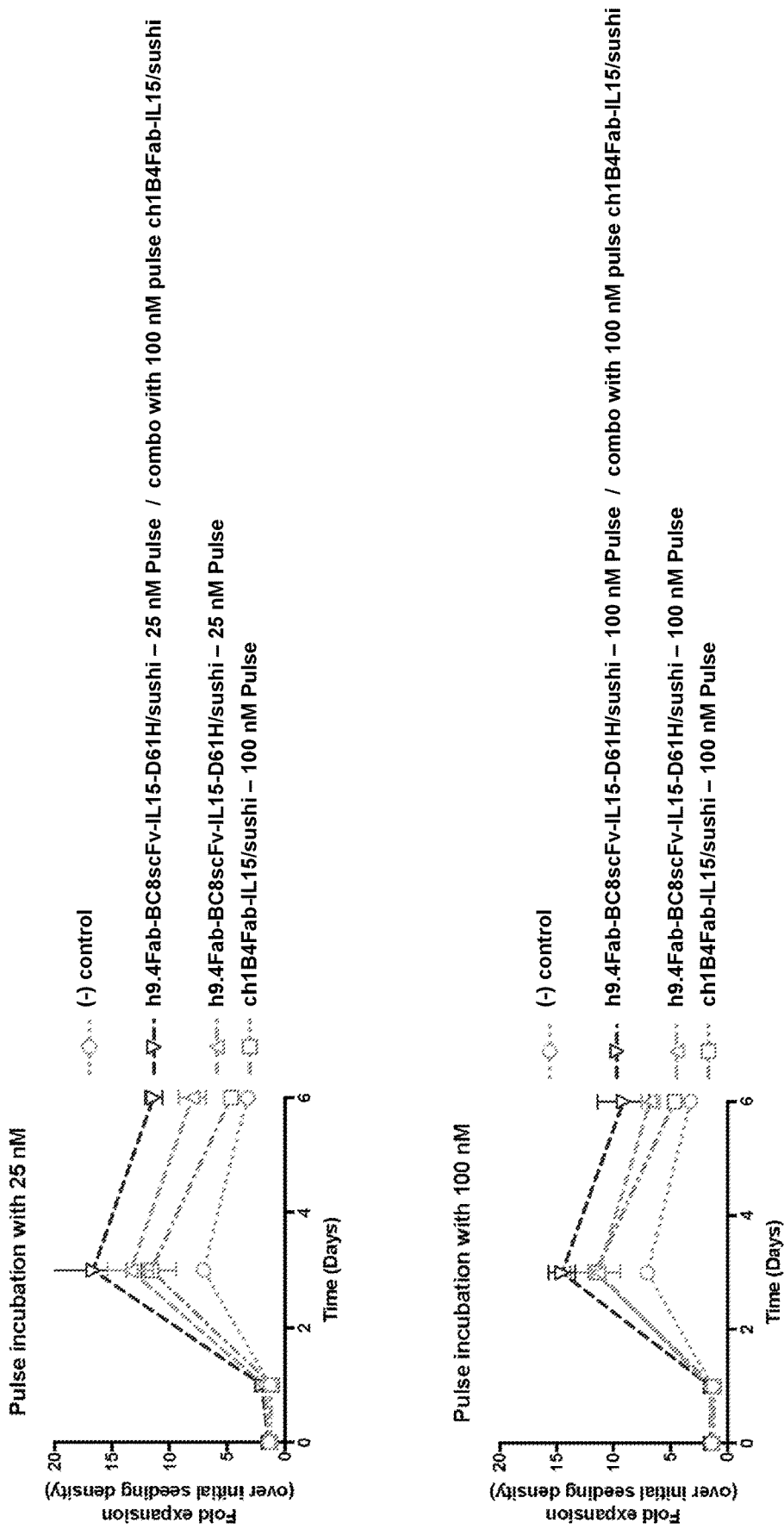
FIG. 30 shows T cell expansion by combination of a CD45-tethered IL-15-D61H IFM and a CD18-tethered wild-type IL-15 IFM.

We further explored the potential for IFM combinations by tethering a single cytokine from multiple different cell surface receptors. In particular, we evaluated the effects of combining a CD45-targeted IL-15 point mutant that delivers improved cell surface persistence with a CD18-targeted wild-type IL-15 on T cell expansion and viability. Briefly, total CD3 human T cells were activated as described in Example 13. Cells were then incubated with 25 or 100 nM CD45-tethered IL-15 containing D61H mutation (h9.4Fab-BC8scFv-IL15-D61H/sushi), 100 nM CD18-tethered wild-type IL-15 (ch1B4Fab-IL15/sushi), or a combination of the two IFMs. After 1 hr at 37 C cells were washed two times in full media, plated at a cell density of 200,000 cells per mL and incubated at 37 C and 5% CO2. Viable cell density was monitored over time using CountBright Absolute flow cytometry counting beads (ThermoFisher) on a FACSCelesta flow cytometer using DiVa software; data were analyzed using Cytobank. Combination of h9.4Fab-BC8scFv-IL15-D61H/sushi and ch1B4Fab-IL15/sushi resulted in greater T cell proliferation than a single tethered cytokine (FIG. 30). We conclude that individual cytokines or cytokine variants can be tethered from multiple cell surface receptors to improve biological potency.

We have shown here that cytokines can be tethered to the cell surface both from a single receptor (for example, both cytokines tethered from the CD45 receptor) or from combinations of different receptors. While these studies examined combination cytokine loading using antibodies targeting CD8, CD18, or CD45 receptors, other combinations of cell surface receptors are possible (optionally including, CD4, CD11a, and/or CD2, for example). Tethering three or more cytokines onto a single cell is also possible and would add further benefits (combined loading of IL-12, IL-15, and IL-21, for example, onto a single immune cell could augment both STAT4 and STAT5 signaling based on our observations here). We additionally demonstrated that tethering cytokines from different receptors enabled 'additive' cytokine loading, in which the second cytokine is loaded onto the T cell surface without reducing the levels of the first cytokine. Without being bound by theory we reason that the additivity observed when loading from different receptors is the result of the antibody component of the IFMs not having to compete for loading onto a single cell surface receptor. We further demonstrated that additive loading can be combined with cell-specific targeting. We showed the ability to combine IL-15 and IL-21, for example, wherein IL-21 was selectively loaded onto CD8 T cells, while IL-15 was loaded onto both CD4 and CD8 T cells. This is advantageous because IL-21 has been shown to promote differentiation of CD4 T cells into a Th2 phenotype, while inhibiting CD4 T cell differentiation into the IFNg-producing Th1 phenotype (Tian et al., Trends Immunol. 2016 August; 37(8): 557-568). Thus, redirecting IL-21 away from CD4 T cells would be desirable for anti-cancer therapy, as Th1 CD4 T cells are considered the more productive anti-cancer CD4 T cell subset. Finally, we demonstrated that individual cytokines and/or cytokine variants can be loaded onto multiple different receptors to facilitate further improved biological activity. Specifically, we showed improved cell expansion by combining CD18- and CD45-targeted tethered fusions comprising IL-15 and an enhanced-activity tethered fusion comprising an IL-15 mutant. Overall, these data support the broad versatility of the tethered fusion platform to provide immune stimulating activity through non-genetic engineering of the immune cell surface.

Example 15: Tethering IL-15 or IL-12 from CD11a or CD18 Receptors

Figure 31B:
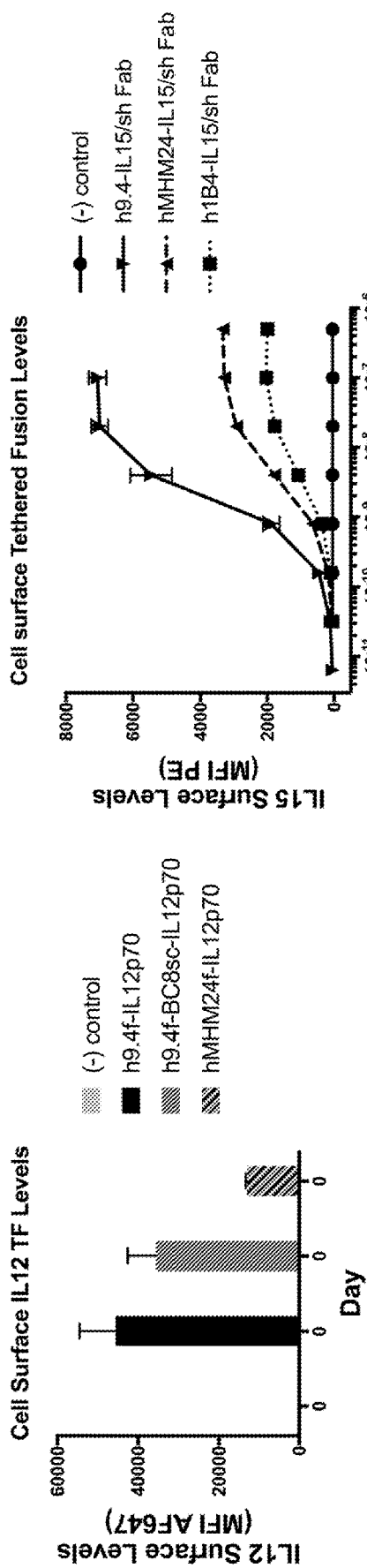
FIG. 31 shows surface loading of IL-12 or IL-15 using various humanized antibodies targeting CD45, CD11a, or CD18.
Figure 31A:
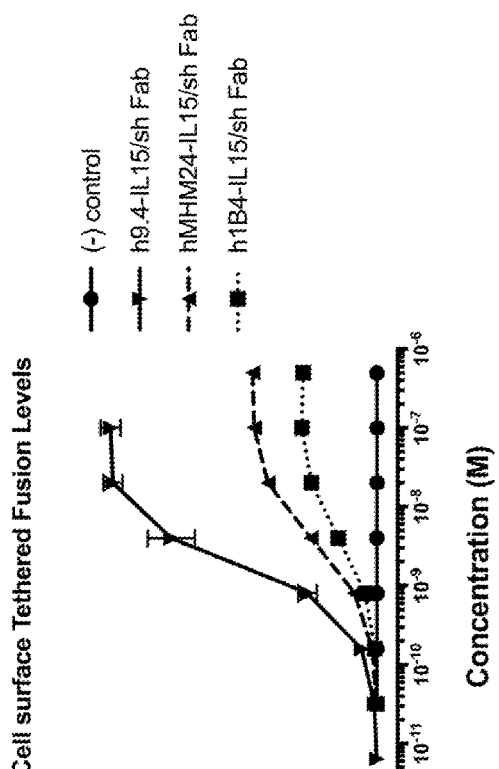

In Example 3 we demonstrated that multiple different abundant or persistent cell surface receptors are capable of generating IFMs (also referred to as tethered fusions) with improved biological activity and persistence. Here, we evaluated the ability of humanized forms of selected receptor-targeted antibodies to support high cell surface loading of IL-15 and IL-12. Briefly, CD3 human T cells were activated as described in Example 1. Activated CD3 T cells were incubated with 500 nM of a CD11a-targeted IL-12 IFM comprising humanized MHM24 variable domains (hMHM24Fab-scIL-12p70); CD45-targeted IL-12 IFMs were included for comparison (h9.4Fab-scIL-12p70 and h9.4Fab-BC8scFv-scIL-12p70; each at 500 nM). After 1 hr at 37 C cells were washed two times in full media and then stained for flow cytometry analysis with a AlexaFluor-647-conjugated anti-human IL-12 antibody. FIG. 31A shows pulse incubation with tethered fusions comprising the humanized antibodies supported loading of IL-12 onto the cell surface.

In a separate experiment we assessed the cell surface loading of IL-15 tethered fusions to humanized antibodies targeting either the CD45, CD11a, or CD18 receptors. Briefly, CD3 human T cells were activated as described in Example 1, and then incubated with five-fold serial dilutions of IFMs comprising IL-15 fused to the C-terminus of the light chain of various humanized antibodies: an anti-CD45 Fab fragment (h9.4Fab-IL15/sushi), an anti-CD11a Fab fragment (hHMH24Fab-IL15/sushi), or an anti-CD18 Fab fragment (h1B4Fab-IL15/sushi). After 1 hr at 37 C cells were washed two times in full media and then stained for flow cytometry analysis with a PE-conjugated anti-human IL-15 antibody to detect surface IFM levels. FIG. 31B shows pulse incubation with the tethered fusions comprising various humanized antibodies supported dose-dependent loading of IL-15 onto the cell surface.

Example 16: Surface Persistence and Quantification of Mouse T-Cell Tethered IL-12

Figure 32:
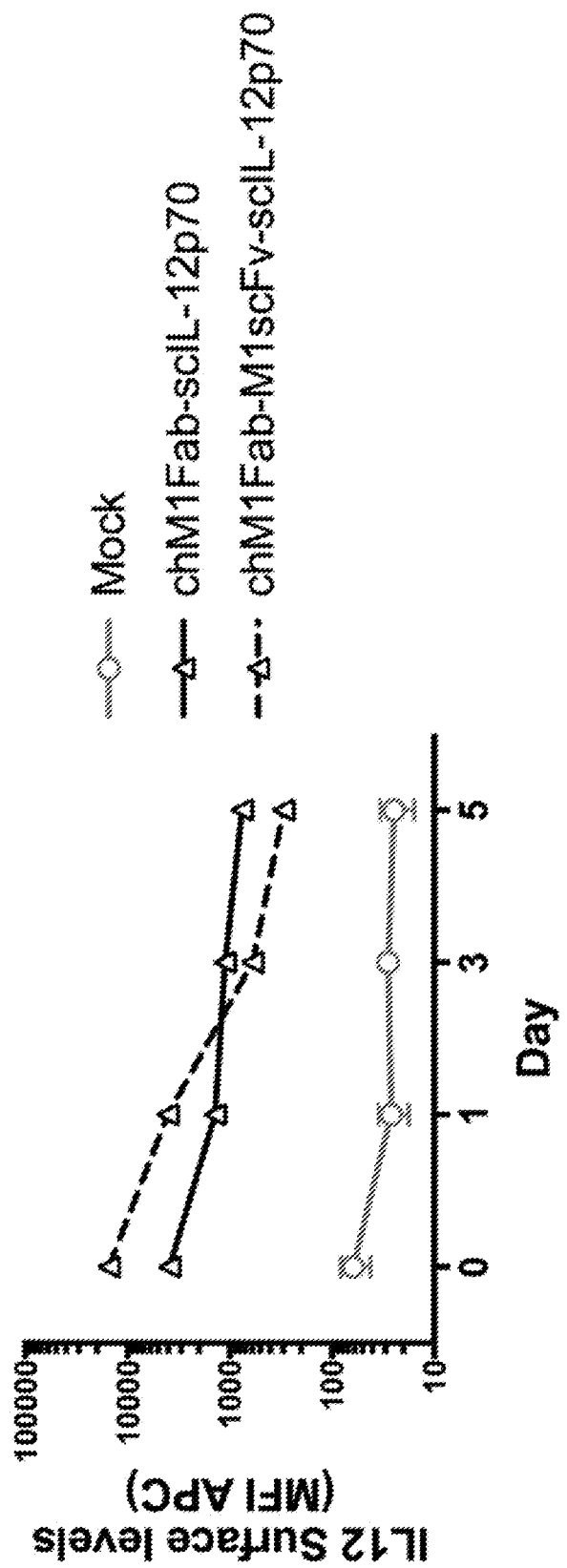
FIG. 32 shows surface persistence of mouse T cell tethered IL-12.

We evaluated the ability of tethered fusions comprising an antibody specific for mouse CD45 and the mouse scIL- 12p70 cytokine to facilitate loading and persistence of IL-12 on the surface of mouse T cells. Prior to incubation with the mouse IL12-TFs, mouse CD8 T cells were isolated from Pmel mice, activated for two days using antibodies against mouse CD3 and CD28 receptors, and then expanded in the presence of IL-21 for two days. Briefly, isolated CD8 T cells were incubated in full medium (containing RPMI 1640, 10% FBS, insulin-transferrin-selenium, penicillin/streptomycin, and 50 uM beta-mercaptoethanol) in Nunc HighBind plates that were previously coated with antibodies against mouse CD3 and CD28 receptors; the CD3 and CD28 antibodies were coated at concentrations of 0.5 ug/mL and 5 ug/mL, respectively. After approximately 24 hr incubation on the antibody-coated plates IL-2 and IL-7 were added to a final concentrations of 20 ng/mL and 0.5 ng/mL respectively. After a second day of incubation, cells were recovered from the antibody-coated plates and diluted to a density of approximately 200,000 cells/mL into medium containing IL-21 at a final concentration of 20 ng/mL. After one day expansion in IL-21 cells were diluted again to a density of approximately 20,000 cells/mL into medium containing IL-21 at a final concentration of 20 ng/mL. Cells were then recovered, washed, and incubated with IL-12 tethered fusion (chM1Fab-scIL-12p70 or chM1Fab-M1scFv-scIL-12p70) at a concentration of 125 nM for 1 hr at 37 C, followed by 3 washes in full media. Cells were plated in full media at a density of 500,000 cells/mL in 24-well dishes. On Days 0, 1, 3, and 5 after the pulse incubation cells were immunostained using antibodies specific to mouse IL-12 and analyzed on a FACSCelesta using Diva Software; data was analyzed using FlowJo. As shown in FIG. 32, the IL-12 tethered fusions support loading of IL-12 onto mouse T cells at high levels. The IL-12 is detectable above the background of the Mock condition for the duration of the five-day experiment.

Figure 33:
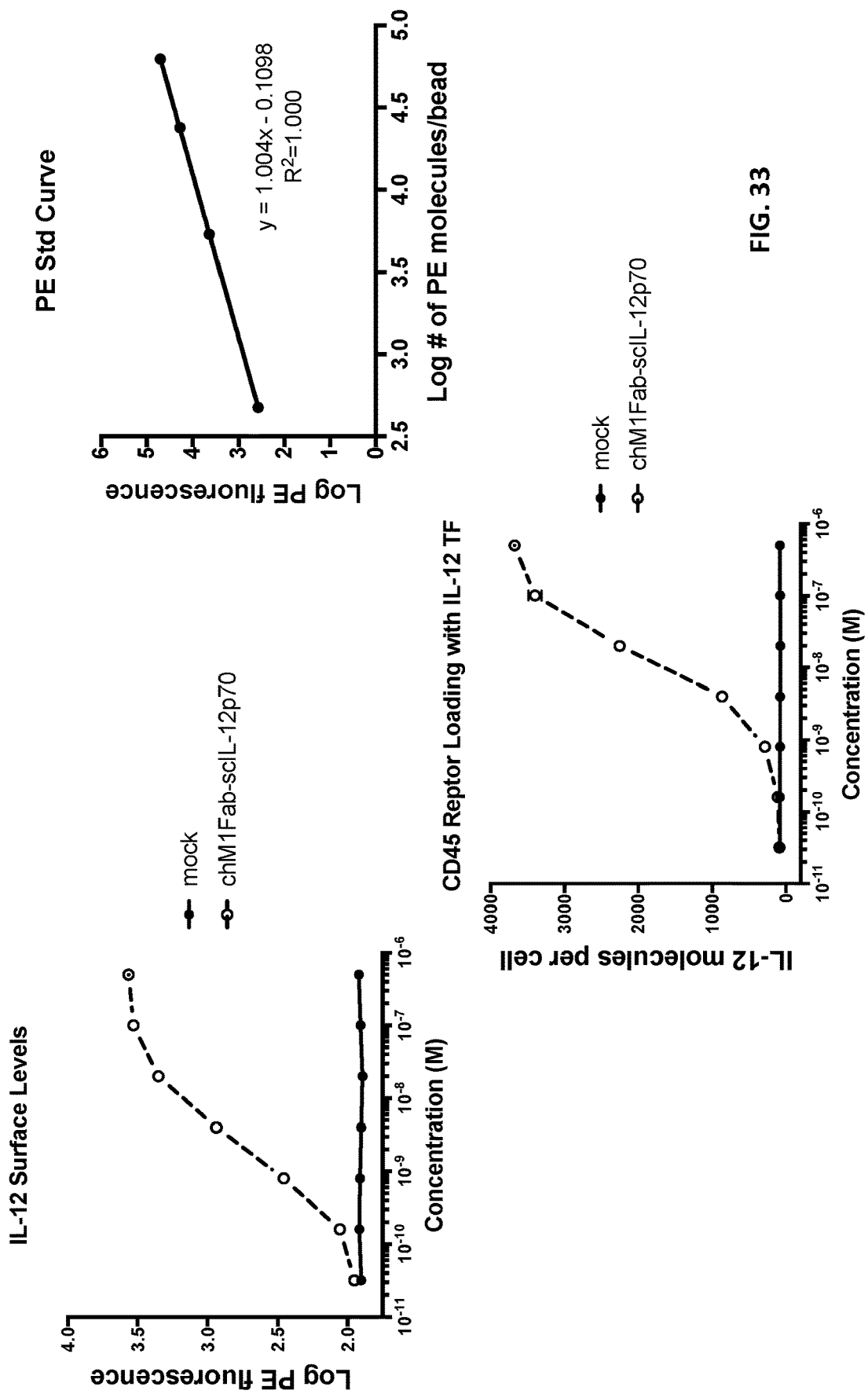
FIG. 33 shows quantification of mouse T cell tethered IL-12.

In a separate experiment we quantified the amounts of IL-12 tethered to the mouse T cells following the pulse incubation. Briefly, mouse CD8 T cells were pulse incubated with serially diluted chM1Fab-scIL-12p70 for 1 hr at 37 C, and unbound tethered fusion was removed by washing. Cell surface bound IL-12 levels were quantified by flow cytometry analysis with a PE-conjugated monoclonal anti-IL-12 antibody and QUANTBrite™ PE quantification kit (BD Biosciences). As shown in FIG. 33, at saturating concentrations of pulsed IL-12 tethered fusion, approximately 3600 IL-12 tethered fusion molecules were bound to the surface of the mouse T cells. This corresponds to approximately 650 pg chM1Fab-scIL-12p70 per 1E6 cells, and approximately 430 pg IL-12 p70 per one million cells.

Figure 34B:
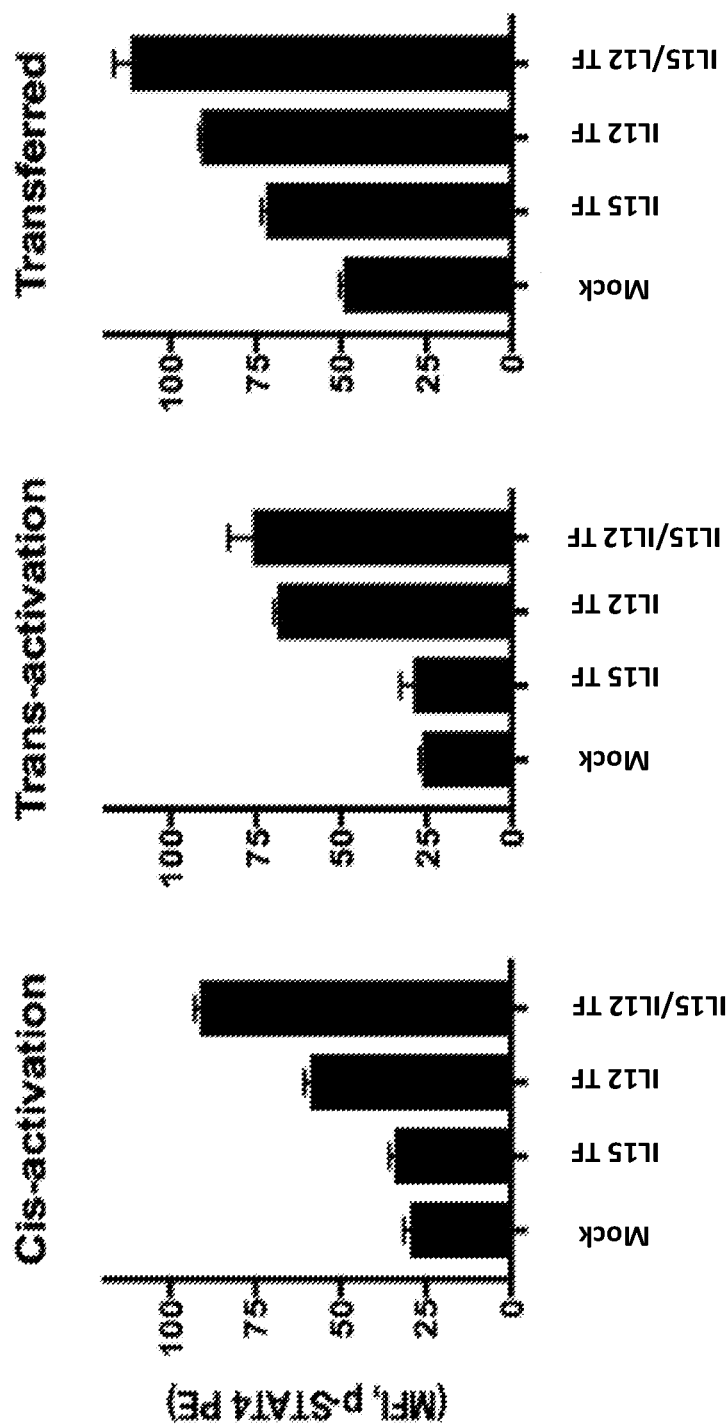

Example 17: Activation of STAT4 Phosphorylation in Non-Loaded Target Cells by IL-12 Tethered Fusion A tethered fusion can activate both the loaded cell and non-loaded target cells (FIG. 34A). We therefore evaluated an IL-12 tethered fusion for its ability to support activity in human T cells in cis/autocrine, trans, and paracrine manner. Briefly, STAT4 phosphorylation was measured in three separate assays one day after pulse incubation with an IL-12 tethered fusion (h9.4Fab-scIL-12p70) to probe cis, trans, and paracrine activity. Total CD3 T cells were activated as described in Example 13. The activated human T cells were incubated with an IL12-TF (h9.4Fab-scIL-12p70) for 1 hr at 37° C., unbound tethered fusion was removed by washing and cells were seeded at a density of 4E5 cells/mL and incubated overnight at 37° C. and 5% CO2. Non-loaded cells were propagated in full media for an additional day in the absence of cytokine, and were used on the following day as "target" cells for the trans and paracrine assays. For cis-presentation/autocrine activity cells were fixed, permeabilized and immunostained for STAT4 phosphorylation as described above. For trans-presentation evaluation, non-IL12-TF-loaded target cells were labeled with CellTrace Far Red dye (ThermoFisher) in order allow differentiation from IL12-TF-loaded cells using flow cytometry. IL12-TF-loaded cells were mixed with the fluorescently labeled non-loaded cells, pelleted and incubated together for 30 min. Cells were then fixed, permeabilized and immunostained for STAT4 phosphorylation. For transfer/paracrine conditioned media from IL12-TF-loaded cells was recovered one day following pulse incubation and transferred to non-loaded cells, incubated for 30 min, and then fixed permeabilized and immunostained for STAT4 phosphorylation. In all assays cells were analyzed on a FACSCelesta flow cytometer using DiVa software, and data was analyzed using Cytobank. For all assays the IL12-TF induces STAT4 phosphorylation above the background of "mock" pulsed cells, which were pulsed with media not containing a tethered fusion (FIG. 34B). IL-15 has been reported to augment the activity of IL-12 and we show above that combinations of IL-15 and IL-12 tethered fusions can augment STAT4 phosphorylation; we therefore also evaluated STAT4 phosphorylation for combined pulse incubation with IL-12 (h9.4Fab-scIL-12p70) and IL-15 (h9.4Fab-IL-15/sushi) tethered fusions in the three assays described here. While the IL-15 tethered fusion did not induce strong STAT4 phosphorylation on its own, STAT4 phosphorylation was augmented by combination of IL-12 and IL-15 tethered fusions in the cis and transferred assays, as shown in FIG. 34B.

Example 18: Effects of IL12-TF in Tumor-Specific T Cell Therapy

Surface tethered IL-12 was evaluated for the ability to augment tumor-specific cell therapy for cancer when pre-loaded on the cells prior to adoptive cell therapy (ACT). Briefly, C57BL/6J mice were inoculated intradermally with 400,000 B16-F10 melanoma cells. Separately CD8 T cells were isolated from Pmel-1 mice, which express a T cell receptor specific for the mouse gp100 antigen in B16-F10 melanoma cells. Cells were activated and expanded as described in Example 16. A mouse IL12-TF (chM1Fab-scIL-12p70) was loaded onto activated CD8 Pmel T cells by incubating with cells at a concentration of 50 nM; unbound cytokine was removed by washing and cells were resuspended in HBSS (Hanks Balanced Salt Solution). We also evaluated an IL15-TF (chY169Fab-M1scFv-IL15/sushi) either alone (at a concentration of 250 nM) or in combination with the IL-12 tethered fusion (at a concentration of 50 nM). After 1 hr incubation at 37° C. with the tethered fusions cells were washed twice with complete media, resuspended in HBSS, and adoptively transferred ($5 \times 10^6$ cell/mouse) to the B16-F10 tumor-bearing mice by tail vein injection. As controls, mice were also treated with HBSS or Pmel T cells alone. While myeloablative lymphodepletion is commonly used for anti-tumor T cell therapies, all treatment conditions in this study were conducted in the absence of myeloablative lymphodepletion.

Figure 35A:
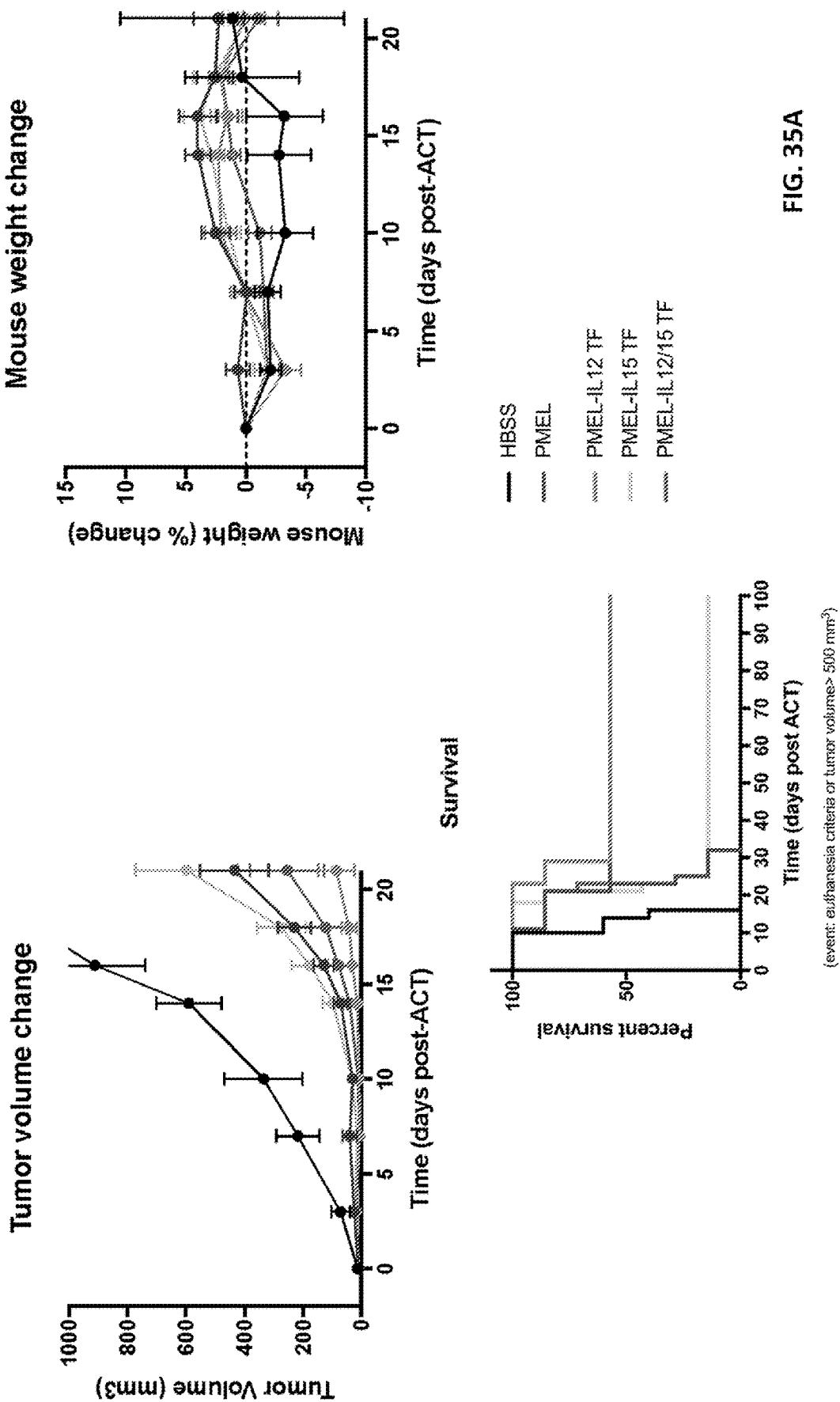
FIG. 35A shows tumor growth, mouse weight change, survival (up to day 100 post ACT).

FIG. 35A shows tumor growth, mouse weight change, and survival (up to day 100 post ACT). The TL-12 containing regimens (IL12-TF and IL12/15 TF) showed the highest anti-tumor activity, both in terms of anti-tumor growth and long-term survival. Four out of the seven (57%) mice from groups treated with Pmel carrying the IL12-TFs (either alone or in combination with the IL15-TF) exhibited complete responses. Notably, there is one long-term survivor in the IL15-TF-containing group. All treatment groups showed peak body weight loss less than 5%, and this was consistent with weight loss observed in the HBSS-treated group, indicating an absence of overt toxicities for the treatment strategies tested here.

Figure 35B:
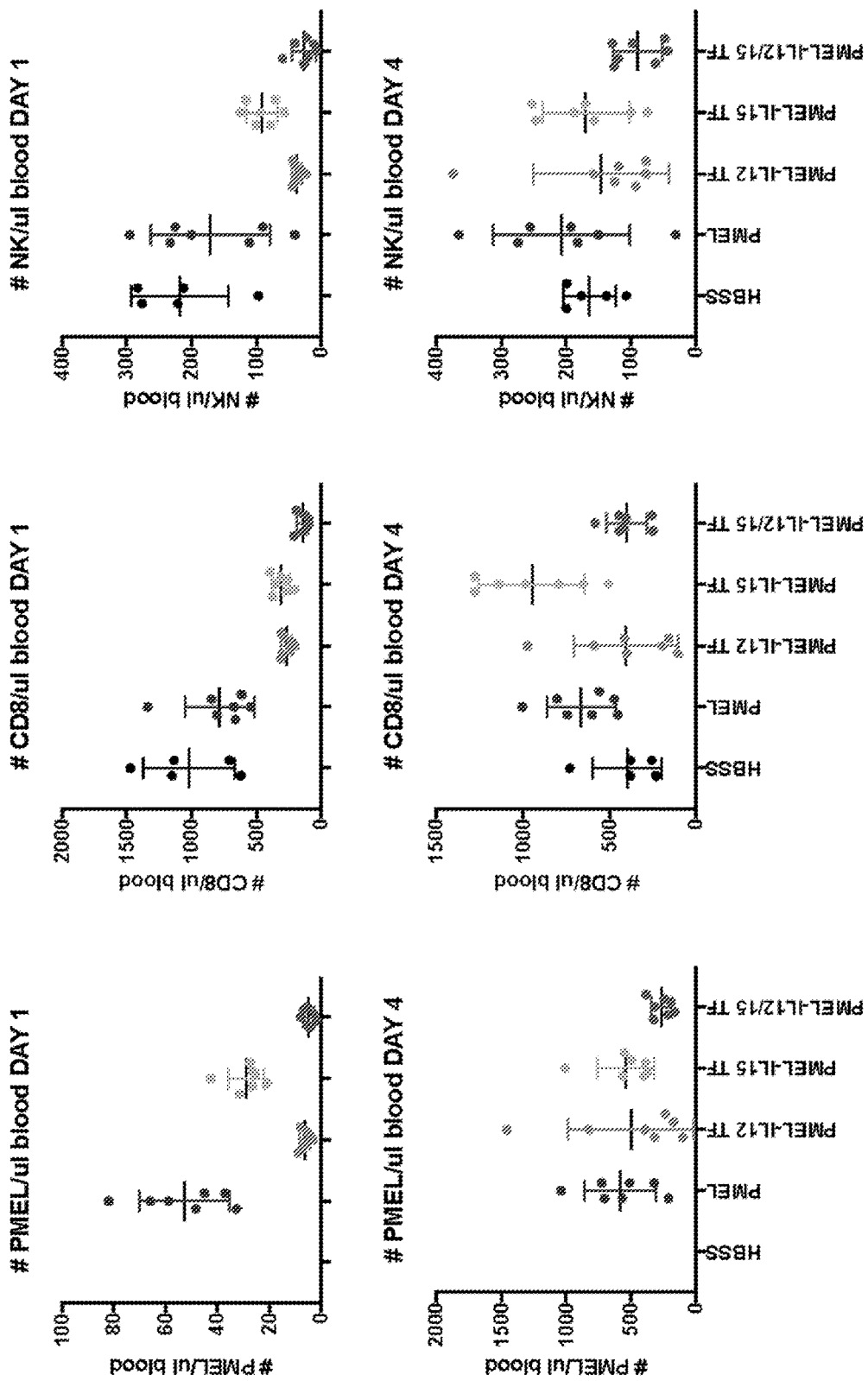
FIG. 35B shows Pmel cells carrying a surrogate IL12-TF lead candidate induce transient lymphopenia of transferred and endogenous immune cells.
Figure 35C:
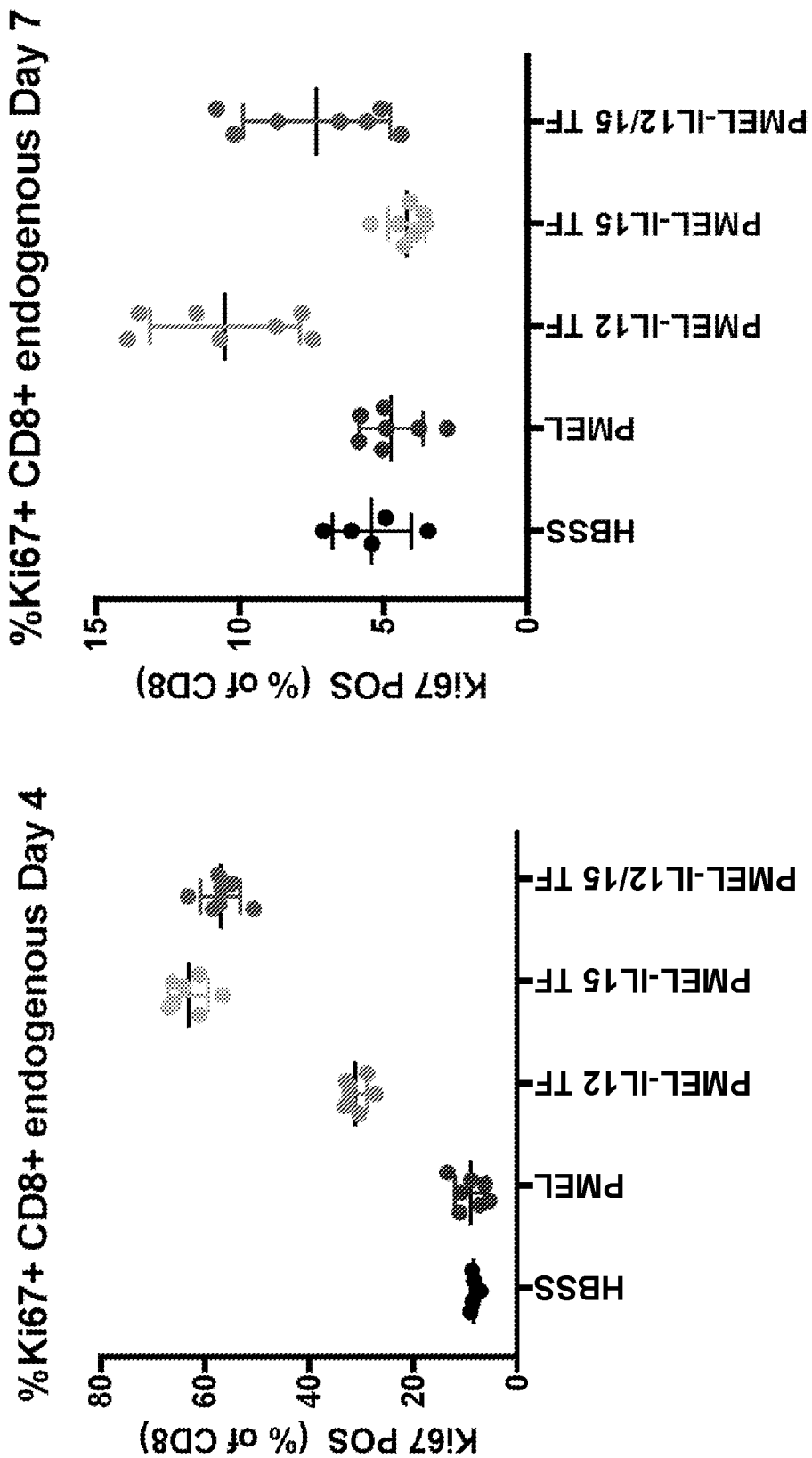
FIGS. 35C-35D show proliferation (via KI67 positivity) of circulating endogenous CD8 T cells.
Figure 35D:
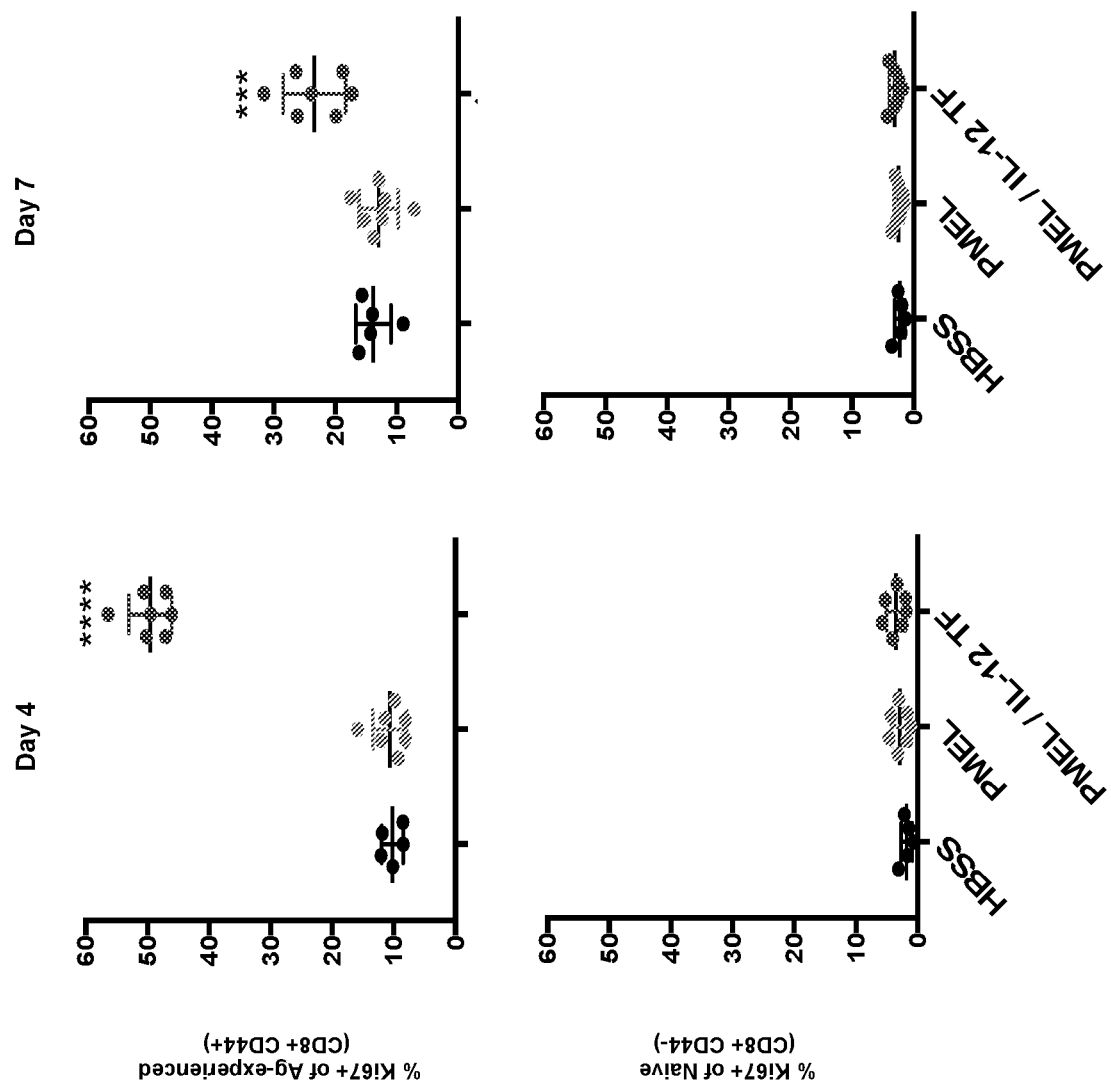
Figure 35E:
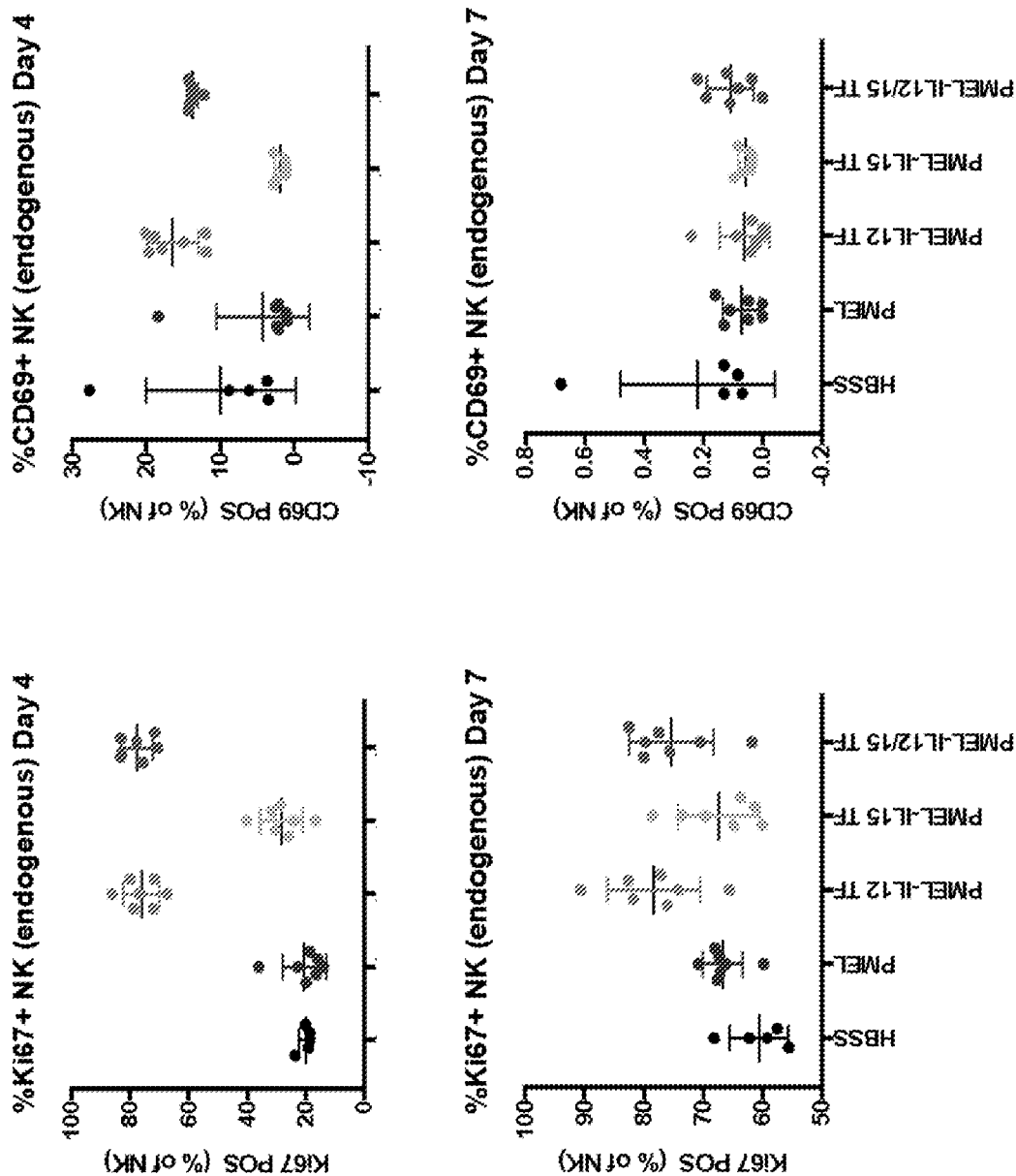
FIG. 35E shows endogenous NK cell proliferation (via Ki67 positivity) and activation (via CD69 positivity).

Pmel cells carrying a mouse IL12-TF show signs of activity towards the endogenous immune system. They induce transient lymphopenia of transferred and endogenous immune cells including CD8 T cells and NK cells (FIG. 35B). This is followed by proliferation (as defined by Ki67 positivity) and differentiation of endogenous CD8 T cells (FIG. 35C). Further subdivision of the endogenous CD8 T cells reveals that the proliferating cells are almost exclusively encompassed within the antigen-experienced endogenous CD8 T cell population (by flow cytometry, populations are both negative for the congenic Pmel T cell marker CD90.1 and double-positive for CD8 and CD44), suggesting that the presence of the IL12-TF is activating a specific compartment of the endogenous immune system (FIG. 35D). The transient lymphopenia of endogenous NK cells shown in FIG. 35B is followed by their increased proliferation (via Ki67 positivity) and activation (via CD69 positivity) as shown in FIG. 35E. We conclude that tumor-specific T cells carrying IL12-TFs hold the potential to both augment ACT for cancer and prime the endogenous immune system.

Example 19: IL12-TF Augments Tumor-Specific T Cell Therapy when Either Pre-Loaded onto Adoptively Transferred T Cells or when Solubly Co-Administered Surface tethered IL-12 was evaluated for the ability to augment adoptive cell therapy (ACT) for cancer. Briefly, C57BL/6J mice were inoculated intradermally with 400,000 B16-F10 melanoma cells. One day prior to adoptive cell therapy with tumor-specific T cells (9 days after inoculation with B16-F10 cells) tumor-bearing mice were treated with 4 mg cyclophosphamide. Separately, CD8 T cells were isolated from Pmel-1 mice, which express a T cell receptor specific for the gp100 antigen in B16-F10 melanoma cells, and activated and expanded as described for T cells in Example 16. Cells were then harvested for ACT and incubated with an IL-12 tethered fusion (chM1Fab-scIL-12p70) at a concentration of 125 nM. Unbound tethered fusion was removed by washing, cells were resuspended in HBSS, and the CD8 Pmel T cells were then adoptively transferred (3E6 cells/mouse) by intravenous (i.v.) injection into the B16-F10 tumor-bearing mice. As controls, mice were also treated with HBSS, CD8 Pmel T cells alone, or the CD8 Pmel T cells followed by a single dose of soluble IL-12p70 (at dose levels of 10, 50, or 250 ng, which corresponds to 0.143, 0.715, and 3.575 pmoles of IL-12p70) or with soluble IL-12 tethered fusion (0.143, 0.715, or 3.575 pmoles of tethered fusion), which was administered intravenously for all conditions. Not wishing to be bound by theory, based on preliminary calculations in Example 16, the highest dose tested so far corresponds to greater than 100-fold amounts of the surface-tethered IL-12 dose.

Figure 36:
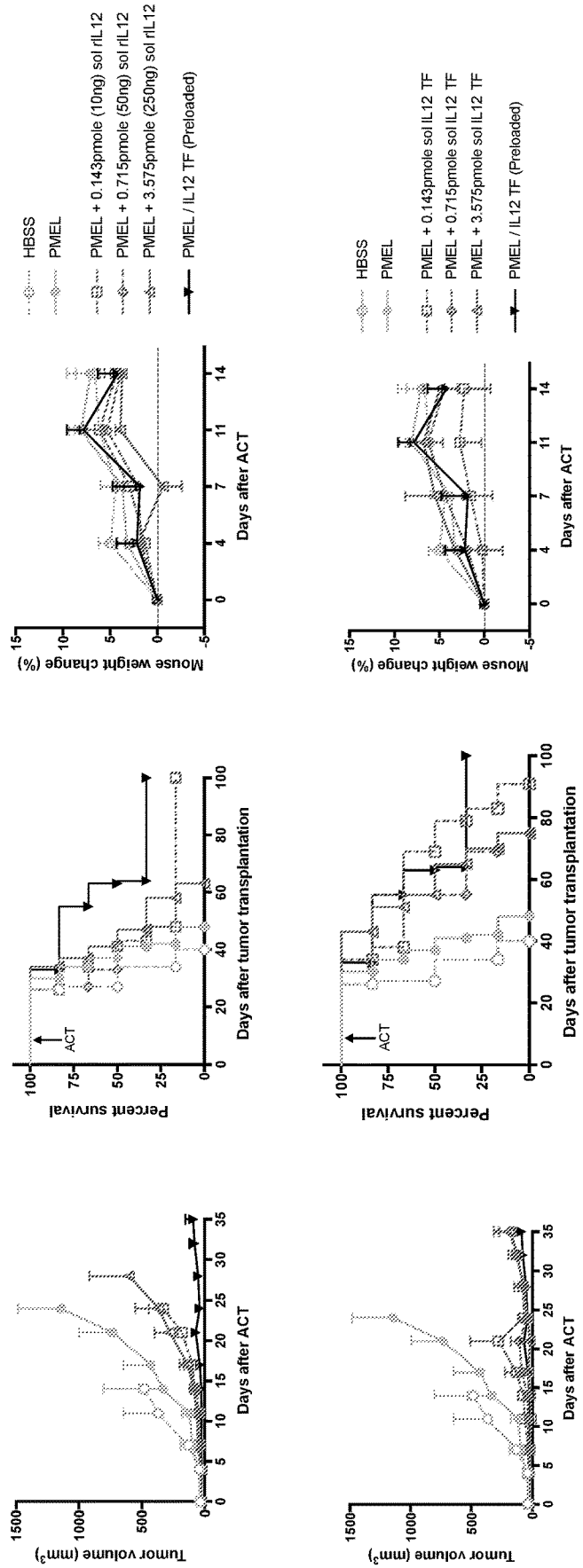
FIG. 36 shows IL12-TF augments tumor-specific T cell therapy when either pre-loaded onto adoptively transferred T cells or when solubly co-administered.

As shown in FIG. 36, both pre-loaded or solubly co-administered IL-12 tethered fusions significantly inhibited tumor growth and supported prolonged survival. In each case the tethered fusions more strongly inhibited tumor growth and prolonged survival than co-administration of free IL-12. Minimal overt toxicity in the form of body weight loss was observed. The data are plotted in two separate figures for clarity; in the second set of figures the HBSS, Pmel only, and Pmel carrying IL12-TF groups are replotted for comparison. Tumor growth kinetics are shown for the first 35 days after ACT or until two mice in a given group die.

Figure 37A:
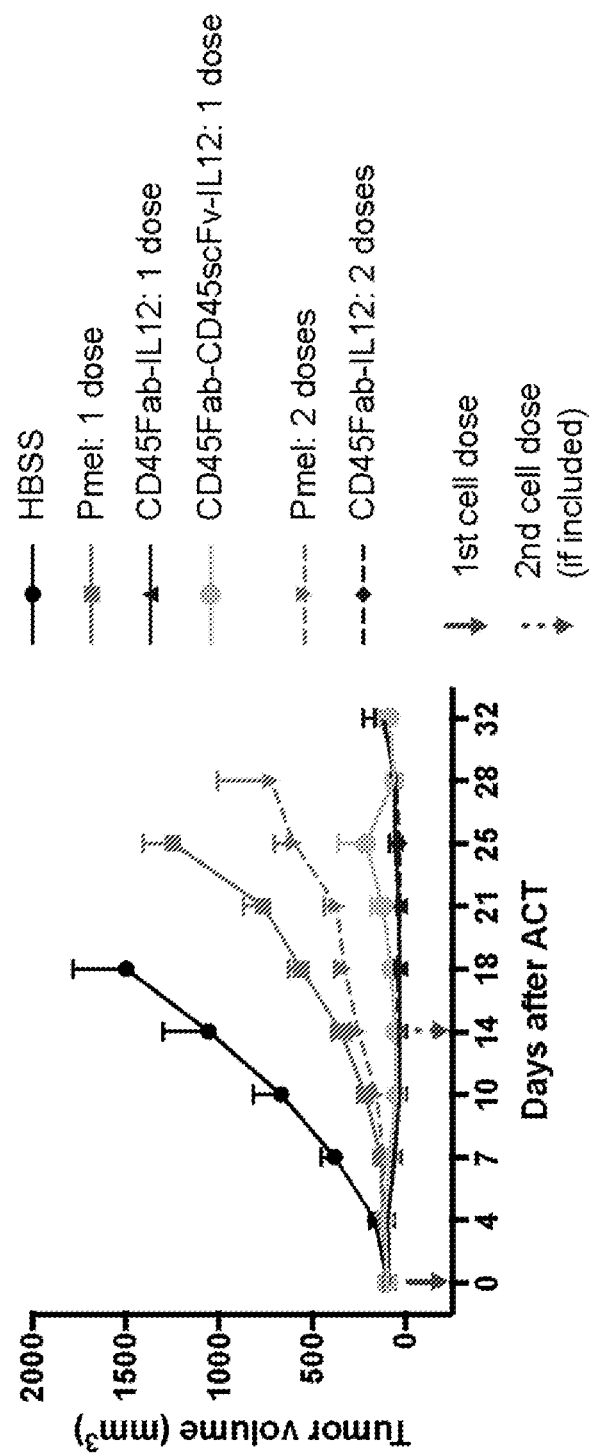
FIG. 37A shows tumor growth curves following single or multiple doses of tumor-specific T cells carrying IL12-TFs.
Figure 37B:
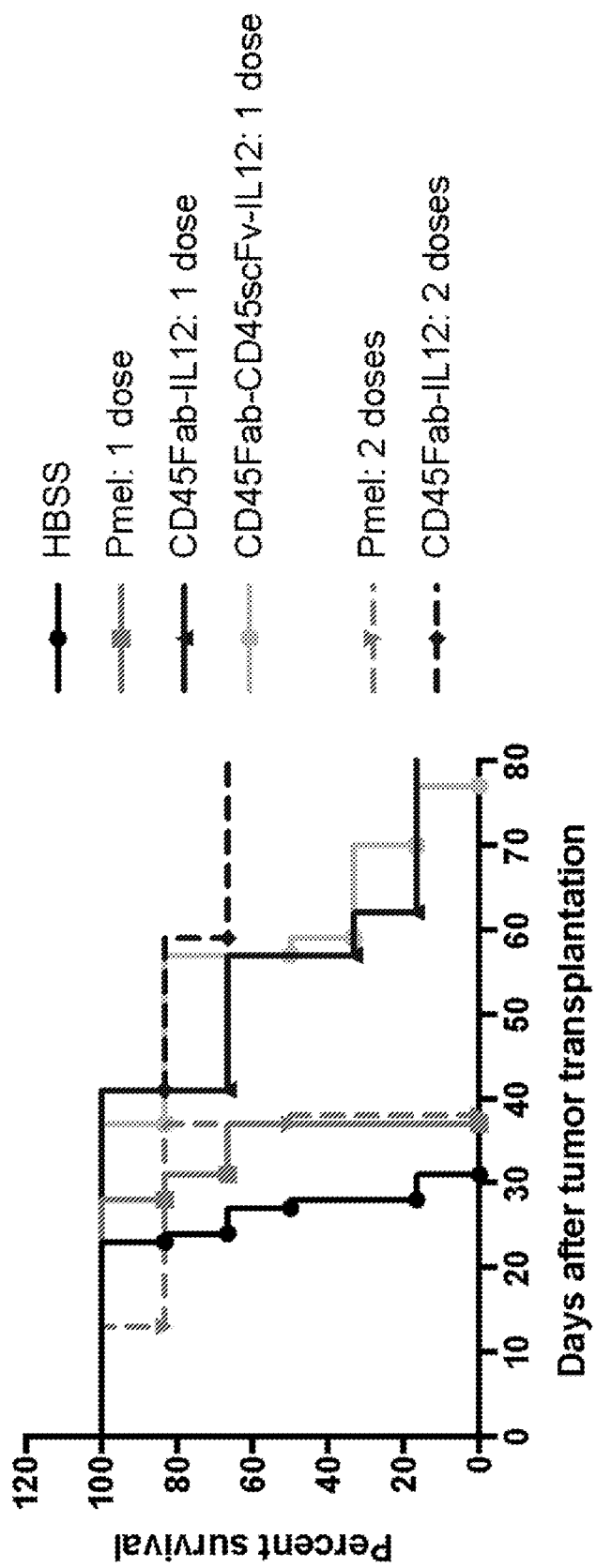
FIG. 37B shows survival from single or multiple doses of tumor-specific T cells carrying IL12-TFs.

Example 20: IL12-TF Candidate Enables Further Improved Tumor Control with Multiple Cell Doses Most cell therapies require preconditioning regimens involving myeloablative chemotherapy prior to ACT for robust anti-tumor responses. This approach, however, has limitations including the inability to administer multiple cell doses due to risks of depleting the activity of previously administered cells by successive rounds of preconditioning chemotherapy. In Example 18 we demonstrated the potential for the IL12-TF to augment tumor-specific T cell therapy in the absence of preconditioning in a solid tumor model. Given these effects we evaluated the ability for IL12-TF to further augment anti-tumor control through the use of multiple cell doses. Briefly, C57BL/6J mice were inoculated intradermally with 400,000 B16-F10 melanoma cells. Separately, CD8 T cells from Pmel mice were isolated, activated, expanded, and loaded with an IL12-TF (chM1Fab-scIL-12p70) as described in Example 18. Nine days following tumor inoculation mice were treated with the CD8 Pmel T cells by i.v. injection. Lymphodepletion with cyclophosphamide was used one day prior to the first cell dose; the second cell dose was given 14 days after the first dose in the absence of additional lymphodepletion. We additionally evaluated the ability of an alternative configuration for the IL12-TF (chM1Fab-M1scFv-scIL-12p70) to augment efficacy of a single dose of tumor-specific cell therapy. Both of the IL12-TFs (chM1Fab-scIL-12p70 and chM1Fab-M1scFv-scIL-12p70) improved the tumor growth inhibition and survival with a single cell dose loaded ex vivo with the tethered fusions (FIG. 37A). Multiple doses of tumor-specific T cells loaded ex vivo with chM1Fab-scIL-12p70—but not multiple doses of the tumor-specific T cells alone—further augmented anti-tumor survival (FIG. 37B).

Figure 37C:
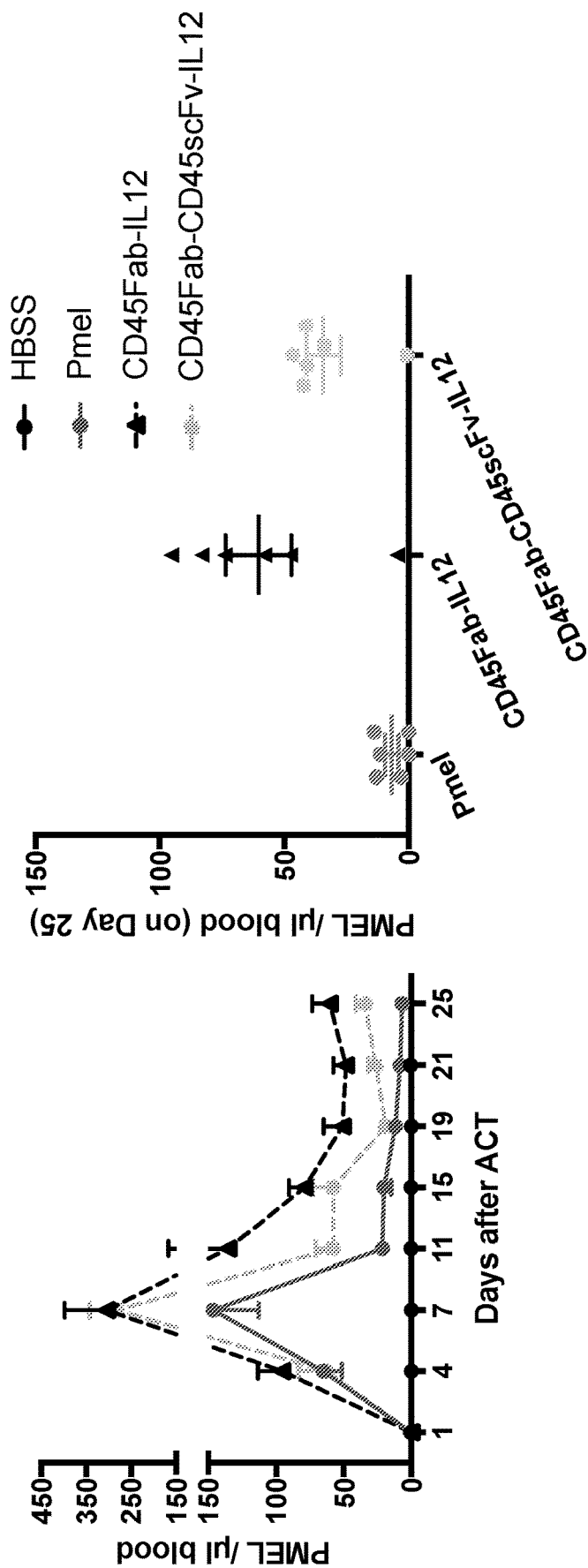
FIG. 37C shows IL12-TFs enhance tumor-specific T cell expansion and engraftment in vivo.
Figure 37D:
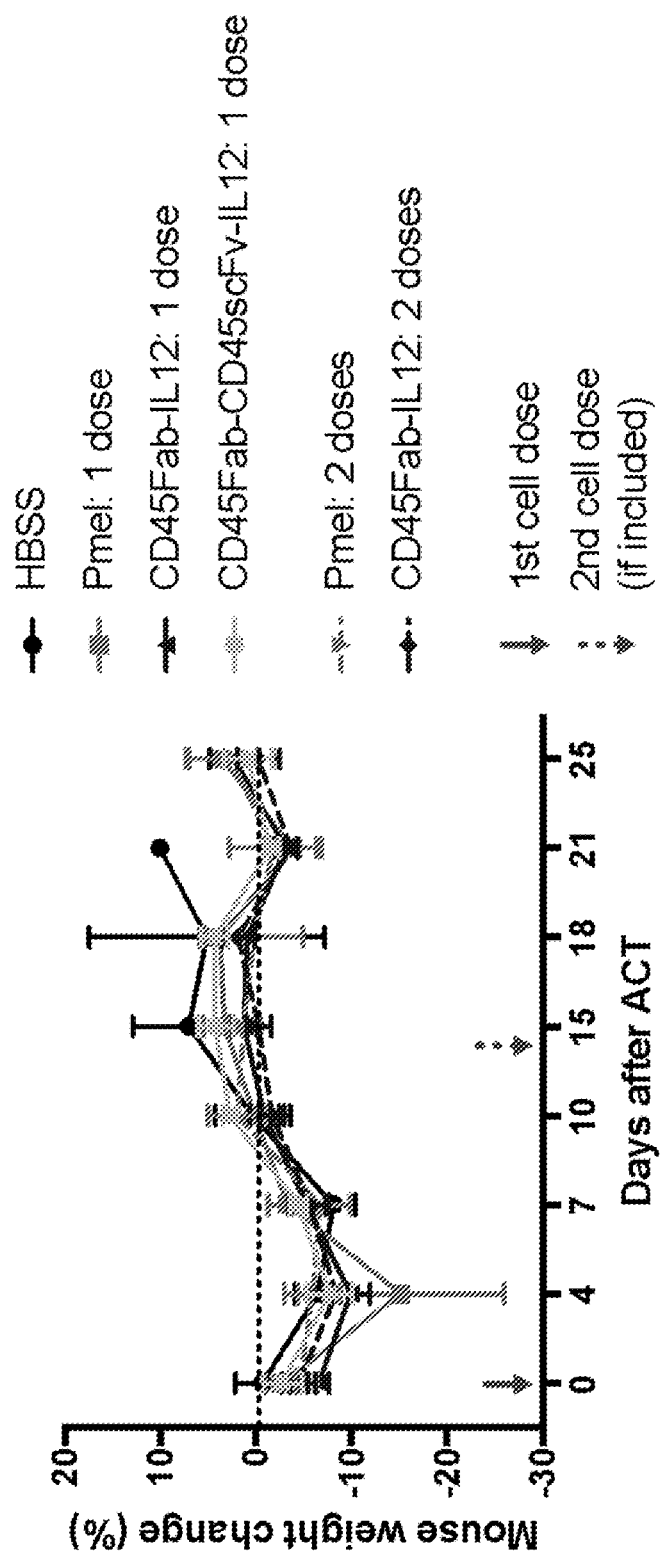
FIG. 37D shows body weight changes following treatment with one or two doses of tumor-specific T cells carrying IL12-TFs.
Figure 38:
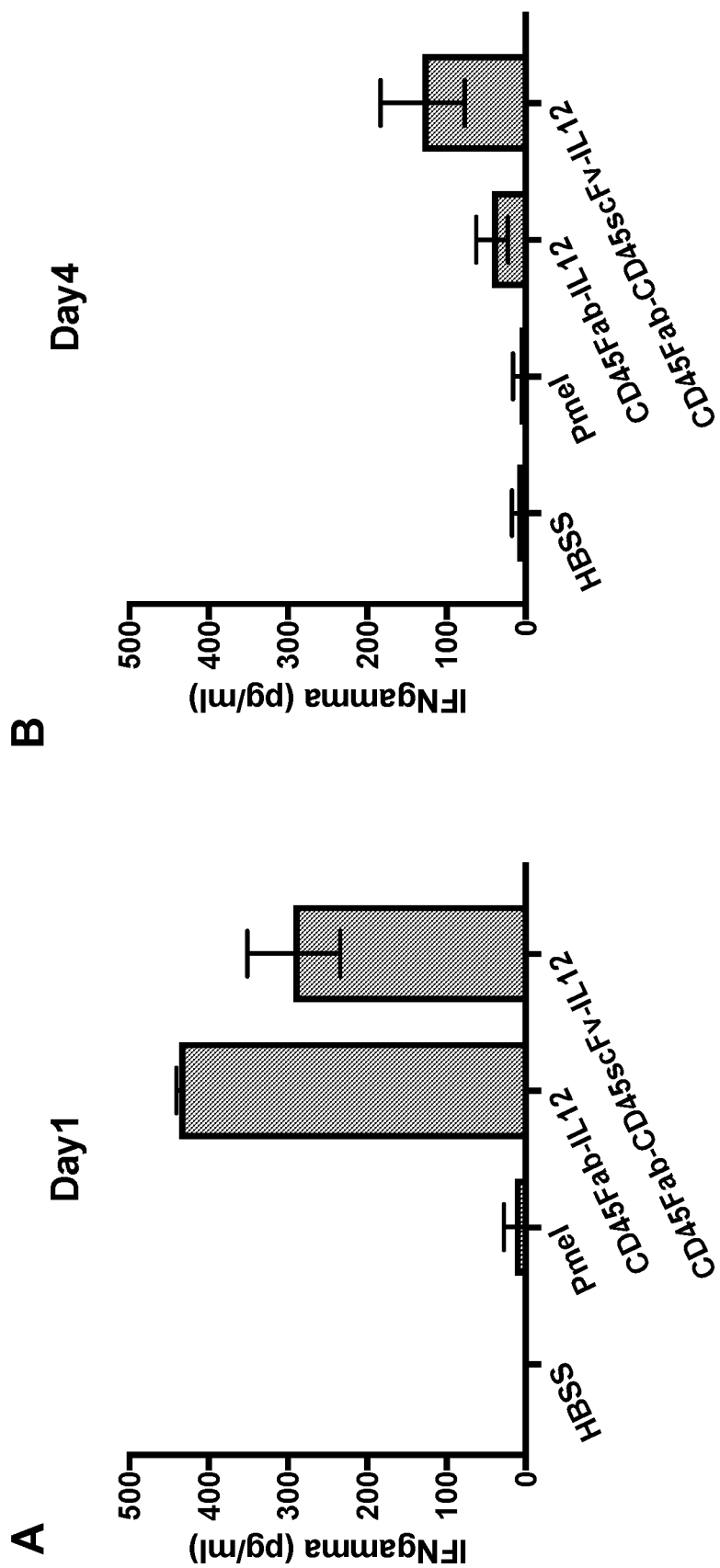
FIG. 38 shows IFN-γ plasma levels following ACT with Pmel carrying one of two IL12-TFs.
Figure 39:
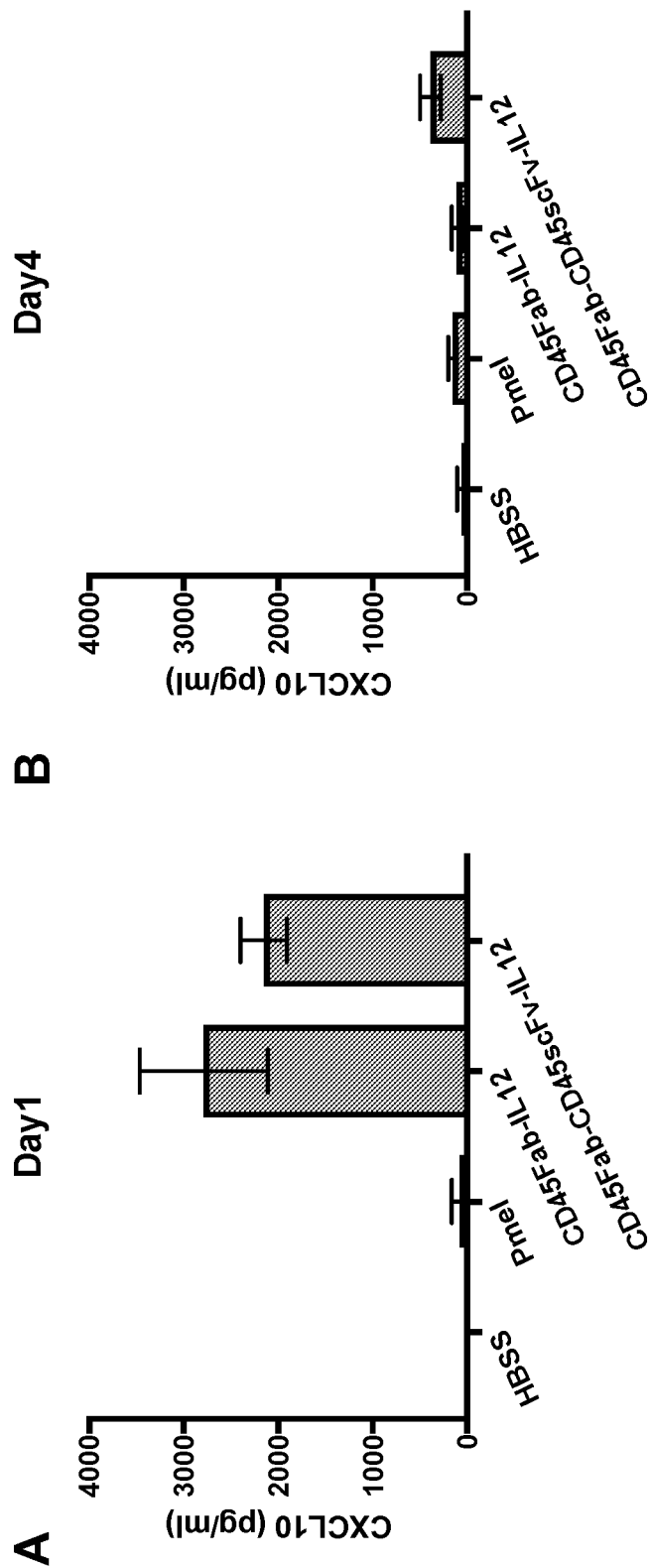
FIG. 39 shows CXCL10 plasma levels following ACT with Pmel carrying one of two IL12-TFs.

The IL12-TFs increased both the peak expansion of circulating Pmel T cells and the their long-term persistence (FIG. 37C). We did not observe signs of overt toxicity in the form of body weight loss (FIG. 37D). Any observed body weight loss appeared to be predominantly driven by lymphodepletion with cyclophosphamide: mice lost approximately 10% body weight in each treatment group (FIG. 37D), while in Example 18, which was conducted in the absence of lymphodepletion, we observed less than 5% body weight loss across all treatment groups (FIG. 35A). We additionally observed modest levels of systemic IFN-γ (FIG. 38) and CXCL10 (FIG. 39) in plasma one day after ACT with Pmel carrying the IL12-TF; circulating levels returned to baseline within four days of the adoptive cell transfer (FIGS. 38-39).

In summary, we have demonstrated in preclinical studies that multiple configurations of antibody-mediated cytokine tethering enable strong loading and persistence of IL-12 on the T cell surface. Furthermore, surface-tethered IL-12 substantially improves efficacy of adoptively transferred tumor-specific T cells in an aggressive solid tumor model, including better tumor control and survival than >100 fold molar excess of systemically administered IL-12. Efficacy of tumor-specific T cells loaded with an IL12-TF in the absence of lymphodepletion enabled further improved efficacy through administration of multiple cell doses.

Surface-tethered IL-12 also supports activation of the endogenous immune system—including increased proliferation of antigen-experienced CD8 T cells—with an absence of overt toxicities in the form of body weight loss and sustained systemic cytokine release.

We conclude that cell surface tethered immunostimulatory cytokines are a powerful approach to augment the efficacy of cell therapy for cancer, including for solid tumors. This approach does not require genetic engineering and can be readily incorporated onto cell therapies that are currently under clinical exploration, such as CAR-T, TCR-T, tumor associated antigen-specific T cells, and NK cells.

Example 21: Tethered Fusion Platform Enables Specific Cell Targeting In Vivo

Having established the ability for selective CD8 T cell loading in vitro using CD8-targeted IL-7 or IL-15 tethered fusions (see Example 9), we tested selective targeting of CD8 T cells in vivo using a CD8-targeted IL-15 IFM. Given our previous observations in human T cells demonstrating improved CD8 affinity using a bivalent Fab-scFv construct (FIG. 17D-FIG. 17F) we generated a mouse CD8-targeted IL-15 variant comprising a similar Fab-scFv antibody configuration (chY169Fab-M1scFv-IL15/sushi). The CD8-targeting Fab is designed to provide specificity, while the CD45-targeting scFv improves persistence on the targeted cell.

Figure 40A:
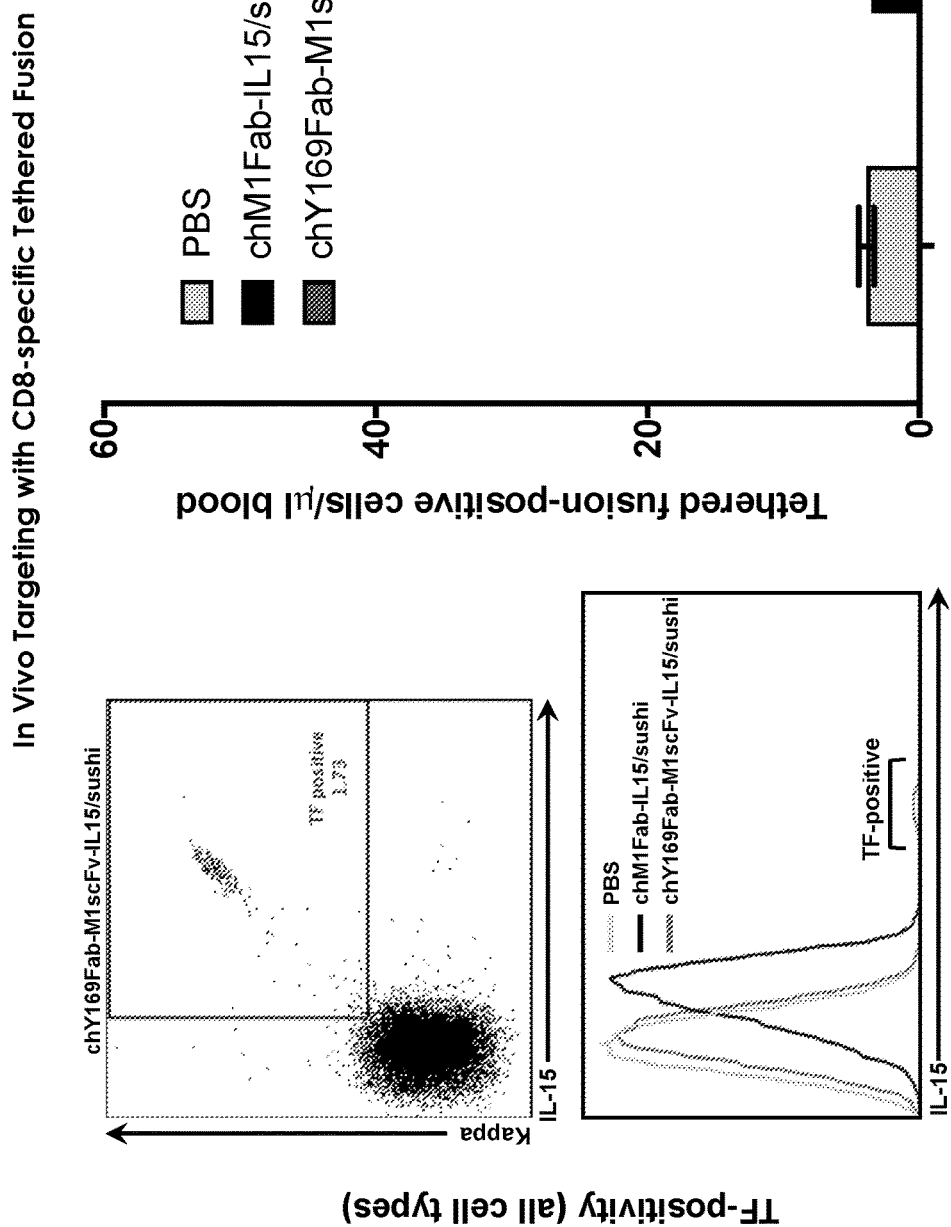
FIGS. 40A-40D shows specific binding of CD8-targeted IFMs comprising wild-type or mutated IL-15 to CD8 T cells in vivo and activity of CD8-targeted IFMs on circulating CD4 T, CD8 T, and NK cells.
Figure 40B:
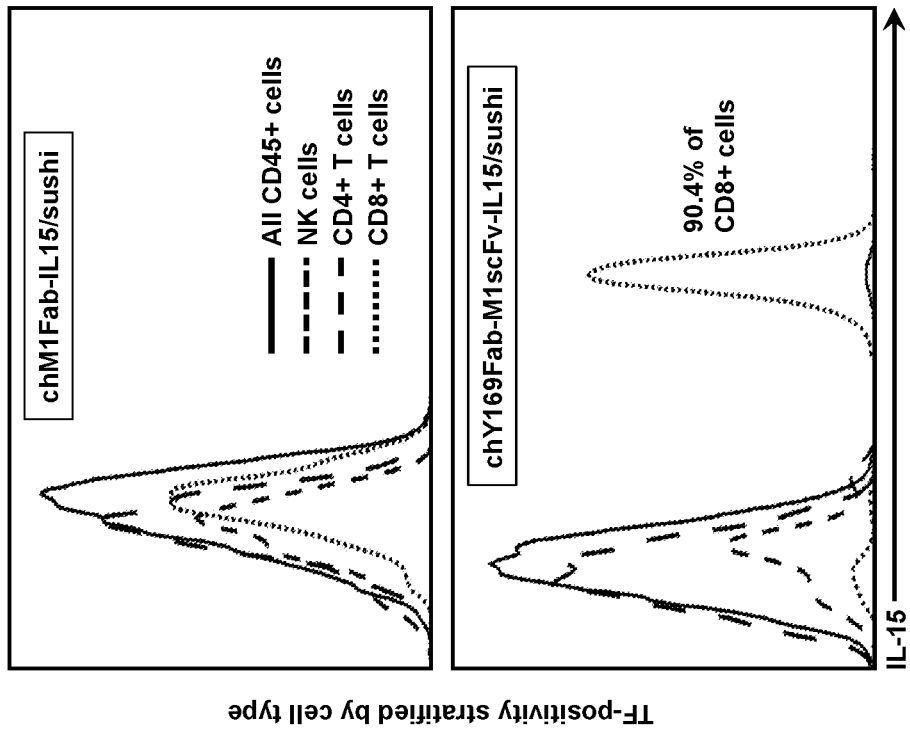

In the first experiment described in this example, we tested whether intravenously administered tethered fusion could be specifically target on mouse CD8 T cells in vivo. Two C57BL/6J mice/group were injected with chY169Fab-M1scFv-IL15/sushi (2 µg/mouse), chM1Fab-IL15/sushi (CD45-targeted IFM, 2 µg/mouse), or PBS vehicle control. One hour after injection, blood was drawn and tethered fusion cell surface binding was assessed by flow cytometry. Red blood cells were lysed, and remaining cells were stained with fluorescently conjugated antibodies against kappa and IL-15 for detection of tethered fusion. Antibodies specific for mouse CD4, CD8, NK1.1, and CD45 were additionally included to enable immune cell subset analysis. Tethered fusion surface binding was defined by positivity for both kappa and IL-15. Both the vehicle control and the chM1Fab-IL15/sushi-treated animals had minimal positive staining cells (3.5-3.9/µl), while the chY169Fab-M1scFv-IL15/sushi-treated animals had greater than 10-fold higher concentration of circulating tethered-fusion positive cells (FIG. 40A). The histogram plot in FIG. 40A shows a bulked shift in fluorescence for the chM1Fab-IL15/sushi-treated animals; however, there was not a distinct TF-positive population. Because CD45 is found on all immune cells, it is likely that there was specific binding, but the tethered fusion signal was spread out over a much larger number of cells. For the mice treated with the CD8-targeted IL-15 (chY169Fab-M1scFv-IL15/sushi), while only a small percentage of total cells were positive for tethered fusion (1.73%), the majority of CD8 T cells were positive (FIG. 40B). Furthermore, none of the other analyzed subsets (CD4 T cells, NK cells) exhibited TF-staining. Together these data show specific, high-level targeting of CD8 cells by the chY169Fab-M1scFv-IL15/sushi tethered fusion, and non-specific, low-level targeting by the CD45-specific chM1Fab-IL15/sushi tethered fusion.

Figure 40C:
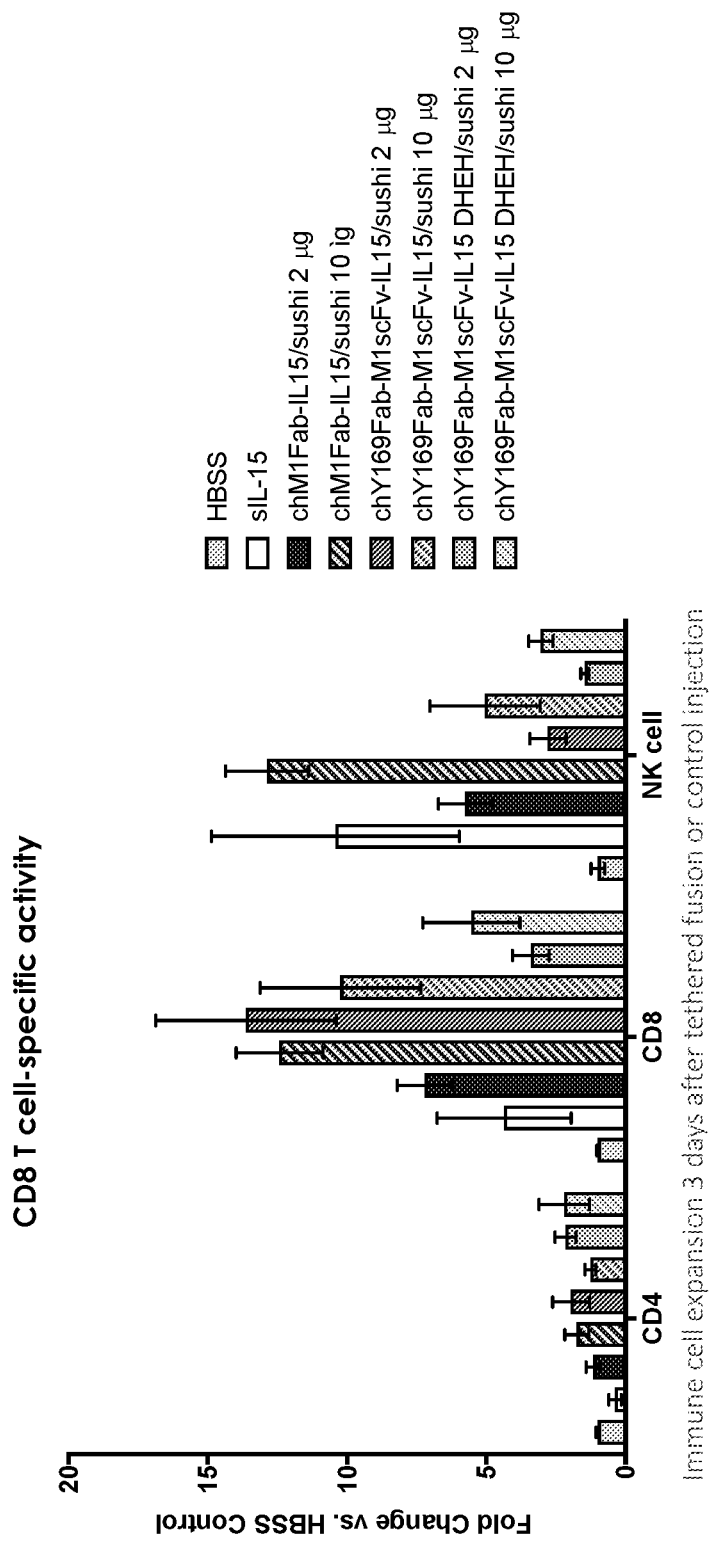
Figure 40D:
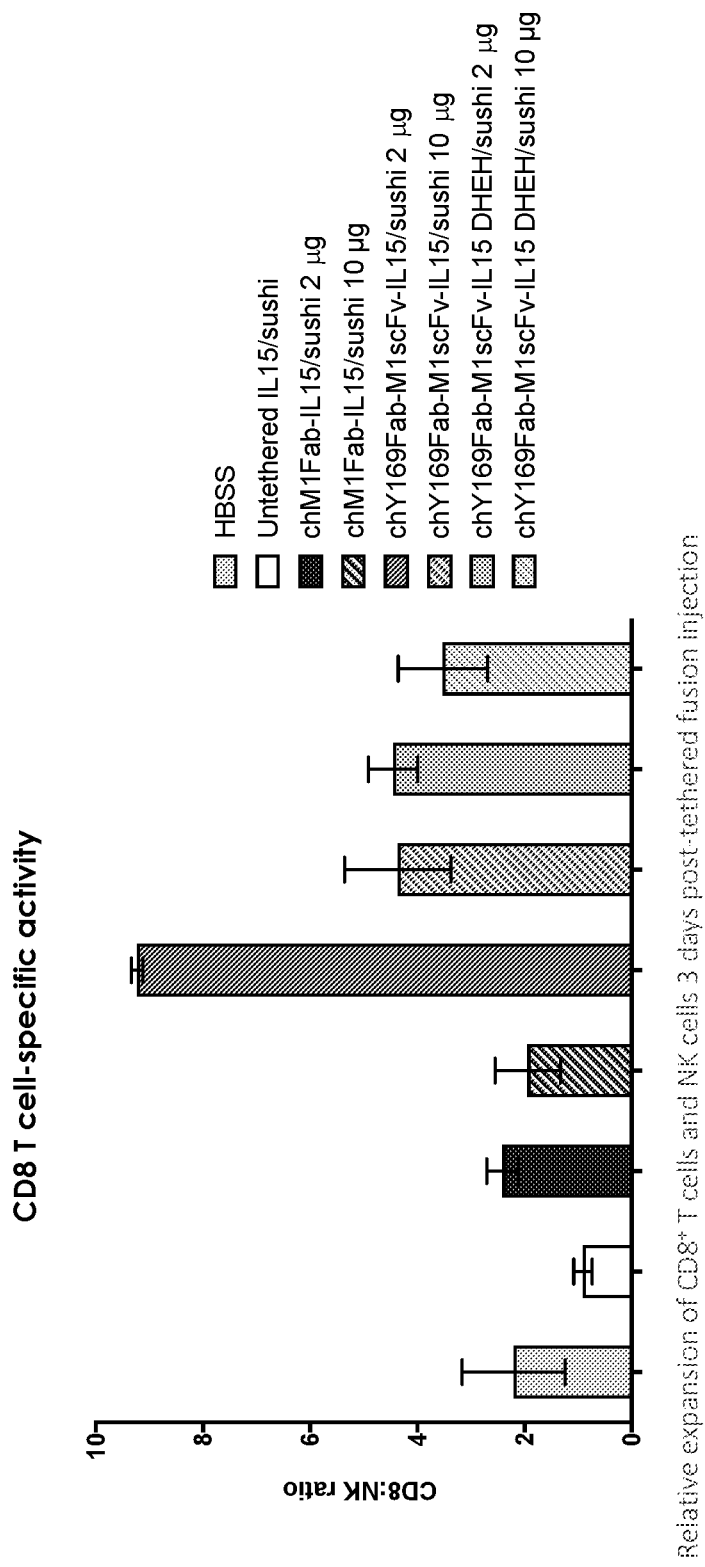

In a second experiment we evaluated the effects of a single dose (2 or 10 ug) of CD45- or CD8-targeted IL-15 IFMs on circulating immune cells. We additionally included a non-targeted IL-15/sushi-Fc construct and a CD8-targeted IL-15 variant comprising D61H and E64H mutations (chY169Fab-M1scFv-IL15-DHEH/sushi; see Example 9 for further description of these mutations). Blood was drawn on Day 3 post-injection, red blood cells were lysed, and remaining cells were stained with fluorescently conjugated antibodies directed against CD45, CD4, CD8 and NK1.1. By Day 3 post-injection there were minimal changes in CD4 T cell numbers for any of the tethered fusion formats or concentrations (FIG. 40C). In contrast, CD8 numbers were increased by all of the tethered fusion formats and concentrations with a range of 3.4-13.6-fold. The effects of the CD45- and CD8-targeting tethered fusions were similar on CD8 cells and were increased relative to non-targeted IL15/sushi-Fc. Corresponding with it's reduced biological activity, the DHEH mutant drove less CD8 expansion than the wildtype IL-15 IFMs. While there was no enhancement of CD8 T cell expansion for the CD8-targeting tethered fusion relative to CD45, there were reduced off-target effects on NK cells (as measured by quantification of NK1.1+ cells in circulation). NK cells are also highly sensitive to IL-15, and their numbers were dramatically increased by the IL-15/sushi-Fc and the pan-CD45 targeting chM1Fab-IL15/sushi tethered fusion (6-13-fold expansion relative to HBSS treated group). In contrast, the CD8-targeting chY169Fab-M1scFv-IL15/sushi led to only modest increases (3-5-fold) in NK cell number. The DHEH mutant off-target effects on NK cells was even more attenuated with only 1.5-3-fold expansion relative to the vehicle control. These effects can be seen most clearly by comparing the CD8 T cell to NK cell ratio (FIG. 40D). The non-targeted IL15/sushi actually reduces the ratio of CD8 T cells to NK cells, suggesting that without targeting there is a preference for NK specific activity. While the pan-CD45-targeting tethered fusion increased CD8 T cell numbers significantly, it had comparable effects on NK cell numbers and the CD8:NK ratio is unchanged from vehicle treated mice. The wildtype CD8-targeting tethered fusion drove a substantial increase in the CD8:NK ratio with 9.2- and 4.4-fold increases for the 2 µg and 10 µg doses, respectively. The DHEH mutant did not have as dramatic effects on CD8 T cells, but it also had reduced off-target effects on NK cells, and mice treated with this construct had similar CD8:NK ratios as the wildtype CD8-targeting tethered fusion. We conclude that IFM targeting can modulate the magnitude and selectivity of CD8 and NK cell effects of IL-15; in particular, IL-15 activity can be biased towards CD8 cells by controlling the targeting (CD8 vs CD45 vs non-targeted), the dose, and activity of IL-15 (via attenuating IL-15 mutations).

Together these experiments indicate that systemic administration of CD8-targeted IL-15 variants can load IL-15 onto CD8 T cells in vivo, can bias IL-15 activity towards these cells, and can further increase circulating levels of CD8 T cells beyond that attainable by treatment with IL-15 constructs described in the art, such as an IL15/sushi-Fc.

Figure 41A:
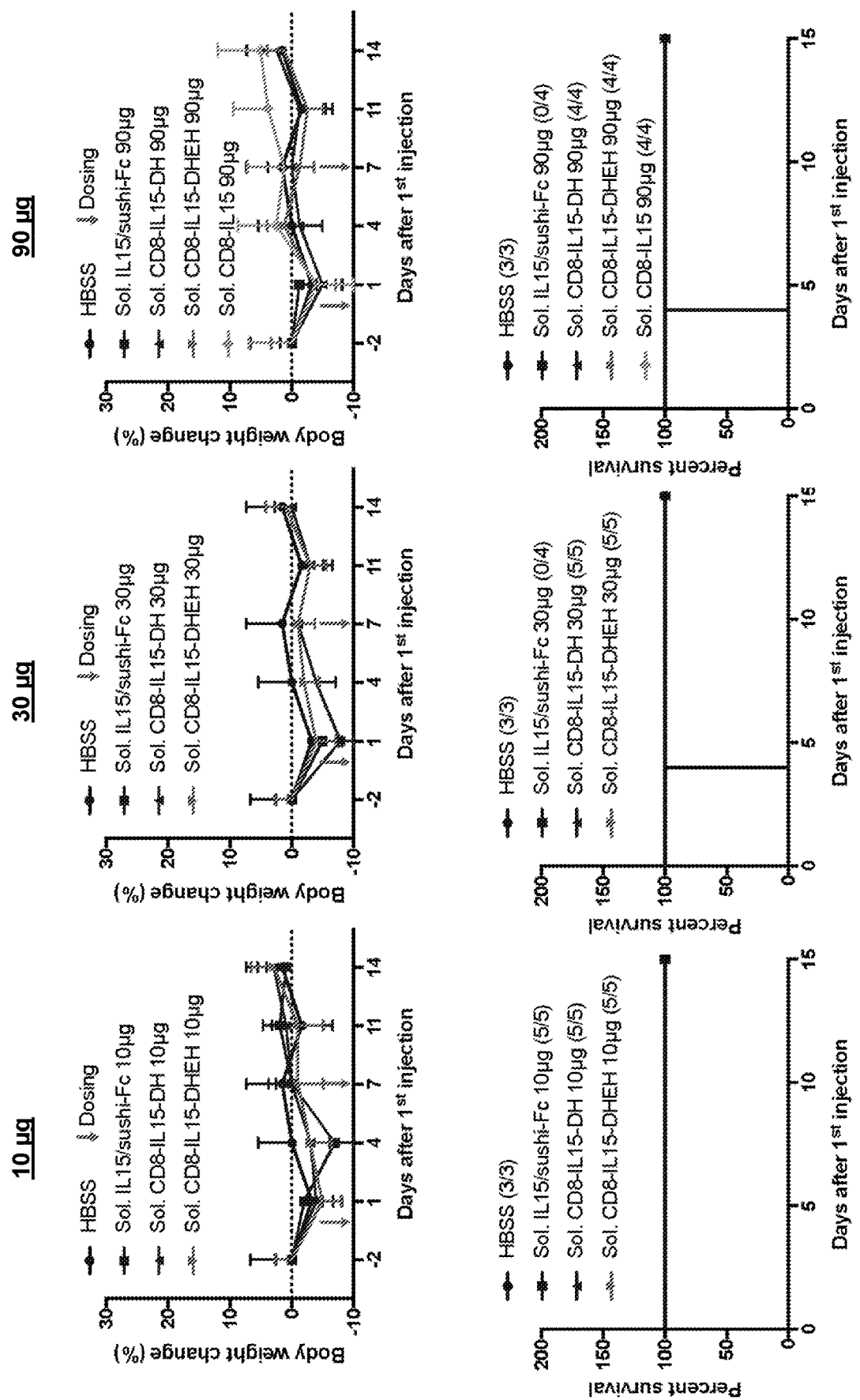
FIGS. 41A-41C shows toxicity of IL-15 following increasing dose or dosing schedule, compared with safety of CD8-targeted IFMs comprising wild-type or mutated IL-15 variants. * indicates after second dosing.
Figure 41B:
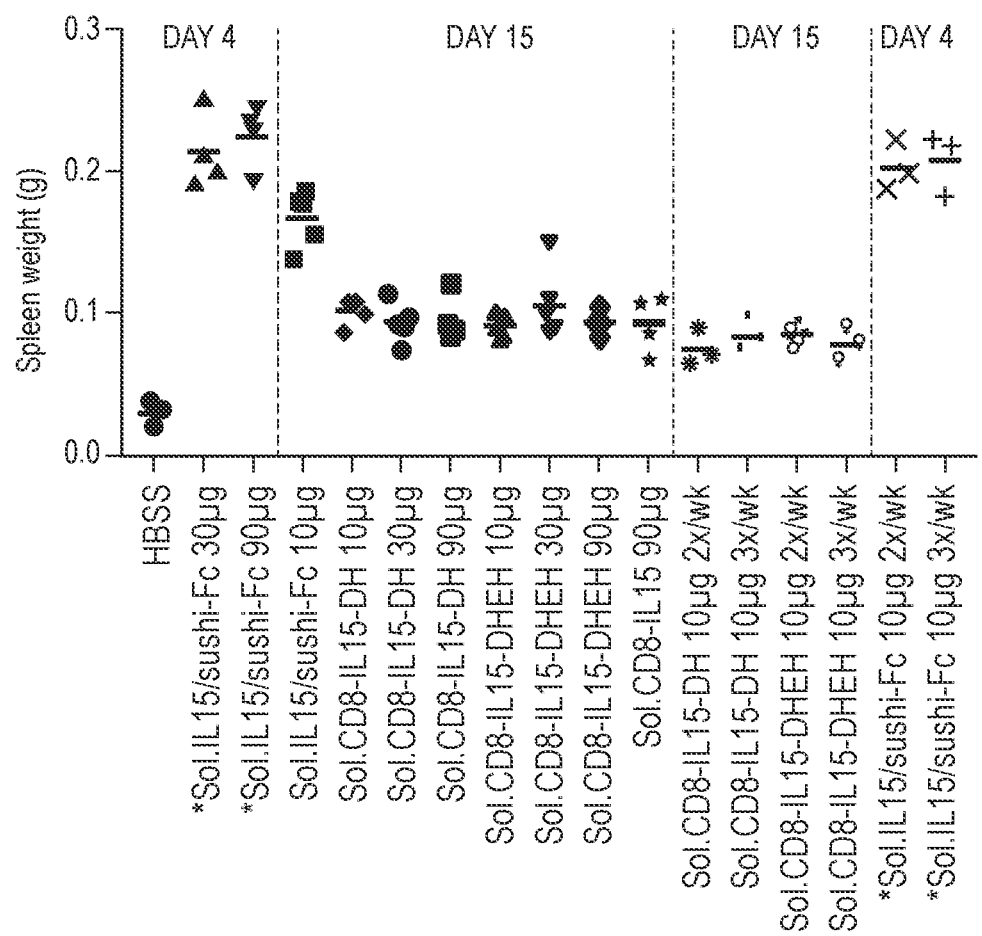
Figure 41C:
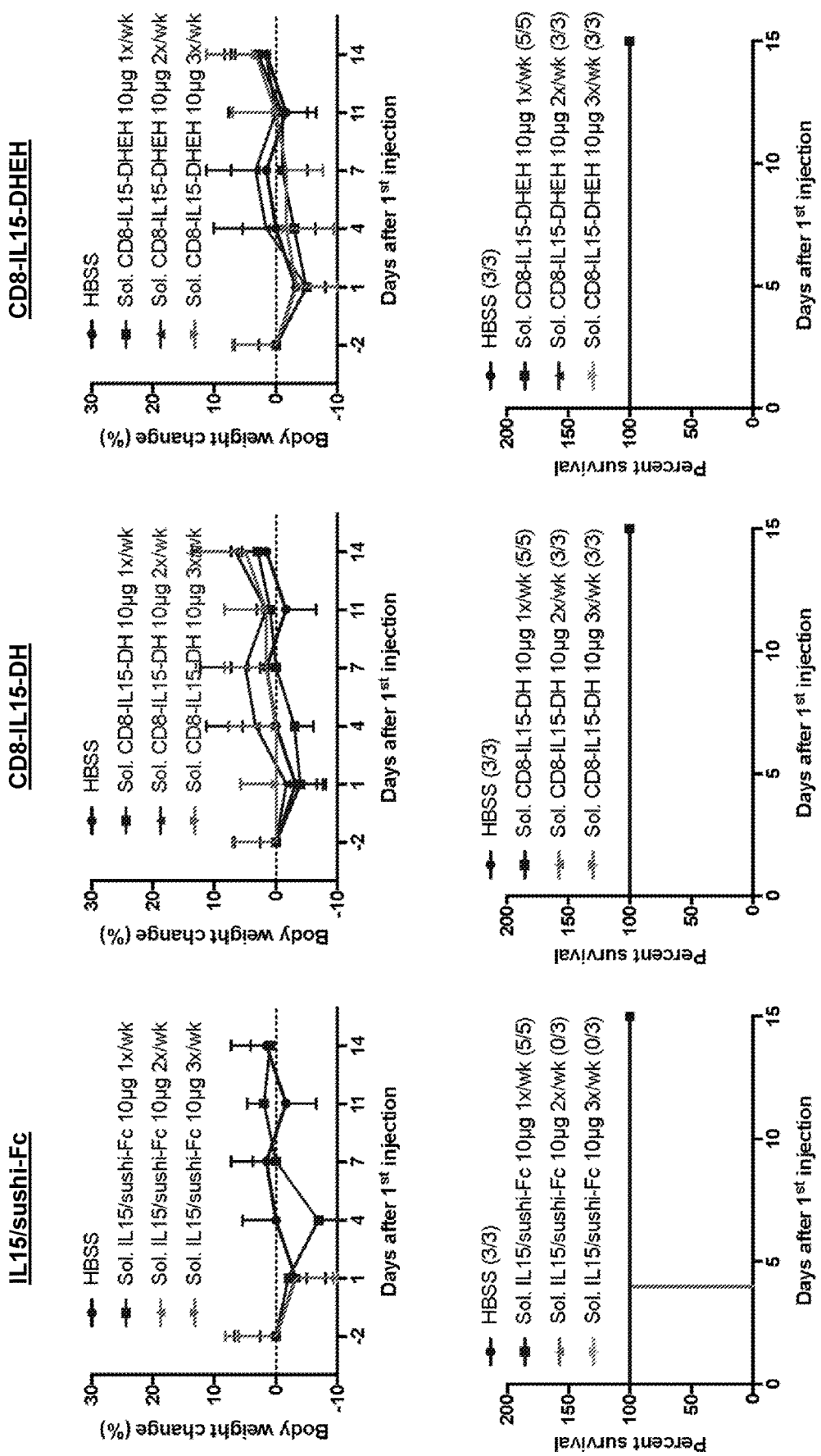

Example 22: Systemic Administration of CD8-Targeted IL-15 Shows Reduced Toxicity We evaluated the effects of retargeting IL-15 to CD8 T cells on systemic toxicities. Briefly, C57BL/6J mice were given two doses administered once per week by intravenous injection of 10, 30 or 90 µg with an IL15/sushi-Fc construct, which is an extended half-life form of IL-15, or two different CD8-targeted IL-15 variants containing a D61H (DH) or D61H and E64H (DHEH) mutations (chY169Fab-M1scFv-IL15-DH/sushi and chY169Fab-M1scFv-IL15-DHEH/sushi); n=5 mice per group. We additionally evaluated a CD8-targeted IFM containing wild-type IL-15, chY169Fab-M1scFv-IL15/sushi at the 90 ag dose level. In Example 21 above we demonstrated that the CD8-targeted constructs bias the loading and activity of IL-15 towards CD8 T cells as compared with IL15/sushi-Fc or CD45-targeted construct, and at the 10 µg dose the CD8-targeted constructs induce expansion of circulating CD8 T cells as well or better than 10 µg IL15/sushi-Fe, while inducing lesser expansion of circulating NK cells. We also evaluated increasing the number of doses per week at a fixed dose-level, in particular, we examined two or three doses per week of 10 µg IL15/sushi-Fc or the CD8-targeted IL-15 IFMs for two weeks (n=3 mice per group). FIG. 41A shows no overt toxicity in the form of body weight loss over time for the dose escalation of the CD8-targeted IL-15 variants. The IL15/sushi-Fc construct, however, had a maximum tolerated dose of 10 µg per week for the IL15/sushi-Fc: the 30 and 90 g doses induced significant toxicity and resulted in death four days post-injection (FIG. 41A, numbers in parentheses in figure legends indicate fraction of surviving mice at the end of the experiment). We further harvested the spleen from the dead mice and found splenomegaly in the mice treated with 30 and 90 µg IL15/sushi-Fc (FIG. 41B). By comparison, each of the CD8-targeted IL-15 variants were able to complete the full two-week study, resulted in minimal body weight loss (FIG. 41A), no deceased animals, and lesser spleen enlargement compared to 10 µg IL15/sushi-Fc following the full two-week dosing regimen examined here (FIG. 41B). Furthermore, while IL15/sushi-Fc was tolerated at a dose of 10 µg one-time per week, increasing this dosing to two or three doses per week resulted in significant toxicity and death after second injection (FIG. 41C, numbers in parentheses in figure legends indicate fraction of surviving mice at the end of the experiment). The deceased mice also exhibited splenomegaly (FIG. 41B). By comparison, dosing the CD8-targeted IL-15 variants two or three times per week at a dose of 10 µg did not result in significant body weight loss, deceased animals, (FIG. 41C) or substantial spleen enlargement (FIG. 41B) over the course of the full two-week dosing regimen. We conclude that retargeting IL-15 to CD8 T cells enables lower toxicity and higher dosing of IL-15 in vivo. Expansion of NK cells by IL-15 has been shown to strongly contribute to IL-15 toxicity in vivo (Guo et al., J Immunol. 2015 September 1;195(5):2353-64). Without wishing to be bound by theory, it is reasoned that biasing activity of IL-15 away from NK cells in vivo can reduce toxicity and enable stronger dosing against CD8 T cells. This is therapeutically advantageous and significant, given that anti-tumor efficacy of IL-15 can be mediated by CD8 T cells (Xu et al., Cancer Res. 2013 May 15; 73(10):3075-86; Cheng et al., J Hepatol. 2014 December; 61(6):1297-303).

Example 23: Anti-Cancer Efficacy from Systemic, CD8 Targeted Administration of IL-12

IL-12 is a potent cytokine that induces strong anti-tumor activity in murine tumor models, but has suffered from high toxicity in human clinical trials. IL-12 supports differentiation of CD4 T cells into a Th1 phenotype, increases cytotoxicity of CD8 T cells, and activates NK cells. Clinical trials of IL-12 for cancer therapy, however, have found that effects of IL-12 in human patients has been most prominent on NK cells (Robertson et al., Clin Cancer Res. 1999 January; 5(1):9-16; Bekaii-Saab et al., Mol Cancer Ther. 2009 November; 8(11): 2983-2991). It is possible that the dominant activity of IL-12 on NK cells—coupled with toxicity associated with activating NK cells—limits the ability to effectively deliver biological effects of IL-12 to CD4 and CD8 T cells. To test this hypothesis we constructed a mouse IL-12 IFM targeted to mouse CD8 T cells (chY169Fab-M1scFv-scIL-12p70) and evaluated its safety and anti-tumor efficacy in a murine melanoma tumor model.

Figure 42A:
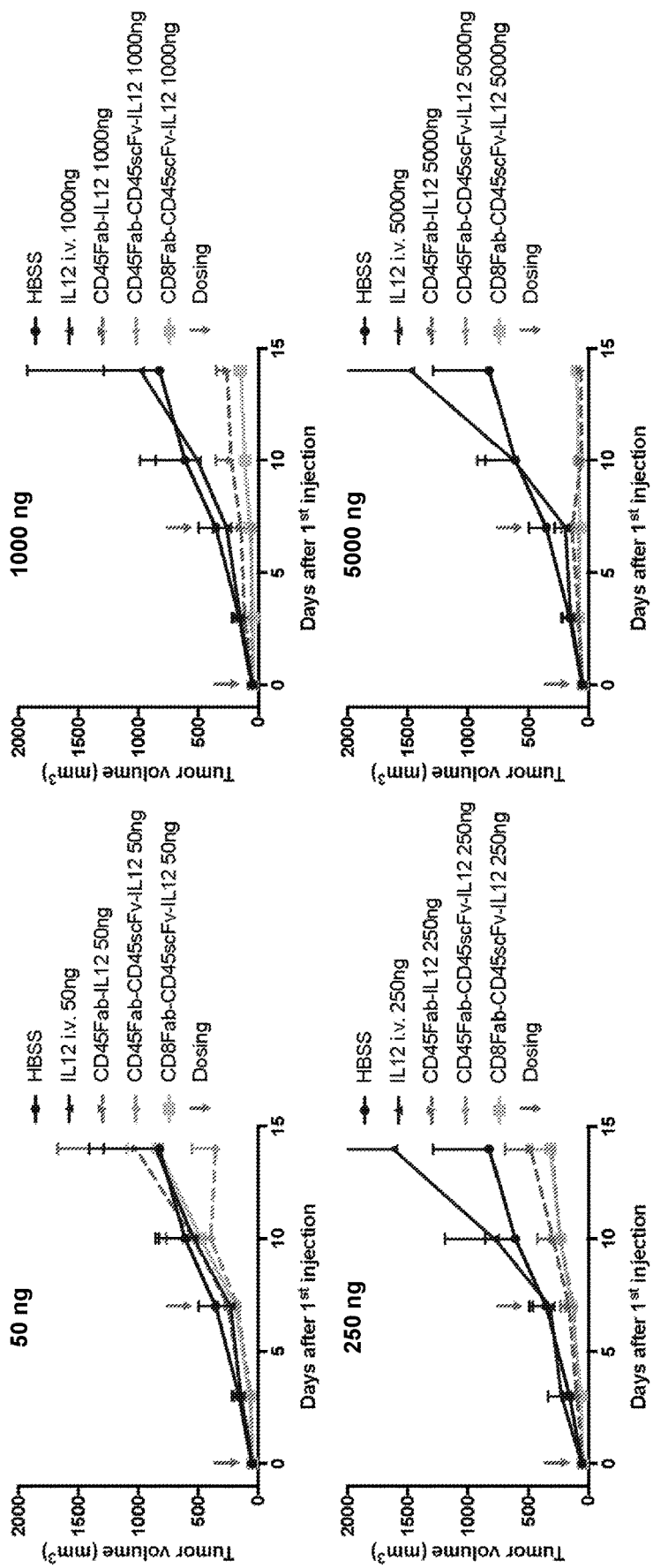
FIGS. 42A-42B shows anti-tumor efficacy and body weight changes from dose escalation with IL-12, a CD8-targeted IL-12 IFM, or two different CD45-targeted IL-12 IFMs.
Figure 42B:
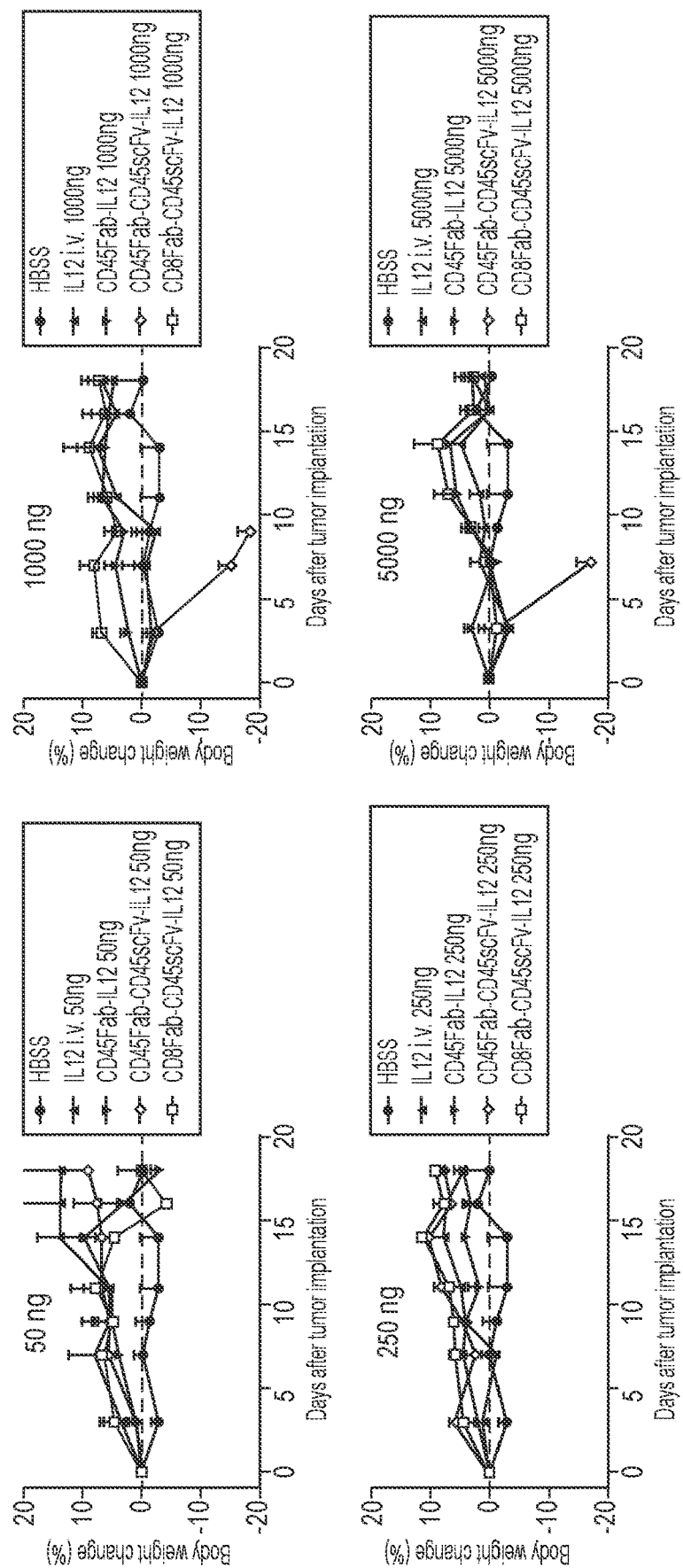

Briefly, B6D2F1/J mice were inoculated by intradermal injection with 400,000 B16-F10 melanoma cells. After 10 days tumor-bearing mice were randomized and treated with two doses (once weekly dosing) of 0.05, 0.25, 1, or 5 µg of recombinant IL-12 (R&D Systems), CD45-targeted IL-12 (chM1Fab-M1scFv-scIL12p70 and chM1Fab-scIL12p70), or CD8-targeted IL-12 by intravenous injection (n=5 mice per group). FIG. 42A demonstrates that weekly injection of the CD45-targeted IL-12 IFMs or the CD8-targeted IL-12 IFM each delivered stronger anti-tumor efficacy than weekly injection of IL-12. The CD8-targeted IL-12 additionally delivered similar tumor growth inhibition as the CD45-targeted IL-12 (FIG. 42A). Notably, mice treated with the Fab-scFv CD45-targeted IL-12 construct suffered toxicity in the form of body weight loss at the 1 and 5 ug dose levels, while mice treated with the Fab-scFv CD8-targeted IL-12 did not exhibit similar toxicities (FIG. 42B). We conclude that IFMs comprising IL-12 can deliver improved anti-tumor efficacy as compared with IL-12 alone, and that cell-specifically-targeted IL-12 can reduce systemic toxicities.

Modifications and variations of the described methods and compositions of the present disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure are intended and understood by those skilled in the relevant field in which this disclosure resides to be within the scope of the disclosure as represented by the following claims.

INCORPORATION BY REFERENCE

All patents and publications mentioned in this specification are herein incorporated by reference to the same extent as if each independent patent and publication was specifically and individually indicated to be incorporated by reference. International Application No. PCT/US2018/040783, filed on Jul. 3, 2018 and titled "POLYNUCLEOTIDES ENCODING IMMUNOSTIMULATORY FUSION MOLECULES AND USES THEREOF" and International Application No. PCT/US2018/040786, filed on Jul. 3, 2018 and titled "FUSION MOLECULES TARGETING IMMUNE REGULATORY CELLS AND USES THEREOF" are both incorporated herein by reference in their entireties.

The invention claimed is:

1. A composition comprising:
   (i) an immunostimulatory fusion molecule comprising:
      (a) an immunostimulatory cytokine molecule selected from the group consisting of IL-12, IL-15, IL-2, IL-6, IL-7, IL-18, IL-21, IL-23, and IL-27; and
      (b) a targeting moiety comprising an antigen-binding fragment of an antibody having an affinity to a cell surface antigen expressed by or displayed on the surface of a T cell, wherein the immunostimulatory cytokine molecule is operably linked to the antigen-binding fragment; and
   (ii) a population of T cells expressing or displaying the cell surface antigen,
   wherein the immunostimulatory fusion molecule is bound to the surface of a T cell in the population of T cells through interaction with the cell surface antigen.

2. The composition of claim 1, wherein the T cells are selected from the group consisting of effector T cells, CD4$^+$ T cells, CD8$^+$ T cells, and cytotoxic T lymphocytes (CTLs).

3. The composition of claim 2, wherein the cell surface antigen is CD45.

4. The composition of claim 1, wherein the targeting moiety comprises a Fab fragment, F(ab')2, Fv, or a single chain Fv comprising:
   (i) a heavy chain variable domain amino acid sequence at least 95% identical to SEQ ID NO: 94 and a light chain variable domain amino acid sequence at least 95% identical to SEQ ID NO: 95;
   (ii) a heavy chain variable domain amino acid sequence at least 95% identical to SEQ ID NO: 59 and a light chain variable domain amino acid sequence at least 95% identical to SEQ ID NO: 60;
   (iii) a heavy chain variable domain amino acid sequence at least 95% identical to SEQ ID NO: 23 and a light chain variable domain amino acid sequence at least 95% identical to SEQ ID NO: 24;
   (iv) a heavy chain variable domain amino acid sequence at least 95% identical to SEQ ID NO: 96 and a light chain variable domain amino acid sequence at least 95% identical to SEQ ID NO: 97;
   (v) a heavy chain variable domain amino acid sequence at least 95% identical to SEQ ID NO: 57 and a light chain variable domain amino acid sequence at least 95% identical to SEQ ID NO: 58; or
   (vi) a heavy chain variable domain amino acid sequence at least 95% identical to SEQ ID NO: 61 and a light chain variable domain amino acid sequence at least 95% identical to SEQ ID NO: 62.

5. The composition of claim 1, wherein the immunostimulatory cytokine molecule comprises an IL-12, a single chain IL-12, or a subunit of IL-12 selected from the group consisting of IL-12A and IL-12B.

6. The composition of claim 1, further comprising a single-chain Fv having an affinity to an antigen on the surface of the T cell.

7. The composition of claim 6, wherein the single-chain Fv has an affinity to the same antigen as the antigen-binding fragment of the targeting moiety.

8. The composition of claim 6, wherein the single-chain Fv has an affinity to a different antigen than the antigen-binding fragment of the targeting moiety.

9. The composition of claim 1, wherein the antigen-binding fragment is a Fab fragment.

10. The composition of claim 9, wherein the Fab fragment comprises a light chain and a heavy chain fragment, and wherein the immunostimulatory cytokine molecule is operably linked to the Fab fragment at a C-terminus of the light chain.

11. The composition of claim 1, wherein the immunostimulatory cytokine molecule is operably linked to the antigen-binding fragment by a linker.

12. The composition of claim 11, wherein the linker is selected from the group consisting of a cleavable linker, a non-cleavable linker, a peptide linker, a flexible linker, a rigid linker, a helical linker, and a non-helical linker.

13. The composition of claim 1, wherein the immunostimulatory fusion molecule has an affinity to a CD45 receptor and comprises a first polypeptide comprising the amino acid sequence of SEQ ID NO: 82 and a second polypeptide comprising the amino acid sequence of SEQ ID NO: 79.

14. The composition of claim 5, wherein the immunostimulatory cytokine molecule comprises a single-chain IL-12 molecule having an amino acid sequence at least 95% identical to SEQ ID NO: 50.

15. The composition of claim 14, wherein the immunostimulatory cytokine molecule comprises a single-chain IL-12 molecule having an IL-12A subunit linked to an IL-12B subunit through a linker having an amino acid sequence at least 95% identical to SEQ ID NO: 70.

16. The composition of claim 12, wherein the linker comprises a peptide linker having the amino acid sequence of SEQ ID NO: 36.

17. The composition of claim 1, wherein the T cells are healthy and/or non-malignant.

18. A pharmaceutical composition comprising the composition of claim 1 and a pharmaceutically acceptable carrier, excipient, or stabilizer.

19. The composition of claim 1, further comprising a nanoparticle.

20. The composition of claim 1, further comprising a liposome.

21. The composition of claim 19, wherein the nanoparticle comprises a protein nanogel, a nucleotide nanogel, a polymer nanoparticle, or a solid nanoparticle.

22. The composition of claim 21, wherein the nanoparticle comprises a protein nanogel.

23. The composition of claim 22, wherein the nanoparticle comprises at least one polymer, cationic polymer, or cationic block co-polymer on the nanoparticle surface.

24. The composition of claim 23, wherein the nanoparticle comprises a nanogel that is cross linked by a reversible linker that is sensitive to redox state, pH, or one or more proteases.

25. The composition of claim 1, further comprising a biodegradable polymer.

26. The composition of claim 1, wherein the cell surface antigen is CD45.

27. The composition of claim 1, wherein the population of T cells have specificity against multiple tumor-associated antigens.

28. The composition of claim 27, wherein the tumor-associated antigens comprise one or more of MART-1, MAGE-A4, NY-ESO-1, SSX2, and Survivin.

29. The composition of claim 1, wherein the cell surface antigen is selected from the group consisting of CD4, CD8, CD3, CD11a, CD11b, CD11c, CD18, CD25, CD127, CD19, CD20, CD22, HLA-DR, CD197, CD38, CD27, CD196, CXCR3, CXCR4, CXCR5, CD84, CD229, CCR1, CCR5, CCR4, CCR6, CCR8, CCR10, CD16, CD56, CD137, OX40, and GITR.

30. The composition of claim 1, wherein the immunostimulatory fusion molecule lacks an Fc domain or comprises an Fc domain in which an antibody-dependent cellular cytotoxicity is reduced by at least 60% relative to a wild-type human IgG1 Fc domain having the amino acid sequence of SEQ ID NO: 67.

* * * * *

SEQUENCE LISTING

<160> NUMBER OF SEQ ID NOS: 131

<210> SEQ ID NO 1
<211> LENGTH: 298
<212> TYPE: PRT
<213> ORGANISM: Unknown
<220> FEATURE:
<223> OTHER INFORMATION: Synthetic

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Gly
    210                 215                 220

Gly Gly Gly Ser Gly Gly Gly Gly Ser Ile Thr Cys Pro Pro Pro Met
225                 230                 235                 240

Ser Val Glu His Ala Asp Ile Trp Val Lys Ser Tyr Ser Leu Tyr Ser
                245                 250                 255

Arg Glu Arg Tyr Ile Cys Asn Ser Gly Phe Lys Arg Lys Ala Gly Thr
            260                 265                 270

Ser Ser Leu Thr Glu Cys Val Leu Asn Lys Ala Thr Asn Val Ala His
        275                 280                 285

Trp Thr Thr Pro Ser Leu Lys Cys Ile Arg
    290                 295

<210> SEQ ID NO 2
<211> LENGTH: 298
<212> TYPE: PRT
<213> ORGANISM: Unknown
<220> FEATURE:
<223> OTHER INFORMATION: Synthetic

<400> SEQUENCE: 2

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Gly Ser Gly Gly Gly Ser Gly Gly Gly Gly Ser
65                  70                  75                  80

Asp Ile Val Leu Thr Gln Ser Pro Ala Ser Leu Ala Val Ser Leu Gly
                85                  90                  95

Gln Arg Ala Thr Ile Ser Cys Arg Ala Ser Lys Ser Val Ser Thr Ser
            100                 105                 110

Gly Tyr Ser Tyr Leu His Trp Tyr Gln Gln Lys Pro Gly Gln Pro Pro
        115                 120                 125

Lys Leu Leu Ile Tyr Leu Ala Ser Asn Leu Glu Ser Gly Val Pro Ala
    130                 135                 140

Arg Phe Ser Gly Ser Gly Ser Gly Thr Asp Phe Thr Leu Asn Ile His
145                 150                 155                 160

Pro Val Glu Glu Glu Asp Ala Ala Thr Tyr Tyr Cys Gln His Ser Arg
                165                 170                 175

Glu Leu Pro Phe Thr Phe Gly Ser Gly Thr Lys Leu Glu Ile Lys Arg
            180                 185                 190

Thr Val Ala Ala Pro Ser Val Phe Ile Phe Pro Pro Ser Asp Glu Gln
        195                 200                 205

Leu Lys Ser Gly Thr Ala Ser Val Val Cys Leu Leu Asn Asn Phe Tyr
    210                 215                 220

Pro Arg Glu Ala Lys Val Gln Trp Lys Val Asp Asn Ala Leu Gln Ser
225                 230                 235                 240

Gly Asn Ser Gln Glu Ser Val Thr Glu Gln Asp Ser Lys Asp Ser Thr
                245                 250                 255

Tyr Ser Leu Ser Ser Thr Leu Thr Leu Ser Lys Ala Asp Tyr Glu Lys
            260                 265                 270

His Lys Val Tyr Ala Cys Glu Val Thr His Gln Gly Leu Ser Ser Pro
        275                 280                 285

Val Thr Lys Ser Phe Asn Arg Gly Glu Cys
    290                 295

<210> SEQ ID NO 3
<211> LENGTH: 347
<212> TYPE: PRT
<213> ORGANISM: Unknown
<220> FEATURE:
<223> OTHER INFORMATION: Synthetic

<400> SEQUENCE: 3

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60
```

```
Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Leu Pro Phe Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Gly
    210                 215                 220

Gly Gly Gly Ser Gly Gly Gly Ser Asn Trp Val Asn Val Ile Ser
225                 230                 235                 240

Asp Leu Lys Lys Ile Glu Asp Leu Ile Gln Ser Met His Ile Asp Ala
                245                 250                 255

Thr Leu Tyr Thr Glu Ser Asp Val His Pro Ser Cys Lys Val Thr Ala
            260                 265                 270

Met Lys Cys Phe Leu Leu Glu Leu Gln Val Ile Ser Leu Glu Ser Gly
        275                 280                 285

Asp Ala Ser Ile His Asp Thr Val Glu Asn Leu Ile Ile Leu Ala Asn
    290                 295                 300

Asn Ser Leu Ser Ser Asn Gly Asn Val Thr Glu Ser Gly Cys Lys Glu
305                 310                 315                 320

Cys Glu Glu Leu Glu Glu Lys Asn Ile Lys Glu Phe Leu Gln Ser Phe
                325                 330                 335

Val His Ile Val Gln Met Phe Ile Asn Thr Ser
            340                 345

<210> SEQ ID NO 4
<211> LENGTH: 347
<212> TYPE: PRT
<213> ORGANISM: Unknown
<220> FEATURE:
<223> OTHER INFORMATION: Synthetic

<400> SEQUENCE: 4

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
 65                  70                  75                  80
```

```
Thr Glu Ser Gly Cys Lys Glu Cys Glu Glu Leu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Gly Gly Gly Ser Gly Gly Gly Gly
            115                 120                 125

Ser Asp Ile Val Leu Thr Gln Ser Pro Ala Ser Leu Ala Val Ser Leu
            130                 135                 140

Gly Gln Arg Ala Thr Ile Ser Cys Arg Ala Ser Lys Ser Val Ser Thr
145                 150                 155                 160

Ser Gly Tyr Ser Tyr Leu His Trp Tyr Gln Gln Lys Pro Gly Gln Pro
                165                 170                 175

Pro Lys Leu Leu Ile Tyr Leu Ala Ser Asn Leu Glu Ser Gly Val Pro
            180                 185                 190

Ala Arg Phe Ser Gly Ser Gly Ser Gly Thr Asp Phe Thr Leu Asn Ile
            195                 200                 205

His Pro Val Glu Glu Glu Asp Ala Ala Thr Tyr Tyr Cys Gln His Ser
            210                 215                 220

Arg Glu Leu Pro Phe Thr Phe Gly Ser Gly Thr Lys Leu Glu Ile Lys
225                 230                 235                 240

Arg Thr Val Ala Ala Pro Ser Val Phe Ile Phe Pro Pro Ser Asp Glu
                245                 250                 255

Gln Leu Lys Ser Gly Thr Ala Ser Val Val Cys Leu Leu Asn Asn Phe
            260                 265                 270

Tyr Pro Arg Glu Ala Lys Val Gln Trp Lys Val Asp Asn Ala Leu Gln
            275                 280                 285

Ser Gly Asn Ser Gln Glu Ser Val Thr Glu Gln Asp Ser Lys Asp Ser
            290                 295                 300

Thr Tyr Ser Leu Ser Ser Thr Leu Thr Leu Ser Lys Ala Asp Tyr Glu
305                 310                 315                 320

Lys His Lys Val Tyr Ala Cys Glu Val Thr His Gln Gly Leu Ser Ser
                325                 330                 335

Pro Val Thr Lys Ser Phe Asn Arg Gly Glu Cys
            340                 345

<210> SEQ ID NO 5
<211> LENGTH: 224
<212> TYPE: PRT
<213> ORGANISM: Unknown
<220> FEATURE:
<223> OTHER INFORMATION: Synthetic

<400> SEQUENCE: 5

Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
            35                  40                  45

Gly Glu Ile Asn Pro Thr Ser Ser Thr Ile Asn Phe Thr Pro Ser Leu
        50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
            85                  90                  95
```

```
Ala Arg Gly Asn Tyr Tyr Arg Tyr Gly Asp Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 6
<211> LENGTH: 448
<212> TYPE: PRT
<213> ORGANISM: Unknown
<220> FEATURE:
<223> OTHER INFORMATION: Synthetic

<400> SEQUENCE: 6

```
Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 7
<211> LENGTH: 218
<212> TYPE: PRT
<213> ORGANISM: Unknown
<220> FEATURE:
<223> OTHER INFORMATION: Synthetic

<400> SEQUENCE: 7

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 8
<211> LENGTH: 577
<212> TYPE: PRT
<213> ORGANISM: Unknown
<220> FEATURE:
<223> OTHER INFORMATION: Synthetic

<400> SEQUENCE: 8

```
Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

Gly Gly Gly Gly Ser Gly Gly Gly Ser Gly Gly Gly Gly Ser Asn
450                 455                 460

Trp Val Asn Val Ile Ser Asp Leu Lys Lys Ile Glu Asp Leu Ile Gln
465                 470                 475                 480

Ser Met His Ile Asp Ala Thr Leu Tyr Thr Glu Ser Asp Val His Pro
                485                 490                 495

Ser Cys Lys Val Thr Ala Met Lys Cys Phe Leu Leu Glu Leu Gln Val
            500                 505                 510

Ile Ser Leu Glu Ser Gly Asp Ala Ser Ile His Asp Thr Val Glu Asn
        515                 520                 525

Leu Ile Ile Leu Ala Asn Asn Ser Leu Ser Ser Asn Gly Asn Val Thr
530                 535                 540

Glu Ser Gly Cys Lys Glu Cys Glu Glu Leu Glu Glu Lys Asn Ile Lys
545                 550                 555                 560

Glu Phe Leu Gln Ser Phe Val His Ile Val Gln Met Phe Ile Asn Thr
                565                 570                 575

Ser

<210> SEQ ID NO 9
<211> LENGTH: 65
<212> TYPE: PRT
<213> ORGANISM: Homo sapiens

<400> SEQUENCE: 9

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg
65

<210> SEQ ID NO 10
<211> LENGTH: 114
```

<212> TYPE: PRT
<213> ORGANISM: Homo sapiens

<400> SEQUENCE: 10

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 11
<211> LENGTH: 114
<212> TYPE: PRT
<213> ORGANISM: Unknown
<220> FEATURE:
<223> OTHER INFORMATION: Synthetic

<400> SEQUENCE: 11

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 12
<211> LENGTH: 297
<212> TYPE: PRT
<213> ORGANISM: Unknown
<220> FEATURE:
<223> OTHER INFORMATION: Synthetic

<400> SEQUENCE: 12

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Ile Asn
            35                  40                  45
```

Lys Ala Thr Asn Val Ala His Trp Thr Thr Pro Ser Leu Lys Cys Ile
         50                  55                  60

Arg Glu Pro Lys Ser Cys Asp Lys Thr His Thr Cys Pro Pro Cys Pro
 65                  70                  75                  80

Ala Pro Glu Leu Leu Gly Gly Pro Ser Val Phe Leu Phe Pro Pro Lys
                 85                  90                  95

Pro Lys Asp Thr Leu Met Ile Ser Arg Thr Pro Glu Val Thr Cys Val
             100                 105                 110

Val Val Asp Val Ser His Glu Asp Pro Glu Val Lys Phe Asn Trp Tyr
         115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 13
<211> LENGTH: 297
<212> TYPE: PRT
<213> ORGANISM: Unknown
<220> FEATURE:
<223> OTHER INFORMATION: Synthetic

<400> SEQUENCE: 13

Ile Thr Cys Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
                 20                  25                  30

Phe Lys Arg Lys Ala Gly Thr Ser Ser Leu Thr Glu Cys Val Leu Asn
             35                  40                  45

Lys Ala Thr Asn Val Ala His Trp Thr Thr Pro Ser Leu Lys Cys Ile
         50                  55                  60

Arg Glu Pro Lys Ser Cys Asp Lys Thr His Thr Cys Pro Pro Cys Pro
 65                  70                  75                  80

Ala Pro Glu Leu Leu Gly Gly Pro Ser Val Phe Leu Phe Pro Pro Lys
                 85                  90                  95

Pro Lys Asp Thr Leu Met Ile Ser Arg Thr Pro Glu Val Thr Cys Val
             100                 105                 110

Val Val Asp Val Ser His Glu Asp Pro Glu Val Lys Phe Asn Trp Tyr
            115                 120                 125

Val Asp Gly Val Glu Val His Asn Ala Lys Thr Lys Pro Arg Glu Glu
130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
            165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
            245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
            290                 295

<210> SEQ ID NO 14
<211> LENGTH: 220
<212> TYPE: PRT
<213> ORGANISM: Unknown
<220> FEATURE:
<223> OTHER INFORMATION: Synthetic

<400> SEQUENCE: 14

Gln Val Gln Leu Gln Gln Leu Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Ser Ile Gln Trp Val Lys Gln Arg Pro Gly Gln Gly Leu Glu Trp Ile
        35                  40                  45

Gly Tyr Ile Asn Pro Ser Ser Gly Tyr Ile Lys Tyr Asn Gln His Phe
    50                  55                  60

Arg Asp Arg Ala Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Ser Gly Ser Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 15
<211> LENGTH: 348
<212> TYPE: PRT
<213> ORGANISM: Unknown
<220> FEATURE:
<223> OTHER INFORMATION: Synthetic

<400> SEQUENCE: 15

Asp Ile Val Met Thr Gln Ala Ala Pro Ser Val Pro Val Thr Pro Gly
1               5                   10                  15

Glu Ser Leu Ser Ile Ser Cys Arg Ser Ser Lys Ser Leu Leu His Ser
            20                  25                  30

Ser Gly Ile Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Asn Trp Val Asn Val Ile
225                 230                 235                 240

Ser Asp Leu Lys Lys Ile Glu Asp Leu Ile Gln Ser Met His Ile Asp
                245                 250                 255

Ala Thr Leu Tyr Thr Glu Ser Asp Val His Pro Ser Cys Lys Val Thr
            260                 265                 270

Ala Met Lys Cys Phe Leu Leu Glu Leu Gln Val Ile Ser Leu Glu Ser
        275                 280                 285

Gly Asp Ala Ser Ile His Asp Thr Val Glu Asn Leu Ile Ile Leu Ala
    290                 295                 300

Asn Asn Ser Leu Ser Ser Asn Gly Asn Val Thr Glu Ser Gly Cys Lys
305                 310                 315                 320
```

Glu Cys Glu Glu Leu Glu Lys Asn Ile Lys Glu Phe Leu Gln Ser
              325                 330                 335

Phe Val His Ile Val Gln Met Phe Ile Asn Thr Ser
              340                 345

<210> SEQ ID NO 16
<211> LENGTH: 220
<212> TYPE: PRT
<213> ORGANISM: Unknown
<220> FEATURE:
<223> OTHER INFORMATION: Synthetic

<400> SEQUENCE: 16

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met Gln Trp Val Lys Gln Arg Pro Gly Gln Gly Leu Glu Trp Ile
            35                  40                  45

Gly Tyr Ile Asn Pro Ser Ser Gly Tyr Ile Lys Tyr Asn Gln Lys Phe
    50                  55                  60

Lys Asp Lys Val Thr Leu Thr Ala Asp Lys Ser Ser Thr Thr Ala Tyr
65                  70                  75                  80

Met Gln Leu Ser Arg Leu Thr Ser Glu Asp Ser Ala Val Tyr Tyr Cys
                85                  90                  95

Ala Arg Arg Gly Ser Tyr Phe Phe Asp Phe Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 17
<211> LENGTH: 348
<212> TYPE: PRT
<213> ORGANISM: Unknown
<220> FEATURE:
<223> OTHER INFORMATION: Synthetic

<400> SEQUENCE: 17

Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
                20                  25                  30

Asp Gly Lys Thr Tyr Leu Asn Trp Phe Leu Gln Arg Pro Gly Gln Ser
            35                  40                  45

Pro Gln Leu Leu Ile Tyr Leu Met Ser Thr Arg Ala Ser Gly Val Ser

```
                    50                  55                  60
Asp Arg Phe Ser Gly Ser Gly Ser Gly Thr Asp Phe Thr Leu Glu Ile
 65                  70                  75                  80

Ser Arg Val Lys Ala Glu Asp Val Gly Val Tyr Tyr Cys Gln Gln Leu
                 85                  90                  95

Val Glu Tyr Pro Phe Thr Phe Gly Gly Gly Thr Lys Leu Glu Val Lys
             100                 105                 110

Arg Thr Val Ala Ala Pro Ser Val Phe Ile Phe Pro Pro Ser Asp Glu
         115                 120                 125

Gln Leu Lys Ser Gly Thr Ala Ser Val Val Cys Leu Leu Asn Asn Phe
     130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Asn Trp Val Asn Val Ile
225                 230                 235                 240

Ser Asp Leu Lys Lys Ile Glu Asp Leu Ile Gln Ser Met His Ile Asp
                245                 250                 255

Ala Thr Leu Tyr Thr Glu Ser Asp Val His Pro Ser Cys Lys Val Thr
            260                 265                 270

Ala Met Lys Cys Phe Leu Leu Glu Leu Gln Val Ile Ser Leu Glu Ser
        275                 280                 285

Gly Asp Ala Ser Ile His Asp Thr Val Glu Asn Leu Ile Ile Leu Ala
    290                 295                 300

Asn Asn Ser Leu Ser Ser Asn Gly Asn Val Thr Glu Ser Gly Cys Lys
305                 310                 315                 320

Glu Cys Glu Glu Leu Glu Glu Lys Asn Ile Lys Glu Phe Leu Gln Ser
                325                 330                 335

Phe Val His Ile Val Gln Met Phe Ile Asn Thr Ser
            340                 345

<210> SEQ ID NO 18
<211> LENGTH: 224
<212> TYPE: PRT
<213> ORGANISM: Unknown
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asp Phe Ser Arg Tyr
             20                  25                  30

Trp Met Ser Trp Val Arg Gln Ala Pro Gly Lys Gly Leu Glu Trp Ile
         35                  40                  45

Gly Glu Ile Asn Pro Thr Ser Ser Thr Ile Asn Phe Ala Asp Ser Val
     50                  55                  60

Lys Gly Arg Phe Thr Ile Ser Arg Asp Asn Ala Lys Asn Ser Leu Tyr
```

```
            65                  70                  75                  80
Leu Gln Met Asn Ser Val Arg Asp Glu Asp Thr Ala Val Tyr Tyr Cys
                85                  90                  95

Ala Arg Gly Asn Tyr Tyr Arg Tyr Gly Asp Ala Met Asp Tyr Trp Gly
               100                 105                 110

Gln Gly Thr Leu Val Thr Val Ser Ala Ser Thr Lys Gly Pro Ser
               115                 120                 125

Val Phe Pro Leu Ala Pro Ser Ser Lys Ser Thr Ser Gly Gly Thr Ala
   130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
               165                 170                 175

Val Leu Gln Ser Ser Gly Leu Tyr Ser Leu Ser Ser Val Val Thr Val
               180                 185                 190

Pro Ser Ser Ser Leu Gly Thr Gln Thr Tyr Ile Cys Asn Val Asn His
               195                 200                 205

Lys Pro Ser Asn Thr Lys Val Asp Lys Lys Val Glu Pro Lys Ser Cys
   210                 215                 220

<210> SEQ ID NO 19
<211> LENGTH: 347
<212> TYPE: PRT
<213> ORGANISM: Unknown
<220> FEATURE:
<223> OTHER INFORMATION: Synthetic

<400> SEQUENCE: 19

Glu Ile Val Leu Thr Gln Ser Pro Ala Thr Leu Ser Leu Ser Leu Gly
1               5                   10                  15

Glu Arg Ala Thr Ile Ser Cys Arg Ala Ser Lys Ser Val Ser Thr Ser
                20                  25                  30

Gly Tyr Ser Tyr Leu His Trp Tyr Gln Gln Lys Pro Gly Gln Ala Pro
            35                  40                  45

Lys Leu Leu Ile Tyr Leu Ala Ser Asn Arg Ala Thr Gly Val Pro Ala
   50                  55                  60

Arg Phe Ser Gly Ser Gly Pro Gly Thr Asp Phe Thr Leu Thr Ile Ser
65                  70                  75                  80

Ser Leu Glu Pro Glu Asp Phe Ala Thr Tyr Tyr Cys Gln His Ser Arg
                85                  90                  95

Glu Leu Pro Phe Thr Phe Gly Gln Gly Thr Lys Leu Glu Ile Lys Arg
               100                 105                 110

Thr Val Ala Ala Pro Ser Val Phe Ile Phe Pro Pro Ser Asp Glu Gln
               115                 120                 125

Leu Lys Ser Gly Thr Ala Ser Val Val Cys Leu Leu Asn Asn Phe Tyr
   130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
               165                 170                 175

Tyr Ser Leu Ser Ser Thr Leu Thr Leu Ser Lys Ala Asp Tyr Glu Lys
               180                 185                 190

His Lys Val Tyr Ala Cys Glu Val Thr His Gln Gly Leu Ser Ser Pro
               195                 200                 205

Val Thr Lys Ser Phe Asn Arg Gly Glu Cys Gly Gly Gly Gly Ser Gly
```

```
                    210                 215                 220
Gly Gly Gly Ser Gly Gly Gly Ser Asn Trp Val Asn Val Ile Ser
225                 230                 235                 240

Asp Leu Lys Lys Ile Glu Asp Leu Ile Gln Ser Met His Ile Asp Ala
                245                 250                 255

Thr Leu Tyr Thr Glu Ser Asp Val His Pro Ser Cys Lys Val Thr Ala
                260                 265                 270

Met Lys Cys Phe Leu Leu Glu Leu Gln Val Ile Ser Leu Glu Ser Gly
            275                 280                 285

Asp Ala Ser Ile His Asp Thr Val Glu Asn Leu Ile Ile Leu Ala Asn
            290                 295                 300

Asn Ser Leu Ser Ser Asn Gly Asn Val Thr Glu Ser Gly Cys Lys Glu
305                 310                 315                 320

Cys Glu Glu Leu Glu Glu Lys Asn Ile Lys Glu Phe Leu Gln Ser Phe
                325                 330                 335

Val His Ile Val Gln Met Phe Ile Asn Thr Ser
                340                 345

<210> SEQ ID NO 20
<211> LENGTH: 224
<212> TYPE: PRT
<213> ORGANISM: Unknown
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Thr Ser Ser Thr Ile Asn Phe Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Val Arg Asp Glu Asp Thr Ala Val Tyr Tyr Cys
                85                  90                  95

Ala Arg Gly Ser Gly Gly Ser Gly Asp Ala Met Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220
```

<210> SEQ ID NO 21
<211> LENGTH: 340
<212> TYPE: PRT
<213> ORGANISM: Unknown
<220> FEATURE:
<223> OTHER INFORMATION: Synthetic

<400> SEQUENCE: 21

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Ser Gly Gly
    210                 215                 220

Gly Ser Asn Trp Val Asn Val Ile Ser Asp Leu Lys Lys Ile Glu Asp
225                 230                 235                 240

Leu Ile Gln Ser Met His Ile Asp Ala Thr Leu Tyr Thr Glu Ser Asp
                245                 250                 255

Val His Pro Ser Cys Lys Val Thr Ala Met Lys Cys Phe Leu Leu Glu
            260                 265                 270

Leu Gln Val Ile Ser Leu Glu Ser Gly Asp Ala Ser Ile His Asp Thr
        275                 280                 285

Val Glu Asn Leu Ile Ile Leu Ala Asn Asn Ser Leu Ser Ser Asn Gly
    290                 295                 300

Asn Val Thr Glu Ser Gly Cys Lys Glu Cys Glu Glu Leu Glu Glu Lys
305                 310                 315                 320

Asn Ile Lys Glu Phe Leu Gln Ser Phe Val His Ile Val Gln Met Phe
                325                 330                 335

Ile Asn Thr Ser
            340
```

<210> SEQ ID NO 22
<211> LENGTH: 344
<212> TYPE: PRT

<213> ORGANISM: Unknown
<220> FEATURE:
<223> OTHER INFORMATION: Synthetic

<400> SEQUENCE: 22

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Ser
    210                 215                 220

Pro Pro Ser Pro Ala Pro Asn Trp Val Asn Val Ile Ser Asp Leu Lys
225                 230                 235                 240

Lys Ile Glu Asp Leu Ile Gln Ser Met His Ile Asp Ala Thr Leu Tyr
                245                 250                 255

Thr Glu Ser Asp Val His Pro Ser Cys Lys Val Thr Ala Met Lys Cys
            260                 265                 270

Phe Leu Leu Glu Leu Gln Val Ile Ser Leu Glu Ser Gly Asp Ala Ser
        275                 280                 285

Ile His Asp Thr Val Glu Asn Leu Ile Leu Ala Asn Asn Ser Leu
    290                 295                 300

Ser Ser Asn Gly Asn Val Thr Glu Ser Gly Cys Lys Glu Cys Glu Glu
305                 310                 315                 320

Leu Glu Glu Lys Asn Ile Lys Glu Phe Leu Gln Ser Phe Val His Ile
                325                 330                 335

Val Gln Met Phe Ile Asn Thr Ser
            340
```

<210> SEQ ID NO 23
<211> LENGTH: 121
<212> TYPE: PRT
<213> ORGANISM: Unknown
<220> FEATURE:
<223> OTHER INFORMATION: Synthetic

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Val Arg Asp Glu Asp Thr Ala Val Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Leu Val Thr Val Ser Ser
            115                 120

<210> SEQ ID NO 24
<211> LENGTH: 111
<212> TYPE: PRT
<213> ORGANISM: Unknown
<220> FEATURE:
<223> OTHER INFORMATION: Synthetic

<400> SEQUENCE: 24

Glu Ile Val Leu Thr Gln Ser Pro Ala Thr Leu Ser Leu Ser Leu Gly
1               5                   10                  15

Glu Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Ala Pro
        35                  40                  45

Lys Leu Leu Ile Tyr Leu Ala Ser Asn Arg Ala Thr Gly Val Pro Ala
    50                  55                  60

Arg Phe Ser Gly Ser Gly Pro Gly Thr Asp Phe Thr Leu Thr Ile Ser
65                  70                  75                  80

Ser Leu Glu Pro Glu Asp Phe Ala Thr Tyr Tyr Cys Gln His Ser Arg
                85                  90                  95

Glu Leu Pro Phe Thr Phe Gly Gln Gly Thr Lys Leu Glu Ile Lys
            100                 105                 110

<210> SEQ ID NO 25
<211> LENGTH: 121
<212> TYPE: PRT
<213> ORGANISM: Unknown
<220> FEATURE:
<223> OTHER INFORMATION: Synthetic

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Val Arg Asp Glu Asp Thr Ala Val Tyr Tyr Cys
                85                  90                  95

Ala Arg Gly Ser Gly Gly Ser Gly Asp Ala Met Asp Tyr Trp Gly
            100                 105                 110

Gln Gly Thr Leu Val Thr Val Ser Ser
        115                 120

<210> SEQ ID NO 26
<211> LENGTH: 224
<212> TYPE: PRT
<213> ORGANISM: Unknown
<220> FEATURE:
<223> OTHER INFORMATION: Synthetic

<400> SEQUENCE: 26

Glu Val Gln Leu Gln Gln Pro Gly Ala Glu Leu Met Arg Pro Gly Ala
1               5                   10                  15

Ser Val Lys Leu Ser Cys Lys Ala Ser Gly Tyr Ser Phe Thr Gly His
            20                  25                  30

Trp Met Asn Trp Val Arg Gln Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Ser Ala Tyr
65                  70                  75                  80

Met Gln Leu Ser Ser Pro Thr Ser Glu Asp Ser Ala Val Tyr Tyr Cys
                85                  90                  95

Ala Arg Gly Ile Tyr Phe Tyr Gly Thr Thr Tyr Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 27
<211> LENGTH: 343
<212> TYPE: PRT
<213> ORGANISM: Unknown
<220> FEATURE:
<223> OTHER INFORMATION: Synthetic

<400> SEQUENCE: 27

Asp Val Gln Ile Thr Gln Ser Pro Ser Tyr Leu Ala Ala Ser Pro Gly
1               5                   10                  15

Glu Thr Ile Ser Ile Asn Cys Arg Ala Ser Lys Thr Ile Ser Lys Tyr

```
            20                  25                  30
Leu Ala Trp Tyr Gln Glu Lys Pro Gly Lys Thr Asn Lys Leu Leu Ile
         35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Leu
                 85                  90                  95

Thr Phe Gly Thr Gly Thr Lys Leu Glu Leu Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Asn Trp Val Asn Val Ile Ser Asp Leu Lys Lys
225                 230                 235                 240

Ile Glu Asp Leu Ile Gln Ser Met His Ile Asp Ala Thr Leu Tyr Thr
                245                 250                 255

Glu Ser Asp Val His Pro Ser Cys Lys Val Thr Ala Met Lys Cys Phe
            260                 265                 270

Leu Leu Glu Leu Gln Val Ile Ser Leu Glu Ser Gly Asp Ala Ser Ile
        275                 280                 285

His Asp Thr Val Glu Asn Leu Ile Ile Leu Ala Asn Asn Ser Leu Ser
    290                 295                 300

Ser Asn Gly Asn Val Thr Glu Ser Gly Cys Lys Glu Cys Glu Glu Leu
305                 310                 315                 320

Glu Glu Lys Asn Ile Lys Glu Phe Leu Gln Ser Phe Val His Ile Val
                325                 330                 335

Gln Met Phe Ile Asn Thr Ser
            340

<210> SEQ ID NO 28
<211> LENGTH: 223
<212> TYPE: PRT
<213> ORGANISM: Unknown
<220> FEATURE:
<223> OTHER INFORMATION: Synthetic

<400> SEQUENCE: 28

Asp Val Lys Leu Val Glu Ser Gly Gly Asp Leu Val Lys Leu Gly Gly
 1               5                  10                  15

Ser Leu Lys Leu Ser Cys Ala Ala Ser Gly Phe Thr Phe Ser Asp Tyr
             20                  25                  30

Tyr Met Ser Trp Val Arg Gln Thr Pro Glu Lys Arg Leu Glu Leu Val
```

```
                35                  40                  45
Ala Ala Ile Asp Asn Asp Gly Gly Ser Ile Ser Tyr Pro Asp Thr Val
 50                  55                  60
Lys Gly Arg Phe Thr Ile Ser Arg Asp Asn Ala Lys Asn Thr Leu Tyr
 65                  70                  75                  80
Leu Gln Met Ser Ser Leu Arg Ser Glu Asp Thr Ala Leu Tyr Tyr Cys
                 85                  90                  95
Ala Arg Gln Gly Arg Leu Arg Asp Tyr Phe Asp Tyr Trp Gly Gln
                100                 105                 110
Gly Thr Thr Leu Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys
                210                 215                 220

<210> SEQ ID NO 29
<211> LENGTH: 347
<212> TYPE: PRT
<213> ORGANISM: Unknown
<220> FEATURE:
<223> OTHER INFORMATION: Synthetic

<400> SEQUENCE: 29

Asp Ile Val Leu Thr Gln Ser Pro Ala Ser Leu Ala Val Ser Leu Gly
  1               5                  10                  15
Gln Arg Ala Thr Ile Ser Cys Arg Ala Ser Glu Ser Val Asp Ser Tyr
                 20                  25                  30
Gly Asn Ser Phe Met His Trp Tyr Gln Gln Lys Pro Gly Gln Pro Pro
                 35                  40                  45
Lys Leu Leu Ile Tyr Arg Ala Ser Asn Leu Glu Ser Gly Ile Pro Ala
 50                  55                  60
Arg Phe Ser Gly Ser Gly Ser Arg Thr Asp Phe Thr Leu Thr Ile Asn
 65                  70                  75                  80
Pro Val Glu Ala Asp Asp Val Ala Thr Tyr Tyr Cys Gln Gln Ser Asn
                 85                  90                  95
Glu Asp Pro Leu Thr Phe Gly Ala Gly Thr Lys Leu Glu Leu Lys Arg
                100                 105                 110
Thr Val Ala Ala Pro Ser Val Phe Ile Phe Pro Pro Ser Asp Glu Gln
                115                 120                 125
Leu Lys Ser Gly Thr Ala Ser Val Val Cys Leu Leu Asn Asn Phe Tyr
                130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
```

```
            180                 185                 190
His Lys Val Tyr Ala Cys Glu Val Thr His Gln Gly Leu Ser Ser Pro
            195                 200                 205
Val Thr Lys Ser Phe Asn Arg Gly Glu Cys Gly Gly Gly Ser Gly
        210                 215                 220
Gly Gly Gly Ser Gly Gly Gly Ser Asn Trp Val Asn Val Ile Ser
225                 230                 235                 240
Asp Leu Lys Lys Ile Glu Asp Leu Ile Gln Ser Met His Ile Asp Ala
                245                 250                 255
Thr Leu Tyr Thr Glu Ser Asp Val His Pro Ser Cys Lys Val Thr Ala
            260                 265                 270
Met Lys Cys Phe Leu Leu Glu Leu Gln Val Ile Ser Leu Glu Ser Gly
        275                 280                 285
Asp Ala Ser Ile His Asp Thr Val Glu Asn Leu Ile Ile Leu Ala Asn
        290                 295                 300
Asn Ser Leu Ser Ser Asn Gly Asn Val Thr Glu Ser Gly Cys Lys Glu
305                 310                 315                 320
Cys Glu Glu Leu Glu Glu Lys Asn Ile Lys Glu Phe Leu Gln Ser Phe
                325                 330                 335
Val His Ile Val Gln Met Phe Ile Asn Thr Ser
            340                 345
```

<210> SEQ ID NO 30
<211> LENGTH: 221
<212> TYPE: PRT
<213> ORGANISM: Unknown
<220> FEATURE:
<223> OTHER INFORMATION: Synthetic
<400> SEQUENCE: 30

```
Gln Val Gln Leu Gln Gln Ser Gly Ala Glu Leu Val Lys Pro Gly Ala
1               5                   10                  15
Ser Val Lys Leu Ser Cys Thr Ala Ser Gly Phe Asn Ile Lys Asp Thr
            20                  25                  30
Tyr Ile His Phe Val Arg Gln Arg Pro Glu Gln Gly Leu Glu Trp Ile
        35                  40                  45
Gly Arg Ile Asp Pro Ala Asn Asp Asn Thr Leu Tyr Ala Ser Lys Phe
    50                  55                  60
Gln Gly Lys Ala Thr Ile Thr Ala Asp Thr Ser Asn Thr Ala Tyr
65                  70                  75                  80
Met His Leu Ser Ser Leu Thr Ser Gly Asp Thr Ala Val Tyr Tyr Cys
                85                  90                  95
Gly Arg Gly Tyr Gly Tyr Tyr Val Phe Asp His Trp Gly Gln Gly Thr
            100                 105                 110
Thr Leu Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
```

```
                195                 200                 205
Asn Thr Lys Val Asp Lys Lys Val Glu Pro Lys Ser Cys
    210                 215                 220
```

<210> SEQ ID NO 31
<211> LENGTH: 343
<212> TYPE: PRT
<213> ORGANISM: Unknown
<220> FEATURE:
<223> OTHER INFORMATION: Synthetic

<400> SEQUENCE: 31

```
Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Gly Leu Glu Pro
65                  70                  75                  80

Glu Asp Phe Ala Met Tyr Tyr Cys Gln Gln His Asn Glu Asn Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Ser
210                 215                 220

Gly Gly Gly Gly Ser Asn Trp Val Asn Val Ile Ser Asp Leu Lys Lys
225                 230                 235                 240

Ile Glu Asp Leu Ile Gln Ser Met His Ile Asp Ala Thr Leu Tyr Thr
                245                 250                 255

Glu Ser Asp Val His Pro Ser Cys Lys Val Thr Ala Met Lys Cys Phe
            260                 265                 270

Leu Leu Glu Leu Gln Val Ile Ser Leu Glu Ser Gly Asp Ala Ser Ile
        275                 280                 285

His Asp Thr Val Glu Asn Leu Ile Ile Leu Ala Asn Asn Ser Leu Ser
290                 295                 300

Ser Asn Gly Asn Val Thr Glu Ser Gly Cys Lys Glu Cys Glu Glu Leu
305                 310                 315                 320

Glu Glu Lys Asn Ile Lys Glu Phe Leu Gln Ser Phe Val His Ile Val
                325                 330                 335

Gln Met Phe Ile Asn Thr Ser
```

<210> SEQ ID NO 32
<211> LENGTH: 380
<212> TYPE: PRT
<213> ORGANISM: Unknown
<220> FEATURE:
<223> OTHER INFORMATION: Synthetic

<400> SEQUENCE: 32

```
Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser Gly Gly Gly Ser Gly Gly
        115                 120                 125

Gly Ser Gly Gly Gly Thr Gly Asp Ile Val Leu Thr Gln Ser Pro Ala
130                 135                 140

Ser Leu Ala Val Ser Leu Gly Gln Arg Ala Thr Ile Ser Cys Arg Ala
145                 150                 155                 160

Ser Lys Ser Val Ser Thr Ser Gly Tyr Ser Tyr Leu His Trp Tyr Gln
                165                 170                 175

Gln Lys Pro Gly Gln Pro Pro Lys Leu Leu Ile Tyr Leu Ala Ser Asn
            180                 185                 190

Leu Glu Ser Gly Val Pro Ala Arg Phe Ser Gly Ser Gly Ser Gly Thr
        195                 200                 205

Asp Phe Thr Leu Asn Ile His Pro Val Glu Glu Asp Ala Ala Thr
    210                 215                 220

Tyr Tyr Cys Gln His Ser Arg Glu Leu Pro Phe Thr Phe Gly Ser Gly
225                 230                 235                 240

Thr Lys Leu Glu Ile Lys Arg Ser Gly Ser Gly Gly Gly Ser Leu
                245                 250                 255

Gln Asn Trp Val Asn Val Ile Ser Asp Leu Lys Lys Ile Glu Asp Leu
            260                 265                 270

Ile Gln Ser Met His Ile Asp Ala Thr Leu Tyr Thr Glu Ser Asp Val
        275                 280                 285

His Pro Ser Cys Lys Val Thr Ala Met Lys Cys Phe Leu Leu Glu Leu
    290                 295                 300

Gln Val Ile Ser Leu Glu Ser Gly Asp Ala Ser Ile His Asp Thr Val
305                 310                 315                 320

Glu Asn Leu Ile Ile Leu Ala Asn Asn Ser Leu Ser Asn Gly Asn
                325                 330                 335

Val Thr Glu Ser Gly Cys Lys Glu Cys Glu Glu Leu Glu Glu Lys Asn
            340                 345                 350

Ile Lys Glu Phe Leu Gln Ser Phe Val His Ile Val Gln Met Phe Ile
```

```
                355                 360                 365
Asn Thr Ser Ala Ala Ala His His His His His His
    370                 375                 380

<210> SEQ ID NO 33
<211> LENGTH: 22
<212> TYPE: PRT
<213> ORGANISM: Unknown
<220> FEATURE:
<223> OTHER INFORMATION: Synthetic

<400> SEQUENCE: 33

Met Asp Met Arg Val Pro Ala Gln Leu Leu Gly Leu Leu Leu Leu Trp
1               5                   10                  15

Leu Pro Gly Ala Lys Cys
            20

<210> SEQ ID NO 34
<211> LENGTH: 19
<212> TYPE: PRT
<213> ORGANISM: Unknown
<220> FEATURE:
<223> OTHER INFORMATION: Synthetic

<400> SEQUENCE: 34

Met Glu Leu Gly Leu Cys Trp Val Phe Leu Val Ala Ile Leu Glu Gly
1               5                   10                  15

Val Gln Cys

<210> SEQ ID NO 35
<211> LENGTH: 30
<212> TYPE: PRT
<213> ORGANISM: Unknown
<220> FEATURE:
<223> OTHER INFORMATION: Synthetic

<400> SEQUENCE: 35

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly
            20                  25                  30

<210> SEQ ID NO 36
<211> LENGTH: 15
<212> TYPE: PRT
<213> ORGANISM: Unknown
<220> FEATURE:
<223> OTHER INFORMATION: Synthetic

<400> SEQUENCE: 36

Gly Gly Gly Gly Ser Gly Gly Gly Gly Ser Gly Gly Gly Gly Ser
1               5                   10                  15

<210> SEQ ID NO 37
<211> LENGTH: 8
<212> TYPE: PRT
<213> ORGANISM: Unknown
<220> FEATURE:
<223> OTHER INFORMATION: Synthetic

<400> SEQUENCE: 37

Gly Gly Gly Ser Gly Gly Gly Ser
1               5
```

<210> SEQ ID NO 38
<211> LENGTH: 12
<212> TYPE: PRT
<213> ORGANISM: Unknown
<220> FEATURE:
<223> OTHER INFORMATION: Synthetic

<400> SEQUENCE: 38

Asp Lys Thr His Thr Ser Pro Pro Ser Pro Ala Pro
1               5                   10

<210> SEQ ID NO 39
<211> LENGTH: 11
<212> TYPE: PRT
<213> ORGANISM: Unknown
<220> FEATURE:
<223> OTHER INFORMATION: Synthetic

<400> SEQUENCE: 39

Arg Ser Gly Ser Gly Gly Gly Gly Ser Leu Gln
1               5                   10

<210> SEQ ID NO 40
<211> LENGTH: 162
<212> TYPE: PRT
<213> ORGANISM: Homo sapiens

<400> SEQUENCE: 40

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 41
<211> LENGTH: 267
<212> TYPE: PRT
<213> ORGANISM: Homo sapiens

<400> SEQUENCE: 41

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
                20                  25                  30

Cys Pro Pro Met Ser Val Glu His Ala Asp Ile Trp Val Lys Ser
         35                  40                  45

Tyr Ser Leu Tyr Ser Arg Glu Arg Tyr Ile Cys Asn Ser Gly Phe Lys
 50                  55                  60

Arg Lys Ala Gly Thr Ser Leu Thr Glu Cys Val Leu Asn Lys Ala
65                  70                  75                  80

Thr Asn Val Ala His Trp Thr Thr Pro Ser Leu Lys Cys Ile Arg Asp
                 85                  90                  95

Pro Ala Leu Val His Gln Arg Pro Ala Pro Ser Thr Val Thr Thr
                100                 105                 110

Ala Gly Val Thr Pro Gln Pro Glu Ser Leu Ser Pro Ser Gly Lys Glu
            115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Val Ala Ile
            195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
                260                 265

<210> SEQ ID NO 42
<211> LENGTH: 177
<212> TYPE: PRT
<213> ORGANISM: Homo sapiens

<400> SEQUENCE: 42

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

```
Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 43
<211> LENGTH: 152
<212> TYPE: PRT
<213> ORGANISM: Homo sapiens

<400> SEQUENCE: 43

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150

<210> SEQ ID NO 44
<211> LENGTH: 162
<212> TYPE: PRT
<213> ORGANISM: Homo sapiens

<400> SEQUENCE: 44

Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
                20                  25                  30

Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
        50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125
```

-continued

```
Glu Lys Lys Pro Pro Lys Glu Phe Leu Glu Arg Phe Lys Ser Leu Leu
130                 135                 140

Gln Lys Met Ile His Gln His Leu Ser Ser Arg Thr His Gly Ser Glu
145                 150                 155                 160

Asp Ser
```

<210> SEQ ID NO 45
<211> LENGTH: 132
<212> TYPE: PRT
<213> ORGANISM: Homo sapiens

<400> SEQUENCE: 45

```
Gly Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
                20                  25                  30

Ala Pro Glu Asp Val Glu Thr Asn Cys Glu Trp Ser Ala Phe Ser Cys
            35                  40                  45

Phe Gln Lys Ala Gln Leu Lys Ser Ala Asn Thr Gly Asn Asn Glu Arg
    50                  55                  60

Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
        130
```

<210> SEQ ID NO 46
<211> LENGTH: 219
<212> TYPE: PRT
<213> ORGANISM: Homo sapiens

<400> SEQUENCE: 46

```
Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
                20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
```

| | | | |
|---|---|---|---|
| 145 | 150 | 155 | 160 |

Ala Val Ile Asp Glu Leu Met Gln Ala Leu Asn Phe Asn Ser Glu Thr
                165                      170                  175

Val Pro Gln Lys Ser Ser Leu Glu Glu Pro Asp Phe Tyr Lys Thr Lys
            180                      185                  190

Ile Lys Leu Cys Ile Leu Leu His Ala Phe Arg Ile Arg Ala Val Thr
            195                      200                  205

Ile Asp Arg Val Met Ser Tyr Leu Asn Ala Ser
            210                      215

<210> SEQ ID NO 47
<211> LENGTH: 197
<212> TYPE: PRT
<213> ORGANISM: Homo sapiens

<400> SEQUENCE: 47

Arg Asn Leu Pro Val Ala Thr Pro Asp Pro Gly Met Phe Pro Cys Leu
1                  5                      10                  15

His His Ser Gln Asn Leu Leu Arg Ala Val Ser Asn Met Leu Gln Lys
            20                      25                  30

Ala Arg Gln Thr Leu Glu Phe Tyr Pro Cys Thr Ser Glu Glu Ile Asp
              35                      40                  45

His Glu Asp Ile Thr Lys Asp Lys Thr Ser Thr Val Glu Ala Cys Leu
  50                    55                      60

Pro Leu Glu Leu Thr Lys Asn Glu Ser Cys Leu Asn Ser Arg Glu Thr
65                      70                      75                  80

Ser Phe Ile Thr Asn Gly Ser Cys Leu Ala Ser Arg Lys Thr Ser Phe
              85                      90                  95

Met Met Ala Leu Cys Leu Ser Ser Ile Tyr Glu Asp Leu Lys Met Tyr
            100                      105                  110

Gln Val Glu Phe Lys Thr Met Asn Ala Lys Leu Leu Met Asp Pro Lys
            115                      120                  125

Arg Gln Ile Phe Leu Asp Gln Asn Met Leu Ala Val Ile Asp Glu Leu
            130                      135                  140

Met Gln Ala Leu Asn Phe Asn Ser Glu Thr Val Pro Gln Lys Ser Ser
145                    150                      155                  160

Leu Glu Glu Pro Asp Phe Tyr Lys Thr Lys Ile Lys Leu Cys Ile Leu
            165                      170                  175

Leu His Ala Phe Arg Ile Arg Ala Val Thr Ile Asp Arg Val Met Ser
            180                      185                  190

Tyr Leu Asn Ala Ser
            195

<210> SEQ ID NO 48
<211> LENGTH: 328
<212> TYPE: PRT
<213> ORGANISM: Homo sapiens

<400> SEQUENCE: 48

Met Cys His Gln Gln Leu Val Ile Ser Trp Phe Ser Leu Val Phe Leu
1                  5                      10                  15

Ala Ser Pro Leu Val Ala Ile Trp Glu Leu Lys Lys Asp Val Tyr Val
            20                      25                  30

Val Glu Leu Asp Trp Tyr Pro Asp Ala Pro Gly Glu Met Val Val Leu
              35                      40                  45

Thr Cys Asp Thr Pro Glu Glu Asp Gly Ile Thr Trp Thr Leu Asp Gln

```
Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 49
<211> LENGTH: 306
<212> TYPE: PRT
<213> ORGANISM: Homo sapiens

<400> SEQUENCE: 49

Ile Trp Glu Leu Lys Lys Asp Val Tyr Val Val Glu Leu Asp Trp Tyr
 1                5                   10                  15

Pro Asp Ala Pro Gly Glu Met Val Val Leu Thr Cys Asp Thr Pro Glu
                 20                  25                  30

Glu Asp Gly Ile Thr Trp Thr Leu Asp Gln Ser Ser Glu Val Leu Gly
             35                  40                  45

Ser Gly Lys Thr Leu Thr Ile Gln Val Lys Glu Phe Gly Asp Ala Gly
         50                  55                  60

Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                 85                  90                  95
```

```
Asp Gln Lys Glu Pro Lys Asn Lys Thr Phe Leu Arg Cys Glu Ala Lys
                100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
            245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
290                 295                 300

Cys Ser
305

<210> SEQ ID NO 50
<211> LENGTH: 519
<212> TYPE: PRT
<213> ORGANISM: Unknown
<220> FEATURE:
<223> OTHER INFORMATION: Synthetic

<400> SEQUENCE: 50

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
                100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
        130                 135                 140
```

-continued

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
            165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
            245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
290                 295                 300

Cys Ser Gly Gly Gly Ser Gly Gly Gly Ser Gly Gly Gly Ser Gly Gly
305                 310                 315                 320

Gly Ser Arg Asn Leu Pro Val Ala Thr Pro Asp Pro Gly Met Phe Pro
            325                 330                 335

Cys Leu His His Ser Gln Asn Leu Leu Arg Ala Val Ser Asn Met Leu
            340                 345                 350

Gln Lys Ala Arg Gln Thr Leu Glu Phe Tyr Pro Cys Thr Ser Glu Glu
            355                 360                 365

Ile Asp His Glu Asp Ile Thr Lys Asp Lys Thr Ser Thr Val Glu Ala
            370                 375                 380

Cys Leu Pro Leu Glu Leu Thr Lys Asn Glu Ser Cys Leu Asn Ser Arg
385                 390                 395                 400

Glu Thr Ser Phe Ile Thr Asn Gly Ser Cys Leu Ala Ser Arg Lys Thr
            405                 410                 415

Ser Phe Met Met Ala Leu Cys Leu Ser Ser Ile Tyr Glu Asp Leu Lys
            420                 425                 430

Met Tyr Gln Val Glu Phe Lys Thr Met Asn Ala Lys Leu Leu Met Asp
            435                 440                 445

Pro Lys Arg Gln Ile Phe Leu Asp Gln Asn Met Leu Ala Val Ile Asp
            450                 455                 460

Glu Leu Met Gln Ala Leu Asn Phe Asn Ser Glu Thr Val Pro Gln Lys
465                 470                 475                 480

Ser Ser Leu Glu Glu Pro Asp Phe Tyr Lys Thr Lys Ile Lys Leu Cys
            485                 490                 495

Ile Leu Leu His Ala Phe Arg Ile Arg Ala Val Thr Ile Asp Arg Val
            500                 505                 510

Met Ser Tyr Leu Asn Ala Ser
        515

<210> SEQ ID NO 51
<211> LENGTH: 519
<212> TYPE: PRT
<213> ORGANISM: Unknown
<220> FEATURE:
<223> OTHER INFORMATION: Synthetic

<400> SEQUENCE: 51

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Ser Gly Gly Gly Ser Gly Gly Gly
        195                 200                 205

Ser Gly Gly Ser Ile Trp Glu Leu Lys Lys Asp Val Tyr Val Val
    210                 215                 220

Glu Leu Asp Trp Tyr Pro Asp Ala Pro Gly Glu Met Val Val Leu Thr
225                 230                 235                 240

Cys Asp Thr Pro Glu Glu Asp Gly Ile Thr Trp Thr Leu Asp Gln Ser
                245                 250                 255

Ser Glu Val Leu Gly Ser Gly Lys Thr Leu Thr Ile Gln Val Lys Glu
            260                 265                 270

Phe Gly Asp Ala Gly Gln Tyr Thr Cys His Lys Gly Gly Glu Val Leu
        275                 280                 285

Ser His Ser Leu Leu Leu Leu His Lys Lys Glu Asp Gly Ile Trp Ser
    290                 295                 300

Thr Asp Ile Leu Lys Asp Gln Lys Glu Pro Lys Asn Lys Thr Phe Leu
305                 310                 315                 320

Arg Cys Glu Ala Lys Asn Tyr Ser Gly Arg Phe Thr Cys Trp Trp Leu
                325                 330                 335

Thr Thr Ile Ser Thr Asp Leu Thr Phe Ser Val Lys Ser Ser Arg Gly
            340                 345                 350

Ser Ser Asp Pro Gln Gly Val Thr Cys Gly Ala Ala Thr Leu Ser Ala
        355                 360                 365

Glu Arg Val Arg Gly Asp Asn Lys Glu Tyr Glu Tyr Ser Val Glu Cys
    370                 375                 380

Gln Glu Asp Ser Ala Cys Pro Ala Ala Glu Glu Ser Leu Pro Ile Glu
385                 390                 395                 400

Val Met Val Asp Ala Val His Lys Leu Lys Tyr Glu Asn Tyr Thr Ser
```

```
                    405                 410                 415
Ser Phe Phe Ile Arg Asp Ile Ile Lys Pro Asp Pro Lys Asn Leu
                420                 425                 430

Gln Leu Lys Pro Leu Lys Asn Ser Arg Gln Val Glu Val Ser Trp Glu
            435                 440                 445

Tyr Pro Asp Thr Trp Ser Thr Pro His Ser Tyr Phe Ser Leu Thr Phe
        450                 455                 460

Cys Val Gln Val Gln Gly Lys Ser Lys Arg Glu Lys Lys Asp Arg Val
465                 470                 475                 480

Phe Thr Asp Lys Thr Ser Ala Thr Val Ile Cys Arg Lys Asn Ala Ser
                485                 490                 495

Ile Ser Val Arg Ala Gln Asp Arg Tyr Tyr Ser Ser Ser Trp Ser Glu
            500                 505                 510

Trp Ala Ser Val Pro Cys Ser
            515

<210> SEQ ID NO 52
<211> LENGTH: 61
<212> TYPE: PRT
<213> ORGANISM: Homo sapiens

<400> SEQUENCE: 52

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Val Ala His Trp Thr Thr Pro Ser Leu Lys Cys
    50                  55                  60

<210> SEQ ID NO 53
<211> LENGTH: 232
<212> TYPE: PRT
<213> ORGANISM: Homo sapiens

<400> SEQUENCE: 53

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
```

```
            145                 150                 155                 160
Asp Ile Ala Val Glu Trp Glu Ser Asn Gly Gln Pro Glu Asn Asn Tyr
                    165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 54
<211> LENGTH: 228
<212> TYPE: PRT
<213> ORGANISM: Homo sapiens

<400> SEQUENCE: 54

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
                35                  40                  45

His Glu Asp Pro Glu Val Gln Phe Asn Trp Tyr Val Asp Gly Val Glu
            50                  55                  60

Val His Asn Ala Lys Thr Lys Pro Arg Glu Glu Gln Phe Asn Ser Thr
65              70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
                115                 120                 125

Val Tyr Thr Leu Pro Pro Ser Arg Glu Glu Met Thr Lys Asn Gln Val
                130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
                195                 200                 205

Met His Glu Ala Leu His Asn His Tyr Thr Gln Lys Ser Leu Ser Leu
            210                 215                 220

Ser Pro Gly Lys
225

<210> SEQ ID NO 55
<211> LENGTH: 228
<212> TYPE: PRT
<213> ORGANISM: Unknown
<220> FEATURE:
<223> OTHER INFORMATION: Synthetic

<400> SEQUENCE: 55
```

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65              70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ser Ser
                100                 105                 110

Ile Glu Lys Thr Ile Ser Lys Thr Lys Gly Gln Pro Arg Glu Pro Gln
                115                 120                 125

Val Tyr Thr Leu Pro Pro Ser Arg Glu Glu Met Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
                210                 215                 220

Ser Pro Gly Lys
225

<210> SEQ ID NO 56
<211> LENGTH: 293
<212> TYPE: PRT
<213> ORGANISM: Unknown
<220> FEATURE:
<223> OTHER INFORMATION: Synthetic

<400> SEQUENCE: 56

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
    50                  55                  60

Arg Glu Arg Lys Cys Cys Val Glu Cys Pro Pro Cys Pro Ala Pro Pro
65              70                  75                  80

Val Ala Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
                100                 105                 110

Ser His Glu Asp Pro Glu Val Gln Phe Asn Trp Tyr Val Asp Gly Val
            115                 120                 125
```

Glu Val His Asn Ala Lys Thr Lys Pro Arg Glu Gln Phe Asn Ser
    130                 135                 140

Thr Phe Arg Val Val Ser Val Leu Thr Val His Gln Asp Trp Leu
145                 150                 155                 160

Asn Gly Lys Glu Tyr Lys Cys Lys Val Ser Asn Lys Gly Leu Pro Ser
                    165                 170                 175

Ser Ile Glu Lys Thr Ile Ser Lys Thr Lys Gly Gln Pro Arg Glu Pro
                180                 185                 190

Gln Val Tyr Thr Leu Pro Pro Ser Arg Glu Glu Met Thr Lys Asn Gln
                195                 200                 205

Val Ser Leu Thr Cys Leu Val Lys Gly Phe Tyr Pro Ser Asp Ile Ala
210                 215                 220

Val Glu Trp Glu Ser Asn Gly Gln Pro Glu Asn Asn Tyr Lys Thr Thr
225                 230                 235                 240

Pro Pro Met Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
                260                 265                 270

Val Met His Glu Ala Leu His Asn His Tyr Thr Gln Lys Ser Leu Ser
                275                 280                 285

Leu Ser Pro Gly Lys
    290

<210> SEQ ID NO 57
<211> LENGTH: 121
<212> TYPE: PRT
<213> ORGANISM: Unknown
<220> FEATURE:
<223> OTHER INFORMATION: Synthetic

<400> SEQUENCE: 57

Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser Ser
        115                 120

<210> SEQ ID NO 58
<211> LENGTH: 111
<212> TYPE: PRT
<213> ORGANISM: Unknown
<220> FEATURE:
<223> OTHER INFORMATION: Synthetic

<400> SEQUENCE: 58

Asp Ile Val Leu Thr Gln Ser Pro Ala Ser Leu Ala Val Ser Leu Gly

```
            1               5                  10                 15
Gln Arg Ala Thr Ile Ser Cys Arg Ala Ser Lys Ser Val Ser Thr Ser
                20                  25                  30

Gly Tyr Ser Tyr Leu His Trp Tyr Gln Gln Lys Pro Gly Gln Pro Pro
                35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
                100                 105                 110
```

<210> SEQ ID NO 59
<211> LENGTH: 117
<212> TYPE: PRT
<213> ORGANISM: Unknown
<220> FEATURE:
<223> OTHER INFORMATION: Synthetic

<400> SEQUENCE: 59

```
Gln Val Gln Leu Gln Gln Leu Gly Ala Glu Leu Ala Arg Pro Gly Ala
1               5                  10                  15

Ser Val Lys Met Ser Cys Lys Ala Ser Gly Tyr Thr Phe Thr Ser Tyr
                20                  25                  30

Ser Ile Gln Trp Val Lys Gln Arg Pro Gly Gln Gly Leu Glu Trp Ile
                35                  40                  45

Gly Tyr Ile Asn Pro Ser Ser Gly Tyr Ile Lys Tyr Asn Gln His Phe
    50                  55                  60

Arg Asp Arg Ala Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Ser Gly Ser Phe Asp Tyr Trp Gly Gln Gly Thr Thr
                100                 105                 110

Leu Thr Val Ser Ser
        115
```

<210> SEQ ID NO 60
<211> LENGTH: 112
<212> TYPE: PRT
<213> ORGANISM: Unknown
<220> FEATURE:
<223> OTHER INFORMATION: Synthetic

<400> SEQUENCE: 60

```
Asp Ile Val Met Thr Gln Ala Ala Pro Ser Val Pro Val Thr Pro Gly
1               5                  10                  15

Glu Ser Leu Ser Ile Ser Cys Arg Ser Ser Lys Ser Leu Leu His Ser
                20                  25                  30

Ser Gly Ile Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80
```

Ser Arg Val Glu Ala Glu Asp Val Gly Val Tyr Tyr Cys Met Gln His
            85                  90                  95

Leu Glu Tyr Pro Phe Thr Phe Gly Gly Gly Thr Lys Leu Glu Ile Lys
        100                 105                 110

<210> SEQ ID NO 61
<211> LENGTH: 117
<212> TYPE: PRT
<213> ORGANISM: Unknown
<220> FEATURE:
<223> OTHER INFORMATION: Synthetic

<400> SEQUENCE: 61

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met Gln Trp Val Lys Gln Arg Pro Gly Gln Gly Leu Glu Trp Ile
        35                  40                  45

Gly Tyr Ile Asn Pro Ser Ser Gly Tyr Ile Lys Tyr Asn Gln Lys Phe
    50                  55                  60

Lys Asp Lys Val Thr Leu Thr Ala Asp Lys Ser Ser Thr Thr Ala Tyr
65                  70                  75                  80

Met Gln Leu Ser Arg Leu Thr Ser Glu Asp Ser Ala Val Tyr Tyr Cys
                85                  90                  95

Ala Arg Arg Gly Ser Tyr Phe Phe Asp Phe Trp Gly Gln Gly Thr Ser
                100                 105                 110

Val Thr Val Ser Ser
            115

<210> SEQ ID NO 62
<211> LENGTH: 112
<212> TYPE: PRT
<213> ORGANISM: Unknown
<220> FEATURE:
<223> OTHER INFORMATION: Synthetic

<400> SEQUENCE: 62

Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro Phe Thr Phe Gly Gly Gly Thr Lys Leu Glu Val Lys
                100                 105                 110

<210> SEQ ID NO 63
<211> LENGTH: 205
<212> TYPE: PRT
<213> ORGANISM: Homo sapiens

<400> SEQUENCE: 63

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
            115                 120                 125

Pro Ala Ala Ser Ser Pro Ser Ser Asn Asn Thr Ala Ala Thr Thr Ala
            130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
            165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr
            195                 200                 205

<210> SEQ ID NO 64
<211> LENGTH: 172
<212> TYPE: PRT
<213> ORGANISM: Homo sapiens

<400> SEQUENCE: 64

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Lys Pro
                85                  90                  95

Ala Ala Ser Ser Pro Ser Ser Asn Asn Thr Ala Ala Thr Thr Ala Ala
            100                 105                 110

Ile Val Pro Gly Ser Gln Leu Met Pro Ser Lys Ser Pro Ser Thr Gly
            115                 120                 125

Thr Thr Glu Ile Ser Ser His Glu Ser Ser His Gly Thr Pro Ser Gln
            130                 135                 140

Thr Thr Ala Lys Asn Trp Glu Leu Thr Ala Ser Ala Ser His Gln Pro
145                 150                 155                 160

Pro Gly Val Tyr Pro Gln Gly His Ser Asp Thr Thr
            165                 170
```

<210> SEQ ID NO 65
<211> LENGTH: 62
<212> TYPE: PRT
<213> ORGANISM: Unknown
<220> FEATURE:
<223> OTHER INFORMATION: Synthetic

<400> SEQUENCE: 65

Cys Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Ile Asn Lys Ala
        35                  40                  45

Thr Asn Val Ala His Trp Thr Thr Pro Ser Leu Lys Cys Ile
    50                  55                  60

<210> SEQ ID NO 66
<211> LENGTH: 65
<212> TYPE: PRT
<213> ORGANISM: Unknown
<220> FEATURE:
<223> OTHER INFORMATION: Synthetic

<400> SEQUENCE: 66

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Ile Asn
        35                  40                  45

Lys Ala Thr Asn Val Ala His Trp Thr Thr Pro Ser Leu Lys Cys Ile
    50                  55                  60

Arg
65

<210> SEQ ID NO 67
<211> LENGTH: 232
<212> TYPE: PRT
<213> ORGANISM: unknown
<220> FEATURE:
<223> OTHER INFORMATION: Synthetic

<400> SEQUENCE: 67

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 68
<211> LENGTH: 326
<212> TYPE: PRT
<213> ORGANISM: Homo sapiens

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 69
<211> LENGTH: 224
<212> TYPE: PRT
<213> ORGANISM: Unknown
<220> FEATURE:
<223> OTHER INFORMATION: Synthetic

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly His
            20                  25                  30

Trp Met Asn Trp Val Arg Gln Ala Pro Gly Lys Gly Leu Glu Trp Val
        35                  40                  45

Gly Met Ile His Pro Ser Asp Ser Glu Thr Arg Tyr Asn Gln Lys Phe
    50                  55                  60

Lys Asp Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Tyr Phe Tyr Gly Thr Thr Tyr Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 70
<211> LENGTH: 16
<212> TYPE: PRT
<213> ORGANISM: Unknown
<220> FEATURE:
<223> OTHER INFORMATION: Synthetic

<400> SEQUENCE: 70

Gly Gly Gly Ser Gly Gly Gly Ser Gly Gly Gly Ser Gly Gly Gly Ser

<210> SEQ ID NO 71
<211> LENGTH: 20
<212> TYPE: PRT
<213> ORGANISM: Unknown
<220> FEATURE:
<223> OTHER INFORMATION: Synthetic

<400> SEQUENCE: 71

Gly Gly Gly Gly Ser Gly Gly Gly Ser Gly Gly Gly Gly Ser Gly
1               5                   10                  15
Gly Gly Gly Ser
            20

<210> SEQ ID NO 72
<211> LENGTH: 523
<212> TYPE: PRT
<213> ORGANISM: Unknown
<220> FEATURE:
<223> OTHER INFORMATION: Synthetic

<400> SEQUENCE: 72

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

```
Ser Ala Thr Val Ile Cys Arg Lys Asn Ala Ser Ile Ser Val Arg Ala
            275                 280                 285

Gln Asp Arg Tyr Tyr Ser Ser Trp Ser Glu Trp Ala Ser Val Pro
290                 295                 300

Cys Ser Gly Gly Gly Ser Gly Gly Gly Ser Gly Gly Gly
305                 310                 315                 320

Ser Gly Gly Gly Ser Arg Asn Leu Pro Val Ala Thr Pro Asp Pro
            325                 330                 335

Gly Met Phe Pro Cys Leu His His Ser Gln Asn Leu Leu Arg Ala Val
                340                 345                 350

Ser Asn Met Leu Gln Lys Ala Arg Gln Thr Leu Glu Phe Tyr Pro Cys
            355                 360                 365

Thr Ser Glu Glu Ile Asp His Glu Asp Ile Thr Lys Asp Lys Thr Ser
370                 375                 380

Thr Val Glu Ala Cys Leu Pro Leu Glu Leu Thr Lys Asn Glu Ser Cys
385                 390                 395                 400

Leu Asn Ser Arg Glu Thr Ser Phe Ile Thr Asn Gly Ser Cys Leu Ala
                405                 410                 415

Ser Arg Lys Thr Ser Phe Met Met Ala Leu Cys Leu Ser Ser Ile Tyr
            420                 425                 430

Glu Asp Leu Lys Met Tyr Gln Val Glu Phe Lys Thr Met Asn Ala Lys
            435                 440                 445

Leu Leu Met Asp Pro Lys Arg Gln Ile Phe Leu Asp Gln Asn Met Leu
450                 455                 460

Ala Val Ile Asp Glu Leu Met Gln Ala Leu Asn Phe Asn Ser Glu Thr
465                 470                 475                 480

Val Pro Gln Lys Ser Ser Leu Glu Glu Pro Asp Phe Tyr Lys Thr Lys
                485                 490                 495

Ile Lys Leu Cys Ile Leu Leu His Ala Phe Arg Ile Arg Ala Val Thr
            500                 505                 510

Ile Asp Arg Val Met Ser Tyr Leu Asn Ala Ser
            515                 520

<210> SEQ ID NO 73
<211> LENGTH: 523
<212> TYPE: PRT
<213> ORGANISM: Unknown
<220> FEATURE:
<223> OTHER INFORMATION: Synthetic

<400> SEQUENCE: 73

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110
```

-continued

```
Gln Val Glu Phe Lys Thr Met Asn Ala Lys Leu Leu Met Asp Pro Lys
            115                 120                 125

Arg Gln Ile Phe Leu Asp Gln Asn Met Leu Ala Val Ile Asp Glu Leu
130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Ser Gly Gly Gly Ser Gly
            195                 200                 205

Gly Gly Gly Ser Gly Gly Gly Ser Ile Trp Glu Leu Lys Lys Asp
210                 215                 220

Val Tyr Val Val Glu Leu Asp Trp Tyr Pro Asp Ala Pro Gly Glu Met
225                 230                 235                 240

Val Val Leu Thr Cys Asp Thr Pro Glu Glu Asp Gly Ile Thr Trp Thr
                245                 250                 255

Leu Asp Gln Ser Ser Glu Val Leu Gly Ser Gly Lys Thr Leu Thr Ile
            260                 265                 270

Gln Val Lys Glu Phe Gly Asp Ala Gly Gln Tyr Thr Cys His Lys Gly
            275                 280                 285

Gly Glu Val Leu Ser His Ser Leu Leu Leu Leu His Lys Lys Glu Asp
            290                 295                 300

Gly Ile Trp Ser Thr Asp Ile Leu Lys Asp Gln Lys Glu Pro Lys Asn
305                 310                 315                 320

Lys Thr Phe Leu Arg Cys Glu Ala Lys Asn Tyr Ser Gly Arg Phe Thr
                325                 330                 335

Cys Trp Trp Leu Thr Thr Ile Ser Thr Asp Leu Thr Phe Ser Val Lys
            340                 345                 350

Ser Ser Arg Gly Ser Ser Asp Pro Gln Gly Val Thr Cys Gly Ala Ala
            355                 360                 365

Thr Leu Ser Ala Glu Arg Val Arg Gly Asp Asn Lys Glu Tyr Glu Tyr
            370                 375                 380

Ser Val Glu Cys Gln Glu Asp Ser Ala Cys Pro Ala Ala Glu Glu Ser
385                 390                 395                 400

Leu Pro Ile Glu Val Met Val Asp Ala Val His Lys Leu Lys Tyr Glu
                405                 410                 415

Asn Tyr Thr Ser Ser Phe Phe Ile Arg Asp Ile Ile Lys Pro Asp Pro
            420                 425                 430

Pro Lys Asn Leu Gln Leu Lys Pro Leu Lys Asn Ser Arg Gln Val Glu
            435                 440                 445

Val Ser Trp Glu Tyr Pro Asp Thr Trp Ser Thr Pro His Ser Tyr Phe
450                 455                 460

Ser Leu Thr Phe Cys Val Gln Val Gln Gly Lys Ser Lys Arg Glu Lys
465                 470                 475                 480

Lys Asp Arg Val Phe Thr Asp Lys Thr Ser Ala Thr Val Ile Cys Arg
                485                 490                 495

Lys Asn Ala Ser Ile Ser Val Arg Ala Gln Asp Arg Tyr Tyr Ser Ser
            500                 505                 510

Ser Trp Ser Glu Trp Ala Ser Val Pro Cys Ser
            515                 520
```

<210> SEQ ID NO 74
<211> LENGTH: 107
<212> TYPE: PRT
<213> ORGANISM: Homo sapiens

<400> SEQUENCE: 74

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 75
<211> LENGTH: 106
<212> TYPE: PRT
<213> ORGANISM: Homo sapiens

<400> SEQUENCE: 75

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 76
<211> LENGTH: 106
<212> TYPE: PRT
<213> ORGANISM: Homo sapiens

<400> SEQUENCE: 76

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
            85                  90                  95

Glu Lys Thr Val Ala Pro Thr Glu Cys Ser
            100                 105

<210> SEQ ID NO 77
<211> LENGTH: 106
<212> TYPE: PRT
<213> ORGANISM: Homo sapiens

<400> SEQUENCE: 77

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
            85                  90                  95

Glu Lys Thr Val Ala Pro Thr Glu Cys Ser
            100                 105

<210> SEQ ID NO 78
<211> LENGTH: 106
<212> TYPE: PRT
<213> ORGANISM: Homo sapiens

<400> SEQUENCE: 78

Ser Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
            85                  90                  95

Glu Lys Thr Val Ala Pro Ala Glu Cys Ser
            100                 105

<210> SEQ ID NO 79
<211> LENGTH: 220
<212> TYPE: PRT
<213> ORGANISM: Unknown
<220> FEATURE:
<223> OTHER INFORMATION: Synthetic

<400> SEQUENCE: 79

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
                20                  25                  30
Ser Ile Gln Trp Val Arg Gln Ala Pro Gly Gln Arg Leu Glu Trp Ile
             35                  40                  45

Gly Tyr Ile Asn Pro Ser Ser Gly Tyr Ile Lys Tyr Asn Gln His Phe
         50                  55                  60

Arg Gly Arg Ala Thr Leu Thr Ala Asp Arg Ser Ala Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Gly Asn Ser Gly Ser Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
210                 215                 220

<210> SEQ ID NO 80
<211> LENGTH: 484
<212> TYPE: PRT
<213> ORGANISM: Unknown
<220> FEATURE:
<223> OTHER INFORMATION: Synthetic

<400> SEQUENCE: 80

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Ile Gln Trp Val Arg Gln Ala Pro Gly Gln Arg Leu Glu Trp Ile
         35                  40                  45

Gly Tyr Ile Asn Pro Ser Ser Gly Tyr Ile Lys Tyr Asn Gln His Phe
     50                  55                  60

Arg Gly Arg Ala Thr Leu Thr Ala Asp Arg Ser Ala Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Gly Asn Ser Gly Ser Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

```
                165                 170                 175
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Gly Gly Gly Gly
    210                 215                 220

Ser Gly Gly Gly Gly Ser Gly Gly Gly Gly Ser Glu Val Gln Leu Val
225                 230                 235                 240

Gln Ser Gly Ala Glu Val Lys Lys Pro Gly Ala Ser Val Lys Val Ser
                245                 250                 255

Cys Lys Ala Ser Gly Tyr Thr Phe Thr Ser Tyr Ser Ile Gln Trp Val
            260                 265                 270

Arg Gln Ala Pro Gly Gln Arg Leu Glu Trp Ile Gly Tyr Ile Asn Pro
        275                 280                 285

Ser Ser Gly Tyr Ile Lys Tyr Asn Gln His Phe Arg Gly Arg Ala Thr
    290                 295                 300

Leu Thr Ala Asp Arg Ser Ala Ser Thr Ala Tyr Met Glu Leu Ser Ser
305                 310                 315                 320

Leu Arg Ser Glu Asp Thr Ala Val Tyr Tyr Cys Ala Arg Gly Asn Ser
                325                 330                 335

Gly Ser Phe Asp Tyr Trp Gly Gln Gly Thr Leu Val Thr Val Ser Ser
            340                 345                 350

Gly Gly Gly Gly Ser Gly Gly Gly Ser Gly Gly Gly Gly Ser Gly
                355                 360                 365

Gly Gly Gly Ser Asp Ile Val Met Thr Gln Ser Pro Leu Ser Leu Pro
        370                 375                 380

Val Thr Pro Gly Glu Pro Ala Ser Ile Ser Cys Arg Ser Ser Gln Ser
385                 390                 395                 400

Leu Leu His Ser Ser Gly Ile Thr Tyr Leu Tyr Trp Phe Leu Gln Lys
                405                 410                 415

Pro Gly Gln Ser Pro Gln Leu Leu Ile Tyr Arg Met Ser Asn Leu Ala
            420                 425                 430

Ser Gly Val Pro Asp Arg Phe Ser Gly Ser Gly Ser Gly Thr Asp Phe
        435                 440                 445

Thr Leu Lys Ile Ser Arg Val Glu Ala Glu Asp Val Gly Val Tyr Tyr
    450                 455                 460

Cys Met Gln His Leu Glu Tyr Pro Phe Thr Phe Gly Gln Gly Thr Lys
465                 470                 475                 480

Leu Glu Ile Lys

<210> SEQ ID NO 81
<211> LENGTH: 487
<212> TYPE: PRT
<213> ORGANISM: Unknown
<220> FEATURE:
<223> OTHER INFORMATION: Synthetic

<400> SEQUENCE: 81

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Ile Gln Trp Val Arg Gln Ala Pro Gly Gln Arg Leu Glu Trp Ile
        35                  40                  45
```

```
Gly Tyr Ile Asn Pro Ser Ser Gly Tyr Ile Lys Tyr Asn Gln His Phe
 50                  55                  60

Arg Gly Arg Ala Thr Leu Thr Ala Asp Arg Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asn Ser Gly Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Gly Gly Gly Gly
210                 215                 220

Ser Gly Gly Gly Gly Ser Gly Gly Gly Gly Ser Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Asp Phe Ser Arg Tyr Trp Met Ser Trp Val
            260                 265                 270

Arg Gln Ala Pro Gly Lys Gly Leu Glu Trp Ile Gly Glu Ile Asn Pro
        275                 280                 285

Thr Ser Ser Thr Ile Asn Phe Ala Asp Ser Val Lys Gly Arg Phe Thr
290                 295                 300

Ile Ser Arg Asp Asn Ala Lys Asn Ser Leu Tyr Leu Gln Met Asn Ser
305                 310                 315                 320

Val Arg Asp Glu Asp Thr Ala Val Tyr Tyr Cys Ala Arg Gly Asn Tyr
                325                 330                 335

Tyr Arg Tyr Gly Asp Ala Met Asp Tyr Trp Gly Gln Gly Thr Leu Val
            340                 345                 350

Thr Val Ser Ser Gly Gly Gly Gly Ser Gly Gly Gly Gly Ser Gly Gly
        355                 360                 365

Gly Gly Ser Gly Gly Gly Gly Ser Glu Ile Val Leu Thr Gln Ser Pro
370                 375                 380

Ala Thr Leu Ser Leu Ser Leu Gly Glu Arg Ala Thr Ile Ser Cys Arg
385                 390                 395                 400

Ala Ser Lys Ser Val Ser Thr Ser Gly Tyr Ser Tyr Leu His Trp Tyr
                405                 410                 415

Gln Gln Lys Pro Gly Gln Ala Pro Lys Leu Leu Ile Tyr Leu Ala Ser
            420                 425                 430

Asn Arg Ala Thr Gly Val Pro Ala Arg Phe Ser Gly Ser Gly Pro Gly
        435                 440                 445

Thr Asp Phe Thr Leu Thr Ile Ser Ser Leu Glu Pro Glu Asp Phe Ala
450                 455                 460
```

```
Thr Tyr Tyr Cys Gln His Ser Arg Glu Leu Pro Phe Thr Phe Gly Gln
465                 470                 475                 480

Gly Thr Lys Leu Glu Ile Lys
            485

<210> SEQ ID NO 82
<211> LENGTH: 753
<212> TYPE: PRT
<213> ORGANISM: Unknown
<220> FEATURE:
<223> OTHER INFORMATION: Synthetic

<400> SEQUENCE: 82

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Ser Gly Ile Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Ile Trp Glu Leu Lys Lys
225                 230                 235                 240

Asp Val Tyr Val Val Glu Leu Asp Trp Tyr Pro Asp Ala Pro Gly Glu
                245                 250                 255

Met Val Val Leu Thr Cys Asp Thr Pro Glu Glu Asp Gly Ile Thr Trp
            260                 265                 270

Thr Leu Asp Gln Ser Ser Glu Val Leu Gly Ser Gly Lys Thr Leu Thr
        275                 280                 285

Ile Gln Val Lys Glu Phe Gly Asp Ala Gly Gln Tyr Thr Cys His Lys
    290                 295                 300

Gly Gly Glu Val Leu Ser His Ser Leu Leu Leu Leu His Lys Lys Glu
305                 310                 315                 320

Asp Gly Ile Trp Ser Thr Asp Ile Leu Lys Asp Gln Lys Glu Pro Lys
                325                 330                 335
```

-continued

```
Asn Lys Thr Phe Leu Arg Cys Glu Ala Lys Asn Tyr Ser Gly Arg Phe
                340                 345                 350

Thr Cys Trp Trp Leu Thr Thr Ile Ser Thr Asp Leu Thr Phe Ser Val
        355                 360                 365

Lys Ser Ser Arg Gly Ser Ser Asp Pro Gln Gly Val Thr Cys Gly Ala
    370                 375                 380

Ala Thr Leu Ser Ala Glu Arg Val Arg Gly Asp Asn Lys Glu Tyr Glu
385                 390                 395                 400

Tyr Ser Val Glu Cys Gln Glu Asp Ser Ala Cys Pro Ala Ala Glu Glu
                405                 410                 415

Ser Leu Pro Ile Glu Val Met Val Asp Ala Val His Lys Leu Lys Tyr
            420                 425                 430

Glu Asn Tyr Thr Ser Ser Phe Phe Ile Arg Asp Ile Ile Lys Pro Asp
        435                 440                 445

Pro Pro Lys Asn Leu Gln Leu Lys Pro Leu Lys Asn Ser Arg Gln Val
    450                 455                 460

Glu Val Ser Trp Glu Tyr Pro Asp Thr Trp Ser Thr Pro His Ser Tyr
465                 470                 475                 480

Phe Ser Leu Thr Phe Cys Val Gln Val Gln Gly Lys Ser Lys Arg Glu
                485                 490                 495

Lys Lys Asp Arg Val Phe Thr Asp Lys Thr Ser Ala Thr Val Ile Cys
            500                 505                 510

Arg Lys Asn Ala Ser Ile Ser Val Arg Ala Gln Asp Arg Tyr Tyr Ser
        515                 520                 525

Ser Ser Trp Ser Glu Trp Ala Ser Val Pro Cys Ser Gly Gly Gly Ser
    530                 535                 540

Gly Gly Gly Ser Gly Gly Gly Ser Gly Gly Gly Ser Arg Asn Leu Pro
545                 550                 555                 560

Val Ala Thr Pro Asp Pro Gly Met Phe Pro Cys Leu His His Ser Gln
                565                 570                 575

Asn Leu Leu Arg Ala Val Ser Asn Met Leu Gln Lys Ala Arg Gln Thr
            580                 585                 590

Leu Glu Phe Tyr Pro Cys Thr Ser Glu Glu Ile Asp His Glu Asp Ile
        595                 600                 605

Thr Lys Asp Lys Thr Ser Thr Val Glu Ala Cys Leu Pro Leu Glu Leu
    610                 615                 620

Thr Lys Asn Glu Ser Cys Leu Asn Ser Arg Glu Thr Ser Phe Ile Thr
625                 630                 635                 640

Asn Gly Ser Cys Leu Ala Ser Arg Lys Thr Ser Phe Met Met Ala Leu
                645                 650                 655

Cys Leu Ser Ser Ile Tyr Glu Asp Leu Lys Met Tyr Gln Val Glu Phe
            660                 665                 670

Lys Thr Met Asn Ala Lys Leu Leu Met Asp Pro Lys Arg Gln Ile Phe
        675                 680                 685

Leu Asp Gln Asn Met Leu Ala Val Ile Asp Glu Leu Met Gln Ala Leu
    690                 695                 700

Asn Phe Asn Ser Glu Thr Val Pro Gln Lys Ser Ser Leu Glu Glu Pro
705                 710                 715                 720

Asp Phe Tyr Lys Thr Lys Ile Lys Leu Cys Ile Leu Leu His Ala Phe
                725                 730                 735

Arg Ile Arg Ala Val Thr Ile Asp Arg Val Met Ser Tyr Leu Asn Ala
            740                 745                 750

Ser
```

<210> SEQ ID NO 83
<211> LENGTH: 226
<212> TYPE: PRT
<213> ORGANISM: Unknown
<220> FEATURE:
<223> OTHER INFORMATION: Synthetic

<400> SEQUENCE: 83

Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Ile His Trp Val Lys Gln Ser His Gly Lys Ser Leu Glu Trp Val
        35                  40                  45

Ala Tyr Ile Asn Pro Asp Arg Asp Tyr Thr Asn Tyr Asn Glu Lys Phe
    50                  55                  60

Lys Ser Lys Ala Thr Leu Thr Val Asp Lys Ser Thr Asn Thr Ala Tyr
65                  70                  75                  80

Met Glu Leu Ser Arg Leu Thr Ser Glu Asp Ser Ala Thr Phe Tyr Cys
                85                  90                  95

Thr Arg Arg Leu Tyr Asp Gly Ala Tyr Tyr Ser Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 84
<211> LENGTH: 755
<212> TYPE: PRT
<213> ORGANISM: Unknown
<220> FEATURE:
<223> OTHER INFORMATION: Synthetic

<400> SEQUENCE: 84

Asp Ile Gln Met Thr Gln Ser Pro His Ser Leu Ser Ala Ser Leu Gly
1               5                   10                  15

Glu Thr Val Ser Ile Glu Cys Leu Ala Ser Glu Gly Ile Ser Asn Tyr
            20                  25                  30

Leu Ala Trp Tyr Gln Gln Lys Pro Gly Lys Ser Pro Gln Leu Leu Ile
        35                  40                  45

Tyr Tyr Gly Ser Arg Leu Gln Asp Gly Val Pro Ser Arg Phe Ser Gly
    50                  55                  60

Ser Gly Ser Gly Thr Gln Tyr Ser Leu Arg Ile Thr Asn Met Gln Pro

```
                65                  70                  75                  80
Glu Asp Glu Gly Val Tyr Tyr Cys Gln Gln Gly Tyr Lys Tyr Pro Tyr
                    85                  90                  95

Thr Phe Gly Ala Gly Thr Lys Leu Glu Leu Lys Arg Thr Val Ala Ala
        100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Gly Gly Ser
    210                 215                 220

Gly Gly Gly Gly Ser Met Trp Glu Leu Glu Lys Asp Val Tyr Val Val
225                 230                 235                 240

Glu Val Asp Trp Thr Pro Asp Ala Pro Gly Glu Thr Val Asn Leu Thr
                245                 250                 255

Cys Asp Thr Pro Glu Glu Asp Asp Ile Thr Trp Thr Ser Asp Gln Arg
        260                 265                 270

His Gly Val Ile Gly Ser Gly Lys Thr Leu Thr Ile Thr Val Lys Glu
            275                 280                 285

Phe Leu Asp Ala Gly Gln Tyr Thr Cys His Lys Gly Gly Glu Thr Leu
    290                 295                 300

Ser His Ser His Leu Leu Leu His Lys Lys Glu Asn Gly Ile Trp Ser
305                 310                 315                 320

Thr Glu Ile Leu Lys Asn Phe Lys Asn Lys Thr Phe Leu Lys Cys Glu
                325                 330                 335

Ala Pro Asn Tyr Ser Gly Arg Phe Thr Cys Ser Trp Leu Val Gln Arg
        340                 345                 350

Asn Met Asp Leu Lys Phe Asn Ile Lys Ser Ser Ser Ser Pro Asp
            355                 360                 365

Ser Arg Ala Val Thr Cys Gly Met Ala Ser Leu Ser Ala Glu Lys Val
    370                 375                 380

Thr Leu Asp Gln Arg Asp Tyr Glu Lys Tyr Ser Val Ser Cys Gln Glu
385                 390                 395                 400

Asp Val Thr Cys Pro Thr Ala Glu Glu Thr Leu Pro Ile Glu Leu Ala
                405                 410                 415

Leu Glu Ala Arg Gln Gln Asn Lys Tyr Glu Asn Tyr Ser Thr Ser Phe
        420                 425                 430

Phe Ile Arg Asp Ile Ile Lys Pro Asp Pro Pro Lys Asn Leu Gln Met
            435                 440                 445

Lys Pro Leu Lys Asn Ser Gln Val Glu Val Ser Trp Glu Tyr Pro Asp
    450                 455                 460

Ser Trp Ser Thr Pro His Ser Tyr Phe Ser Leu Lys Phe Phe Val Arg
465                 470                 475                 480

Ile Gln Arg Lys Lys Glu Lys Met Lys Glu Thr Glu Glu Gly Cys Asn
                485                 490                 495
```

```
Gln Lys Gly Ala Phe Leu Val Glu Lys Thr Ser Thr Glu Val Gln Cys
            500                 505                 510
Lys Gly Gly Asn Val Cys Val Gln Ala Gln Asp Arg Tyr Tyr Asn Ser
            515                 520                 525
Ser Cys Ser Lys Trp Ala Cys Val Pro Cys Arg Val Arg Ser Gly Gly
            530                 535                 540
Gly Gly Ser Gly Gly Gly Ser Gly Gly Gly Ser Gly Gly
545                 550                 555                 560
Gly Ser Arg Val Ile Pro Val Ser Gly Pro Ala Arg Cys Leu Ser Gln
                565                 570                 575
Ser Arg Asn Leu Leu Lys Thr Thr Asp Asp Met Val Lys Thr Ala Arg
            580                 585                 590
Glu Lys Leu Lys His Tyr Ser Cys Thr Ala Glu Asp Ile Asp His Glu
            595                 600                 605
Asp Ile Thr Arg Asp Gln Thr Ser Thr Leu Lys Thr Cys Leu Pro Leu
            610                 615                 620
Glu Leu His Lys Asn Glu Ser Cys Leu Ala Thr Arg Glu Thr Ser Ser
625                 630                 635                 640
Thr Thr Arg Gly Ser Cys Leu Pro Pro Gln Lys Thr Ser Leu Met Met
                645                 650                 655
Thr Leu Cys Leu Gly Ser Ile Tyr Glu Asp Leu Lys Met Tyr Gln Thr
                660                 665                 670
Glu Phe Gln Ala Ile Asn Ala Ala Leu Gln Asn His Asn His Gln Gln
            675                 680                 685
Ile Ile Leu Asp Lys Gly Met Leu Val Ala Ile Asp Glu Leu Met Gln
            690                 695                 700
Ser Leu Asn His Asn Gly Glu Thr Leu Arg Gln Lys Pro Pro Val Gly
705                 710                 715                 720
Glu Ala Asp Pro Tyr Arg Val Lys Met Lys Leu Cys Ile Leu Leu His
                725                 730                 735
Ala Phe Ser Thr Arg Val Val Thr Ile Asn Arg Val Met Gly Tyr Leu
                740                 745                 750
Ser Ser Ala
        755

<210> SEQ ID NO 85
<211> LENGTH: 343
<212> TYPE: PRT
<213> ORGANISM: Unknown
<220> FEATURE:
<223> OTHER INFORMATION: Synthetic

<400> SEQUENCE: 85

Asp Ile Gln Met Thr Gln Ser Pro His Ser Leu Ser Ala Ser Leu Gly
1               5                   10                  15
Glu Thr Val Ser Ile Glu Cys Leu Ala Ser Glu Gly Ile Ser Asn Tyr
            20                  25                  30
Leu Ala Trp Tyr Gln Gln Lys Pro Gly Lys Ser Pro Gln Leu Leu Ile
        35                  40                  45
Tyr Tyr Gly Ser Arg Leu Gln Asp Gly Val Pro Ser Arg Phe Ser Gly
    50                  55                  60
Ser Gly Ser Gly Thr Gln Tyr Ser Leu Arg Ile Thr Asn Met Gln Pro
65                  70                  75                  80
Glu Asp Glu Gly Val Tyr Tyr Cys Gln Gln Gly Tyr Lys Tyr Pro Tyr
                85                  90                  95
```

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Gly Gly Ser
            210                 215                 220

Gly Gly Gly Gly Ser Asn Trp Val Asn Val Ile Ser Asp Leu Lys Lys
225                 230                 235                 240

Ile Glu Asp Leu Ile Gln Ser Met His Ile Asp Ala Thr Leu Tyr Thr
            245                 250                 255

Glu Ser Asp Val His Pro Ser Cys Lys Val Thr Ala Met Lys Cys Phe
            260                 265                 270

Leu Leu Glu Leu Gln Val Ile Ser Leu Glu Ser Gly Asp Ala Ser Ile
            275                 280                 285

His Asp Thr Val Glu Asn Leu Ile Ile Leu Ala Asn Asn Ser Leu Ser
            290                 295                 300

Ser Asn Gly Asn Val Thr Glu Ser Gly Cys Lys Glu Cys Glu Glu Leu
305                 310                 315                 320

Glu Glu Lys Asn Ile Lys Glu Phe Leu Gln Ser Phe Val His Ile Val
            325                 330                 335

Gln Met Phe Ile Asn Thr Ser
            340

<210> SEQ ID NO 86
<211> LENGTH: 491
<212> TYPE: PRT
<213> ORGANISM: Unknown
<220> FEATURE:
<223> OTHER INFORMATION: Synthetic

<400> SEQUENCE: 86

Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Ile His Trp Val Lys Gln Ser His Gly Lys Ser Leu Glu Trp Val
            35                  40                  45

Ala Tyr Ile Asn Pro Asp Arg Asp Tyr Thr Asn Tyr Asn Glu Lys Phe
        50                  55                  60

Lys Ser Lys Ala Thr Leu Thr Val Asp Lys Ser Thr Asn Thr Ala Tyr
65                  70                  75                  80

Met Glu Leu Ser Arg Leu Thr Ser Glu Asp Ser Ala Thr Phe Tyr Cys
                85                  90                  95

Thr Arg Arg Leu Tyr Asp Gly Ala Tyr Tyr Tyr Ser Trp Phe Ala Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Gly Gly Gly Ser Gly Gly Gly Ser Gly Gly Gly Gly
225                 230                 235                 240

Ser Gln Val Asn Leu Leu Gln Ser Gly Ala Ala Leu Val Lys Pro Gly
                245                 250                 255

Ala Ser Val Lys Leu Ser Cys Lys Ala Ser Gly Tyr Thr Phe Thr Asp
            260                 265                 270

Tyr Tyr Ile His Trp Val Lys Gln Ser His Gly Lys Ser Leu Glu Trp
        275                 280                 285

Val Ala Tyr Ile Asn Pro Asp Arg Asp Tyr Thr Asn Tyr Asn Glu Lys
        290                 295                 300

Phe Lys Ser Lys Ala Thr Leu Thr Val Asp Lys Ser Asn Thr Ala
305                 310                 315                 320

Tyr Met Glu Leu Ser Arg Leu Thr Ser Glu Asp Ser Ala Thr Phe Tyr
                325                 330                 335

Cys Thr Arg Arg Leu Tyr Asp Gly Ala Tyr Tyr Ser Trp Phe Ala
            340                 345                 350

Tyr Trp Gly Gln Gly Thr Leu Val Thr Val Ser Ser Gly Gly Gly Gly
        355                 360                 365

Ser Gly Gly Gly Gly Ser Gly Gly Gly Ser Gly Gly Gly Gly Ser
        370                 375                 380

Asp Ile Gln Met Thr Gln Ser Pro His Ser Leu Ser Ala Ser Leu Gly
385                 390                 395                 400

Glu Thr Val Ser Ile Glu Cys Leu Ala Ser Glu Gly Ile Ser Asn Tyr
                405                 410                 415

Leu Ala Trp Tyr Gln Gln Lys Pro Gly Lys Ser Pro Gln Leu Leu Ile
            420                 425                 430

Tyr Tyr Gly Ser Arg Leu Gln Asp Gly Val Pro Ser Arg Phe Ser Gly
        435                 440                 445

Ser Gly Ser Gly Thr Gln Tyr Ser Leu Arg Ile Thr Asn Met Gln Pro
        450                 455                 460

Glu Asp Glu Gly Val Tyr Tyr Cys Gln Gln Gly Tyr Lys Tyr Pro Tyr
465                 470                 475                 480

Thr Phe Gly Ala Gly Thr Lys Leu Glu Leu Lys
                485                 490

<210> SEQ ID NO 87
<211> LENGTH: 227
<212> TYPE: PRT
<213> ORGANISM: Unknown
<220> FEATURE:

-continued

<223> OTHER INFORMATION: Synthetic

<400> SEQUENCE: 87

Glu Val Lys Leu Gln Glu Ser Gly Gly Gly Leu Val Gln Pro Gly Arg
1               5                   10                  15

Ser Leu Lys Leu Ser Cys Ala Ala Ser Gly Phe Asn Phe Asn Asp Tyr
            20                  25                  30

Trp Met Gly Trp Val Arg Gln Ala Pro Gly Lys Gly Leu Glu Trp Ile
        35                  40                  45

Gly Glu Ile Asn Lys Asp Ser Ser Thr Ile Asn Tyr Thr Pro Ser Leu
    50                  55                  60

Lys Asp Lys Phe Thr Ile Ser Arg Asp Asn Ala Gln Asn Thr Leu Tyr
65                  70                  75                  80

Leu Gln Met Ser Lys Leu Gly Ser Glu Asp Thr Ala Ile Tyr Tyr Cys
                85                  90                  95

Ala Arg Ala Arg Gly Met Met Val Leu Ile Ile Pro His Tyr Phe Asp
            100                 105                 110

Tyr Trp Gly Gln Gly Val Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225

<210> SEQ ID NO 88
<211> LENGTH: 342
<212> TYPE: PRT
<213> ORGANISM: Unknown
<220> FEATURE:
<223> OTHER INFORMATION: Synthetic

<400> SEQUENCE: 88

Asp Ile Val Leu Thr Gln Ser Pro Ala Met Ala Met Ser Pro Gly Glu
1               5                   10                  15

Arg Ile Thr Ile Ser Cys Arg Ala Ser Glu Ser Val Ser Thr Arg Met
            20                  25                  30

His Trp Tyr Gln Gln Lys Pro Gly Gln Pro Lys Leu Leu Ile Tyr
        35                  40                  45

Gly Ala Ser Asn Leu Glu Ser Gly Val Pro Ala Arg Phe Ser Gly Ser
    50                  55                  60

Gly Ser Gly Thr Asp Phe Thr Leu Thr Ile Asp Pro Val Glu Ala Asn
65                  70                  75                  80

Asp Thr Ala Thr Tyr Phe Cys Gln Gln Ser Trp Tyr Asp Pro Trp Thr
                85                  90                  95

Phe Gly Gly Gly Thr Lys Leu Glu Leu Lys Arg Thr Val Ala Ala Pro
            100                 105                 110

```
Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Ser Gly Gly Gly Gly Ser Gly
    210                 215                 220

Gly Gly Gly Ser Asn Trp Val Asn Val Ile Ser Asp Leu Lys Lys Ile
225                 230                 235                 240

Glu Asp Leu Ile Gln Ser Met His Ile Asp Ala Thr Leu Tyr Thr Glu
                245                 250                 255

Ser Asp Val His Pro Ser Cys Lys Val Thr Ala Met Lys Cys Phe Leu
            260                 265                 270

Leu Glu Leu Gln Val Ile Ser Leu Glu Ser Gly Asp Ala Ser Ile His
        275                 280                 285

Asp Thr Val Glu Asn Leu Ile Ile Leu Ala Asn Asn Ser Leu Ser Ser
    290                 295                 300

Asn Gly Asn Val Thr Glu Ser Gly Cys Lys Glu Cys Glu Glu Leu Glu
305                 310                 315                 320

Glu Lys Asn Ile Lys Glu Phe Leu Gln Ser Phe Val His Ile Val Gln
                325                 330                 335

Met Phe Ile Asn Thr Ser
            340

<210> SEQ ID NO 89
<211> LENGTH: 492
<212> TYPE: PRT
<213> ORGANISM: Unknown
<220> FEATURE:
<223> OTHER INFORMATION: Synthetic

<400> SEQUENCE: 89

Glu Val Lys Leu Gln Glu Ser Gly Gly Gly Leu Val Gln Pro Gly Arg
1               5                   10                  15

Ser Leu Lys Leu Ser Cys Ala Ala Ser Gly Phe Asn Phe Asn Asp Tyr
                20                  25                  30

Trp Met Gly Trp Val Arg Gln Ala Pro Gly Lys Gly Leu Glu Trp Ile
            35                  40                  45

Gly Glu Ile Asn Lys Asp Ser Ser Thr Ile Asn Tyr Thr Pro Ser Leu
        50                  55                  60

Lys Asp Lys Phe Thr Ile Ser Arg Asp Asn Ala Gln Asn Thr Leu Tyr
65                  70                  75                  80

Leu Gln Met Ser Lys Leu Gly Ser Glu Asp Thr Ala Ile Tyr Tyr Cys
                85                  90                  95

Ala Arg Ala Arg Gly Met Met Val Leu Ile Ile Pro His Tyr Phe Asp
            100                 105                 110

Tyr Trp Gly Gln Gly Val Met Val Thr Val Ser Ser Ala Ser Thr Lys
        115                 120                 125
```

-continued

Gly Pro Ser Val Phe Pro Leu Ala Pro Ser Ser Lys Ser Thr Ser Gly
         130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Gly Gly Gly Gly Ser Gly Gly Gly Gly Ser Gly Gly Gly
225                 230                 235                 240

Gly Ser Gln Val Asn Leu Leu Gln Ser Gly Ala Ala Leu Val Lys Pro
                245                 250                 255

Gly Ala Ser Val Lys Leu Ser Cys Lys Ala Ser Gly Tyr Thr Phe Thr
            260                 265                 270

Asp Tyr Tyr Ile His Trp Val Lys Gln Ser His Gly Lys Ser Leu Glu
        275                 280                 285

Trp Val Ala Tyr Ile Asn Pro Asp Arg Asp Tyr Thr Asn Tyr Asn Glu
    290                 295                 300

Lys Phe Lys Ser Lys Ala Thr Leu Thr Val Asp Lys Ser Thr Asn Thr
305                 310                 315                 320

Ala Tyr Met Glu Leu Ser Arg Leu Thr Ser Glu Asp Ser Ala Thr Phe
                325                 330                 335

Tyr Cys Thr Arg Arg Leu Tyr Asp Gly Ala Tyr Tyr Ser Trp Phe
            340                 345                 350

Ala Tyr Trp Gly Gln Gly Thr Leu Val Thr Val Ser Ser Gly Gly Gly
        355                 360                 365

Gly Ser Gly Gly Gly Gly Ser Gly Gly Gly Gly Ser Gly Gly Gly Gly
    370                 375                 380

Ser Asp Ile Gln Met Thr Gln Ser Pro His Ser Leu Ser Ala Ser Leu
385                 390                 395                 400

Gly Glu Thr Val Ser Ile Glu Cys Leu Ala Ser Glu Gly Ile Ser Asn
                405                 410                 415

Tyr Leu Ala Trp Tyr Gln Gln Lys Pro Gly Lys Ser Pro Gln Leu Leu
            420                 425                 430

Ile Tyr Tyr Gly Ser Arg Leu Gln Asp Gly Val Pro Ser Arg Phe Ser
        435                 440                 445

Gly Ser Gly Ser Gly Thr Gln Tyr Ser Leu Arg Ile Thr Asn Met Gln
    450                 455                 460

Pro Glu Asp Glu Gly Val Tyr Tyr Cys Gln Gln Gly Tyr Lys Tyr Pro
465                 470                 475                 480

Tyr Thr Phe Gly Ala Gly Thr Lys Leu Glu Leu Lys
                485                 490

<210> SEQ ID NO 90
<211> LENGTH: 754
<212> TYPE: PRT
<213> ORGANISM: Unknown
<220> FEATURE:
<223> OTHER INFORMATION: Synthetic

<400> SEQUENCE: 90

-continued

```
Asp Ile Val Leu Thr Gln Ser Pro Ala Met Ala Met Ser Pro Gly Glu
1               5                   10                  15

Arg Ile Thr Ile Ser Cys Arg Ala Ser Glu Ser Val Ser Thr Arg Met
            20                  25                  30

His Trp Tyr Gln Gln Lys Pro Gly Gln Gln Pro Lys Leu Leu Ile Tyr
            35                  40                  45

Gly Ala Ser Asn Leu Glu Ser Gly Val Pro Ala Arg Phe Ser Gly Ser
        50                  55                  60

Gly Ser Gly Thr Asp Phe Thr Leu Thr Ile Asp Pro Val Glu Ala Asn
65                  70                  75                  80

Asp Thr Ala Thr Tyr Phe Cys Gln Gln Ser Trp Tyr Asp Pro Trp Thr
                85                  90                  95

Phe Gly Gly Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys Gly Gly Gly Ser Gly Gly Gly Ser Gly
210                 215                 220

Gly Gly Gly Ser Met Trp Glu Leu Glu Lys Asp Val Tyr Val Val Glu
225                 230                 235                 240

Val Asp Trp Thr Pro Asp Ala Pro Gly Glu Thr Val Asn Leu Thr Cys
                245                 250                 255

Asp Thr Pro Glu Glu Asp Ile Thr Trp Thr Ser Asp Gln Arg His
            260                 265                 270

Gly Val Ile Gly Ser Gly Lys Thr Leu Thr Ile Thr Val Lys Glu Phe
            275                 280                 285

Leu Asp Ala Gly Gln Tyr Thr Cys His Lys Gly Gly Glu Thr Leu Ser
        290                 295                 300

His Ser His Leu Leu Leu His Lys Lys Glu Asn Gly Ile Trp Ser Thr
305                 310                 315                 320

Glu Ile Leu Lys Asn Phe Lys Asn Lys Thr Phe Leu Lys Cys Glu Ala
                325                 330                 335

Pro Asn Tyr Ser Gly Arg Phe Thr Cys Ser Trp Leu Val Gln Arg Asn
            340                 345                 350

Met Asp Leu Lys Phe Asn Ile Lys Ser Ser Ser Ser Pro Asp Ser
            355                 360                 365

Arg Ala Val Thr Cys Gly Met Ala Ser Leu Ser Ala Glu Lys Val Thr
        370                 375                 380

Leu Asp Gln Arg Asp Tyr Glu Lys Tyr Ser Val Ser Cys Gln Glu Asp
385                 390                 395                 400

Val Thr Cys Pro Thr Ala Glu Glu Thr Leu Pro Ile Glu Leu Ala Leu
                405                 410                 415
```

Glu Ala Arg Gln Gln Asn Lys Tyr Glu Asn Tyr Ser Thr Ser Phe Phe
                420                 425                 430

Ile Arg Asp Ile Ile Lys Pro Asp Pro Lys Asn Leu Gln Met Lys
            435                 440                 445

Pro Leu Lys Asn Ser Gln Val Glu Val Ser Trp Glu Tyr Pro Asp Ser
    450                 455                 460

Trp Ser Thr Pro His Ser Tyr Phe Ser Leu Lys Phe Phe Val Arg Ile
465                 470                 475                 480

Gln Arg Lys Lys Lys Met Lys Glu Thr Glu Glu Gly Cys Asn Gln
                485                 490                 495

Lys Gly Ala Phe Leu Val Glu Lys Thr Ser Thr Glu Val Gln Cys Lys
                500                 505                 510

Gly Gly Asn Val Cys Val Gln Ala Gln Asp Arg Tyr Tyr Asn Ser Ser
                515                 520                 525

Cys Ser Lys Trp Ala Cys Val Pro Cys Arg Val Arg Ser Gly Gly Gly
    530                 535                 540

Gly Ser Gly Gly Gly Ser Gly Gly Gly Ser Gly Gly Gly Gly
545                 550                 555                 560

Ser Arg Val Ile Pro Val Ser Gly Pro Ala Arg Cys Leu Ser Gln Ser
                565                 570                 575

Arg Asn Leu Leu Lys Thr Thr Asp Asp Met Val Lys Thr Ala Arg Glu
            580                 585                 590

Lys Leu Lys His Tyr Ser Cys Thr Ala Glu Asp Ile Asp His Glu Asp
                595                 600                 605

Ile Thr Arg Asp Gln Thr Ser Thr Leu Lys Thr Cys Leu Pro Leu Glu
610                 615                 620

Leu His Lys Asn Glu Ser Cys Leu Ala Thr Arg Glu Thr Ser Ser Thr
625                 630                 635                 640

Thr Arg Gly Ser Cys Leu Pro Pro Gln Lys Thr Ser Leu Met Met Thr
            645                 650                 655

Leu Cys Leu Gly Ser Ile Tyr Glu Asp Leu Lys Met Tyr Gln Thr Glu
                660                 665                 670

Phe Gln Ala Ile Asn Ala Ala Leu Gln Asn His Asn His Gln Gln Ile
            675                 680                 685

Ile Leu Asp Lys Gly Met Leu Val Ala Ile Asp Glu Leu Met Gln Ser
            690                 695                 700

Leu Asn His Asn Gly Glu Thr Leu Arg Gln Lys Pro Pro Val Gly Glu
705                 710                 715                 720

Ala Asp Pro Tyr Arg Val Lys Met Lys Leu Cys Ile Leu Leu His Ala
                725                 730                 735

Phe Ser Thr Arg Val Val Thr Ile Asn Arg Val Met Gly Tyr Leu Ser
                740                 745                 750

Ser Ala

<210> SEQ ID NO 91
<211> LENGTH: 249
<212> TYPE: PRT
<213> ORGANISM: Unknown
<220> FEATURE:
<223> OTHER INFORMATION: Synthetic

<400> SEQUENCE: 91

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
                20                  25                  30
Ser Ile Gln Trp Val Arg Gln Ala Pro Gly Gln Arg Leu Glu Trp Ile
             35                  40                  45

Gly Tyr Ile Asn Pro Ser Ser Gly Tyr Ile Lys Tyr Asn Gln His Phe
 50                  55                  60

Arg Gly Arg Ala Thr Leu Thr Ala Asp Arg Ser Ala Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Gly Asn Ser Gly Ser Phe Asp Tyr Trp Gly Gln Gly Thr Leu
                100                 105                 110

Val Thr Val Ser Ser Gly Gly Gly Ser Gly Gly Gly Ser Gly
            115                 120                 125

Gly Gly Gly Ser Gly Gly Gly Ser Asp Ile Val Met Thr Gln Ser
            130                 135                 140

Pro Leu Ser Leu Pro Val Thr Pro Gly Glu Pro Ala Ser Ile Ser Cys
145                 150                 155                 160

Arg Ser Ser Gln Ser Leu Leu His Ser Gly Ile Thr Tyr Leu Tyr
                165                 170                 175

Trp Phe Leu Gln Lys Pro Gly Gln Ser Pro Gln Leu Leu Ile Tyr Arg
                180                 185                 190

Met Ser Asn Leu Ala Ser Gly Val Pro Asp Arg Phe Ser Gly Ser Gly
                195                 200                 205

Ser Gly Thr Asp Phe Thr Leu Lys Ile Ser Arg Val Glu Ala Glu Asp
            210                 215                 220

Val Gly Val Tyr Tyr Cys Met Gln His Leu Glu Tyr Pro Phe Thr Phe
225                 230                 235                 240

Gly Gln Gly Thr Lys Leu Glu Ile Lys
                245

<210> SEQ ID NO 92
<211> LENGTH: 252
<212> TYPE: PRT
<213> ORGANISM: Unknown
<220> FEATURE:
<223> OTHER INFORMATION: Synthetic

<400> SEQUENCE: 92

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asp Phe Ser Arg Tyr
             20                  25                  30

Trp Met Ser Trp Val Arg Gln Ala Pro Gly Lys Gly Leu Glu Trp Ile
             35                  40                  45

Gly Glu Ile Asn Pro Thr Ser Ser Thr Ile Asn Phe Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Val Arg Asp Glu Asp Thr Ala Val Tyr Tyr Cys
             85                  90                  95

Ala Arg Gly Asn Tyr Tyr Arg Tyr Gly Asp Ala Met Asp Tyr Trp Gly
                100                 105                 110

Gln Gly Thr Leu Val Thr Val Ser Ser Gly Gly Gly Ser Gly Gly
            115                 120                 125

Gly Gly Ser Gly Gly Gly Gly Ser Gly Gly Gly Gly Ser Glu Ile Val
```

```
                130                 135                 140
Leu Thr Gln Ser Pro Ala Thr Leu Ser Leu Ser Leu Gly Glu Arg Ala
145                 150                 155                 160

Thr Ile Ser Cys Arg Ala Ser Lys Ser Val Ser Thr Ser Gly Tyr Ser
                165                 170                 175

Tyr Leu His Trp Tyr Gln Gln Lys Pro Gly Gln Ala Pro Lys Leu Leu
                180                 185                 190

Ile Tyr Leu Ala Ser Asn Arg Ala Thr Gly Val Pro Ala Arg Phe Ser
                195                 200                 205

Gly Ser Gly Pro Gly Thr Asp Phe Thr Leu Thr Ile Ser Ser Leu Glu
                210                 215                 220

Pro Glu Asp Phe Ala Thr Tyr Tyr Cys Gln His Ser Arg Glu Leu Pro
225                 230                 235                 240

Phe Thr Phe Gly Gln Gly Thr Lys Leu Glu Ile Lys
                245                 250

<210> SEQ ID NO 93
<211> LENGTH: 250
<212> TYPE: PRT
<213> ORGANISM: Unknown
<220> FEATURE:
<223> OTHER INFORMATION: Synthetic

<400> SEQUENCE: 93

Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr Asp Tyr
                20                  25                  30

Tyr Ile His Trp Val Lys Gln Ser His Gly Lys Ser Leu Glu Trp Val
                35                  40                  45

Ala Tyr Ile Asn Pro Asp Arg Asp Tyr Thr Asn Tyr Asn Glu Lys Phe
                50                  55                  60

Lys Ser Lys Ala Thr Leu Thr Val Asp Lys Ser Thr Asn Thr Ala Tyr
65                  70                  75                  80

Met Glu Leu Ser Arg Leu Thr Ser Glu Asp Ser Ala Thr Phe Tyr Cys
                85                  90                  95

Thr Arg Arg Leu Tyr Asp Gly Ala Tyr Tyr Ser Trp Phe Ala Tyr
                100                 105                 110

Trp Gly Gln Gly Thr Leu Val Thr Val Ser Ser Gly Gly Gly Gly Ser
                115                 120                 125

Gly Gly Gly Gly Ser Gly Gly Gly Ser Gly Gly Gly Gly Ser Asp
                130                 135                 140

Ile Gln Met Thr Gln Ser Pro His Ser Leu Ser Ala Ser Leu Gly Glu
145                 150                 155                 160

Thr Val Ser Ile Glu Cys Leu Ala Ser Glu Gly Ile Ser Asn Tyr Leu
                165                 170                 175

Ala Trp Tyr Gln Gln Lys Pro Gly Lys Ser Pro Gln Leu Leu Ile Tyr
                180                 185                 190

Tyr Gly Ser Arg Leu Gln Asp Gly Val Pro Ser Arg Phe Ser Gly Ser
                195                 200                 205

Gly Ser Gly Thr Gln Tyr Ser Leu Arg Ile Thr Asn Met Gln Pro Glu
                210                 215                 220

Asp Glu Gly Val Tyr Tyr Cys Gln Gln Gly Tyr Lys Tyr Pro Tyr Thr
225                 230                 235                 240

Phe Gly Ala Gly Thr Lys Leu Glu Leu Lys
                245                 250
```

245                 250

<210> SEQ ID NO 94
<211> LENGTH: 117
<212> TYPE: PRT
<213> ORGANISM: Unknown
<220> FEATURE:
<223> OTHER INFORMATION: Synthetic

<400> SEQUENCE: 94

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Ile Gln Trp Val Arg Gln Ala Pro Gly Gln Arg Leu Glu Trp Ile
        35                  40                  45

Gly Tyr Ile Asn Pro Ser Ser Gly Tyr Ile Lys Tyr Asn Gln His Phe
    50                  55                  60

Arg Gly Arg Ala Thr Leu Thr Ala Asp Arg Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Ser Gly Ser Phe Asp Tyr Trp Gly Gln Gly Thr Leu
            100                 105                 110

Val Thr Val Ser Ser
        115

<210> SEQ ID NO 95
<211> LENGTH: 112
<212> TYPE: PRT
<213> ORGANISM: Unknown
<220> FEATURE:
<223> OTHER INFORMATION: Synthetic

<400> SEQUENCE: 95

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Ser Gly Ile Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

<210> SEQ ID NO 96
<211> LENGTH: 121
<212> TYPE: PRT
<213> ORGANISM: Unknown
<220> FEATURE:
<223> OTHER INFORMATION: Synthetic

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Val Arg Asp Glu Asp Thr Ala Val Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Leu Val Thr Val Ser Ser
        115                 120

<210> SEQ ID NO 97
<211> LENGTH: 111
<212> TYPE: PRT
<213> ORGANISM: Unknown
<220> FEATURE:
<223> OTHER INFORMATION: Synthetic

<400> SEQUENCE: 97

Glu Ile Val Leu Thr Gln Ser Pro Ala Thr Leu Ser Leu Ser Leu Gly
1               5                   10                  15

Glu Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Ala Pro
        35                  40                  45

Lys Leu Leu Ile Tyr Leu Ala Ser Asn Arg Ala Thr Gly Val Pro Ala
50                  55                  60

Arg Phe Ser Gly Ser Gly Pro Gly Thr Asp Phe Thr Leu Thr Ile Ser
65                  70                  75                  80

Ser Leu Glu Pro Glu Asp Phe Ala Thr Tyr Tyr Cys Gln His Ser Arg
                85                  90                  95

Glu Leu Pro Phe Thr Phe Gly Gln Gly Thr Lys Leu Glu Ile Lys
            100                 105                 110

<210> SEQ ID NO 98
<211> LENGTH: 123
<212> TYPE: PRT
<213> ORGANISM: Unknown
<220> FEATURE:
<223> OTHER INFORMATION: Synthetic

<400> SEQUENCE: 98

Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Ile His Trp Val Lys Gln Ser His Gly Lys Ser Leu Glu Trp Val
        35                  40                  45

Ala Tyr Ile Asn Pro Asp Arg Asp Tyr Thr Asn Tyr Asn Glu Lys Phe
50                  55                  60

Lys Ser Lys Ala Thr Leu Thr Val Asp Lys Ser Thr Asn Thr Ala Tyr
65                  70                  75                  80

Met Glu Leu Ser Arg Leu Thr Ser Glu Asp Ser Ala Thr Phe Tyr Cys

```
                    85                  90                  95

Thr Arg Arg Leu Tyr Asp Gly Ala Tyr Tyr Tyr Ser Trp Phe Ala Tyr
                100                 105                 110

Trp Gly Gln Gly Thr Leu Val Thr Val Ser Ser
        115                 120
```

<210> SEQ ID NO 99
<211> LENGTH: 107
<212> TYPE: PRT
<213> ORGANISM: Unknown
<220> FEATURE:
<223> OTHER INFORMATION: Synthetic

<400> SEQUENCE: 99

```
Asp Ile Gln Met Thr Gln Ser Pro His Ser Leu Ser Ala Ser Leu Gly
1               5                   10                  15

Glu Thr Val Ser Ile Glu Cys Leu Ala Ser Glu Gly Ile Ser Asn Tyr
                20                  25                  30

Leu Ala Trp Tyr Gln Gln Lys Pro Gly Lys Ser Pro Gln Leu Leu Ile
            35                  40                  45

Tyr Tyr Gly Ser Arg Leu Gln Asp Gly Val Pro Ser Arg Phe Ser Gly
50                  55                  60

Ser Gly Ser Gly Thr Gln Tyr Ser Leu Arg Ile Thr Asn Met Gln Pro
65                  70                  75                  80

Glu Asp Glu Gly Val Tyr Tyr Cys Gln Gln Gly Tyr Lys Tyr Pro Tyr
                85                  90                  95

Thr Phe Gly Ala Gly Thr Lys Leu Glu Leu Lys
                100                 105
```

<210> SEQ ID NO 100
<211> LENGTH: 124
<212> TYPE: PRT
<213> ORGANISM: Unknown
<220> FEATURE:
<223> OTHER INFORMATION: Synthetic

<400> SEQUENCE: 100

```
Glu Val Lys Leu Gln Glu Ser Gly Gly Gly Leu Val Gln Pro Gly Arg
1               5                   10                  15

Ser Leu Lys Leu Ser Cys Ala Ala Ser Gly Phe Asn Phe Asn Asp Tyr
                20                  25                  30

Trp Met Gly Trp Val Arg Gln Ala Pro Gly Lys Gly Leu Glu Trp Ile
            35                  40                  45

Gly Glu Ile Asn Lys Asp Ser Ser Thr Ile Asn Tyr Thr Pro Ser Leu
        50                  55                  60

Lys Asp Lys Phe Thr Ile Ser Arg Asp Asn Ala Gln Asn Thr Leu Tyr
65                  70                  75                  80

Leu Gln Met Ser Lys Leu Gly Ser Glu Asp Thr Ala Ile Tyr Tyr Cys
                85                  90                  95

Ala Arg Ala Arg Gly Met Met Val Leu Ile Ile Pro Tyr Phe Asp
                100                 105                 110

Tyr Trp Gly Gln Gly Val Met Val Thr Val Ser Ser
        115                 120
```

<210> SEQ ID NO 101
<211> LENGTH: 106
<212> TYPE: PRT
<213> ORGANISM: Unknown
<220> FEATURE:

<223> OTHER INFORMATION: Synthetic

<400> SEQUENCE: 101

```
Asp Ile Val Leu Thr Gln Ser Pro Ala Met Ala Ser Pro Gly Glu
1               5                   10                  15

Arg Ile Thr Ile Ser Cys Arg Ala Ser Glu Ser Val Ser Thr Arg Met
            20                  25                  30

His Trp Tyr Gln Gln Lys Pro Gly Gln Pro Lys Leu Leu Ile Tyr
            35                  40                  45

Gly Ala Ser Asn Leu Glu Ser Gly Val Pro Ala Arg Phe Ser Gly Ser
50                  55                  60

Gly Ser Gly Thr Asp Phe Thr Leu Thr Ile Asp Pro Val Glu Ala Asn
65                  70                  75                  80

Asp Thr Ala Thr Tyr Phe Cys Gln Gln Ser Trp Tyr Asp Pro Trp Thr
                85                  90                  95

Phe Gly Gly Gly Thr Lys Leu Glu Leu Lys
                100                 105
```

<210> SEQ ID NO 102
<211> LENGTH: 753
<212> TYPE: PRT
<213> ORGANISM: Unknown
<220> FEATURE:
<223> OTHER INFORMATION: Synthetic

<400> SEQUENCE: 102

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Ser Gly Ile Thr Tyr Leu Tyr Trp Phe Leu Gln Lys Pro Gly Gln Ser
            35                  40                  45

Pro Gln Leu Leu Ile Tyr Arg Met Ser Asn Leu Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
        210                 215                 220

Gly Gly Gly Gly Ser Gly Gly Gly Ser Arg Asn Leu Pro Val Ala
225                 230                 235                 240
```

```
Thr Pro Asp Pro Gly Met Phe Pro Cys Leu His His Ser Gln Asn Leu
            245                 250                 255
Leu Arg Ala Val Ser Asn Met Leu Gln Lys Ala Arg Gln Thr Leu Glu
            260                 265                 270
Phe Tyr Pro Cys Thr Ser Glu Glu Ile Asp His Glu Asp Ile Thr Lys
            275                 280                 285
Asp Lys Thr Ser Thr Val Glu Ala Cys Leu Pro Leu Glu Leu Thr Lys
            290                 295                 300
Asn Glu Ser Cys Leu Asn Ser Arg Glu Thr Ser Phe Ile Thr Asn Gly
305                 310                 315                 320
Ser Cys Leu Ala Ser Arg Lys Thr Ser Phe Met Met Ala Leu Cys Leu
                325                 330                 335
Ser Ser Ile Tyr Glu Asp Leu Lys Met Tyr Gln Val Glu Phe Lys Thr
                340                 345                 350
Met Asn Ala Lys Leu Leu Met Asp Pro Lys Arg Gln Ile Phe Leu Asp
                355                 360                 365
Gln Asn Met Leu Ala Val Ile Asp Glu Leu Met Gln Ala Leu Asn Phe
            370                 375                 380
Asn Ser Glu Thr Val Pro Gln Lys Ser Ser Leu Glu Glu Pro Asp Phe
385                 390                 395                 400
Tyr Lys Thr Lys Ile Lys Leu Cys Ile Leu Leu His Ala Phe Arg Ile
                405                 410                 415
Arg Ala Val Thr Ile Asp Arg Val Met Ser Tyr Leu Asn Ala Ser Gly
                420                 425                 430
Gly Gly Ser Gly Gly Ser Gly Gly Ser Gly Gly Ser Ile
                435                 440                 445
Trp Glu Leu Lys Lys Asp Val Tyr Val Val Glu Leu Asp Trp Tyr Pro
            450                 455                 460
Asp Ala Pro Gly Glu Met Val Val Leu Thr Cys Asp Thr Pro Glu Glu
465                 470                 475                 480
Asp Gly Ile Thr Trp Thr Leu Asp Gln Ser Ser Glu Val Leu Gly Ser
                485                 490                 495
Gly Lys Thr Leu Thr Ile Gln Val Lys Glu Phe Gly Asp Ala Gly Gln
                500                 505                 510
Tyr Thr Cys His Lys Gly Gly Glu Val Leu Ser His Ser Leu Leu Leu
                515                 520                 525
Leu His Lys Lys Glu Asp Gly Ile Trp Ser Thr Asp Ile Leu Lys Asp
            530                 535                 540
Gln Lys Glu Pro Lys Asn Lys Thr Phe Leu Arg Cys Glu Ala Lys Asn
545                 550                 555                 560
Tyr Ser Gly Arg Phe Thr Cys Trp Trp Leu Thr Thr Ile Ser Thr Asp
                565                 570                 575
Leu Thr Phe Ser Val Lys Ser Ser Arg Gly Ser Ser Asp Pro Gln Gly
                580                 585                 590
Val Thr Cys Gly Ala Ala Thr Leu Ser Ala Glu Arg Val Arg Gly Asp
                595                 600                 605
Asn Lys Glu Tyr Glu Tyr Ser Val Glu Cys Gln Glu Asp Ser Ala Cys
            610                 615                 620
Pro Ala Ala Glu Glu Ser Leu Pro Ile Glu Val Met Val Asp Ala Val
625                 630                 635                 640
His Lys Leu Lys Tyr Glu Asn Tyr Thr Ser Ser Phe Phe Ile Arg Asp
                645                 650                 655
```

-continued

```
Ile Ile Lys Pro Asp Pro Pro Lys Asn Leu Gln Leu Lys Pro Leu Lys
            660                 665                 670

Asn Ser Arg Gln Val Glu Val Ser Trp Glu Tyr Pro Asp Thr Trp Ser
        675                 680                 685

Thr Pro His Ser Tyr Phe Ser Leu Thr Phe Cys Val Gln Val Gln Gly
    690                 695                 700

Lys Ser Lys Arg Glu Lys Asp Arg Val Phe Thr Asp Lys Thr Ser
705                 710                 715                 720

Ala Thr Val Ile Cys Arg Lys Asn Ala Ser Ile Ser Val Arg Ala Gln
                725                 730                 735

Asp Arg Tyr Tyr Ser Ser Ser Trp Ser Glu Trp Ala Ser Val Pro Cys
            740                 745                 750

Ser
```

<210> SEQ ID NO 103
<211> LENGTH: 431
<212> TYPE: PRT
<213> ORGANISM: Unknown
<220> FEATURE:
<223> OTHER INFORMATION: Synthetic

<400> SEQUENCE: 103

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Ser Gly Ile Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Arg Asn Leu Pro Val Ala
225                 230                 235                 240

Thr Pro Asp Pro Gly Met Phe Pro Cys Leu His His Ser Gln Asn Leu
                245                 250                 255

Leu Arg Ala Val Ser Asn Met Leu Gln Lys Ala Arg Gln Thr Leu Glu
```

-continued

```
                260                 265                 270
Phe Tyr Pro Cys Thr Ser Glu Glu Ile Asp His Glu Asp Ile Thr Lys
            275                 280                 285

Asp Lys Thr Ser Thr Val Glu Ala Cys Leu Pro Leu Glu Leu Thr Lys
        290                 295                 300

Asn Glu Ser Cys Leu Asn Ser Arg Glu Thr Ser Phe Ile Thr Asn Gly
305                 310                 315                 320

Ser Cys Leu Ala Ser Arg Lys Thr Ser Phe Met Met Ala Leu Cys Leu
                325                 330                 335

Ser Ser Ile Tyr Glu Asp Leu Lys Met Tyr Gln Val Glu Phe Lys Thr
            340                 345                 350

Met Asn Ala Lys Leu Leu Met Asp Pro Lys Arg Gln Ile Phe Leu Asp
        355                 360                 365

Gln Asn Met Leu Ala Val Ile Asp Glu Leu Met Gln Ala Leu Asn Phe
                375                 380
        370

Asn Ser Glu Thr Val Pro Gln Lys Ser Ser Leu Glu Glu Pro Asp Phe
385                 390                 395                 400

Tyr Lys Thr Lys Ile Lys Leu Cys Ile Leu Leu His Ala Phe Arg Ile
                405                 410                 415

Arg Ala Val Thr Ile Asp Arg Val Met Ser Tyr Leu Asn Ala Ser
            420                 425                 430
```

<210> SEQ ID NO 104
<211> LENGTH: 540
<212> TYPE: PRT
<213> ORGANISM: Unknown
<220> FEATURE:
<223> OTHER INFORMATION: Synthetic

<400> SEQUENCE: 104

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Ser Gly Ile Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
            195                 200                 205
Pro Val Thr Lys Ser Phe Asn Arg Gly Glu Cys Gly Gly Gly Ser
    210                 215                 220

Gly Gly Gly Gly Ser Gly Gly Gly Ser Ile Trp Glu Leu Lys Lys
225                 230                 235                 240

Asp Val Tyr Val Val Glu Leu Asp Trp Tyr Pro Asp Ala Pro Gly Glu
                245                 250                 255

Met Val Val Leu Thr Cys Asp Thr Pro Glu Glu Asp Gly Ile Thr Trp
            260                 265                 270

Thr Leu Asp Gln Ser Ser Glu Val Leu Gly Ser Gly Lys Thr Leu Thr
        275                 280                 285

Ile Gln Val Lys Glu Phe Gly Asp Ala Gly Gln Tyr Thr Cys His Lys
    290                 295                 300

Gly Gly Glu Val Leu Ser His Ser Leu Leu Leu Leu His Lys Lys Glu
305                 310                 315                 320

Asp Gly Ile Trp Ser Thr Asp Ile Leu Lys Asp Gln Lys Glu Pro Lys
                325                 330                 335

Asn Lys Thr Phe Leu Arg Cys Glu Ala Lys Asn Tyr Ser Gly Arg Phe
            340                 345                 350

Thr Cys Trp Trp Leu Thr Thr Ile Ser Thr Asp Leu Thr Phe Ser Val
        355                 360                 365

Lys Ser Ser Arg Gly Ser Ser Asp Pro Gln Gly Val Thr Cys Gly Ala
    370                 375                 380

Ala Thr Leu Ser Ala Glu Arg Val Arg Gly Asp Asn Lys Glu Tyr Glu
385                 390                 395                 400

Tyr Ser Val Glu Cys Gln Glu Asp Ser Ala Cys Pro Ala Ala Glu Glu
                405                 410                 415

Ser Leu Pro Ile Glu Val Met Val Asp Ala Val His Lys Leu Lys Tyr
            420                 425                 430

Glu Asn Tyr Thr Ser Ser Phe Phe Ile Arg Asp Ile Ile Lys Pro Asp
        435                 440                 445

Pro Pro Lys Asn Leu Gln Leu Lys Pro Leu Lys Asn Ser Arg Gln Val
    450                 455                 460

Glu Val Ser Trp Glu Tyr Pro Asp Thr Trp Ser Thr Pro His Ser Tyr
465                 470                 475                 480

Phe Ser Leu Thr Phe Cys Val Gln Val Gln Gly Lys Ser Lys Arg Glu
                485                 490                 495

Lys Lys Asp Arg Val Phe Thr Asp Lys Thr Ser Ala Thr Val Ile Cys
            500                 505                 510

Arg Lys Asn Ala Ser Ile Ser Val Arg Ala Gln Asp Arg Tyr Tyr Ser
        515                 520                 525

Ser Ser Trp Ser Glu Trp Ala Ser Val Pro Cys Ser
    530                 535                 540

<210> SEQ ID NO 105
<211> LENGTH: 4
<212> TYPE: PRT
<213> ORGANISM: Unknown
<220> FEATURE:
<223> OTHER INFORMATION: Synthetic

<400> SEQUENCE: 105

Gly Phe Ser Gly
1
```

```
<210> SEQ ID NO 106
<211> LENGTH: 4
<212> TYPE: PRT
<213> ORGANISM: Unknown
<220> FEATURE:
<223> OTHER INFORMATION: Synthetic

<400> SEQUENCE: 106

Gly Lys Val Ser
1

<210> SEQ ID NO 107
<211> LENGTH: 4
<212> TYPE: PRT
<213> ORGANISM: Unknown
<220> FEATURE:
<223> OTHER INFORMATION: Synthetic

<400> SEQUENCE: 107

Gly Trp Ile Gly
1

<210> SEQ ID NO 108
<211> LENGTH: 4
<212> TYPE: PRT
<213> ORGANISM: Unknown
<220> FEATURE:
<223> OTHER INFORMATION: Synthetic

<400> SEQUENCE: 108

Gly Lys Lys Trp
1

<210> SEQ ID NO 109
<211> LENGTH: 4
<212> TYPE: PRT
<213> ORGANISM: Unknown
<220> FEATURE:
<223> OTHER INFORMATION: Synthetic

<400> SEQUENCE: 109

Gly Ala Tyr Met
1

<210> SEQ ID NO 110
<211> LENGTH: 8
<212> TYPE: PRT
<213> ORGANISM: Unknown
<220> FEATURE:
<223> OTHER INFORMATION: Synthetic

<400> SEQUENCE: 110

Val Pro Leu Ser Leu Tyr Ser Gly
1               5

<210> SEQ ID NO 111
<211> LENGTH: 8
<212> TYPE: PRT
<213> ORGANISM: Unknown
<220> FEATURE:
<223> OTHER INFORMATION: Synthetic

<400> SEQUENCE: 111

Gly Pro Gln Gly Ile Ala Gly Gln
1               5

<210> SEQ ID NO 112
```

```
<211> LENGTH: 8
<212> TYPE: PRT
<213> ORGANISM: Unknown
<220> FEATURE:
<223> OTHER INFORMATION: Synthetic

<400> SEQUENCE: 112

Val Pro Met Ser Met Arg Gly Gly
1               5

<210> SEQ ID NO 113
<211> LENGTH: 8
<212> TYPE: PRT
<213> ORGANISM: Unknown
<220> FEATURE:
<223> OTHER INFORMATION: Synthetic

<400> SEQUENCE: 113

Ile Pro Val Ser Leu Arg Ser Gly
1               5

<210> SEQ ID NO 114
<211> LENGTH: 8
<212> TYPE: PRT
<213> ORGANISM: Unknown
<220> FEATURE:
<223> OTHER INFORMATION: Synthetic

<400> SEQUENCE: 114

Arg Pro Phe Ser Met Ile Met Gly
1               5

<210> SEQ ID NO 115
<211> LENGTH: 8
<212> TYPE: PRT
<213> ORGANISM: Unknown
<220> FEATURE:
<223> OTHER INFORMATION: Synthetic

<400> SEQUENCE: 115

Val Pro Leu Ser Leu Thr Met Gly
1               5

<210> SEQ ID NO 116
<211> LENGTH: 8
<212> TYPE: PRT
<213> ORGANISM: Unknown
<220> FEATURE:
<223> OTHER INFORMATION: Synthetic

<400> SEQUENCE: 116

Ile Pro Glu Ser Leu Arg Ala Gly
1               5

<210> SEQ ID NO 117
<211> LENGTH: 10
<212> TYPE: PRT
<213> ORGANISM: Unknown
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Nva

<400> SEQUENCE: 117

Arg Pro Lys Pro Val Glu Xaa Trp Arg Lys
1               5                   10
```

<210> SEQ ID NO 118
<211> LENGTH: 10
<212> TYPE: PRT
<213> ORGANISM: Unknown
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Nva

<400> SEQUENCE: 118

Arg Pro Lys Pro Tyr Ala Xaa Trp Met Lys
1               5                   10

<210> SEQ ID NO 119
<211> LENGTH: 8
<212> TYPE: PRT
<213> ORGANISM: Unknown
<220> FEATURE:
<223> OTHER INFORMATION: Synthetic

<400> SEQUENCE: 119

Pro Gln Gly Ile Ala Gly Gln Arg
1               5

<210> SEQ ID NO 120
<211> LENGTH: 7
<212> TYPE: PRT
<213> ORGANISM: Unknown
<220> FEATURE:
<223> OTHER INFORMATION: Synthetic

<400> SEQUENCE: 120

Pro Leu Gly Ile Ala Gly Arg
1               5

<210> SEQ ID NO 121
<211> LENGTH: 5
<212> TYPE: PRT
<213> ORGANISM: Unknown
<220> FEATURE:
<223> OTHER INFORMATION: Synthetic

<400> SEQUENCE: 121

Gly Pro Leu Gly Pro
1               5

<210> SEQ ID NO 122
<211> LENGTH: 5
<212> TYPE: PRT
<213> ORGANISM: Unknown
<220> FEATURE:
<223> OTHER INFORMATION: Synthetic

<400> SEQUENCE: 122

Gly Pro Ile Gly Pro
1               5

<210> SEQ ID NO 123
<211> LENGTH: 5
<212> TYPE: PRT
<213> ORGANISM: Unknown
<220> FEATURE:
<223> OTHER INFORMATION: Synthetic

<400> SEQUENCE: 123

Ser Gly Gly Gly Ser
1               5

<210> SEQ ID NO 124
<211> LENGTH: 4
<212> TYPE: PRT
<213> ORGANISM: Unknown
<220> FEATURE:
<223> OTHER INFORMATION: Synthetic

<400> SEQUENCE: 124

Gly Gly Gly Ser
1

<210> SEQ ID NO 125
<211> LENGTH: 5
<212> TYPE: PRT
<213> ORGANISM: Unknown
<220> FEATURE:
<223> OTHER INFORMATION: Synthetic

<400> SEQUENCE: 125

Gly Gly Gly Gly Ser
1               5

<210> SEQ ID NO 126
<211> LENGTH: 13
<212> TYPE: PRT
<213> ORGANISM: Unknown
<220> FEATURE:
<223> OTHER INFORMATION: Synthetic

<400> SEQUENCE: 126

Asp Lys Thr His Thr Cys Pro Pro Ser Cys Ala Pro Glu
1               5                   10

<210> SEQ ID NO 127
<211> LENGTH: 18
<212> TYPE: PRT
<213> ORGANISM: Unknown
<220> FEATURE:
<223> OTHER INFORMATION: Synthetic

<400> SEQUENCE: 127

Glu Pro Lys Ser Ser Asp Lys Thr His Thr Ser Pro Pro Ser Pro Ala
1               5                   10                  15

Pro Glu

<210> SEQ ID NO 128
<211> LENGTH: 8
<212> TYPE: PRT
<213> ORGANISM: Unknown
<220> FEATURE:
<223> OTHER INFORMATION: Synthetic

<400> SEQUENCE: 128

Ser Val Glu Ser Pro Pro Ser Pro
1               5

<210> SEQ ID NO 129
<211> LENGTH: 12
<212> TYPE: PRT
<213> ORGANISM: Unknown
<220> FEATURE:
<223> OTHER INFORMATION: Synthetic

```
<400> SEQUENCE: 129

Glu Arg Lys Ser Ser Val Glu Ser Pro Pro Ser Pro
1               5                   10

<210> SEQ ID NO 130
<211> LENGTH: 7
<212> TYPE: PRT
<213> ORGANISM: Unknown
<220> FEATURE:
<223> OTHER INFORMATION: Synthetic

<400> SEQUENCE: 130

Pro Pro Ser Pro Ser Ser Pro
1               5

<210> SEQ ID NO 131
<211> LENGTH: 12
<212> TYPE: PRT
<213> ORGANISM: Unknown
<220> FEATURE:
<223> OTHER INFORMATION: Synthetic

<400> SEQUENCE: 131

Glu Ser Lys Tyr Gly Pro Pro Ser Pro Ser Ser Pro
1               5                   10
```